(12) United States Patent
Mattes et al.

(10) Patent No.: US 8,507,472 B2
(45) Date of Patent: Aug. 13, 2013

(54) BICYCLIC PYRIDINYLPYRAZOLES

(75) Inventors: Amos Mattes, Langenfeld (DE); Hendrik Helmke, Liederbach (DE); Stefan Hillebrand, Neuss (DE); Gorka Peris, Köln (DE); Alexander Sudau, Leichlingen (DE); Lars Rodefeld, Leverkusen (DE); Stefan Gauger, Leverkusen (DE); Jürgen Benting, Leichlingen (DE); Peter Dahmen, Neuss (DE); Ruth Meissner, Leverkusen (DE); Ulrike Wachendorff-Neumann, Neuwied (DE); Hiroyuki Hadano, Tochigi (JP)

(73) Assignee: Bayer CropScience AG, Monheim (DE)

( * ) Notice: Subject to any disclaimer, the term of this patent is extended or adjusted under 35 U.S.C. 154(b) by 157 days.

(21) Appl. No.: 13/080,257

(22) Filed: Apr. 5, 2011

(65) Prior Publication Data

US 2011/0251178 A1    Oct. 13, 2011

Related U.S. Application Data

(60) Provisional application No. 61/321,704, filed on Apr. 7, 2010.

(30) Foreign Application Priority Data

Apr. 7, 2010    (EP) ..................... 10159210

(51) Int. Cl.
*A01N 43/84* (2006.01)
*A01N 43/40* (2006.01)
*A01N 43/46* (2006.01)
*A01N 43/42* (2006.01)
*C07D 401/14* (2006.01)
*C07D 487/14* (2006.01)
*C07D 471/04* (2006.01)
*C07D 498/04* (2006.01)

(52) U.S. Cl.
USPC ... 514/214.02; 514/300; 514/338; 514/230.5; 514/226.8; 544/55; 544/105; 546/121; 546/276.7; 540/579

(58) Field of Classification Search
USPC .............. 514/214.02, 300, 338, 230.5, 226.8; 544/105, 55; 546/121, 276.7; 540/579
See application file for complete search history.

(56) References Cited

U.S. PATENT DOCUMENTS

| 4,245,432 A | 1/1981 | Dannelly |
| 4,272,417 A | 6/1981 | Barke et al. |
| 4,808,430 A | 2/1989 | Kouno |
| 5,876,739 A | 3/1999 | Turnblad et al. |
| 5,932,576 A | 8/1999 | Anantanarayan et al. |
| 6,335,336 B1 | 1/2002 | Anantanarayan et al. |
| 6,423,713 B1 | 7/2002 | Anantanarayan et al. |
| 6,511,997 B1 | 1/2003 | Minami et al. |
| 6,667,325 B1 | 12/2003 | Minami et al. |
| 6,979,686 B1 | 12/2005 | Naraian et al. |
| 2003/0176428 A1 | 9/2003 | Schneidersmann et al. |
| 2004/0147525 A1 | 7/2004 | Kimura et al. |
| 2006/0063934 A1 | 3/2006 | Hagihara et al. |
| 2007/0155779 A1 | 7/2007 | Verhoest et al. |
| 2008/0039633 A1 | 2/2008 | Jung et al. |
| 2009/0018156 A1 | 1/2009 | Tang et al. |

FOREIGN PATENT DOCUMENTS

| EP | 1 188 754 A1 | 3/2002 |
| EP | 1 553 096 A1 | 7/2005 |
| EP | 2 044 957 A1 | 4/2009 |
| WO | WO 89/10396 A1 | 11/1989 |
| WO | WO 95/31451 A1 | 11/1995 |
| WO | WO 96/33270 A1 | 10/1996 |
| WO | WO 98/52937 A2 | 11/1998 |
| WO | WO 98/52940 A1 | 11/1998 |
| WO | WO 00/31063 A1 | 6/2000 |
| WO | WO 01/03015 A1 | 1/2001 |
| WO | WO 02/28186 A2 | 4/2002 |
| WO | WO 02/080675 A1 | 10/2002 |
| WO | WO 02/088124 A2 | 11/2002 |
| WO | WO 02/094833 A1 | 11/2002 |
| WO | WO 03/049542 A1 | 6/2003 |
| WO | WO 03/076441 A1 | 9/2003 |

(Continued)

OTHER PUBLICATIONS

Cheung et al. Bioorganic and Medicinal Chemistry Letters (2008), 18(2), 5428-5430.*

(Continued)

*Primary Examiner* — Kahsay T Habte
(74) *Attorney, Agent, or Firm* — Sterne, Kessler, Goldstein & Fox P.L.L.C.

(57) ABSTRACT

Bicyclic pyridinylpyrazoles of the formula (I)

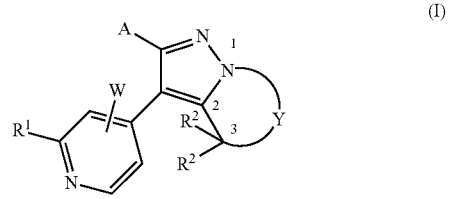

in which the symbols have the meanings given in the description and agrochemically active salts thereof and their use for controlling unwanted microorganisms in crop protection and the protection of materials and for reducing mycotoxins in plants and plant parts, and also processes for preparing compounds of the formula (I).

20 Claims, No Drawings

(56) References Cited

FOREIGN PATENT DOCUMENTS

| WO | WO 03/095455 A2 | 11/2003 |
|---|---|---|
| WO | WO 2004/013135 A1 | 2/2004 |
| WO | WO 2004/016606 A1 | 2/2004 |
| WO | WO 2005/041879 A2 | 5/2005 |
| WO | WO 2005/044194 A2 | 5/2005 |
| WO | WO 2007/018314 A2 | 2/2007 |
| WO | WO 2007/018818 A1 | 2/2007 |
| WO | WO 2007/024782 A2 | 3/2007 |
| WO | WO 2007/027777 A2 | 3/2007 |
| WO | WO 2007/105058 A2 | 9/2007 |
| WO | WO 2008/024978 A2 | 2/2008 |
| WO | WO 2008/132434 A2 | 11/2008 |
| WO | WO 2009/076440 A2 | 6/2009 |
| WO | WO 2010/010154 A1 | 1/2010 |

OTHER PUBLICATIONS

Abdel-Aziz, M. and Abdel-Rahman, H.M., "Synthesis and antimycobacterial evaluation of some pyrazine-2-carboxylic acid hydrazide derivatives," *European Journal of Medicinal Chemistry* 45:3384-3388, Elsevier Masson SAS, France (2010).

Ashimori, A., et al., "Novel 1,4-Dihydropyridine Calcium Antagonists. I. Synthesis and Hypotensive Activity of 4-(Substituted Pyridyl)-1,4-dihydropyridine Derivatives," *Chem. Pharm. Bull.* 38(9):2446-2458, Pharmaceutical Society of Japan, Japan (1990).

Barbachyn, M.R., et al., "Identification of Phenylisoxazolines as Novel and Viable Antibacterial Agents Active against Gram-Positive Pathogens," *J. Med. Chem.* 46(2):284-302, American Chemical Society, United States (2003).

Cacchi, S., et al., "*N*-Propargylic β-Enaminones: Common Intermediated for the Synthesis of Polysubstituted Pyrroles and Pyridines," *Organic Letters* 10(13):2629-2632, American Chemical Society, United States (2008).

Carling, R.W., et al., "2,3,7-Trisubstituted pyrazolo[1,5-*d*][1,2,4]triazines: Functionally selective $GABA_A$ α3-subtype agonists," *Bioorganic & Medicinal Chemistry Letters* 16:3550-3554, Elsevier Ltd., England (2006).

Deshayes, C. and Gelin, S., "Synthesis of Some 3-Ethoxycarbonyl-2-methyl-4,5-dihydro-7*H*-pyrazolo[1,5-*c*]-1,3-oxazines from 4-Ethoxycarbonyl-5(or 3)-(2-hydroxyalkyl)-3(or 5)-methylpyrazoles," *Synthesis* 440-441, Georg Thieme Publishers, Germany (1979).

Draber W., "Chemie der Pflanzenschutz-und Schadlingsbekampfungsmittel [Chemistry of Plant Protection and Pest Control Agents]," *R. Wegler ed.* 2:400-412, Springer-Verlag, Berlin (1970).

English language translation of Draber W., "Chemie der Pflanzenschutz-und Schadlingsbekampfungsmittel [Chemistry of Plant Protection and Pest Control Agents]," *R. Wegler ed.* 2:400-412, Springer-Verlag, Berlin (1970).

Elangovan, A., et al., "Sonogashira Coupling Reaction with Diminished Homocoupling,"*Organic Letters* 5(11):1841-1844, American Chemical Society, United States (2003).

Girgis, A.S., et al., "A Convenient Regioselective Synthesis of 6-Amino-2-oxo-3,5-pyridinedicarbonitriles," *Z. Naturforsch.* 58:678-685, Verlag der Zeitschrift fur Naturforschung, Germany (2003).

Graneto, M.J., et al., "Synthesis, Crystal Structure, and Activity of Pyrazole-Based Inhibitors of p38 Kinase," *J. Med. Chem.* 50:5712-5719, American Chemical Society, United States (2007).

Kumar, G. and Boyer, J.H., "Alkyl N-Nitro- and N-Nitrosopiperidin-2-Ylcarbamates," *Heterocycles* 31(3):481-484, Elsevier, Amsterdam, Netherlands (1990).

Kumar, K. et al., "Biologically Active Compounds through Catalysis: Efficient Synthesis of *N*-(Heteroarylcarbonyl)-*N*'-(arylalkyl)piperazines," *Chem. Eur. J.* 10:746-757, Wiley-VCH Verlag GmbH & Co. KGaA, Weinheim, Germany (2004).

Larock, R.C., "Interconversion of Nitriles, Carboxylic Acids and Derivatives," *Comprehensive Organic Transformations*:1929-1930, Wiley-VCH, Germany (1999).

Li,H-Y., et al., "A concise synthesis of quinazolinone TGF-β RI inhibitor through one-pot three-component Suzuki-Miyaura/ etherification and imidate-amide rearrangement reactions," *Tetrahedron* 63:11763-11770, Elsevier Ltd., England (2007).

Linderman, R.J. and Kirollos, K.S., "An Efficient Method for the Synthesis of Trifluoromethyl Substituted Heterocycles," *Tetrahedron Letters* 30(16):2049-2052, Pergamon Press plc, England (1989).

Montalbetti, C.A.G.N. and Falque, V., "Amide bond formation and peptide coupling," *Tetrahedron* 61:10827-10852, Elsevier Ltd., England (2005).

Montiel, L.E., et al., "Efficient Total Synthesis of Racemic Bisabolane.Sesquiterpenes Curcuphenol and Xanthorrhizol Starting from Substituted Acetophenones," *HELVETICA CHIMICA ACTA* 93:1261-1273, Verlag Helvetica Chimica Acta AG, Zürich, Switzerland (2010).

Profft, V.E. and Richter, H., "Über die Darstellung der 4-Halogenide des 2•Methylpyridins," *Journal für praktische Chemie. 4th Series* 9:164-172, Wiley-VCH, Germany (1959).

Saitton, S., et al., "A synthetic approach to 2,3,4-substituted pyridines useful as scaffolds for tripeptidomimetics," *Tetrahedron* 60:6113-6120, Elsevier Ltd., England (2004).

Sakthivel, K. and Cook, P.D., "Direct $S_NAr$ amination of fluorinated imidazo[4,5-c]-pyridine nucleoside: efficient synthesis of 3-fluoro-3-deazaadenosine analogs," *Tetrahedron Letters* 46:3883-3887, Elsevier Ltd., England (2005).

Sashida, H., et al., "A New One-Pot Synthetic Method for Selenium-Containing Medium-Sized α,β—Unsaturated Cyclic Ketones," *Synthesis* 2008(20):3229-3236, Georg Thieme Verlag Stuttgart, New York, U.S.A. (2008).

Sawyer, J.S., et al., "Synthesis and Activity of New Aryl- and Heteroaryl-Substituted Pyrazole Inhibitors of the Transforming Growth Factor-β Type I Receptor Kinase Domain," *Journal of Medicinal Chemistry* 46(19):3953-3956, American Chemical Society, United States(2003).

Schumacher, R.F., et al., "Synthesis of 2,3-Dihydroselenophene and Selenophene Derivatives by Electrophilic Cyclization of Homopropargyl Selenides," *Organic Letters* 12(9):1952-1955, American Chemical Society, United States (2010).

Seefeld, M.A., et al., "Discovery of 5-pyrrolopyridinyl-2-thiophenecarboxamides as potent AKT kinase inhibitors," *Bioorganic & Medicinal Chemistry Letters* 19:2244-2248, Elsevier Ltd., England (2009).

Shiro, Y., et al., "First synthesis of polyoxin M," *Tetrahedron* 62:8687-8695, Elsevier Ltd., England (2006).

Stevens, K.L., et al., "Pyrazolo[1,5-a]pyridines as p38 Kinase Inhibitors," *Organic Letters* 7(21):4753-4756, American Chemical Society, United States (2005).

Sun, A., et al., "Non-nucleoside inhibitors of the measles virus RNA-dependent RNA polymerase complex activity: Synthesis and in nitro evaluation," *Bioorganic & Medicinal Chemistry Letters* 17:5199-5203, Elsevier Ltd., England (2007).

Szczepankiewicz, B.G., et al., "Aminopyridine-Based c-Jun N-Terminal Kinase Inhibitors with Cellular Activity and Minimal Cross-Kinase Activity," *J. Med. Chem.* 49:3563-3580, American Chemical Society, United States (2006).

Taylor, E.C., et al., "Synthesis and Properties of 3-Oxo-1,2-diazetidinium Ylides," *J. Am. Chem. Soc.* 103:7743-7752, American Chemical Society, United States (1981).

Thomas, A.A., et al., "Non-charged thiamine analogs as inhibitors of enzyme transketolase," *Bioorganic & Medicinal Chemistry Letters* 18509-512, Elsevier Ltd., England (2008).

Tyrrell, E. and Brookes,P., "The Synthesis and Applications of Heterocyclic Boronic Acids," *Synthesis* 2004(4):469-483, Georg Thieme Verlag Stuttgart, New York, United States (2004).

Venkatesan, A.M., et al., "Structure-Activity Relationship of 6-Methylidene Penems Bearing 6,5 Bicyclic Heterocycles as Broad-Spectrum β-Lactamase Inhibitors: Evidence for 1,4-Thiazepine Intermediates with C7 R Stereochemistry by Computational Methods," *J. Med. Chem.* 494623-4637, American Chemical Society, United States (2010).

Wang, S., et al., "Structure Based Drug Design: Development of Potent and Selective Factor IXa (FIXa) Inhibitors," *J. Med. Chem.* 53:1473-1482, American Chemical Society, United States (2010).

Wiles, J.A., et al., "Biological evaluation of isothiazoloquinolones containing aromatic heterocycles at the 7-position: In vitro activity of a series of potent antibacterial agents that are effective against methicillin-resistant *Staphylococcus aureus*," *Bioorganic & Medicinal Chemistry Letters* 16:1277-1281, Elsevier Ltd., England (2006).

Winters, G., et al., "Synthesis and pregnancy terminating activity of pyrazolo[1,5-a]indoles and quinolines," *Eur. J. Med. Chem.—Chim. Ther.* 19(3); 215-218, Sociéte d'études de Chimie therapeutique, France (1984).

Zhang, J-H., et al., "Synthesis and preliminary biological evaluation of novel pyrazolo[1,5-*a*]pyrazin-4(5*H*)—one derivatives as potential agents against A549 lung cancer cells," *Bioorganic & Medicinal Chemistry* 16:10165-10171, Elsevier Ltd., England (2008).

Tu, M., et al., "Synthesis of novel organic intermediate substituded pyrazole ethyl formate and pyrazolecarboxylic acid," *Journal of Zheijiang University (Science edition)* 35(6):641-643, zeijuabg Daxue Xuebaim Lixueban, China (2008) (Only Abstract in English).

International Search Report for International Application No. PCT/EP2011/055153, European Patent Office, The Hague, Netherlands, mailed on May 24, 2011.

\* cited by examiner

BICYCLIC PYRIDINYLPYRAZOLES

The present invention relates to novel bicyclic pyridinylpyrazoles, to a plurality of processes for their preparation and to their use for controlling unwanted microorganisms in crop protection and in the protection of materials, and also for reducing mycotoxins in plants and plant parts. The present invention furthermore relates to a process for controlling phytopathogenic fungi and for reducing mycotoxins in plants and plant parts in crop protection and also to crop protection compositions comprising bicyclic pyridinylpyrazoles.

It is already known that certain arylpyrazoles have fungicidal properties (cf., for example, WO 2009/076440, WO 2003/049542 and WO 2001/03015). The activity of the substances described in these publications is good; however, in some cases it is unsatisfactory.

WO 2002/094833 describes certain heteroaryl-substituted pyrazoles suitable for medicinal use, here as inhibitors of TGF-beta signal transduction. Similar compounds are also described in WO 1998/052937, WO 2002/094833, EP-A 1 553 096, WO 2004/029043, WO 1998/052940, WO 2000/031063, WO 1995/031451, WO 2002/057265 and WO 2000/039116. However, an effect on fungal pathogens is not described.

WO 2007/105058 describes certain heteroaryl-substituted pyrazoles which can be used as modulators or inhibitors of the human Raf enzyme. However, an effect on fungal pathogens is not described.

Since the ecological and economical demands made on modern crop protection agents are increasing constantly, for example with respect to activity spectrum, toxicity, selectivity, application rate, formation of residues and favourable manufacture, and there can furthermore be problems, for example, with resistances, there is a constant need to develop novel crop protection agents, in particular fungicides, which, at least in some areas, have advantages over the known ones.

Surprisingly, it has now been found that the bicyclic pyridinylpyrazoles according to the invention achieve at least some aspects of the objects mentioned and are suitable for use as crop protection agents, in particular as fungicides.

The invention relates to compounds of the formula (I)

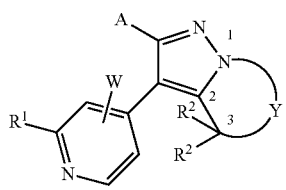

(I)

in which the symbols have the following meanings:

Y together with the adjacent nitrogen atom "1" and the two carbon atoms "2" and "3" forms a 5- to 7-membered non-aromatic heterocyclic ring whose further ring members are selected from the group consisting of $C(R^2)_2$, O, S, $NR^3$, $C(R^2)=C(R^2)$, $C(R^2)=N$, $N=N$, $C(=O)$, $C(=S)$, $C(=NR^4)$, $S(=O)_p(=NR^4)_q$ and $SiR^{5a}R^{5b}$;

$R^2$ represent in each case independently of one another H, halogen, cyano, hydroxyl, —CHO, —NHCHO, —N$_3$, —N=C=O, —N=C=S, —SH, —C(=O)NH$_2$, —C(=O)NHCN, —C(=O)OR$^6$, —C(=O)NHOR$^{6a}$, $C_1$-$C_5$-alkyl, $C_2$-$C_5$-alkenyl, $C_2$-$C_5$-alkynyl, $C_3$-$C_6$-cycloalkyl, $C_3$-$C_6$-halocycloalkyl, $C_3$-$C_6$-cycloalkenyl, $C_1$-$C_5$-haloalkyl, $C_1$-$C_5$-alkoxy, $C_1$-$C_5$-haloalkoxy, $C_3$-$C_6$-cycloalkoxy, $C_2$-$C_5$-alkenyloxy, $C_3$-$C_5$-haloalkenyloxy, $C_2$-$C_5$-alkynyloxy, $C_2$-$C_5$-alkylcarbonyl, $C_2$-$C_5$-alkylcarbonyloxy, $C_2$-$C_5$-haloalkylcarbonyloxy, $C_3$-$C_5$-alkoxycarbonylalkoxy, $C_1$-$C_5$-alkylthio, $C_1$-$C_5$-haloalkylthio, $C_3$-$C_6$-cycloalkylthio, $C_2$-$C_5$-alkyl(thiocarbonyl), $C_2$-$C_5$-alkylthio(thiocarbonyl), $C_1$-$C_5$-alkylsulphinyl, $C_1$-$C_5$-haloalkylsulphinyl, $C_3$-$C_6$-cycloalkylsulphinyl, $C_1$-$C_5$-alkylsulphonyl, $C_1$-$C_5$-haloalkylsulphonyl, $C_3$-$C_6$-cycloalkylsulphonyl, $C_3$-$C_5$-trialkylsilyl, $C_3$-$C_5$-halotrialkylsilyl, $C_1$-$C_5$-alkylamino, $C_2$-$C_5$-haloalkylamino, $C_3$-$C_6$-cycloalkylamino, $C_2$-$C_5$-dialkylamino or $C_3$-$C_5$-halodialkylamino;

$R^3$ represents H, —CN, —C(=O)NH$_2$, —C(=O)NHCN, —CHO, —NHCHO, —C(=O)OR$^6$, —C(=O)NHOR$^{6a}$, hydroxyl, $C_1$-$C_5$-alkyl, $C_2$-$C_5$-alkenyl, $C_2$-$C_5$-alkynyl, $C_3$-$C_6$-cycloalkyl, $C_3$-$C_6$-halocycloalkyl, $C_3$-$C_6$-cycloalkenyl, $C_4$-$C_{10}$-cycloalkylalkyl, $C_4$-$C_7$-alkylcycloalkyl, $C_5$-$C_7$-alkylcycloalkylalkyl, $C_2$-$C_5$-haloalkyl, $C_1$-$C_4$-alkylcarbonyl, $C_1$-$C_4$-haloalkylcarbonyl, $C_3$-$C_7$-cycloalkylcarbonyl, $C_1$-$C_6$-alkoxycarbonyl, $C_1$-$C_4$-haloalkoxycarbonyl, $C_3$-$C_6$-cycloalkoxycarbonyl, $C_2$-$C_6$-alkoxyalkylcarbonyl, $C_2$-$C_6$-alkoxyalkoxycarbonyl, $C_1$-$C_6$-(alkylthio)carbonyl, $C_1$-$C_6$-alkoxy(thiocarbonyl), $C_1$-$C_6$-alkyl(thiocarbonyl), $C_1$-$C_6$-alkylthio(thiocarbonyl), $C_1$-$C_6$-alkylaminocarbonyl, $C_3$-$C_6$-cycloalkylaminocarbonyl, $C_2$-$C_6$-dialkylaminocarbonyl, $C_1$-$C_6$-alkylamino(thiocarbonyl), $C_2$-$C_6$-dialkylamino(thiocarbonyl), $C_2$-$C_6$-alkoxy(alkyl)aminocarbonyl, $C_1$-$C_5$-alkoxy, $C_1$-$C_5$-haloalkoxy, $C_1$-$C_5$-alkylthio, $C_1$-$C_5$-haloalkylthio, $C_3$-$C_6$-cycloalkylthio, $C_1$-$C_5$-alkylaminosulphonyl, $C_3$-$C_5$-trialkylsilyl or $C_3$-$C_5$-halotrialkylsilyl;

$R^4$ in each case represents H, cyano, amino, hydroxyl, $C_1$-$C_6$-alkyl, $C_3$-$C_6$-cycloalkyl, $C_1$-$C_4$-alkylcarbonyl, $C_1$-$C_4$-haloalkylcarbonyl, $C_1$-$C_4$-alkoxy, phenyl or benzoyl;

$R^{5a}$, $R^{5b}$ independently of one another represent $C_1$-$C_4$-alkyl, $C_2$-$C_5$-alkenyl, $C_2$-$C_5$-alkynyl, $C_3$-$C_5$-cycloalkyl, $C_3$-$C_6$-halocycloalkyl, $C_4$-$C_7$-cycloalkylalkyl, $C_4$-$C_7$-alkylcycloalkyl, $C_5$-$C_7$-alkylcycloalkylalkyl, $C_1$-$C_5$-haloalkyl, $C_1$-$C_5$-alkoxy or $C_1$-$C_5$-haloalkoxy;

$R^6$ in each case represents H, $C_1$-$C_6$-alkyl, $C_1$-$C_6$-haloalkyl, $C_3$-$C_6$-cycloalkyl, $C_4$-$C_7$-cycloalkylalkyl, $C_4$-$C_7$-alkylcycloalkyl or benzyl;

$R^{6a}$ in each case represents $C_1$-$C_6$-alkyl, $C_1$-$C_6$-haloalkyl, $C_3$-$C_6$-cycloalkyl, $C_4$-$C_7$-cycloalkylalkyl or $C_4$-$C_7$-alkylcycloalkyl;

A represents a phenyl ring which may optionally be mono- or polysubstituted by $R^7$ or represents a thiophenyl ring which may optionally be mono- or polysubstituted by $R^8$;

$R^7$ independently of one another represent halogen, $C_1$-$C_6$-alkyl, $C_2$-$C_6$-alkenyl, $C_2$-$C_6$-alkynyl, $C_3$-$C_6$-cycloalkyl, $C_3$-$C_6$-halocycloalkyl, $C_4$-$C_7$-alkylcycloalkyl, $C_1$-$C_6$-haloalkyl, $C_2$-$C_6$-haloalkenyl, cyano, nitro, $C_1$-$C_6$-alkoxy, $C_1$-$C_6$-haloalkoxy, $C_1$-$C_6$-alkylthio, $C_1$-$C_6$-alkylsulphinyl, $C_1$-$C_6$-alkylsulphonyl, $C_1$-$C_6$-haloalkylthio, $C_1$-$C_6$-haloalkylsulphinyl, $C_1$-$C_6$-haloalkylsulphonyl, $C_1$-$C_6$-alkylamino, $C_2$-$C_6$-dialkylamino, $C_1$-$C_6$-alkylcarbonyl, $C_1$-$C_6$-alkoxycarbonyl, $C_1$-$C_6$-alkylaminocarbonyl, $C_2$-$C_6$-dialkylaminocarbonyl or $C_3$-$C_6$-trialkylsilyl;

$R^8$ independently of one another represent halogen, cyano, $C_1$-$C_3$-alkyl; $C_1$-$C_3$-alkoxy, $C_1$-$C_3$-haloalkyl, $C_1$-$C_3$-haloalkoxy, $R^1$ represents H, halogen, cyano, hydroxyl, $C_1$-$C_4$-alkyl, $CONR^{9a}R^{9b}$, COOH, $COOR^{12}$, $—NR^{9a}R^{9b}$, $—N(R^{9b})COR^{9a}$, $—N(R^{9b})CSR^{9a}$, $N(R^{9b})COOR^{12}$, $—NR^{9b})SO_2R^{12}$, $—NR^{10}—NR^{11a}R^{11b}$, $—S(O)_mR^{12}$, $—OR^{12}$, $—N=CR^{13a}R^{13b}$ or $—NR^{10}N=CR^{14a}R^{14b}$;

$R^{9a}$ and $R^{11a}$ independently of one another each represent H, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_2$-$C_6$-alkoxyalkyl, $C_3$-$C_6$-alkoxyalkoxyalkyl, $C_3$-$C_6$-alkoxyalkenyl, $C_3$-$C_6$-alkoxyalkynyl, $C_3$-$C_6$-dialkoxyalkyl, $C_4$-$C_{10}$-trialkoxyalkyl, $C_2$-$C_6$-haloalkoxyalkyl, $C_2$-$C_6$-alkoxyhaloalkyl, $C_2$-$C_6$-haloalkoxyhaloalkyl, $C_1$-$C_6$-hydroxyalkyl, $C_1$-$C_{10}$-cyanoalkyl, $C_2$-$C_6$-alkylthioalkyl, $C_2$-$C_6$-alkylsulphinylalkyl, $C_3$-$C_6$-alkylaminoalkyl, $C_3$-$C_6$-haloalkylaminoalkyl, $C_5$-$C_{10}$-cycloalkylaminoalkyl, $C_4$-$C_{10}$-dialkylaminoalkyl, $C_4$-$C_{10}$-halodialkylaminoalkyl, $C_5$-$C_{10}$-cycloalkyl(alkyl)aminoalkyl or —$(CR^{15a}R^{15b})_mR^{16}$;

$R^{9b}$ and $R^{11b}$ independently of one another each represent H, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_2$-$C_6$-alkoxyalkyl, $C_3$-$C_6$-alkoxyalkoxyalkyl, $C_3$-$C_6$-alkoxyalkenyl, $C_3$-$C_6$-alkoxyalkynyl, $C_3$-$C_6$-dialkoxyalkyl, $C_4$-$C_{10}$-trialkoxyalkyl, $C_2$-$C_6$-haloalkoxyalkyl, $C_2$-$C_6$-alkoxyhaloalkyl, $C_2$-$C_6$-haloalkoxyhaloalkyl, $C_1$-$C_6$-hydroxyalkyl, $C_1$-$C_{10}$-cyanoalkyl, $C_2$-$C_6$-alkylthioalkyl, $C_2$-$C_6$-alkylsulphinylalkyl, $C_3$-$C_6$-alkylaminoalkyl, $C_3$-$C_6$-haloalkylaminoalkyl, $C_5$-$C_{10}$-cycloalkylaminoalkyl, $C_4$-$C_{10}$-dialkylaminoalkyl, $C_4$-$C_{10}$-halodialkylaminoalkyl, $C_5$-$C_{10}$-cycloalkyl(alkyl)aminoalkyl or —$(CR^{15a}R^{15b})_mR^{16}$;

or $R^{9a}$ and $R^{9b}$ or $R^{11a}$ and $R^{11b}$ in each case together with the nitrogen atom or the (NCO) unit or the (NCS) unit to which they are attached form a 3- to 6-membered ring which may optionally additionally comprise ring members selected from the group consisting of O, $NR^3$, C(=O), C(=S), C(=$NR^4$), $SiR^{5a}R^{5b}$ and S(=O)$_p$(=$NR^4$)$_q$ and which may optionally be substituted at the ring carbon atoms by 1 to 4 substituents selected from the group consisting of halogen, —CN, $C_1$-$C_2$-alkyl and $C_1$-$C_2$-alkoxy;

$R^{12}$ in each case represents $C_1$-$C_{10}$-alkyl, $C_2$-$C_{10}$-alkenyl, $C_2$-$C_{10}$-alkynyl, $C_1$-$C_{10}$-haloalkyl, $C_2$-$C_{10}$-haloalkenyl, $C_2$-$C_{10}$-haloalkynyl, $C_2$-$C_{10}$-alkoxyalkyl, $C_3$-$C_{10}$-alkoxyalkoxyalkyl, $C_3$-$C_{10}$-alkoxyalkenyl, $C_3$-$C_{10}$-alkoxyalkynyl, $C_3$-$C_{10}$-dialkoxyalkyl, $C_4$-$C_{10}$-trialkoxyalkyl, $C_2$-$C_{10}$-haloalkoxyalkyl, $C_2$-$C_{10}$-alkoxyhaloalkyl, $C_2$-$C_{10}$-haloalkoxyhaloalkyl, $C_2$-$C_{10}$-hydroxyalkyl, $C_2$-$C_{10}$-cyanoalkyl, $C_2$-$C_{10}$-alkylthioalkyl, $C_2$-$C_{10}$-alkylsulphinylalkyl, $C_3$-$C_{10}$-alkylaminoalkyl, $C_3$-$C_{10}$-haloalkylaminoalkyl, $C_5$-$C_{10}$-cycloalkylaminoalkyl, $C_4$-$C_{10}$-dialkcylaminoalkyl, $C_4$-$C_{10}$-halodialkylaminoalkyl, $C_6$-$C_{10}$-cycloalkyl(alkyl)-aminoalkyl or —$(CR^{15a}R^{15b})_mR^{16}$;

$R^{15a}$, $R^{15b}$ independently of one another represent H, halogen, $C_1$-$C_5$-alkyl, $C_1$-$C_5$-haloalkyl or $C_1$-$C_5$-alkoxy;

or a geminal pair of $R^{15a}$ and $R^{15b}$ together with the carbon atom to which it is attached forms C(=O) or a $C_3$-$C_6$-cycloalkyl ring or a $C_3$-$C_6$-halocycloalkyl ring;

$R^{16}$ represents phenyl, $C_3$-$C_8$-cycloalkyl, $C_3$-$C_8$-cycloalkenyl, a 5- or 6-membered heteroaromatic ring or naphthalenyl or an 8-, 9- or 10-membered heteroaromatic bicyclic ring system; or a 5- or 6-membered heterocyclic non-aromatic ring which optionally contains ring members selected from the group consisting of C(=O), C(=S), C(=$NR^4$), $SiR^{5a}R^{5b}$ and S(=O)$_p$(=$NR^4$)$_q$; where each ring or each ring system may optionally be substituted at the ring carbon atoms by up to 5 substituents independently of one another selected from $R^{17}$;

$R^{17}$ in each case independently of one another represent halogen, $C_1$-$C_6$-alkyl, $C_2$-$C_6$-alkenyl, $C_2$-$C_6$-alkynyl, $C_3$-$C_6$-cycloalkyl, $C_4$-$C_{10}$-alkylcycloalkyl, $C_3$-$C_6$-halocycloalkyl, $C_1$-$C_6$-haloalkyl, $C_2$-$C_6$-haloalkenyl, cyano, nitro, $C_1$-$C_6$-alkoxy, $C_3$-$C_8$-cycloalkoxy, $C_3$-$C_8$-halocycloalkoxy, $C_1$-$C_6$-haloalkoxy, $C_1$-$C_6$-alkylthio, $C_1$-$C_6$-alkylsulphinyl, $C_1$-$C_6$-alkylsulphonyl, $C_1$-$C_6$-haloalkylthio, $C_1$-$C_6$-haloalkylsulphinyl, $C_1$-$C_6$-haloalkylsulphonyl, $C_1$-$C_6$-alkylamino, $C_1$-$C_6$-dialkylamino, $C_1$-$C_6$-alkylcarbonyl, $C_1$-$C_6$-alkoxycarbonyl, $C_1$-$C_6$-alkylaminocarbonyl, $C_3$-$C_6$-dialkylaminocarbonyl, $C_3$-$C_6$-trialkylsilyl, phenyl, naphthalenyl or a 5- or 6-membered heteroaromatic ring;

m represents 0, 1 or 2;

$R^{10}$ in each case represents H, $C_1$-$C_5$-alkyl, $C_2$-$C_5$-alkenyl, $C_2$-$C_5$-alkynyl, $C_3$-$C_6$-cycloalkyl, $C_3$-$C_6$-halocycloalkyl, $C_1$-$C_5$-haloalkyl, $C_2$-$C_5$-haloalkenyl, $C_2$-$C_5$-haloalkynyl, $C_2$-$C_5$-alkoxyalkyl, $C_2$-$C_5$-alkylcarbonyl or $C_1$-$C_5$-alkoxy;

$R^{13a}$, $R^{13b}$ independently of one another represent H, —CN, —C(=O)$OR^{18}$, $C_1$-$C_6$-alkyl, $C_2$-$C_6$-alkenyl, $C_2$-$C_6$-alkynyl, $C_3$-$C_8$-cycloalkyl, $C_3$-$C_8$-halocycloalkyl, $C_3$-$C_8$-cycloalkenyl, $C_4$-$C_{10}$-cycloalkylalkyl, $C_4$-$C_{10}$-alkylcycloalkyl, $C_5$-$C_{10}$-alkylcycloalkylalkyl, $C_1$-$C_6$-alkylamino, $C_2$-$C_6$-dialkylamino, $C_2$-$C_6$-alkylaminoalkyl, $C_2$-$C_6$-haloalkylaminoalkyl, $C_4$-$C_6$-cycloalkylaminoalkyl, $C_3$-$C_6$-dialkylaminoalkyl, $C_3$-$C_6$-halodialkylaminoalkyl, $C_5$-$C_{10}$-cycloalkyl(alkyl)aminoalkyl, $C_1$-$C_6$-alkoxy, $C_1$-$C_6$-haloalkoxy, $C_3$-$C_{10}$-cycloalkoxy, $C_1$-$C_{10}$-alkylthio, $C_1$-$C_{10}$-haloalkylthio, $C_3$-$C_{10}$-cycloalkylthio, $C_3$-$C_{10}$-trialkylsilyl or $C_3$-$C_{10}$-halotrialkylsilyl, or phenyl or a 5- or 6-membered heteroaromatic ring, an 8-, 9- or 10-membered heteroaromatic bicyclic ring system, or a 5- or 6-membered heterocyclic non-aromatic ring which optionally contains ring members selected from the group consisting of $NR^3$, C(=O), C(=S), C(=$NR^4$), $SiR^{5a}R^{5b}$ and S(=O)$_p$(=$NR^4$)$_q$; where each ring or each ring system may optionally be substituted at the ring carbon atoms by 1 to 5 substituents selected from the group consisting of $C_1$-$C_3$-alkyl, halogen, —CN and $C_1$-$C_3$-alkoxy;

or $R^{13a}$ and $R^{13b}$ together with the carbon atom to which they are attached form a 3- to 6-membered ring, where said ring may optionally contain ring members selected from the group consisting of $NR^3$, C(=O), C(=S), C(=$NR^4$), $SiR^{5a}R^{5b}$ and S(=O)p(=$NR^4$)$_q$ and may optionally be substituted at the ring carbon atoms by 1 to 4 substituents selected from the group consisting of $C_1$-$C_2$-alkyl, halogen, —CN and $C_1$-$C_2$-alkoxy;

$R^{14a}$, $R^{14b}$ independently of one another represent H, —CN, —C(=O)$OR^{18}$, $C_1$-$C_6$-alkyl, $C_2$-$C_6$-alkenyl, $C_2$-$C_6$-alkynyl, $C_3$-$C_8$-cycloalkyl, $C_3$-$C_8$-halocycloalkyl, $C_3$-$C_8$-cycloalkenyl, $C_4$-$C_{10}$-cycloalkylalkyl, $C_4$-$C_{10}$-alkylcycloalkyl, $C_5$-$C_{10}$-alkylcycloalkylalkyl, $C_1$-$C_6$-alkylamino, $C_2$-$C_6$-dialkylamino, $C_2$-$C_6$-alkylaminoalkyl, $C_2$-$C_6$-haloalkylaminoalkyl, $C_4$-$C_6$-cycloalkylaminoalkyl, $C_3$-$C_6$-dialkylaminoalkyl, $C_3$-$C_6$-halodialkylaminoalkyl, $C_5$-$C_{10}$-cycloalkyl(alkyl)aminoalkyl, $C_1$-$C_6$-alkoxy, $C_1$-$C_6$-haloalkoxy, $C_3$-$C_{10}$-cycloalkoxy, $C_1$-$C_{10}$-alkylthio, $C_1$-$C_{10}$-haloalkylthio, $C_3$-$C_{10}$-cycloalkylthio, $C_3$-$C_{10}$-trialkylsilyl or $C_3$-$C_{10}$-halotrialkylsilyl; or phenyl or a 5- or 6-membered heteroaromatic ring, an 8-, 9- or 10-membered heteroaromatic bicyclic ring system, or a 5- or 6-membered heterocyclic non-aromatic ring which optionally contains ring members selected from the group consisting of $NR^3$, C(=O), C(=S), C(=$NR^4$), $SiR^{5a}R^{5b}$ and S(=O)$_p$(=$NR^4$)$_q$; where each ring or each ring system may optionally be substituted at the ring carbon atoms by 1 to 5 substituents selected from the group consisting of $C_1$-$C_3$-alkyl, halogen, —CN and $C_1$-$C_3$-alkoxy;

or $R^{14a}$, $R^{14b}$ together with the carbon atom to which they are attached form a 3- to 6-membered ring, where said ring may optionally contain ring components selected from the group consisting of $NR^3$, C(=O), C(=S), C(=$NR^4$), $SiR^{5a}R^{5b}$ and S(=O)p(=$NR^4$)$_q$ and may optionally be substituted at the ring carbon atoms by 1 to 4 substituents selected from the group consisting of $C_1$-$C_2$-alkyl, halogen, —CN and $C_1$-$C_2$-alkoxy;

p, q independently of one another represent 0, 1 or 2, provided the sum of p and q is 1 or 2, $R^{18}$ represents $C_1$-$C_6$-alkyl, $C_1$-$C_6$-haloalkyl, $C_3$-$C_6$-cycloalkyl, $C_4$-$C_7$-cycloalkylalkyl or $C_4$-$C_7$-alkylcycloalkyl;

W represents H or

W represents halogen, CN, $C_1$-$C_4$-haloalkyl, $C_1$-$C_4$-alkyl, $C_1$-$C_4$-alkoxy;

and agrochemically active salts thereof.

Compounds of the formula (I) are highly suitable for controlling unwanted microorganisms. In particular, they have strong fungicidal activity and can be used both in crop protection and in the protection of materials and also for reducing mycotoxins in plants and plant parts.

The compounds of the formula (I) can be present both in pure form and as mixtures of various possible isomeric forms, in particular of stereoisomers, such as E and Z, threo and erythro, and also optical isomers, such as R and S isomers or atropisomers, and, if appropriate, also of tautomers. What is claimed are both the E and the Z isomers, and also the threo and erythro, and also the optical isomers, any mixtures of these isomers, and also the possible tautomeric forms.

The formula (I) provides a general definition of the compounds according to the invention.

Preference is given to compounds of the formula (I) in which one or more of the symbols have one of the meanings below:

Y together with the adjacent nitrogen atom "1" and the two carbon atoms "2" and "3" forms a 5- to 7-membered non-aromatic heterocyclic ring whose further ring members are selected from the group consisting of $C(R^2)_2$, O, S, $SO_2$, $NR^3$, —$C(R^2)$=$C(R^2)$—, C(=O) and C(=S);

$R^2$ represent in each case independently of one another H, halogen, cyano, hydroxyl, —CHO, —C(=O)$OR^6$, —C(=O)$NHOR^{6a}$, $C_1$-$C_5$-alkyl, $C_2$-$C_5$-alkenyl, $C_2$-$C_5$-alkynyl, $C_3$-$C_6$-cycloalkyl, $C_3$-$C_6$-halocycloalkyl, $C_3$-$C_6$-cycloalkenyl, $C_1$-$C_5$-haloalkyl, $C_1$-$C_5$-alkoxy, $C_1$-$C_5$-haloalkoxy, $C_3$-$C_6$-cycloalkoxy, $C_2$-$C_5$-alkenyloxy, $C_3$-$C_5$-haloalkenyloxy, $C_2$-$C_5$-alkynyloxy, $C_2$-$C_5$-alkylcarbonyl, $C_1$-$C_5$-alkylthio, $C_1$-$C_5$-haloalkylthio or $C_3$-$C_6$-cycloalkylthio;

$R^3$ represents H, —CN, —C(=O)$NH_2$, —C(=O)NHCN, —CHO, —C(=O)$OR^6$, —C(=O)$NHOR^{6a}$, $C_1$-$C_5$-alkyl, $C_2$-$C_5$-haloalkyl, $C_1$-$C_4$-alkylcarbonyl, $C_1$-$C_4$-haloalkylcarbonyl, $C_3$-$C_6$-cycloalkylcarbonyl, $C_1$-$C_4$-alkoxycarbonyl, $C_1$-$C_4$-haloalkoxycarbonyl, $C_3$-$C_6$-cycloalkoxycarbonyl, $C_3$-$C_6$-alkoxyalkylcarbonyl, $C_3$-$C_6$-alkoxyalkoxycarbonyl, $C_1$-$C_4$-(alkylthio)carbonyl, $C_1$-$C_4$-alkoxy(thiocarbonyl), $C_1$-$C_4$-alkyl(thiocarbonyl), $C_1$-$C_4$-alkylthio(thiocarbonyl), $C_1$-$C_4$-alkylaminocarbonyl, $C_3$-$C_6$-cycloalkylaminocarbonyl, $C_2$-$C_6$-dialkylaminocarbonyl, $C_2$-$C_6$-alkylamino(thiocarbonyl), $C_2$-$C_6$-dialkylamino(thiocarbonyl) or $C_3$-$C_6$-alkoxy(alkyl)aminocarbonyl;

$R^6$ in each case represents H or $C_1$-$C_4$-alkyl;

$R^{6a}$ in each case represents $C_1$-$C_4$-alkyl;

A represents a phenyl ring which may optionally be mono- or polysubstituted by $R^7$ or represents a thiophenyl ring which may optionally be mono- or polysubstituted by $R^8$;

$R^7$ independently of one another represent halogen, $C_1$-$C_4$-alkyl, $C_1$-$C_4$-haloalkyl, cyano, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl or $C_1$-$C_4$-haloalkylthio;

$R^8$ independently of one another represent halogen, cyano, $C_1$-$C_3$-alkyl, $C_1$-$C_3$-alkoxy, $C_1$-$C_3$-haloalkyl;

$R^1$ represents H, halogen, $C_1$-$C_3$-alkyl, cyano, —$NR^{9a}R^{9b}$, —$N(R^{9b})COR^{9a}$, —$N(R^{9b})CSR^{9a}$, —$N(R^{9b})COOR^{12}$, —$OR^{12}$, —S(O)m$R^{6a}$, $COOR_{12}$ or —$CONR^{9a}R^{9b}$;

$R^{9a}$ in each case represents H, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_2$-$C_6$-alkoxyalkyl, $C_3$-$C_6$-alkoxyalkoxyalkyl, $C_3$-$C_6$-alkoxyalkenyl, $C_3$-$C_6$-alkoxyalkynyl, $C_3$-$C_6$-dialkoxyalkyl, $C_2$-$C_6$-haloalkoxyalkyl, $C_2$-$C_6$-alkoxyhaloalkyl, $C_2$-$C_6$-haloalkoxyhaloalkyl, $C_1$-$C_6$-hydroxyalkyl, $C_1$-$C_6$-cyanoalkyl, $C_2$-$C_6$-alkylthioalkyl, $C_2$-$C_6$-alkylsulphinylalkyl, $C_3$-$C_6$-alkylaminoalkyl, $C_3$-$C_6$-haloalkylaminoalkyl, $C_5$-$C_{10}$-cycloalkylaminoalkyl, $C_1$-$C_{10}$-dialkylaminoalkyl, $C_4$-$C_{10}$-halodialkylaminoalkyl or —$(CR^{15a}R^{15b})_mR^{16}$;

$R^{9b}$ in each case represents H, $C_1$-$C_6$-alkyl, $C_2$-$C_6$-alkenyl, $C_2$-$C_6$-alkynyl, $C_1$-$C_6$-haloalkyl or —$(CR^{15a}R^{15b})_mR^{16}$;

or $R^{9a}$, $R^{9b}$ in each case together with the nitrogen atom or the (NCO) or the (NCS) unit to which they are attached form a 3- to 6-membered ring which may optionally additionally also comprise ring members selected from the group consisting of $NR^3$, C(=O), C(=S), O and which is optionally substituted at the ring carbon atoms by 1 to 4 substituents selected from the group consisting of halogen, —CN, $C_1$-$C_2$-alkyl and $C_1$-$C_2$-alkoxy;

$R^{12}$ in each case represents $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl or —$(CR^{15a}R^{15b})_mR^{16}$;

$R^{15a}$, $R^{15}$ independently of one another represent H, halogen or $C_1$-$C_4$-alkyl;

$R^{16}$ represents phenyl, $C_3$-$C_8$-cycloalkyl, $C_3$-$C_8$-cycloalkenyl, a 5- or 6-membered heteroaromatic ring or naphthalenyl or an 8-, 9- or 10-membered heteroaromatic bicyclic ring system; or a 5- or 6-membered heterocyclic non-aromatic ring which optionally contains ring members selected from the group consisting of C(=O), C(=S), C(=$NR^4$); where each ring or each ring system may optionally be substituted at the ring carbon atoms by up to 3 substituents independently of one another selected from $R^{17}$;

$R^{17}$ in each case independently of one another represent halogen, cyano, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_1$-$C_6$-alkoxy;

m represents 0, 1 or 2,

W represents H or

W represents fluorine, chlorine, CN, $CF_3$, methyl, ethyl, methoxy.

Particular preference is given to compounds of the formula (I) in which one or more of the symbols have one of the meanings below:

Y together with the adjacent nitrogen atom "1" and the two carbon atoms "2" and "3" forms a 5- to 7-membered non-aromatic heterocyclic ring selected from the group consisting of: H-1, H-2, H-3, H-4, H-5, H-6, H-7, H-8, H-9 and H-10 shown in Scheme 1, where s is a number from 0 to 4.

Scheme 1

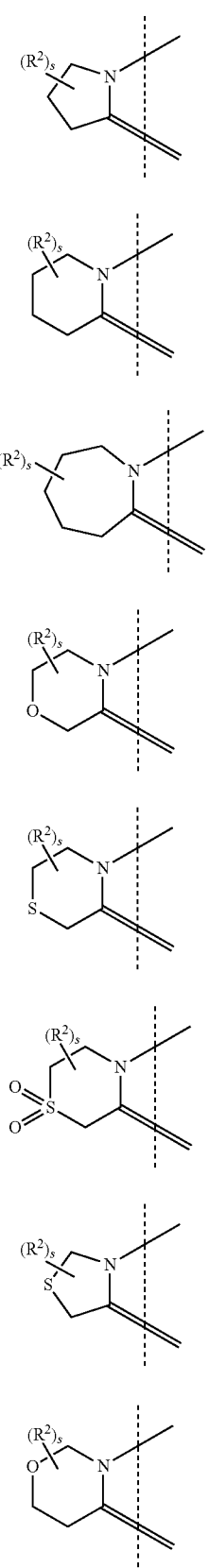

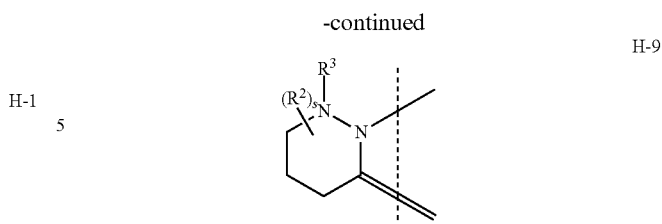

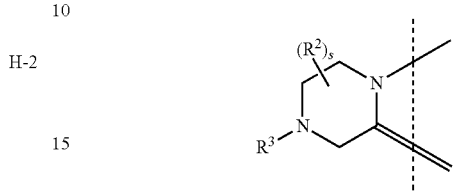

R² in each case independently of one another represent H, F, Cl, Br, I, cyano, hydroxyl, —CHO, —C(=O)OR⁶, methyl, ethyl, isopropyl, n-propyl, trifluoromethyl, difluoromethyl, dichloromethyl, pentafluoroethyl, methoxy, ethoxy, n-propoxy, isopropoxy, trifluoromethoxy, difluoromethoxy or acetyl, propionyl, isobutyryl, 2,2-dimethylpropanoyl;

R³ represents H, —CHO, methyl, ethyl, isopropyl, n-propyl, acetyl, propionyl, isobutyryl, 2,2-dimethylpropanoyl, trifluoroacetyl, difluoroacetyl, CH₃OC(O), CH₃CH₂C(O), (CH₃)₂CHC(O) or CF₃OC(O), CF₂HOC(O);

R⁶ in each case represents H, methyl, ethyl, isopropyl, n-propyl;

A represents a phenyl or thiophene ring which is optionally substituted by radicals selected from the group consisting of F, Cl, Br, I, cyano, methyl, ethyl, isopropyl, n-propyl, trifluoromethyl, difluoromethyl, dichloromethyl, pentafluoroethyl or methoxy, ethoxy, n-propoxy, isopropoxy;

R¹ represents H, F, Cl, Br, I, CH₃, S(O)ₘMe, —NR⁹ᵃR⁹ᵇ, N(R⁹ᵇ)COR⁹ᵃ, N(R⁹ᵇ)COOR¹²;

R⁹ᵃ in each case represents H, methyl, ethyl, isopropyl, n-propyl, n-butyl, sec-butyl, tert-butyl, isobutyl, n-pentyl, n-hexyl, —CH=CH₂, —CH₂CH=CH₂, —CH=CHCH₃, —CH₂C≡CH, —C≡CH, trifluoromethyl, difluoromethyl, dichloromethyl, pentafluoroethyl, methoxymethyl, ethoxymethyl, methoxyethyl, tert-butoxymethyl, hydroxymethyl, 1-hydroxyethyl, 2-hydroxypropan-2-yl or —(CH₂)ₘR¹⁶;

R⁹ᵇ in each case represents H, methyl, ethyl, isopropyl, n-propyl, n-butyl, sec-butyl, tert-butyl, isobutyl, n-pentyl, n-hexyl, —CH₂CH=CH₂, —CH=CHCH₃, —CH₂C≡CH, —C≡CH;

R⁹ᵃ, R⁹ᵇ in each case together with the nitrogen to which they are attached form a 5- or 6-membered ring which is optionally substituted at the ring carbon atoms by 1 or 2 substituents selected from the group consisting of F, Cl, Br, I, —CN and methyl, ethyl;

R¹² represents methyl, ethyl, isopropyl, n-propyl, n-butyl, sec-butyl, tert-butyl, isobutyl, —CH₂CH=CH₂, —CH=CHCH₃, CH₂C≡CH, —C≡CH, trifluoromethyl, difluoromethyl, dichloromethyl or —(CH₂)ₘR¹⁶;

R¹⁶ represents cyclopropyl, cyclobutyl, cyclopentyl, cyclohexyl, cyclopentenyl, cyclohexenyl, phenyl or thienyl, each of which may optionally be substituted by up to 2 radicals selected from group R¹⁷;

R¹⁷ in each case independently of one another represent F, Cl, Br, I, methyl, ethyl, isopropyl, n-propyl, n-butyl, sec-butyl, tert-butyl, isobutyl, trifluoromethyl, difluoromethyl, dichloromethyl, methoxy, ethoxy or cyano;

m represents 0, 1 and 2,
W represents H
or
W represents fluorine, chlorine, CN, CF$_3$, methyl, ethyl.

Very particular preference is given to compounds of the formula (I) in which one or more of the symbols have one of the meanings below:

Y together with the adjacent nitrogen atom "1" and the two carbon atoms "2" and "3" forms a 5- to 7-membered non-aromatic heterocyclic ring selected from the group consisting of: H-1, H-2, H-3, H-4, H-5 and H-8 shown in Scheme 2, where s is a number from 0 to 4;

Scheme 2

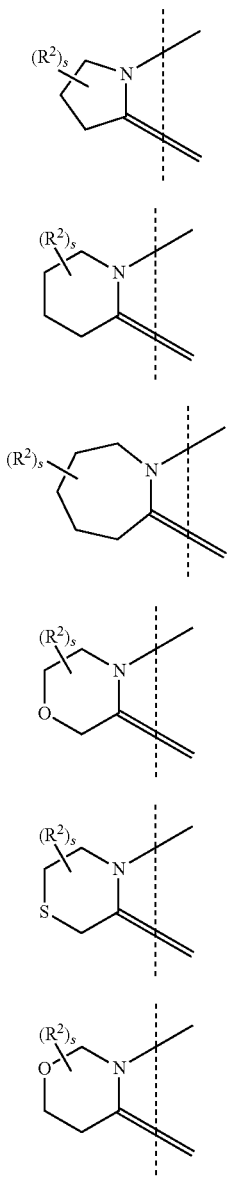

R$^2$ in each case independently of one another represent H, fluorine, chlorine, cyano, CF$_3$, methyl or methoxy;
A represents a phenyl or thiophene ring which is optionally substituted by radicals selected from the group consisting of F, Cl, cyano, CH$_3$, CF$_3$;

R$^1$ represents H, fluorine, chlorine, S(O)$_m$Me, NR$^{9a}$R$^{9b}$, N(R$^{9b}$)COR$^{9a}$, N(R$^{9b}$)COOR$^{12}$;

R$^{9a}$ in each case represents H, methyl, ethyl, n-propyl, isopropyl, n-butyl, isobutyl, sec-butyl, tert-butyl, n-pentyl, n-hexyl, methoxymethyl, ethoxymethyl, ethoxyethyl, methoxyethyl, methoxypropyl, hydroxymethyl, 1-hydroxyethyl, 2-hydroxyethyl, hydroxypropyl or —(CH$_2$)$_m$R$^{16}$;

R$^{9b}$ in each case represents H, methyl, ethyl, n-propyl, isopropyl, n-butyl, allyl or propargyl;

R$^{12}$ represents methyl, ethyl, n-propyl, isopropyl, t-butyl, allyl, propargyl or —(CH$_2$)$_m$R$^{16}$;

R$^{16}$ represents cyclopropyl, cyclopentyl, cyclobutyl, cyclohexyl, thienyl or phenyl, each of which may be substituted by a radical selected from the group R$^{17}$;

m represents 0, 1 or 2;

R$^{17}$ represents methyl, ethyl, fluorine, chlorine, CF$_3$, OMe, cyano

W represents H
or
W represents fluorine, chlorine, cyano
and agrochemically active salts thereof as fungicides.

However, the general or preferred radical definitions and illustrations mentioned above can also be combined with one another as desired, that is including combinations between the respective ranges and preferred ranges. They apply both to the end products and, correspondingly, to precursors and intermediates. Moreover, individual definitions may not apply.

Preference is given to compounds of the formula (I) in which all radicals have the preferred meanings mentioned above.

Particular preference is given to compounds of the formula (I) in which all radicals have the particularly preferred meanings mentioned above.

Very particular preference is given to compounds of the formula (I) in which all radicals have the very particularly preferred meanings mentioned above.

Very particular preference is furthermore given to compounds of the formula (I) in which
R$^1$ represents hydrogen,
where the other substituents have one or more of the meanings mentioned above, and the agrochemically active salts thereof.

Very particular preference is furthermore given to compounds of the formula (I) in which
R$^1$ represents NR$^{9a}$R$^{9b}$,
where the other substituents have one or more of the meanings mentioned above, and the agrochemically active salts thereof.

Very particular preference is furthermore given to compounds of the formula (I) in which
R$^1$ represents N(R$^{9b}$)COR$^{9a}$,
where the other substituents have one or more of the meanings mentioned above, and the agrochemically active salts thereof.

Very particular preference is furthermore given to compounds of the formula (I) in which
W represents hydrogen,
where the other substituents have one or more of the meanings mentioned above, and the agrochemically active salts thereof.

Very particular preference is furthermore given to compounds of the formula (I) in which
A represents a phenyl or thiophene ring which is optionally substituted by radicals selected from the group consisting of F, Cl, cyano, CH$_3$, CF$_3$, where the other substituents have one or more of the meanings mentioned above, and the agrochemically active salts thereof.

Very particular preference is furthermore given to compounds of the formula (I) in which Y together with the adjacent nitrogen atom "1" and the two carbon atoms "2" and "3" forms a 5- to 7-membered non-aromatic heterocyclic ring selected from the group consisting of H-1, H-2, H-3, H-4, H-5 and H-8 (see above in Scheme 2) in which s represents an integer from 0 to 4 and the substituents $R^2$ independently of one another represent H, fluorine, chlorine, cyano, $CF_3$, methyl or methoxy, where the other substituents have one or more of the meanings mentioned above, and the agrochemically active salts thereof.

In the definitions of the symbols given in the formulae above, collective terms were used which are generally representative of the following substituents:

halogen: fluorine, chlorine, bromine and iodine;

alkyl: saturated, straight-chain or branched hydrocarbon radicals having 1 to 8 carbon atoms, for example $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

haloalkyl: straight-chain or branched alkyl groups having 1 to 8 carbon atoms (as mentioned above), where in these groups some or all of the hydrogen atoms may be replaced by halogen atoms as mentioned above, for example $C_1$-$C_3$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl;

thioalkyl: saturated straight-chain or branched alkylthio radicals having 1 to 6 carbon atoms, for example (but not limited thereto) $C_1$-$C_6$-alkylthio, such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

thiohaloalkyl: straight-chain or branched alkylthio groups having 1 to 6 carbon atoms (as mentioned above), where in these groups some or all of the hydrogen atoms may be replaced by halogen atoms as mentioned above, for example (but not limited thereto) $C_1$-$C_2$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, pentafluoroethylthio and 1,1,1-trifluoroprop-2-ylthio;

alkenyl: unsaturated straight-chain or branched hydrocarbon radicals having 2 to 8 carbon atoms and a double bond in any position, for example $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl: straight-chain or branched hydrocarbon groups having 2 to 8 carbon atoms and one triple bond in any position, for example $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

cycloalkyl: monocyclic saturated hydrocarbon groups having 3 to 8 carbon ring members, such as cyclopropyl, cyclobutyl, cyclopentyl and cyclohexyl;

cycloalkenyl: monocyclic non-aromatic hydrocarbon groups having 3 to 8 carbon ring members having at least one double bond, such as cyclopenten-1-yl, cyclohexen-1-yl, cyclohepta-1,3-dien-1-yl;

alkoxycarbonyl: an alkoxy group having 1 to 6 carbon atoms (as mentioned above) which is attached to the skeleton via a carbonyl group (—CO—);

halocycloalkyl: monocyclic saturated hydrocarbon groups having 3 to 8 carbon ring members (as mentioned above), where in these groups some or all of the hydrogen atoms may be replaced by halogen atoms as mentioned above, for example (but not limited thereto) 2-fluorocyclopropyl, 2,2-difluorocyclopropyl, 3,3-difluorocyclobutyl, 2-fluorocyclopentyl, 3-fluorocyclopentyl;

heterocyclyl: a three- to fifteen-membered saturated or partially unsaturated heterocycle which contains one to four heteroatoms from the group consisting of oxygen, nitrogen and sulphur: mono-, bi- or tricyclic heterocycles which contain, in addition to carbon ring members, one to three nitrogen atoms and/or one oxygen or sulphur atom or one or two oxygen and/or sulphur atoms; if the ring contains a plurality of oxygen atoms, these are not directly adjacent; such as, for example (but not limited thereto), oxiranyl, aziridinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl;

aryl: a 6- to 14-membered completely unsaturated carbocyclic ring system, for example (but not limited thereto) phenyl, 1-naphthyl, 2-naphthyl, 2-anthryl, 1-anthryl;

heteroaryl: a 5- or 6-membered fully unsaturated monocyclic ring system comprising one to four heteroatoms from the group consisting of oxygen, nitrogen and sulphur; if the ring contains a plurality of oxygen atoms, these are not directly adjacent;

alkoxy: a straight-chain or branched alkoxy radical such as, for example (but not limited thereto), methoxy, ethoxy, n-propoxy, 1-methylethoxy, n-butoxy, 1-methylpropoxy, 2-methylpropoxy or 1,1-dimethylethoxy, in particular methoxy or ethoxy;

alkylthio: represents straight-chain or branched alkylthio, for example (but not limited thereto) methylthio, ethylthio, n- and isopropylthio, n-, i-, sec- and tert-butylthio, n-pentylthio and its isomers, such as 1-, 2- and 3-methylbutylthio. The alkylthio groups can be substituted by 1 to 3 halogen atoms (preferably chlorine and/or fluorine), for example (but not limited thereto) di- and trifluoromethylthio and difluorochloromethylthio.

Haloalkoxy: represents a straight-chain or branched alkoxy radical in which one or more hydrogen atoms have been replaced by fluorine, chlorine or bromine, for example (but not limited thereto) —$OCF_3$, —$OCHF_2$.

Acyloxy: represents a straight-chain branched, cyclic saturated or unsaturated acyloxy radical connected via the oxygen atom, for example (but not limited thereto) acetyloxy, propionyloxy, isobutyryloxy.

The present invention furthermore provides a process for preparing the bicyclic pyridinylpyrazoles of the formula (I) according to the invention, which comprises at least one of steps (a) to (d) below:

a) the reaction of pyridinylalkynes of the general formula (II) with bicycles of the general formula (III) to give bicyclic pyrazoles of the general formula (Ia), if appropriate in the presence of a solvent, according to the reaction scheme below (Scheme 3).

Scheme 3:

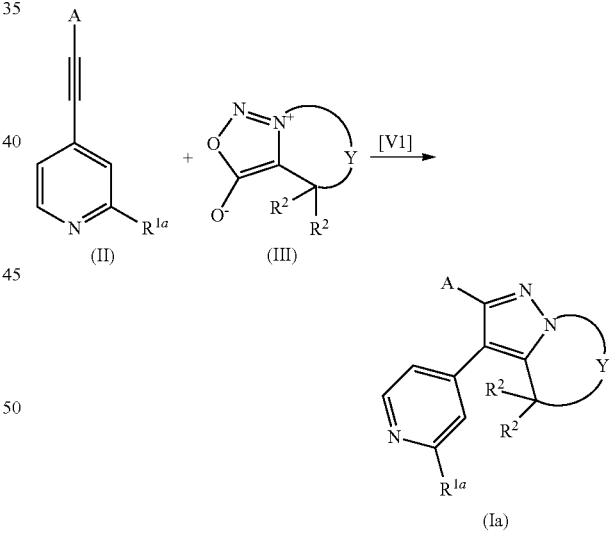

$R^{1a}$ = H, halogen, $S(O)_m$Me, CN, $C_1$-$C_4$-alkyl b) the reaction of 4-halopyridines of the general formula (IV) with (het)arylalkynes of the general formula (V) to give pyridinylalkynes of the general formula (II), if appropriate in the presence of a suitable catalyst and in the presence of a solvent, according to the reaction scheme below (Scheme 4):

Scheme 4:

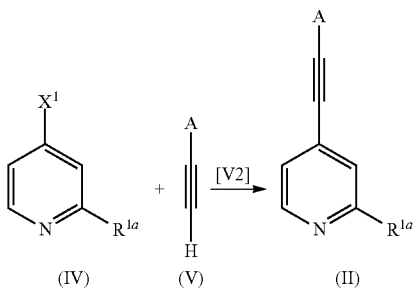

where $X^1$ = Cl, bromine, iodine
$R^{1a}$ = H, haolgen, S(O)$_m$Me, CN, C$_1$-C$_4$-alkyl c) the reaction of amino acids of the general formula (VI) to give compounds of the general formula (III) according to the reaction scheme below (Scheme 5):

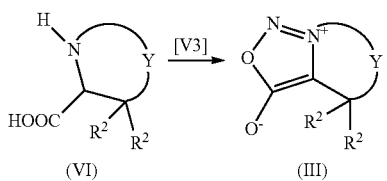

d) the reaction of compounds of the general formula (Ib) to give compounds of the general formula (Ic), if appropriate in the presence of a base, if appropriate in the presence of a solvent, according to the scheme below (Scheme 6):

Scheme 6:

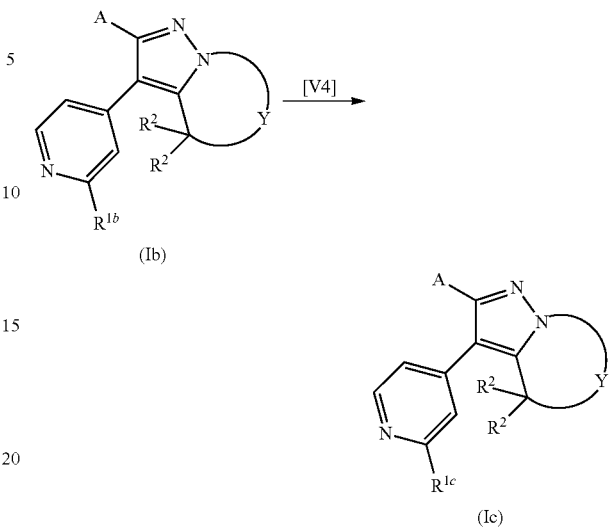

$R^{1b}$ = halogen, S(O)$_m$Me $R^{1c}$ = NR$^{9a}$R$^{9b}$, NR$^{10}$—NR$^{11a}$R$^{11b}$, CN, N=CR$^{13a}$R$^{13b}$, OR$^{12}$, SR$^{12}$ The bicyclic pyridinylpyrazoles of the formula (I) according to the invention may be prepared by various routes. The text which follows initially gives schematic representations of possible processes. Unless stated otherwise, the radicals mentioned have the meanings given above.

A general overview of the synthesis paths is given in Scheme 7:

Scheme 7:

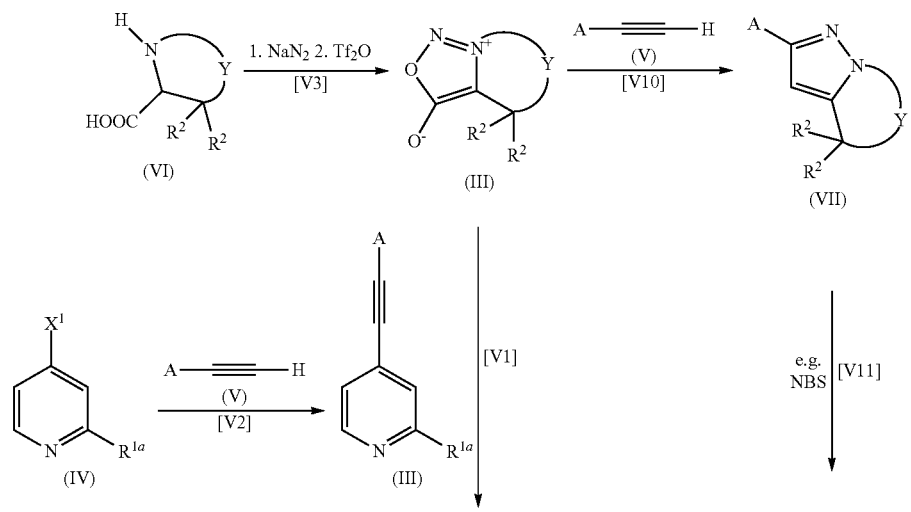

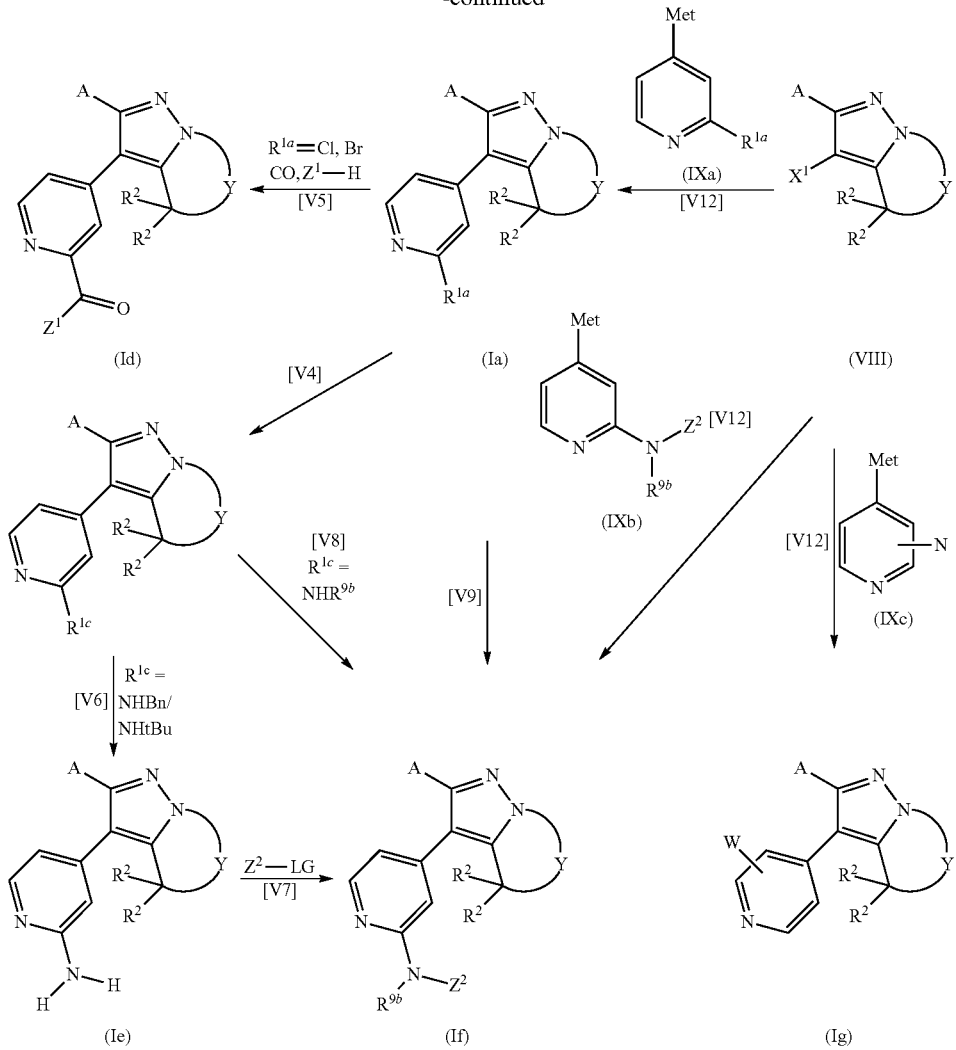

$X_1$ represents chlorine, bromine or iodine, $Z^1$ represents $OR^{12}$, $NR^{9a}R^{9b}$, $Z^2$ represents $R^{9a}CO$, $R^{12}COO$ or $R^{12}SO_2$, LG represents halogen, hydroxyl or $OZ^2$; Met represents $Sn(Bu)_3$, $B(OH)_2$ or 4,4,5,5-tetramethyl-1,3,2-dioxaborolan-2-yl, $R^{1a}$ represents H, halogen, $S(O)_m Me$, CN, $C_1$-$C_4$-alkyl Process Step [V1]:

The reaction of pyridinylalkynes of the general formula (II) with bicycles of the general formula (III), if appropriate in the presence of a solvent, gives the bicyclic pyrazoles of the general formula (Ia).

Suitable solvents for carrying out the process step according to the invention are all solvents which are inert under the reaction conditions, and mixtures thereof. Preference is given to aromatic hydrocarbons (for example benzene, toluene, xylene or mesitylene).

The reaction temperature for carrying out Process step [V1] according to the invention is between 80° C. and 250° C., preferably between 120° C. and the boiling point of the solvent used. The reaction time for carrying out Process step [V1] according to the invention is, depending on the scale of the reaction, between 12 and 96 h, preferably between 16 h and 24 h.

Process Step [V2]:

The reaction of 4-halopyridines of the general formula (IV) ($X^1$=chlorine, bromine, iodine) with (het)arylalkynes of the general formula (V) affords, in a Sonogashira reaction, pyridinylalkynes of the general formula (II). Suitable catalysts and reaction conditions for the Sonogashira reaction can be found in A. de Meijere/F. Diederich, (eds.) Metal-Catalyzed Cross-Coupling Reactions, Wiley-VCh, Weinheim, 2004. The 4-halopyridines (IV) required for this purpose are either commercially available or can be obtained for example by methods known from the literature from the corresponding N-oxides (*Bioorg. Med. Chem. Lett.* 2009, 19, 2244-2248), 4-nitropyridines (*Chem. Pharm. Bull.* 1990, 38, 2446-58) or 4-aminopyridines (*J. Prak. Chem.*, 1959, 9, 164-72). (Het-)arylalkynes (V) are either commercially available or can be obtained from the corresponding (het-)aryl bromides or iodides by reaction with, for example, trimethylsilylacetylene via a Sonogashira reaction as described, for example, in *Org. Lett.* 2003, 42, 1842.

Process Step [V3]:

Amino acids of the general formula (VI) can be nitrosated with sodium nitrite in a diluted aqueous acidic medium (for example hydrochloric acid or acetic acid) and then be reacted with a dehydrating agent to give compounds of the general formula (III), as described, for example, in *Heterocycles*

1990, 31, 481 or *J. Med. Chem.* 2006, 49, 4623. Suitable dehydrating agents are chloroformic esters (for example ClCOOMe) or anhydrides (for example Tf$_2$O). The cyclic amino acids (VI) are either commercially available or can be prepared by methods known from the literature (for example *Tetrahedron* 2006, 62, 8687 or *J. Med. Chem.* 2006, 49, 4623).

Process Step [V4]:

One way of preparing compounds of the general formula (Ic, where R$^{1c}$=NR$^{9a}$R$^{9b}$, NR$^{10}$—NR$^{11a}$R$^{11b}$, CN, N=CR$^{13a}$R$^{13b}$, OR$^{12}$, SR$^{12}$) is described by Process step [V4]. To this end, the suitable leaving groups in (Ia), for example R$^{1a}$=halogen, SMc, SOMe or SO$_2$Me are substituted by corresponding amines HNR$^{9a}$R$^{9b}$, hydrazines HNR$^{10}$—NR$^{11a}$R$^{11b}$, imines HN=CR$^{13a}$R$^{13b}$, alcohols HOR$^{10}$ or cyanide, if appropriate in the presence of a base and if appropriate in the presence of a solvent.

Solvents which can be used for carrying out the Process step [V4] according to the invention from Scheme 7 are the amines HNR$^{9a}$R$^{9b}$ or alcohols OR$^{10}$ themselves or all customary solvents which are inert under the reaction conditions, such as cyclic and acyclic ethers (dimethoxymethane, tetrahydrofuran, dioxane), aromatic hydrocarbons (for example toluene), nitriles (for example acetonitrile, propionitrile) and amides (for example dimethylformamide, dimethylacetamide, N-methylpyrrolidone), or the reaction can be carried out in mixtures of two or more of these solvents. The preferred solvent is dimethylformamide or acetonitrile.

Suitable bases are alkali metal hydroxides, alkali metal hydrides, alkali metal carbonates, alkali metal acetates, alkali metal alkoxides, and also tertiary amines. Preferred bases are sodium hydride, sodium carbonate, potassium carbonate and caesium carbonate.

The reaction temperature for carrying out the Process step [V4] according to the invention is between 0° C. and 180° C., preferably between room temperature and 100° C. The reaction can be carried out under atmospheric pressure or under elevated pressure. The reaction time is, depending on the scale of the reaction, between 5 min and 24 h, preferably between 30 min and 6 h.

Process Step [V5]:

One way of converting halopyridines of the general formula (Ia) (R$^{1a}$=Cl, Br) into the corresponding esters and amides is provided by Process step [V5]. Pd-catalysed carbonylations of (Ia) in the presence of alcohols afford the corresponding esters of the general formula (Id), where Z$^1$=OR$^{12}$, cf. *J. Med. Chem.* 2006, 49, 3563-3580, whereas in the presence of amines the corresponding amides (Id), where Z$^1$=NR$^{9a}$R$^{9b}$ as described, for example, in *Chemistry Euro. J.* 2004, 10, 746-757, are formed. Carbon monoxide itself or metal carbonyls (for example Mo(CO)$_6$) may serve as CO source.

Solvents which can be used for carrying out the Process step [V5] according to the invention from Scheme 7 are the alcohols or amines themselves and in addition all customary solvents which are inert under the reaction conditions, such as cyclic and acyclic ethers (for example dioxane), aromatic hydrocarbons (for example toluene), sulphoxides (for example DMSO) and amides (for example dimethylformamide, dimethylacetamide, N-methylpyrrolidone), or the reaction can be carried out in mixtures of two or more of these solvents. The preferred solvents are the alcohols or amines themselves, and also dimethylformamide.

Suitable bases for carrying out the Process step [V5] according to the invention from Scheme 7 are alkali metal carbonates (for example potassium carbonate), cyclic amidines (for example DBU) and tertiary amines (for example triethylamine).

Preferred for carrying out the Process step [V5] according to the invention are palladium catalysts in which the palladium is present in oxidation number (0) or (II), such as, for example, tetrakis(triphenylphosphine)palladium, bis(triphenylphosphine)palladium dichloride, bis(diphenylphosphino)ferrocenepalladium dichloride and palladium(II) acetate. The catalyst may comprise phosphorus-containing ligands, or phosphorus-containing ligands may be added separately to the reaction mixture. Preferred phosphorus-containing ligands are tri-n-alkylphosphanes, triarylphosphanes, dialkylarylphosphanes, alkyldiarylphosphanes, where the three substituents at phosphorus may be identical or different and where one or more substituents may link the phosphorus groups of a plurality of phosphanes, where a metal atom may also be part of this attachment. Particular preference is given to phosphanes such as triphenylphosphane and 1,4-bis(diphenylphosphino)propane and 1,1'-bis(diphenylphosphino)ferrocene.

The reaction for carrying out the Process step [V5] according to the invention is carried out in a temperature range of from 25° to 150° C., particularly preferably at from 80° to 120° C. The reaction can be carried out under atmospheric pressure or under elevated pressure. The reaction time varies depending on the scale of the reaction and the reaction temperature, but is generally between a few minutes and 20 hours.

Process Step [V6]:

One way of preparing compounds of the general formula (Ie) is described by Process step [V6]. Suitable acid-labile amines (for example R$^{1c}$=NHBn (cf. WO 2008/132434) or NHtBu (cf. *Tetrahedron Lett.* 2005, 46, 3883-3887)) can be cleaved in acidic medium to give (2-aminopyridin-4-yl)pyrazoles (Ie). Suitable acids for this purpose are mineral acids (for example H$_2$SO$_4$, HCl), Lewis acids (for example BBr$_3$, AlCl$_3$) or organic acids (for example F$_3$COOH, CF$_3$SO$_3$H). Suitable solvents are the acids themselves or any customary solvents which are inert under the reaction conditions, such as halogenated hydrocarbons (for example dichloromethane) or aromatic hydrocarbons (for example toluene). The reaction temperature is between 0° C. and 100° C. The reaction time is, depending on the scale of the reaction, between 5 min and 24 h, preferably between 30 min and 12 h.

Process Steps [V7] and [V8]:

Via Process steps [V7] and [V8], starting with the amines (Ie) and (Ic for R$^{1c}$=primary amine) and using carbonyl chlorides or carboxylic anhydrides, the corresponding amides (If, where Z$^2$=R$^{9a}$CO) can be obtained, the corresponding carbamates (If, where Z$^2$=R$^{12}$COO) can be obtained using chloroformic esters and the corresponding sulphonamides (If, where Z$^2$=R$^{12}$SO$_2$) can be obtained using sulphonyl chlorides or sulphonic anhydrides. The compounds of the general formula Z$^2$-LG are either commercially available or can be prepared using methods of organic synthesis known from the literature (R. C. Larock, *Comprehensive Organic Transformations*, 2nd edition, 1999, Wiley-VCH, page 1929 ff. and literature cited therein).

Suitable solvents for carrying out the Process steps [V7] and [V8] according to the invention are all customary solvents which are inert under the reaction conditions, such as, for example, cyclic and acyclic ethers (for example tetrahydrofuran, dioxanes), aromatic hydrocarbons (for example toluene), halogenated hydrocarbons (for example dichloromethane), ketones (for example acetone), amides (for example dimethylformamide) and nitriles (for example acetonitrile), or the reaction can be carried out in mixtures of two or more of these solvents. The preferred solvents are tetrahydrofuran, dichloromethane and acetonitrile.

Acid scavengers which can be used for carrying out Process steps [V7] and [V8] are suitable bases. Preference is given to tertiary amines (for example triethylamine, ethyldiisopropylamine), alkali metal carbonates (for example sodium carbonate) or alkali metal hydroxides (sodium hydroxide).

The reaction for carrying out the Process steps [V7] and [V8] is usually carried out at temperatures of 0° C.-100° C. and preferably at room temperature, but it can also be carried out up to the reflux temperature of the reaction mixture. The reaction time varies depending on the scale of the reaction and the reaction temperature, but is generally between a few minutes and 48 hours.

Alternatively, carboxamides and sulphonamides of the general formula (If) where $Z^2=R^{9a}CO$, $R^{12}SO_2$ can also be synthesized from the corresponding acids $Z^2$—OH in the presence of a coupling agent, analogously to procedures described in the literature (for example *Tetrahedron* 2005, 61, 10827-10852, and references cited therein).

Suitable coupling agents for carrying out the Process steps [V7] and [V8] are, for example, carbodiimides (for example N-(3-dimethylaminopropyl)-N'-ethylcarbodiimide, optionally with 4-dimethylaminopyridine or 1-hydroxybenzotriazole), phosphonium ions (for example bromotripyrrolidinophosphonium hexafluorophosphate) or uronium ions (for example O-(7-azabenzotriazol-1-yl)-N,N,N',N'-tetramethyluronium hexafluorophosphate).

If appropriate, a base, such as, for example, triethylamine or ethyldiisopropylamine, can be used in the reaction for carrying out the Process steps [V7] and [V8]. Solvents which can be used for carrying out the Process steps [V7] and [V8] are all customary solvents which are inert under the reaction conditions, as described for the reaction with acid chlorides.

Process Step [V9]:

As described, for example, in DE-A 1 037 399, the introduction of an amide radical can also be carried out directly under Pd catalysis starting with the 2-halopyridines (Ia, where $R^{1a}$=chlorine, bromine, iodine).

Process Step [V10]:

Analogously to the reaction conditions described in Process step [V1], bicycles of the general formula (III) can also be reacted with (het)arylalkynes of the general formula (V) to give bicyclic pyrazoles of the general formula (VII).

Process Step [V11]:

4H-Pyrazoles of the general formula (VII) can be converted with suitable halogenating agents by processes known from the literature (for example *Bioorg. Med. Chem. Lett.* 2008, 18, 509-512) into the corresponding 4-halopyrazoles ($X^1$=Cl, Br, I) of the general formula (VIII). Suitable for use as halogenating agents are, for example, elemental chlorine, bromine, iodine or N-halosuccinimides (NCS, NBS, NIS) or else sulphuryl chloride and pyridinium tribromide.

The halogenation for carrying out the Process step [V11] can be carried out in the presence of a solvent which is inert under the reaction conditions. Preference is given to alcohols (for example methanol, ethanol), cyclic and acyclic ethers (for example diethyl ether, tetrahydrofuran, dioxane), amides (for example dimethylformamide, dimethylacetamide), sulphoxides (for example dimethyl sulphoxide), aromatic hydrocarbons (for example benzene, toluene), halogenated hydrocarbons (for example dichloromethane, chloroform) and carboxylic acids (for example acetic acid).

The reaction temperature is between 0° C. and the boiling point of the solvent, preferably between room temperature and 80° C. The reaction time is, depending on the scale of the reaction, between 5 min and 24 h, preferably between 30 min and 6 h.

Process Step [V12]:

A further way of synthesizing the pyridinylpyrazoles (Ia), (If) and (Ig) according to the invention is provided by Process step [V12]. In a Suzuki reaction (for example analogously to *Organic Lett.* 2005, 7, 4753-4756), the 4-halopyrazoles (VIII) obtained in Process step [V11] are reacted with pyridines of the general formula (IXa/b/c). The 4-pyridinylboronic acids and esters (IXa/b/c, Met=B(OH)$_2$ or 4,4,5,5-tetramethyl-1,3,2-dioxaborolan-2-yl) used for the Suzuki reaction are commercially available or can be prepared from the corresponding 4-bromopyridines by Pd-catalysed reaction with bispinacolatodiborane (for example *Bioorg. Med. Chem. Lett.* 2006, 16, 1277-1281) or by metallation/boronation (for example *Synthesis*, 2003, 469-483).

Suitable solvents for the Suzuki reaction are all customary solvents which are inert under the reaction conditions, such as alcohols (for example ethanol, ethylene glycol), cyclic and acyclic ethers (dimethoxymethane, tetrahydrofuran, dioxane), aromatic hydrocarbons (for example toluene), ketones (for example acetone, ethyl methyl ketone), nitriles (for example acetonitrile, propionitrile) and amides (for example dimethylformamide, dimethylacetamide, N-methylpyrrolidone) and water, or the reaction can be carried out in mixtures of two or more of these solvents. The preferred solvents are dioxane and tetrahydrofuran.

Suitable bases are alkali metal hydroxides, alkali metal carbonates, alkali metal bicarbonates, alkali metal acetates, alkali metal alkoxides, and also tertiary amines. Preferred bases are caesium carbonate, sodium carbonate, potassium carbonate and potassium acetate.

Preferred for carrying out the Process step [V12] are palladium catalysts in which the palladium is present in oxidation number (0) or (II), such as, for example, tetrakis(triphenylphosphine)palladium, bis(triphenylphosphine) palladium dichloride and bis(diphenylphosphino) ferrocenepalladium dichloride, or else palladium(II) acetate and palladium(II) chloride.

The catalyst may comprise phosphorus-containing ligands, or phosphorus-containing ligands may be added separately to the reaction mixture. Preferred phosphorus-containing ligands are tri-n-alkylphosphanes, triarylphosphanes, dialkylarylphosphanes, alkyldiarylphosphanes and/or heteroarylphosphanes, such as tripyridylphosphane and trifurylphosphane, where the three substituents at phosphorus may be identical or different and where one or more substituents may link the phosphorus groups of a plurality of phosphanes, where a metal atom may also be part of this attachment. Particular preference is given to phosphanes such as triphenylphosphane, tri-tert-butylphosphane, tricyclohexylphosphane.

The Suzuki coupling is carried out in a temperature range of from 25° to 200° C., particularly preferably from 80° to 150° C. The reaction time varies depending on the scale of the reaction and the reaction temperature, but is generally between a few minutes and 48 hours.

In an alternative C—C-coupling method for Process step [V12], the 4-halopyrazoles (VIII) can also be reacted in a Stille reaction (for example analogously to *Med. Chem. Lett.* 2006, 16, 3550) with pyridinylstannanes (IXa/b/c, Met=Sn (alkyl)$_3$) to give the pyridinylpyrazoles (Ia), (If) or (Ig). The preparation of 4-pyridinylstannanes (IX) is likewise known from the literature (for example *J. Med. Chem.* 2003, 46, 284-302; *Tetrahedron* 2004, 60, 6113-6120). For the Stille coupling, the choice of catalyst, if appropriate an inorganic or organic halide salt, if appropriate a ligand and a suitable solvent at suitable temperatures may vary depending on the alkyltin substrate used.

Suitable solvents for the Stille coupling are all customary solvents which are inert under the reaction conditions, such as cyclic and acyclic ethers (for example dimethoxymethane, tetrahydrofuran, dioxane), aromatic hydrocarbons (for example toluene), amides (for example dimethylformamide, dimethylacetamide, N-methylpyrrolidone) and sulphoxides (for example dimethyl sulphoxide), or the reaction can be carried out in mixtures of two or more of these solvents.

Halide salts which are preferably used are, for example, copper halides (for example CuBr or CuI), caesium halides (for example CsF) and tetraalkylammonium halides (for example TBAF).

Preference is given to palladium catalysts in which the palladium is present in oxidation number (0) or (II), such as, for example, tetrakis(triphenylphosphine)palladium, bis(triphenylphosphine)palladium dichloride and bis(diphenylphosphino)ferrocenepalladium dichloride, or else palladium(II) acetate and palladium(II) chloride.

The catalyst may comprise phosphorus-containing ligands, or phosphorus-containing ligands may be added separately to the reaction mixture. Preferred phosphorus-containing ligands are tri-n-alkylphosphanes, triarylphosphanes, dialkylarylphosphanes, alkyldiarylphosphanes and/or heteroarylphosphanes, such as tripyridylphosphane and trifurylphosphane, where the three substituents at phosphorus may be identical or different and where one or more substituents may link the phosphorus groups of a plurality of phosphanes, where a metal atom may also be part of this attachment. Particular preference is given to phosphanes such as triphenylphosphane, tri-tert-butylphosphane, tricyclohexylphosphane.

The Stille coupling is carried out in a temperature range of from 25°-200° C., particularly preferably at 60°-150° C. The reaction time varies depending on the scale of the reaction and the reaction temperature, but is generally between a few minutes and 48 hours.

Alternatively to the process described in Scheme 7, the bicyclic pyrazole intermediates (VII) and (VIII) can also be prepared according to the following general scheme from the monocyclic pyrazoles (X) provided with suitable substituents $Y^1$ and $Y^2$ (Scheme 8):

Scheme 8:

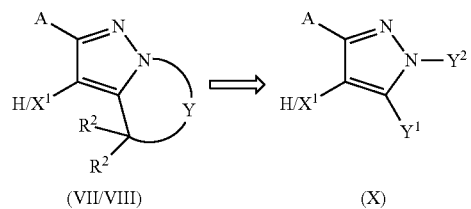

(VII/VIII)    (X)

$X^1$ represents chlorine, bromine and iodine; $Y^1$ and $Y^2$ represent suitable functional groups which can be converted into —C($R^2$)$_2$—Y—.

The following processes are shown here in an exemplary manner for the retrosynthesis described in Scheme 8 (Scheme 9 and Scheme 10):

Scheme 9:

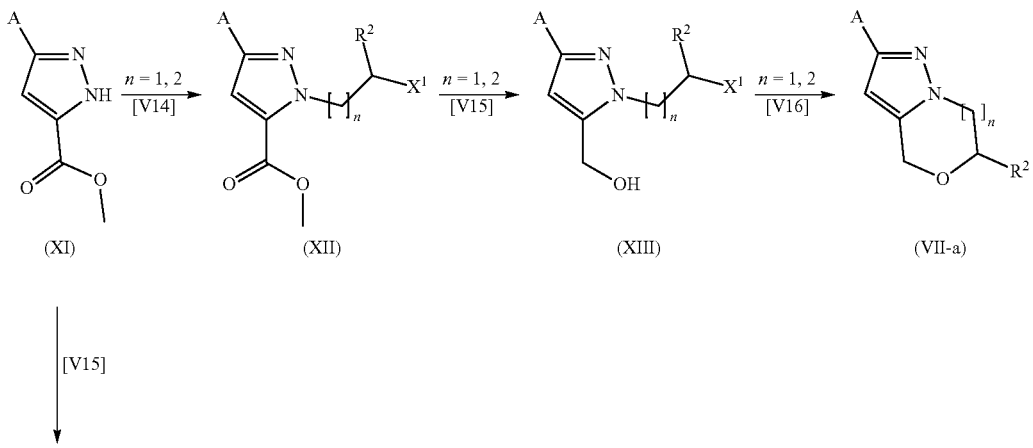

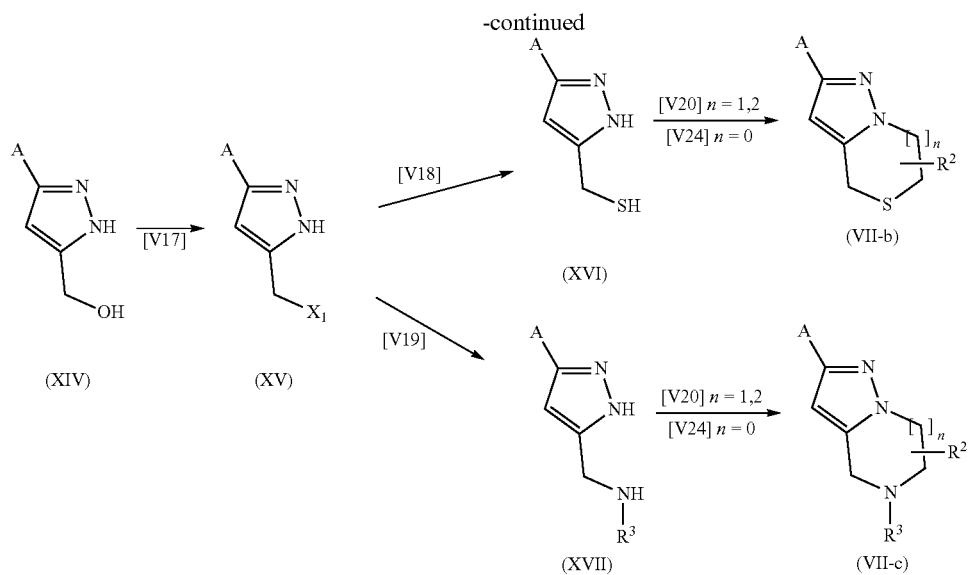

$X^1$ = represents chlorine, bromine and iodine; m and n independently of one another represent 0, 1, 2;

Scheme 10:

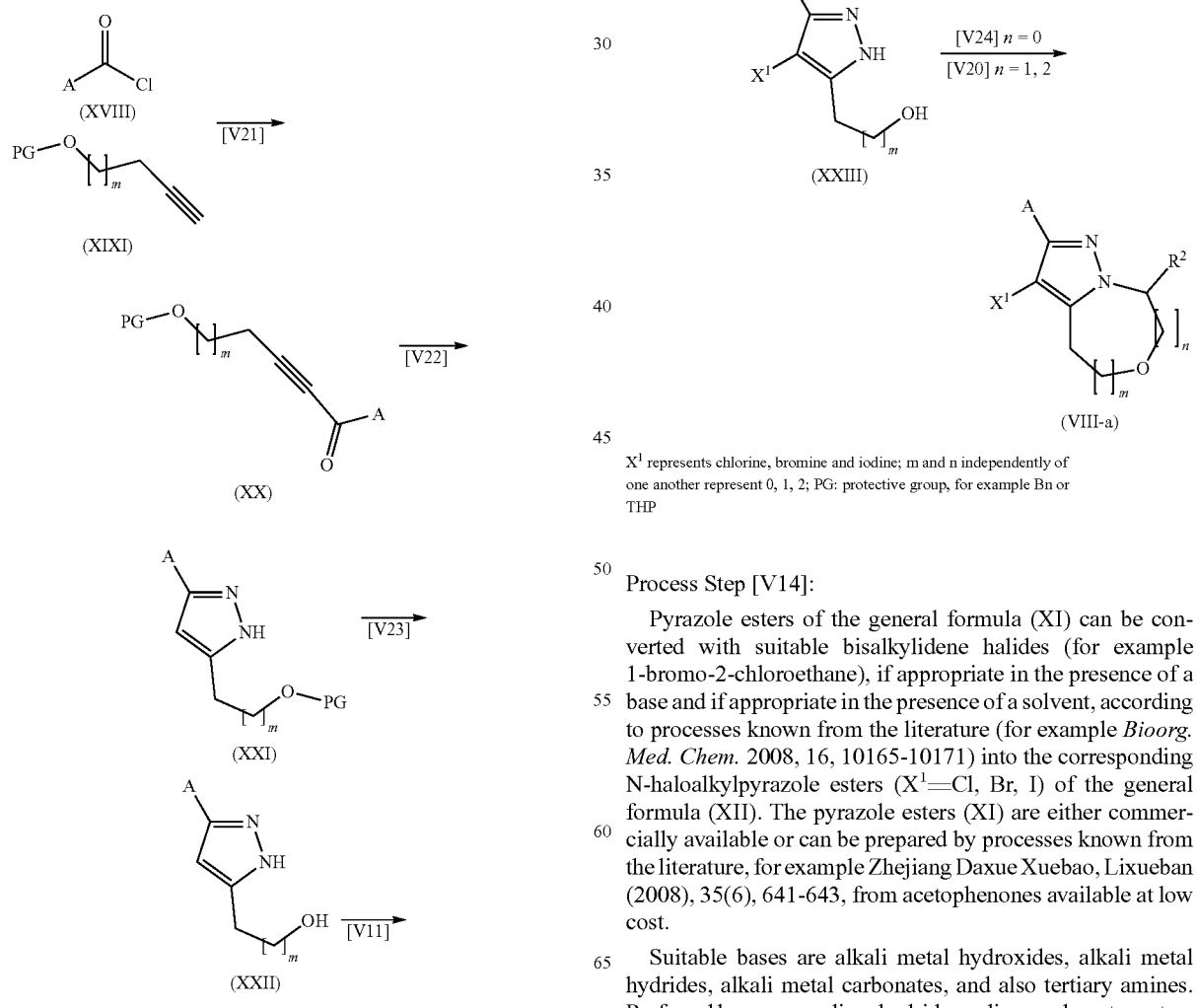

$X^1$ represents chlorine, bromine and iodine; m and n independently of one another represent 0, 1, 2; PG: protective group, for example Bn or THP Process Step [V14]:

Pyrazole esters of the general formula (XI) can be converted with suitable bisalkylidene halides (for example 1-bromo-2-chloroethane), if appropriate in the presence of a base and if appropriate in the presence of a solvent, according to processes known from the literature (for example *Bioorg. Med. Chem.* 2008, 16, 10165-10171) into the corresponding N-haloalkylpyrazole esters ($X^1$=Cl, Br, I) of the general formula (XII). The pyrazole esters (XI) are either commercially available or can be prepared by processes known from the literature, for example Zhejiang Daxue Xuebao, Lixueban (2008), 35(6), 641-643, from acetophenones available at low cost.

Suitable bases are alkali metal hydroxides, alkali metal hydrides, alkali metal carbonates, and also tertiary amines. Preferred bases are sodium hydride, sodium carbonate, potassium carbonate or caesium carbonate. Suitable for use as solvents are all customary solvents which are inert under the reaction conditions, such as cyclic and acyclic ethers (dimethoxymethane, tetrahydrofuran, dioxane), aromatic hydrocarbons (for example toluene), nitriles (for example acetonitrile, propionitrile,), ketones (for example acetone) and amides (for example dimethylformamide, dimethylacetamide, N-methylpyrrolidone), or the reaction can be carried out in mixtures of two or more of these solvents. The preferred solvents are dimethylformamide, acetone or acetonitrile. The reaction temperature is between 0° C. and 180° C., preferably between room temperature and 100° C.

Process Step [V15]:

According to processes known from the literature (for example WO 2007/018314), pyrazole esters of the general formula (XI) or (XII) can be converted with suitable reducing agents into the corresponding alcohols of the general formula (XIII) or (XIV).

Suitable reducing agents for this purpose are alanates or boronates (for example LiAlH$_4$, DIBAL-H, LiBH$_4$, for $R^2$=H) or Grignard compounds (for example MeMgCl for $R^2$=Me).

Suitable for use as solvents are all customary solvents which are inert under the reaction conditions, such as cyclic and acyclic ethers (dimethoxymethane, tetrahydrofuran, dioxane) or hydrocarbons (for example toluene, hexane) or mixtures.

Process Step [V16]:

Hydroxymethylpyrazoles of the general formula (XIII) can, if appropriate, be cyclized in the presence of a base and, if appropriate, in the presence of a solvent to give the corresponding bicyclic pyrazoles of the general formula (VIIa). Suitable bases are alkali metal hydroxides, alkali metal hydrides, alkali metal carbonates, alkali metal acetates, alkali metal alkoxides, and also tertiary amines. Preferred bases are sodium hydride, sodium carbonate, potassium carbonate or caesium carbonate.

Suitable for use as solvents are all customary solvents which are inert under the reaction conditions, such as cyclic and acyclic ethers (dimethoxymethane, tetrahydrofuran, dioxane), aromatic hydrocarbons (for example toluene), nitriles (for example acetonitrile, propionitrile), ketones (for example acetone) and amides (for example dimethylformamide, dimethylacetamide, N-methylpyrrolidone), or the reaction can be carried out in mixtures of two or more of these solvents. The preferred solvents are dimethylformamide, acetone or acetonitrile.

The reaction temperature is between 0° C. and 180° C., preferably between room temperature and 100° C.

Process Step [V17]:

According to processes known from the literature (for example *Bioorg. Med. Chem. Lett.* 2007, 17, 5199-5203), hydroxymethylpyrazoles of the general formula (XIV) can be converted with suitable halogenating agents into the corresponding halomethylpyrazoles ($X^1$=Cl, Br, I) of the general formula (XV). Suitable for use as halogenating agents are, for example, thionyl chloride, pyridinium tribromide, Br$_2$/PPh$_3$ or I$_2$/PPh$_3$. If appropriate, the halogenation can be carried out in the presence of a solvent which is inert under the reaction conditions. Preference is given to cyclic and acyclic ethers (for example diethyl ether, tetrahydrofuran, dimethoxyethane), amides (for example dimethylformamide, dimethylacetamide), sulphoxides (for example dimethyl sulphoxide), aromatic hydrocarbons (for example toluene), halogenated hydrocarbons (for example dichloromethane, chloroform). The reaction temperature is between 0° C. and the boiling point of the solvent, preferably between room temperature and 80° C.

Process Step [V18]:

Halomethylpyrazoles of the general formula (XV) can be converted into the corresponding sulphanylmethylpyrazoles of the general formula (XVI). Suitable for use as sulphurizing agent are, for example, hydrogen sulphide, sodium sulphide, thiourea or potassium thioacetate.

Suitable solvents are all solvents which are inert under the reaction conditions and mixtures thereof. Preference is given to alcohols (for example methanol, ethanol), water, cyclic and acyclic ethers (for example dioxane, dimethoxyethane), amides (for example dimethylformamide, dimethylacetamide), ketones (for example acetone) and nitriles (for example acetonitrile). If appropriate, auxiliary bases, such as, for example, alkali metal carbontes (sodium carbonate, potassium carbonate, sodium bicarbonate), alkali metal hydroxides (for example sodium hydroxide, potassium hydroxide), aromatic amines (for example pyridine) or tertiary amines (triethylamine, ethyldiisopropylamine) can be added to the reaction mixture.

The reaction temperature is between 0° C. and the boiling point of the solvent, preferably between room temperature and 80° C.

Process Step [V19]:

According to processes known from the literature (for example Journal of Medicinal Chemistry 2010, 53, 1473-1482), halomethylpyrazoles of the general formula (XV) can be converted with appropriate amines H$_2$NR$^3$ into aminomethylpyrazoles of the general formula (XVII).

Suitable solvents are all solvents which are inert under the reaction conditions, and mixtures thereof. Preference is given to alcohols (for example methanol, ethanol), water, cyclic and acyclic ethers (for example dioxane, tetrahydrofuran), amides (for example dimethylformamide, dimethylacetamide) and nitriles (for example acetonitrile). If appropriate, auxiliary bases, such as alkali metal carbonates (for example sodium carbonate, potassium carbonate, sodium bicarbonate), aromatic amines (for example pyridine) or tertiary amines (triethylamine, ethyldiisopropylamine) may be added to the reaction mixture.

The reaction temperature is between 0° C. and the boiling point of the solvent, preferably between room temperature and 80° C.

Process Step [V20]:

Using suitable bisalkylidene halides (for example 1,2-dibromoethane) or bisalkylidene mesylates and tosylates (for example ethylene dimesylate), 5-sulphanylmethyl- or 5-aminomethylpyrazoles of the general formulae (XVI) and (XVII) can be cyclized to give the bicyclic pyrazoles (VIIb) and (VIIc). Suitable for use as solvents are all customary solvents which are inert under the reaction conditions, such as cyclic and acyclic ethers (dimethoxymethane, tetrahydrofuran, dioxane), aromatic hydrocarbons (for example toluene), nitriles (for example acetonitrile, propionitrile), ketones (for example acetone) and amides (for example dimethylformamide, dimethylacetamide, N-methylpyrrolidone), or the reaction can be carried out in mixtures of two or more of these solvents. The preferred solvents are dimethylformamide, acetone or acetonitrile.

If appropriate, it is also possible to add suitable bases, such as alkali metal carbonates or tertiary amines, to the reaction mixture. Preferred bases are sodium carbonate or potassium carbonate, and also triethylamine. The reaction temperature is between 0° C. and 180° C., preferably between room temperature and 100° C.

Process Step [V21]:

Starting with commercially available benzoyl chlorides and terminal alkynes of the general formulae (XVIII and XIX), according to processes known from the literature (for example Organic Letters 2008, 10, 2629-2632), it is possible to prepare, in a Sonogashira reaction analogously to Process step [V2] or under basic conditions (for example Organic Letters 2010, 12, 1952-1955), alkynyl aryl ketones of the general formula (XX). Suitable bases for this purpose are preferably butyllithium and Grignard compounds. Suitable for use as solvents are all customary solvents which are inert under the reaction conditions, such as cyclic and acyclic ethers (dimethoxymethane, tetrahydrofuran, diethyl ether), or hydrocarbons (for example toluene, hexane), or the reaction can be carried out in mixtures of two or more of these solvents. The reaction temperature is between −78° C. and the boiling point of the solvent, preferably between −70° C. and room temperature.

Process Step [V22]:

According to processes known from the literature (for example Tetrahedron Letters 1989, 30, 2049-52), alkynyl aryl ketones of the general formula (XX) can be converted with hydrazine into the corresponding pyrazoles (XXI). The preferred solvents for the reaction are alcohols, such as methanol and ethanol, water and acetic acid, and also mixtures thereof. The reaction temperature is between 0° C. and the boiling point of the solvent, preferably between room temperature and 80° C.

Process Step [V23]:

In Process step [V23], the pyrazole alcohols blocked with a suitable protective group can be converted by processes known from the literature (cf. Greene/Wuts Protective Groups in Organic Synthesis, Wiley, 1999 or Kocienski, Protecting Groups, Thieme, 2005) into the free pyrazole alcohols. Thus, for example, a benzyl protective group can be removed hydrogenolytically or using $FeCl_3$, and an acid-labile THP protective group can be removed using toluenesulphonic acid.

Process Step [V24]:

According to processes known from the literature (cf. Synthesis 1979, 440-1), 5-sulphanylalkyl-, 5-aminoalkyl- and 5-hydroxyalkylpyrazoles of the general formulae (XVI), (XVII) and (XIII) can be cyclized to give the bicyclic pyrazoles of the general formulae (VIIb), (VIIc) and (VIIIa). To this end, corresponding aldehydes (for example formaldehyde, acetaldehyde) or ketones (for example acetone) are used as reactants. If appropriate, an acid, such as, for example, p-toluenesulphonic acid, may be added to the reaction mixture as a catalyst. Suitable for use as solvents are the reactant (for example acetone) itself or any other solvents which are inert under the reaction conditions, such as cyclic and acyclic ethers (dimethoxymethane, tetrahydrofuran, dioxane), aromatic hydrocarbons (for example toluene), nitriles (for example acetonitrile, propionitrile), amides (for example dimethylformamide, dimethylacetamide, N-methylpyrrolidone). The reaction temperature is between 0° C. and the boiling point of the solvent, preferably between room temperature and 100° C.

An alternative synthesis route to the compounds VII and VIII is found in Scheme 11:

Scheme 11:

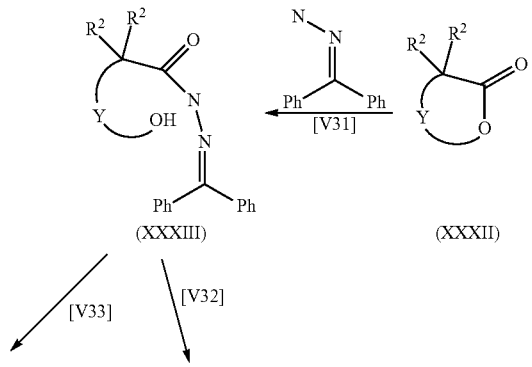

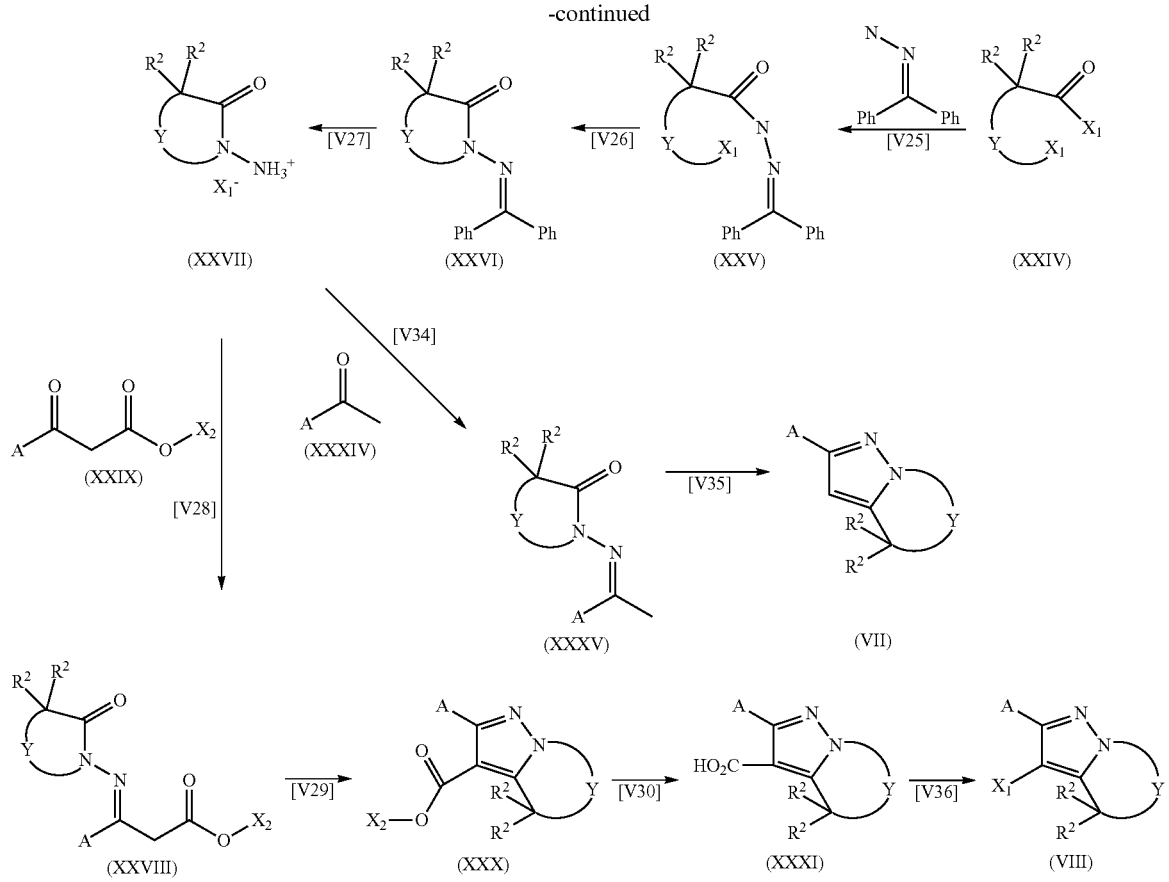

Process Step [V25]:

According to methods known from the literature (for example *J. Am. Chem. Soc.* 1981, 103, 7743-7752), the reaction of compounds of the general formula (XXIV) with benzophenone hydrazone, if appropriate in the presence of a solvent and a base, affords compounds of the general formula (XXV). The compounds (XXIV) required for this purpose are either commercially available or can be obtained, for example, by methods known from the literature from the lactones (*Synthesis* 2008, 20, 3229-3236).

Suitable for use as solvents for carrying out Process step [V25] are all solvents which are inert under the reaction conditions, and mixtures thereof. Preference is given to dichloromethane. Suitable bases are pyridine and tertiary amines. Preference is given to pyridine. The reaction temperature is between 0° C. and 100° C. The time for carrying out the reaction is, depending on the scale of the reaction, between 12 and 96 h, preferably between 16 h and 24 h.

Process Step [V26]:

According to methods known from the literature (for example *J. Am. Chem. Soc.* 1981, 103, 7743-7752), the reaction of compounds of the general formula (XXV), if appropriate in the presence of a solvent and a base, gives compounds of the general formula (XXVI).

Suitable solvents are all solvents which are inert under the reaction conditions, and mixtures thereof. Preference is given to tetrahydrofuran. Suitable bases are alkali metal hydrides. Preference is given to sodium hydride. The reaction temperature is between 0° C. and 50° C. The reaction time is, depending on the scale of the reaction, between 12 and 96 h, preferably between 16 h and 24 h.

Process Step [V27]:

According to methods known from the literature (for example WO2007018818), the reaction of compounds of the general formula (XXVI), if appropriate in the presence of a solvent and an acid, gives N-aminolactams of the general formula (XXVII).

Suitable solvents for carrying out the Process step [V27] are all solvents which are inert under the reaction conditions, and also mixtures thereof. Preference is given to tetrahydrofuran. Suitable acids are inorganic acids, and also organic acids. Preference is given to hydrochloric acid. The reaction temperature for carrying out the Process step [V27] is between 0° C. and 50° C. The reaction time is, depending on the scale of the reaction, between 5 min and 2 h, preferably 30 min.

Process Step [V28]:

According to methods known from the literature (for example *Tetrahedron* 2007, 63, 11763-11770), the reaction of N-aminolactams of the general formula (XXVII) with ketoesters (XXIX) gives compounds of the general formula (XXIX). The ketoesters (XXVIII) required for this purpose are either commercially available, or they can be obtained, for example, by methods known from the literature (*Helv. Chim. Acta* 2010, 93, 1261-1273).

Suitable solvents are all solvents which are inert under the reaction conditions, and mixtures thereof. Preference is given to pyridine. The reaction temperature is between 0° C. and 50° C. The reaction time for carrying out the Process step [V28] is, depending on the scale of the reaction, between 24 h and 72 h, preferably 48 h.

Process Step [V29]:

As described, for example, in *Eur. J. Med. Chem* 1984, 19, 215-218, compounds of the general formula (XXIX) can be cyclized under basic conditions to give pyrazole esters of the general formula (XXX).

Suitable solvents are all solvents which are inert under the reaction conditions, and mixtures thereof. Preference is given to dimethylformamide. Suitable bases are alkali metal hydrides and alkali metal carbonates. Preference is given to caesium carbonate. The reaction temperature is between 0° C. and 150° C. The reaction temperature is, depending on the scale of the reaction, between 2 h and 8 h, preferably between 4 h and 6 h.

Process Step [V30]:

The hydrolysis of pyrazole esters of the general formula (XXX) according to methods known from the literature (for example *Org. Lett.* 2005, 7, 4753-4756) gives pyrazolecarboxylic acids of the general formula (XXXI).

Suitable solvents are all solvents which are inert under the reaction conditions, and mixtures thereof. Preference is given to methanol. Suitable bases are alkali metal hydroxides. Preference is given to sodium hydroxide. The reaction temperature is between 0° C. and 100° C. The reaction time is, depending on the scale of the reaction, between 1 h and 8 h, preferably between 3 h and 6 h.

Process Step [V31]:

The reaction of lactones of the general formula (XXXII) with benzophenone hydrazone in the presence of a Lewis acid gives the compounds of the general formula (XXXIII).

Suitable solvents are all solvents which are inert under the reaction conditions, and mixtures thereof. Preference is given to dichloromethane. Suitable Lewis acids are trialkylaluminium derivatives. Preference is given to trimethylaluminium. The reaction temperature is between 0° C. and 100° C. The reaction time is, depending on the scale of the reaction, between 1 h and 8 h, preferably between 3 h and 6 h.

Process Step [V32]:

The reaction of alcohols of the general formula (XXXIII) with a suitable halogenating agent according to methods known from the literature (for example the article "Triphenylphosphine-Carbon Tetrabromide" in *Encyclopeadia of Reagents for Organic Synthesis*, Wiley, 1995) gives compounds of the general formula (XXV).

Suitable solvents are all solvents which are inert under the reaction conditions, and mixtures thereof. Preference is given to dichloromethane. Suitable halogenating agents are, for example, triphenylphosphane/halogenated hydrocarbon combinations, and halosulphur compounds (for example thionyl chloride). Preference is given to the combination triphenylphosphane/carbon tetrabromide. The reaction temperature is between 0° C. and 100° C. The reaction time is, depending on the scale of the reaction, between 30 min and 8 h, preferably 1 h.

Process Step [V33]:

The reaction of compounds of the general formula (XXXIII) with a halosulponic acid and, if appropriate, a base gives the compounds of the general formula (XXVI).

Suitable solvents are all solvents which are inert under the reaction conditions, and mixtures thereof.

Preference is given to dichloromethane and tetrahydrofuran. Suitable halosulphonic acids are, for example, methylsulphonyl chloride and tolylsulphonyl chloride. Preference is given to methylsulphonyl chloride. Suitable bases are pyridine derivatives and alkali metal hydrides. Preference is given to pyridine and sodium hydride. The reaction temperature is between 0° C. and 100° C. The reaction time is, depending on the scale of the reaction, between 6 h and 48 h, preferably between 12 h and 24 h.

Process Step [V34]:

According to methods known from the literature (for example *Eur. J. Med. Chem.* 2010, 95, 3384-3388), the reaction of N-aminolactams of the general formula (XXVII) With acetophenones of the general formula (XXXIV), if appropriate in the presence of a solvent, gives the compounds of the general formula (XXXV). The acetophenones (XXXIV) required for this purpose are commercially available.

Suitable solvents are all solvents which are inert under the reaction conditions, and mixtures thereof. Preference is given to ethanol. The reaction temperature is between 0° C. and 0.100° C. The reaction time is, depending on the scale of the reaction, between 6 h and 12 h, preferably 12 h.

Process Step [V35]:

According to methods known from the literature (for example *Zeitschrift für Naturforschung-B* 2003, 58, 678-685), the reaction of compounds of the general formula (XXXV) with acetic anhydride, if appropriate in the presence of a solvent, gives pyrazoles of the general formula (VII).

Suitable solvents are all solvents which are inert under the reaction conditions, and mixtures thereof. Preference is given to acetic anhydride. The reaction temperature is between 0° C. and 150° C. The reaction time is, depending on the scale of the reaction, between 2 h and 8 h, preferably between 4 h and 6 h.

Process Step [V36]:

The reaction of pyrazolecarboxylic acids of the general formula (XXXI) with a base and a halogenating agent according to methods known from the literature (for example *Org. Lett.* 2005, 7, 4753-4756) gives 5-halopyrazoles of the general formula (VIII).

Suitable solvents are all solvents which are inert under the reaction conditions, and mixtures thereof. Preference is given to dimethylformamide. Suitable halogenating agents are halosuccinimide reagents. Preference is given to N-iodosuccinimide. Suitable bases are alkali metal carbonates. Preference is given to sodium bicarbonate. The reaction temperature is between 0° C. and 100° C. The reaction time is, depending on the scale of the reaction, between 1 h and 48 h, preferably 12 h.

Novel and also part of the invention are compounds of the general formula (VIIIb)

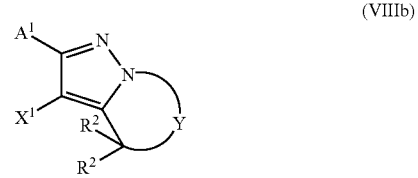

(VIIIb)

in which the symbols have the following meanings:

$A^1$ represents a phenyl ring which may optionally be mono- or polysubstituted at the 3-, 4- or 5-position by $R^7$, or represents a thiophenyl ring which may optionally be mono- or polysubstituted by $R^8$, $R^2$, $R^7$, $R^8$ and Y have the general, preferred, particularly preferred or very particularly preferred meanings given above and $X^1$ represents chlorine, bromine, iodine;

with the proviso that
3-bromo-5,6-dihydro-2-phenyl-4H-pyrrolo[1,2-b]pyrazole, 3-iodo-2-phenylpyrazolo[1,5-c]-pyrimidine-7(6H)-thione and 3-bromo-2-phenylpyrazolo[1,5-c]pyrimidine-7(6H)-thione are excluded.

Novel and also part of the invention are compounds of the general formula (VIIx)

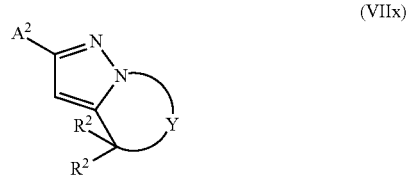

(VIIx)

in which the symbols have the following meanings:
$A^2$ represents an optionally mono- or polysubstituted thiophenyl ring or represents a phenyl ring which is optionally mono- or polysubstituted at the 3-, 4- or 5-position, where the substituents are selected from the group consisting of F, Cl, Br, I, cyano, methyl, ethyl, isopropyl, n-propyl, trifluoromethyl, difluoromethyl, dichloromethyl, pentafluoroethyl, methoxy, ethoxy, n-propoxy, isopropoxy;

Y together with the adjacent nitrogen atom "1" and the two carbon atoms "2" and "3" forms a 5- to 7-membered non-aromatic heterocyclic ring selected from the group consisting of H-2, H-3, H-4, H-5, H-6, H-7, H-8 and H-9 shown in Scheme 1, where s is a number from 0 to 4;

$R^2$ has the particularly preferred or very particularly preferred meanings given above.

The present invention furthermore relates to a crop protection composition for controlling unwanted fungi and for reducing mycotoxins in plants and plant parts, which composition comprises at least one of the bicyclic pyridinylpyrazole derivatives of the formula (I). These are preferably fungicidal compositions which comprise agriculturally suitable auxiliaries, solvents, carriers, surfactants or extenders.

Moreover, the invention relates to a method for controlling unwanted microorganisms and for reducing mycotoxins in plants and plant parts, characterized in that bicyclic pyridinylpyrazole derivatives of the formula (I) according to the invention are applied to the phytopathogenic fungi and/or their habitat.

According to the invention, a carrier is a natural or synthetic organic or inorganic substance with which the active compounds are mixed or bonded for better applicability, in particular for application to plants or plant parts or seed. The carrier, which may be solid or liquid, is generally inert and should be suitable for use in agriculture.

Suitable solid or liquid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and natural or synthetic silicates, resins, waxes, solid fertilizers, water, alcohols, especially butanol, organic solvents, mineral and vegetable oils and derivatives of these. Mixtures of such carriers may also be used. Suitable solid carriers for granules are: for example crushed and fractionated natural rocks such as calcite, marble, pumice, sepiolite, dolomite, and synthetic granules of inorganic and organic meals, and also granules of organic material such as sawdust, coconut shells, maize cobs and tobacco stalks.

Suitable liquefied gaseous extenders or carriers are liquids which are gaseous at ambient temperature and under atmospheric pressure, for example aerosol propellants, such as halogenated hydrocarbons, and also butane, propane, nitrogen and carbon dioxide.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

The compositions according to the invention may additionally comprise further components, such as, for example, surfactants. Suitable surfactants are emulsifiers and/or foam formers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is required if one of the active compounds and/or one of the inert carriers is insoluble in water and when the application takes place in water. The proportion of surfactants is between 5 and 40 percent by weight of the composition according to the invention.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

If appropriate, other additional components may also be present, for example protective colloids, binders, adhesives, thickeners, thixotropic substances, penetrants, stabilizers, sequestering agents, complex formers. In general, the active compounds can be combined with any solid or liquid additive customarily used for formulation purposes.

The formulations generally comprise between 0.05 and 99% by weight, 0.01 and 98% by weight, preferably between 0.1 and 95% by weight, particularly preferably between 0.5 and 90% of active compound, very particularly preferably between 10 and 70% by weight.

The active compounds or compositions according to the invention can be used as such or, depending on their respective physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active compound, and also microencapsulations in polymeric substances and in coating materials for seed, and also ULV cold-fogging and warm-fogging formulations.

The formulations mentioned can be prepared in a manner known per se, for example by mixing the active compounds with at least one customary extender, solvent or diluent, emulsifier, dispersant, and/or binder or fixative, wetting agent, water repellent, if appropriate desiccants and UV stabilizers and, if appropriate, dyes and pigments, antifoams, preservatives, secondary thickeners, adhesives, gibberellins and also further processing auxiliaries.

The compositions according to the invention include not only formulations which are already ready for use and can be applied with a suitable apparatus to the plant or the seed, but also commercial concentrates which have to be diluted with water prior to use.

The active compounds according to the invention can be present as such or in their (commercial) formulations and in the use forms prepared from these formulations as a mixture with other (known) active compounds, such as insecticides, attractants, sterilants, bactericides, acaricides, nematicides, fungicides, growth regulators, herbicides, fertilizers, safeners and/or semiochemicals.

The treatment according to the invention of the plants and plant parts with the active compounds or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more coats, etc. It is furthermore possible to apply the active compounds by the ultra-low volume method or to inject the active compound preparation or the active compound itself into the soil.

The invention furthermore includes a method for treating seed.

The invention furthermore relates to seed which has been treated in accordance with one of the methods described in the previous paragraph. The seeds according to the invention are used in methods for the protection of seed from undesirable fungi. In these methods, seed treated with at least one active compound according to the invention is employed.

The active compounds or compositions according to the invention are also suitable for treating seed. A large part of the damage to crop plants caused by harmful organisms is triggered by the infection of the seed during storage or after sowing and during and after germination of the plant. This phase is particularly critical since the roots and shoots of the growing plant are particularly sensitive, and even small damage may result in the death of the plant. Accordingly, there is great interest in protecting the seed and the germinating plant by using appropriate compositions.

The control of phytopathogenic fungi by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with, or at least reduce considerably, the additional application of crop protection agents after sowing or after emergence of the plants. It is furthermore desirable to optimize the amount of active compound employed in such a way as to provide optimum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

The present invention therefore also relates to a method for the protection of seed and germinating plants from attack by phytopathogenic fungi, by treating the seed with a composition according to the invention. The invention also relates to the use of the compositions according to the invention for treating seed for protecting the seed and the germinating plant against phytopathogenic fungi. Furthermore, the invention relates to seed treated with a composition according to the invention for protection against phytopathogenic fungi.

The control of phytopathogenic fungi which damage plants post-emergence is carried out primarily by treating the soil and the above-ground parts of plants with crop protection agents. Owing to the concerns regarding a possible impact of the crop protection agents on the environment and the health of humans and animals, there are efforts to reduce the amount of active compounds applied.

One of the advantages of the present invention is that the particular systemic properties of the active compounds and compositions according to the invention mean that treatment of the seed with these active compounds and compositions not only protects the seed itself, but also the resulting plants after emergence, from phytopathogenic fungi. In this manner, the immediate treatment of the crop at the time of sowing or shortly thereafter can be dispensed with.

It is also considered to be advantageous that the active compounds or compositions according to the invention can be used in particular also for transgenic seed where the plant growing from this seed is capable of expressing a protein which acts against pests. By treating such seed with the active compounds or compositions according to the invention, even by the expression of the, for example, insecticidal protein, certain pests may be controlled. Surprisingly, a further synergistic effect may be observed here, which additionally increases the effectiveness of the protection against attack by pests.

The compositions according to the invention are suitable for protecting seed of any plant variety which is employed in agriculture, in the greenhouse, in forests or in horticulture and viticulture. In particular, this takes the form of seed of cereals (such as wheat, barley, rye, triticale, millet and oats), maize, cotton, soya beans, rice, potatoes, sunflower, bean, coffee, beet (for example sugar beet and fodder beet), peanut, oilseed rape, poppy, olive, coconut, cacao, sugar cane, tobacco, vegetables (such as tomato, cucumbers, onions and lettuce), turf and ornamentals (see also hereinbelow). The treatment of the seed of cereals (such as wheat, barley, rye, triticale and oats), maize and rice is of particular importance.

As also described further below, the treatment of transgenic seed with the active compounds or compositions according to the invention is of particular importance. This refers to the seed of plants containing at least one heterologous gene which allows the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. Preferably, this heterologous gene is from *Bacillus* sp., the gene product having activity against the European corn borer and/or the Western corn rootworm. Particularly preferably, the heterologous gene originates from *Bacillus thuringiensis*.

Within the context of the present invention, the composition according to the invention is applied to the seed either alone or in a suitable formulation. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits. Thus, it is possible to use, for example, seed which has been harvested, cleaned and dried to a moisture content of less than 15% by weight. Alternatively, it is also possible to use seed which, after drying, has been treated, for example, with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which can have phytotoxic effects at certain application rates.

The compositions according to the invention can be applied directly, i.e. without containing any other components and undiluted. In general, it is preferred to apply the compositions to the seed in the form of a suitable formulation. Suitable formulations and methods for treating seed are known to the person skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compounds which can be used in accordance with the invention can be converted into the customary seed-dressing formulations, such as solutions, emulsions, suspensions, powders, foams, slurries or other coating compositions for seed, and also ULV formulations.

These formulations are prepared in a known manner, by mixing the active compounds with customary additives such as, for example, customary extenders and also solvents or diluents, colorants, wetting agents, dispersants, emulsifiers, antifoams, preservatives, secondary thickeners, adhesives, gibberellins and also water.

Colorants which may be present in the seed-dressing formulations which can be used in accordance with the invention are all colorants which are customary for such purposes. In this context, not only pigments, which are sparingly soluble in water, but also dyes, which are soluble in water, may be used. Examples which may be mentioned are the colorants known by the names Rhodamin B, C.I. Pigment Red 112 and C.I. Solvent Red 1.

Suitable wetting agents which may be present in the seed-dressing formulations which can be used in accordance with the invention are all substances which promote wetting and which are conventionally used for the formulation of agrochemical active compounds. Preference is given to using alkylnaphthalenesulphonates, such as diisopropyl- or diisobutylnaphthalenesulphonates.

Suitable dispersants and/or emulsifiers which may be present in the seed-dressing formulations which can be used in accordance with the invention are all nonionic, anionic and cationic dispersants conventionally used for the formulation of agrochemical active compounds. Preference is given to using nonionic or anionic dispersants or mixtures of nonionic or anionic dispersants. Suitable nonionic dispersants which may be mentioned are, in particular, ethylene oxide/propylene oxide block polymers, alkylphenol polyglycol ethers and tristryrylphenol polyglycol ethers, and their phosphated or sulphated derivatives. Suitable anionic dispersants are, in particular, lignosulphonates, polyacrylic acid salts and arylsulphonate/formaldehyde condensates.

Antifoams which may be present in the seed-dressing formulations which can be used in accordance with the invention are all foam-inhibiting substances conventionally used for the formulation of agrochemical active compounds. Silicone antifoams and magnesium stearate can preferably be used.

Preservatives which may be present in the seed-dressing formulations which can be used in accordance with the invention are all substances which can be employed for such purposes in agrochemical compositions. Dichlorophene and benzyl alcohol hemiformal may be mentioned by way of example.

Secondary thickeners which may be present in the seed-dressing formulations which can be used in accordance with the invention are all substances which can be employed for such purposes in agrochemical compositions. Cellulose derivatives, acrylic acid derivatives, xanthan, modified clays and finely divided silica are preferred.

Adhesives which may be present in the seed-dressing formulations which can be used in accordance with the invention are all customary binders which can be employed in seed-dressing products. Polyvinylpyrrolidone, polyvinyl acetate, polyvinyl alcohol and tylose may be mentioned as being preferred.

Gibberellins which can be present in the seed-dressing formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz- and Schädlingsbekämpfungsmittel" [Chemistry of crop protection agents and pesticides], vol. 2, Springer Verlag, 1970, p. 401-412).

The seed-dressing formulations which can be used in accordance with the invention can be employed for the treatment of a wide range of seed, including the seed of transgenic plants, either directly or after previously having been diluted with water. In this context, additional synergistic effects may also occur in cooperation with the substances formed by expression.

All mixers which can conventionally be employed for the seed-dressing operation are suitable for treating seed with the seed-dressing formulations which can be used in accordance with the invention or with the preparations prepared therefrom by addition of water. Specifically, a procedure is followed during the seed-dressing operation in which the seed is placed into a mixer, the specific desired amount of seed-dressing formulations, either as such or after previously having been diluted with water, is added, and everything is mixed until the formulation is distributed uniformly on the seed. If appropriate, this is followed by a drying process.

The active compounds or compositions according to the invention have a potent fungicidal activity and can be employed for controlling undesirable fungi in crop protection and in the protection of materials.

The bicyclic pyridinylpyrazole derivatives according to the invention can be employed in crop protection for controlling Plasmodiophoromycetes, Oomycetes, Chytridiomycetes, Zygomycetes, Ascomycetes, Basidiomycetes and Deuteromycetes.

The fungicidal compositions according to the invention can be used for the curative or protective control of phytopathogenic fungi. Accordingly, the invention also relates to curative and protective methods for controlling phytopathogenic fungi using the active compounds or compositions according to the invention, which are applied to the seed, the plant or plant parts, the fruit or the soil in which the plants grow.

The compositions according to the invention for controlling phytopathogenic fungi in crop protection comprise an effective, but non-phytotoxic amount of the active compounds according to the invention. "Effective, but non-phytotoxic amount" means an amount of the composition according to the invention which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on a plurality of factors, for example on the fungus to be controlled, the plant, the climatic conditions and the ingredients of the compositions according to the invention.

The fact that the active compounds are well tolerated by plants at the concentrations required for controlling plant diseases permits the treatment of above-ground parts of plants, of propagation stock and seeds, and of the soil.

All plants and plant parts can be treated in accordance with the invention. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. Parts of plants also include harvested plants and vegetative and generative propagation material, for example seedlings, tubers, rhizomes, cuttings and seeds.

The active compounds according to the invention are suitable for the protection of plants and plant organs, for increasing the harvest yields, for improving the quality of the harvested crop, while being well tolerated by plants, having favourable toxicity to warm-blooded species and being environmentally friendly. They may be preferably employed as crop protection agents. They are active against normally sensitive and resistant species and also against all or some stages of development.

The following plants may be mentioned as plants which can be treated according to the invention: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for example banana plants and banana plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Utnbelliferae* sp., *Cruciferae* sp., *Chenopodiaceae* sp., *Cucurbitaceae* sp. (for example cucumber), *Alliaceae* sp. (for example leeks, onions), *Papilionaceae* sp. (for example peas); major crop plants such as *Gramineae* sp. (for example maize, turf, cereals such as wheat, rye, rice, barley, oats, millet and triticale), *Poaceae* sp. (for example sugar cane), *Asteraceae* sp. (for example sunflower), *Brassicaceae* sp. (for example white cabbage, red cabbage, broccoli, cauliflower, Brussels sprouts, pak Choi, kohlrabi, small radishes, and also oilseed rape, mustard, horseradish and cress), *Fabacae* sp. (for example beans, peanuts), *Papilionaceae* sp. (for example soya bean), *Solanaceae* sp. (for example potatoes), *Chenopodiaceae* sp. (for example sugar beet, fodder beet, Swiss chard, beetroot); useful plants and ornamental plants in gardens and forests; and in each case genetically modified types of these plants.

As already mentioned above, it is possible to treat all plants and their parts according to the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above. Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, varieties, bio- or genotypes.

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example antisense technology, cosuppression technology or RNAi technology [RNA interference]). A heterologous gene that is located in the genome is also called a transgene. A transgene that is defined by its particular location in the plant genome is called a transformation or transgenic event.

Depending on the plant species or plant varieties, their location and growth conditions (soils, climate, vegetation period, diet), the treatment according to the invention may also result in superadditive ("synergistic") effects. Possible are thus, for example, the following effects which exceed the effects which were actually to be expected: reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processability of the harvested products.

At certain application rates, the active compound combinations according to the invention may also have a strengthening effect in plants. Accordingly, they are suitable for mobilizing the defence system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) substances are to be understood as meaning, in the present context, also those substances or combinations of substances which are capable of stimulating the defence system of plants in such a way that, when subsequently inoculated with unwanted phytopathogenic fungi, the treated plants display a substantial degree of resistance to these unwanted phytopathogenic fungi. Thus, the substances according to the invention can be employed for protecting plants against attack by the abovementioned pathogens within a certain period of time after the treatment. The period within which protection is brought about generally extends from 1 to 10 days, preferably 1 to 7 days, after the treatment of the plants with the active compounds.

Plants and plant varieties which are preferably treated according to the invention include all plants which have genetic material which imparts particularly advantageous, useful traits to these plants (whether obtained by breeding and/or biotechnological means).

Plants and plant varieties which are also preferably treated according to the invention are resistant against one or more biotic stress factors, i.e. said plants have a better defence against animal and microbial pests, such as against nematodes, insects, mites, phytopathogenic fungi, bacteria, viruses and/or viroids.

Plants and plant varieties which may also be treated according to the invention are those plants which are resistant to one or more abiotic stress factors. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or shade avoidance.

Plants and plant varieties which may also be treated according to the invention are those plants characterized by enhanced yield characteristics. Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristics of heterosis, or hybrid effect, which results in generally higher yield, vigour, health and resistance towards biotic and abiotic stress factors. Such plants are typically made by crossing an inbred male-sterile parent line (the female parent) with another inbred male-fertile parent line (the male parent). Hybrid seed is typically harvested from the male-sterile plants and sold to growers. Male-sterile plants can sometimes (e.g. in corn) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant varieties (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an Eleusine EPSPS. It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyltransferase enzyme. Glyphosate-tolerant plants can also be obtained by selecting plants containing naturally occurring mutations of the abovementioned genes.

Other herbicide-resistant plants are for example plants which have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species for example). Plants expressing an exogenous phosphinothricin acetyltransferase have been described.

Further herbicide-tolerant plants are also plants that have been made tolerant to the herbicides inhibiting the enzyme hydroxyphenylpyruvatedioxygenase (HPPD). Hydroxyphenylpyruvatedioxygenases are enzymes that catalyse the reaction in which para-hydroxyphenylpyruvate (HPP) is transformed into homogentisate. Plants tolerant to HPPD inhibitors can be transformed with a gene encoding a naturally occurring resistant HPPD enzyme, or a gene encoding a mutated HPPD enzyme. Tolerance to HPPD inhibitors can also be obtained by transforming plants with genes encoding certain enzymes enabling the formation of homogentisate despite the inhibition of the native HPPD enzyme by the HPPD inhibitor. Tolerance of plants to HPPD inhibitors can also be improved by transforming plants with a gene encoding a prephenate dehydrogenase enzyme in addition to a gene encoding an HPPD-tolerant enzyme.

Further herbicide-resistant plants are plants that have been made tolerant to acetolactate synthase (ALS) inhibitors. Known ALS inhibitors include, for example, sulphonylurea, imidazolinone, triazolopyrimidines, pyrimidinyl oxy(thio)benzoates, and/or sulphonylaminocarbonyltriazolinone herbicides. Different mutations in the ALS enzyme (also known as acetohydroxy acid synthase, AHAS) are known to confer tolerance to different herbicides and groups of herbicides. The production of sulphonylurea-tolerant plants and imidazolinone-tolerant plants has been described in the international publication WO 1996/033270. Further sulphonylurea- and imidazolinone-tolerant plants have also been described, for example in WO 2007/024782.

Other plants tolerant to imidazolinone and/or sulphonylurea can be obtained by induced mutagenesis, by selection in cell cultures in the presence of the herbicide or by mutation breeding.

Plants or plant varieties (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding:
1) an insecticidal crystal protein from *Bacillus thuringiensis* or an insecticidal portion thereof, such as the insecticidal crystal proteins listed online at:
http://www.lifesci.sussex.ac.uk/Home/Neil_Crickmore/Bt/, or insecticidal portions thereof, for example proteins of the Cry protein classes Cry1Ab, Cry1Ac, Cry1F, Cry2Ab, Cry3Ae or Cry3Bb or insecticidal portions thereof; or
2) a crystal protein from *Bacillus thuringiensis* or a portion thereof which is insecticidal in the presence of a second other crystal protein than *Bacillus thuringiensis* or a portion thereof, such as the binary toxin made up of the Cy34 and Cy35 crystal proteins; or
3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A. 105 protein produced by maize event MON98034 (WO 2007/027777); or
4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in maize events MON863 or MON88017, or the Cry3A protein in maize event MIR 604;
5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/home/Neil_Crickmore/Bt/vip.html, for example proteins from the VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins;
7) a hybrid insecticidal protein comprising parts from different secreted proteins from *Bacillus thuringiensis* or *Bacillus cereus*, such as a hybrid of the proteins in 1) above or a hybrid of the proteins in 2) above; or
8) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

Plants or plant varieties (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:
a. plants which contain a transgene capable of reducing the expression and/or the activity of the poly(ADP-ribose)polymerase (PARP) gene in the plant cells or plants;
b. plants which contain a stress tolerance-enhancing transgene capable of reducing the expression and/or the activity of the PARG-encoding genes of the plants or plant cells;
c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant varieties (obtained by plant biotechnology methods such as genetic engineering) which may also be treated according to the invention show altered quantity, quality and/or storage stability of the harvested product and/or altered properties of specific ingredients of the harvested product such as, for example:
1) Transgenic plants which synthesize a modified starch which is altered with respect to its chemophysical traits, in particular the amylose content or the amylose/amylopectin ratio, the degree of branching, the average chain length, the distribution of the side chains, the viscosity behaviour, the gel resistance, the grain size and/or grain morphology of the starch in comparison to the synthesized starch in wild-type plant cells or plants, such that this modified starch is better suited for certain applications.

2) Transgenic plants which synthesize non-starch carbohydrate polymers or which synthesize non-starch carbohydrate polymers with altered properties in comparison to wild-type plants without genetic modification. Examples are plants which produce polyfructose, especially of the inulin and levan type, plants which produce alpha-1,4-glucans, plants which produce alpha-1,6-branched alpha-1,4-glucans, and plants producing alternan.

3) Transgenic plants which produce hyaluronan.

Plants or plant varieties (obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:

a) plants, such as cotton plants, which contain an altered form of cellulose synthase genes;
b) plants, such as cotton plants, which contain an altered form of rsw2 or rsw3 homologous nucleic acids;
c) plants, such as cotton plants, with an increased expression of sucrose phosphate synthase;
d) plants, such as cotton plants, with an increased expression of sucrose synthase;
e) plants, such as cotton plants, wherein the timing of the plasmodesmatal gating at the basis of the fibre cell is altered, for example through downregulation of fibre-selective β-1,3-glucanase;
f) plants, such as cotton plants, which have fibres with altered reactivity, for example through the expression of the N-acetylglucosaminetransferase gene including nodC and chitin synthase genes.

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants containing a mutation imparting such altered oil characteristics and include:

a) plants, such as oilseed rape plants, which produce oil having a high oleic acid content;
b) plants, such as oilseed rape plants, which produce oil having a low linolenic acid content;
c) plants, such as oilseed rape plants, which produce oil having a low level of saturated fatty acids.

Particularly useful transgenic plants which may be treated according to the invention are plants which comprise one or more genes which encode one or more toxins and are the transgenic plants available under the following trade names: YIELD GARD® (for example maize, cotton, soya beans), KnockOut® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are available under the following trade names: Roundup Ready® (tolerance to glyphosate, for example maize, cotton, soya beans), Liberty Link® (tolerance to phosphinothricin, for example oilseed rape), IMI® (tolerance to imidazolinone) and SCS® (tolerance to sulphonylurea, for example maize). Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or a combination of transformation events, and that are listed for example in the databases for various national or regional regulatory agencies (see for example http://gmoinfo.jrc.it/gmp_browse.aspx and http://www.agbios.com/dbase.php).

Moreover, in the protection of materials, the active compounds or compositions according to the invention can be employed for protecting industrial materials against attack and destruction by unwanted microorganisms, such as, for example, fungi.

Industrial materials in the present context are understood as meaning non-living materials which have been prepared for use in industry. For example, industrial materials which are intended to be protected by active compounds according to the invention from fungal change or destruction can be adhesives, sizes, paper, wallpaper and board, textiles, carpets, leather, wood, paints and plastic articles, cooling lubricants and other materials which can be infected with, or destroyed by, microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood. The active compounds or compositions according to the invention may prevent disadvantageous effects, such as rotting, decay, discoloration, decolouration or formation of mould. Moreover, the compounds according to the invention can be employed for protecting objects which come into contact with saltwater or brackish water, in particular hulls, screens, nets, buildings, moorings and signalling systems, against fouling.

The method according to the invention for controlling unwanted fungi can also be employed for protecting storage goods. Here, storage goods are to be understood as meaning natural substances of vegetable or animal origin or processed products thereof of natural origin, for which long-term protection is desired. Storage goods of vegetable origin, such as, for example, plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, and in the form of finished products, such as furniture. Storage goods of animal origin are, for example, hides, leather, furs and hairs. The active compounds according to the invention may prevent disadvantageous effects, such as rotting, decay, discoloration, decoloration or formation of mould.

Some pathogens of fungal diseases which can be treated according to the invention may be mentioned by way of example, but not by way of limitation:

diseases caused by powdery mildew pathogens, such as, for example, *Blumeria* species, such as, for example, *Blumeria graminis*; *Podosphaera* species, such as, for example, *Podosphaera leucotricha*; *Sphaerotheca* species, such as, for example, *Sphaerotheca fuliginea*; *Uncinula* species, such as, for example, *Uncinula necator*;

diseases caused by rust disease pathogens, such as, for example, *Gymnosporangium* species, such as, for example,

*Gymnosporangium sabinae; Hemileia* species, such as, for example, *Hemileia vastatrix; Phakopsora* species, such as, for example, *Phakopsora pachyrhizi* and *Phakopsora meibomiae; Puccinia* species, such as, for example, *Puccinia recondita* or *Puccinia triticina; Uromyces* species, such as, for example, *Uromyces appendiculatus;* diseases caused by pathogens from the group of the Oomycetes, such as, for example, *Bremia* species, such as, for example, *Bremia lactucae; Peronospora* species, such as, for example, *Peronospora pili* or *P. brassicae; Phytophthora* species, such as, for example, *Phytophthora infestans; Plasmopara* species, such as, for example, *Plasmopara viticola; Pseudoperonospora* species, such as, for example, *Pseudoperonospora humuli* or *Pseudoperonospora cubensis; Pythium* species, such as, for example, *Pythium ultimum;* leaf blotch diseases and leaf wilt diseases caused, for example, by *Alternaria* species, such as, for example, *Alternaria solani; Cercospora* species, such as, for example, *Cercospora beticola; Cladiosporium* species, such as, for example, *Cladiosporium cucumerinum; Cochliobolus* species, such as, for example, *Cochliobolus sativus* (conidia form: *Drechslera*, syn: *Helminthosporium*); *Colletotrichum* species, such as, for example, *Colletotrichum lindemuthanium; Cycloconium* species, such as, for example, *Cycloconium oleaginum; iaporthe* species, such as, for example, *Diaporthe citri; Elsinoe* species, such as, for example, *Elsinoe fawcettii; Gloeosporium* species, such as, for example, *Gloeosporium* laeticolor; *Glomerella* species, such as, for example, *Glomerella cingulata; Guignardia* species, such as, for example, *Guignardia bidwelli; Leptosphaeria* species, such as, for example, *Leptosphaeria maculans; Magnaporthe* species, such as, for example, *Magnaporthe grisea; Microdochium* species, such as, for example, *Microdochium nivale; Mycosphaerella* species, such as, for example, *Mycosphaerella graminicola* and *M. fijiensis; Phaeosphaeria* species, such as, for example, *Phaeosphaeria nodorum; Pyrenophora* species, such as, for example, *Pyrenophora teres; Ramularia* species, such as, for example, *Ramularia collo-cygni; Rhynchosporium* species, such as, for example, *Rhynchosporium secalis; Septoria* species, such as, for example, *Septoria apii; Typhula* species, such as, for example, *Typhula incarnata; Venturia* species, such as, for example, *Venturia inacqualis;* root and stem diseases caused, for example, by *Corticium* species, such as, for example, *Corticium graminearum; Fusarium* species, such as, for example, *Fusarium oxysporum; Gaeumannomyces* species, such as, for example, *Gaeumannomyces graminis; Rhizoctonia* species, such as, for example, *Rhizoctonia solani; Tapesia* species, such as, for example, *Tapesia acuformis; Thielaviopsis* species, such as, for example, *Thielaviopsis basicola;* ear and panicle diseases (including corn cobs) caused, for example, by *Alternaria* species, such as, for example, *Alternaria* spp.; *Aspergillus* species, such as, for example, *Aspergillus flavus; Cladosporium* species, such as, for example, *Cladosporium cladosporioides; Claviceps* species, such as, for example, *Claviceps purpurea; Fusarium* species, such as, for example, *Fusarium culmorum; Gibberella* species, such as, for example, *Gibberella zeae; Monographella* species, such as, for example, *Monographella nivalis; Septoria* species, such as, for example, *Septoria nodorum;* diseases caused by smut fungi, such as, for example, *Sphacelotheca* species, such as, for example, *Sphacelotheca reiliana; Tilletia* species, such as, for example, *Tilletia caries, T. controversa; Urocystis* species, such as, for example, *Urocystis occulta; Ustilago* species, such as, for example, *Ustilago nuda, U. nuda tritici;* fruit rot caused, for example, by *Aspergillus* species, such as, for example, *Aspergillus flavus; Botrytis* species, such as, for example, *Botrytis cinerea; Penicillium* species, such as, for example, *Penicillium expansum* and *P. purpurogenum; Sclerotinia* species, such as, for example, *Sclerotinia sclerotiorum;*

*Verticilium* species, such as, for example, *Verticilium alboatrum;* seed- and soil-borne rot and wilt diseases, and also diseases of seedlings, caused, for example, by *Fusarium* species, such as, for example, *Fusarium culmorum; Phytophthora* species, such as, for example, *Phytophthora cactorum; Pythium* species, such as, for example, *Pythium ultimum; Rhizoctonia* species, such as, for example, *Rhizoctonia solani; Sclerotium* species, such as, for example, *Sclerotium rolfsii;* cancerous diseases, galls and witches' broom caused, for example, by *Nectria* species, such as, for example, *Nectria galligena;* wilt diseases caused, for example, by *Monilinia* species, such as, for example, *Monilinia laxa;* deformations of leaves, flowers and fruits caused, for example, by *Taphrina* species, such as, for example, *Taphrina deformans;* degenerative diseases of woody plants caused, for example, by *Esca* species, such as, for example, *Phaeomoniella chlamydospora* and *Phaeoacremonium aleophilum* and *Fomitiporia mediterranea;* diseases of flowers and seeds caused, for example, by *Botrytis* species, such as, for example, *Botrytis cinerea;* diseases of plant tubers caused, for example, by *Rhizoctonia* species, such as, for example, *Rhizoctonia solani; Helminthosporium* species, such as, for example, *Helminthosporium solani;* diseases caused by bacterial pathogens, such as, for example, *Xanthomonas* species, such as, for example, *Xanthomonas campestris* pv. *oryzae; Pseudomonas* species, such as, for example, *Pseudomonas syringae* pv. *lachrymans; Erwinia* species, such as, for example, *Erwinia amylovora.*

Preference is given to controlling the following diseases of soya beans:

Fungal diseases on leaves, stems, pods and seeds caused, for example, by alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaenilina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*),

*pythium* rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

Organisms which can bring about degradation or modification of the industrial materials and which may be mentioned are fungi. The active compounds according to the invention preferably act against fungi, in particular moulds, wood-discolouring and wood-destroying fungi (Basidiomycetes). Fungi of the following genera may be mentioned as examples: *Alternaria*, such as *Alternaria tenuis*; *Aspergillus*, such as *Aspergillus niger*; *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pityophila*; *Trichoderma*, such as *Trichoderma viride*.

In addition, the active compounds according to the invention also have very good antimycotic activity. They have a very broad antimycotic activity spectrum, in particular against dermatophytes and yeasts, moulds and diphasic fungi (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and *audouinii*. The list of these fungi by no means limits the mycotic spectrum covered, but is only for illustration.

When using the active compounds according to the invention as fungicides, the application rates can be varied within a relatively wide range, depending on the kind of application. The application rate of the active compounds according to the invention is when treating plant parts, for example leaves: from 0.1 to 10 000 g/ha, preferably from 10 to 1000 g/ha, particularly preferably from 50 to 300 g/ha (when the application is carried out by watering or dripping, it is even possible to reduce the application rate, especially when inert substrates such as rock wool or perlite are used);

when treating seed: from 2 to 200 g per 100 kg of seed, preferably from 3 to 150 g per 100 kg of seed, particularly preferably from 2.5 to 25 g per 100 kg of seed, very particularly preferably from 2.5 to 12.5 g per 100 kg of seed;

when treating the soil: from 0.1 to 10 000 g/ha, preferably from 1 to 5000 g/ha.

These application rates are mentioned only by way of example and are not limiting in the sense of the invention.

The active compounds or compositions according to the invention can thus be employed for protecting plants for a certain period of time after treatment against attack by the pathogens mentioned. The period for which protection is provided extends generally for 1 to 28 days, preferably for 1 to 14 days, particularly preferably for 1 to 10 days, very particularly preferably for 1 to 7 days after the treatment of the plants with the active compounds, or for up to 200 days after a seed treatment.

In addition, by the treatment according to the invention it is possible to reduce the mycotoxin content in the harvested material and the foodstuffs and feedstuffs prepared therefrom. Particular, but not exclusive, mention may be made here of the following mycotoxins: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins produced, for example, by the following fungi: *Fusarium* spec., such as *Fusarium acuminatum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides*, inter alia, and also by *Aspergillus* spec., *Penicillium* spec., *Claviceps purpurea, Stachybotrys* spec., inter alia.

The plants listed can be treated according to the invention in a particularly advantageous manner with the bicyclic pyridinylpyrazole derivatives of the formula (I) or the compositions according to the invention. The preferred ranges stated above for the active compounds or compositions also apply to the treatment of these plants. Particular emphasis is given to the treatment of plants with the compounds or compositions specifically mentioned in the present text.

The preparation and the use of the active compounds of the formula (I) according to the invention is illustrated by the examples below. However, the invention is not limited to these examples.

Example of Process step [V1] from Schemes 3 & 7

Example 2

2-(4-Fluorophenyl)-3-(pyridin-4-yl)-4,5,6,7-tetrahydropyrazolo[1,5-a]pyridine

A mixture of 1.64 g (11.1 mmol) of 4,5,6,7-tetrahydro[1,2,3]oxadiazolo[3,4-a]pyridin-8-ium 3-olate and 2.19 g (11.1 mmol) of 4-{[4-fluorophenyl]ethynyl}pyridine in 40 ml of mesitylene is stirred under argon at 165° C. for 16 h. After cooling, the reaction mixture is concentrated under reduced pressure. Purification by column chromatography on silica gel (cyclohexane/ethyl acetate) gives 888 mg (27%) of the desired product; log P(HCOOH): 1.03; $^1$H-NMR (CDCl$_3$-d1): 8.52 (d, 2H), 7.38 (dd, 2H), 7.08 (d, 2H), 7.00 (dd, 2H), 4.25 (dd, 2H), 2.85 (dd, 2H), 2.12 (m, 2H), 1.92 (m, 2H).

Example of Process step [V2] from Schemes 4 & 7

4-{[4-(Trifluoromethyl)phenyl]ethynyl}pyridine (II-1)

Under argon, a mixture of 1.20 g (6.17 mmol) of 4-bromopyridine hydrochloride, 1.57 g (9.26 mmol) of 1-ethynyl-4-(trifluoromethyl)benzene, 88 mg (0.46 mmol) of copper(I) iodide and 251 mg (0.31 mmol) of Pd(dppf)Cl$_2$ in 10 ml of triethylamine is heated at 90° C. for 3 h. After concentration, the reaction mixture is taken up in 100 ml of ethyl acetate and washed with 2×100 ml of 1M HCl. The aqueous phase is adjusted to pH 10 using aqueous sodium hydroxide solution and extracted with 3×100 ml of chloroform. The combined organic phases are washed with saturated aqueous NaCl solution, dried over Na$_2$SO$_4$ and freed from the solvent under reduced pressure. This gives 380 mg (24%) of the desired product; log P(HCOOH): 2.86; $^1$H-NMR (DMSO-d6) δ: 8.66 (d, 2H), 7.84 (s, 4H), 7.58 (d, 2H)

The following compounds can be prepared analogously:

4-{[3-(Trifluoromethyl)phenyl]ethynyl}pyridine (II-2); log P(pH7): 3.50 with MS (ESI): 248.1 ([M+H]$^+$).

4-{[4-(Methoxy)phenyl]ethynyl}pyridine (II-3); log P(pH7): 2.68; $^1$H-NMR (DMSO-d6) δ: 8.60 (d, 2H), 7.55 (d, 2H), 7.48 (d, 2H), 7.02 (d, 2H).

4-{[4-Fluorophenyl]ethynyl}pyridine (II-4); log P(pH7): 2.81; $^1$H-NMR (DMSO-d6) δ: 8.63 (d, 2H), 7.68 (dd, 2H), 7.52 (d, 2H), 7.32 (dd, 2H).

4-{[4-Chlorophenyl]ethynyl}pyridine (II-5); log P(HCOOH): 2.43; with MS (ESI): 214.0/216.0 ([M+H]$^+$).

2-Chloro-4-[(4-fluorophenyl)ethynyl]pyridine (II-6); log P(HCOOH): 3.80 with MS (ESI): 232.1/234.1 ([M+H]$^+$).

Example of Process step [V3] from Schemes 5 & 7

5,6,7,8-Tetrahydro-4H-[1,2,3]oxadiazolo[3,4-a]azepin-9-ium 3-olate (III-1)

At 0° C., a solution of 7.80 g (43.4 mmol) of azepan-2-carboxylic acid and 4.10 g (59.5 mmol) of sodium nitrite in 50 ml of water is acidified to pH 3 using HCl (conc.) and then stirred for 1 h. 50 ml of ethyl acetate are added to the reaction mixture, the organic phase is separated off and the aqueous phase is extracted with 2×50 ml of ethyl acetate. The combined organic phases are dried over MgSO$_4$ and freed from the solvent under reduced pressure. The 1-nitrosoazepan-2-carboxylic acid obtained (6.80 g, 67%) is taken up in 15 ml of acetonitrile without further purification, and 12.4 g (59.2 mmol) of trifluoroacetic anhydride are added dropwise at 0° C. After 2 h of stirring at room temperature, 8.19 g (59.2 mmol) of potassium carbonate are added, and stirring is continued for a further 20 min. 40 ml of ethyl acetate and 20 ml of water are added to the reaction mixture, and the aqueous phase is extracted with 3×40 ml of ethyl acetate. The combined organic phases are dried over MgSO$_4$ and freed from the solvent under reduced pressure. Purification by column chromatography on silica gel (cyclohexane/ethyl acetate) gives 5.50 g (90%) of the desired product; log P(HCOOH): 0.6; $^1$H-NMR (DMSO-d6): 4.45 (m, 2H), 2.56 (m, 2H), 1.83 (m, 4H), 1.57 (m, 2H)

The following compounds can be prepared analogously:

4,5,6,7-Tetrahydro[1,2,3]oxadiazolo[3,4-a]pyridin-8-ium 3-olate (III-2); log P(HCOOH): 0.59; $^1$H-NMR (MeCN-d3) δ: 4.22 (dd, 2H), 2.50 (dd, 2H), 2.02 (m, 2H), 1.87 (m, 2H).

5,6-Dihydro-4H-pyrrolo[1,2-c][1,2,3]oxadiazol-7-ium 3-olate (III-3); $^1$H-NMR (DMSO-d6) δ: 4.47 (dd, 2H), 2.73 (m, 2H), 2.67 (m, 2H).

5-tert-Butoxy-5,6-dihydro-4H-pyrrolo[1,2-c][1,2,3]oxadiazol-7-ium 3-olate (III-4); log P(HCOOH): 1.34; $^1$H-NMR (DMSO-d6) δ: 5.03 (m, 1H), 4.74 (dd, 1H), 4.27 (dd, 1H), 3.11 (dd, 1H), 1.18 (s, 9H).

Example of Process step [V4] from Scheme 7

Example 70

4-[2-(Phenyl)-5,6-dihydro-4H-pyrrolo[1,2-b]pyrazol-3-yl]-N-isopropylpyridine-2-amine (Ic)

In an autoclave, a mixture of 1.10 g (0.39 mmol) of 3-(2-fluoropyridin-4-yl)-2-phenyl-5,6-dihydro-4H-pyrrolo[1,2-b]pyrazole and 1.5 ml of isopropylamine is heated at 140° C. After 16 h, the reaction mixture is concentrated under reduced pressure. After purification by column chromatography on silica gel (cyclohexane/ethyl acetate), 50 mg (35%) of the desired product are obtained; log P(HCOOH): 1.21; $^1$H-NMR (DMSO-d6): 7.81 (d, 1H), 7.36 (m, 5H), 6.28 (s, 1H), 6.21 (m, 2H), 4.15 (dd, 2H), 3.84 (m, 1H), 2.98 (dd, 2H), 2.59 (m, 2H), 1.08 (d, 6H).

Example of Process step [V6] from Scheme 7

Example 3

4-[2-(4-Fluorophenyl)-4,5,6,7-tetrahydropyrazolo[1,5-a]pyridin-3-yl]pyridine-2-amine (Ie)

With ice-cooling, 10 ml of conc. sulphuric acid are added to 1.29 g (1.29 mmol) of N-benzyl-4-[2-(4-fluorophenyl)-4,5,6,7-tetrahydropyrazolo[1,5-a]pyridin-3-yl]pyridine-2-amine, and the mixture is stirred at room temperature for 1 h. The reaction mixture is stirred into ice-water, adjusted to pH 10 using conc. NaOH and extracted with 3×50 ml of dichloromethane. The combined organic phases are washed with water, dried over MgSO$_4$ and freed from the solvent under reduced pressure. This gives 239 mg (35%) of the desired product; log P(HCOOH): 1.21; $^1$H-NMR (DMSO-d6): 7.81 (d, 1H), 7.416 (dd, 2H), 7.15 (dd, 2H), 6.28 (s, 1H), 6.24 (d, 1H), 5.83 (br.s, 2H), 4.15 (dd, 2H), 2.73 (dd, 2H), 2.02 (m, 2H), 1.80 (m, 2H).

Example of Process step [V7] from Scheme 7

Example 26

Methyl{4-[2-(4-fluorophenyl)-4,5,6,7-tetrahydropyrazolo[1,5-a]pyridin-3-yl]-pyridin-2-yl}carbamate (If)

125 mg (1.29 mmol) of methyl chloroformate are added dropwise to a solution of 200 mg (0.51 mmol) of 4-[2-(4-fluorophenyl)-4,5,6,7-tetrahydropyrazolo[1,5-a]pyridin-3-yl]pyridine-2-amine and 167 mg (1.29 mmol) of diisopropylethylamine in 20 ml THF. After 16 h, 10 ml of water are added, and the reaction mixture is extracted with 3×50 ml of ethyl acetate. The combined organic phases are washed with water, dried over MgSO$_4$ and freed from the solvent under reduced pressure. The residue is taken up again in 10 ml of 6N methanolic ammonia solution and stirred for 12 h. The reaction mixture is concentrated and the residue obtained is purified by column chromatography on silica gel (cyclohexane/ethyl acetate). This gives 167 mg (87%) of the desired product; log P(HCOOH): 2.11; $^1$H-NMR (MeCN-d3): 8.13 (br.s, 1H), 8.10 (d, 1H), 7.76 (s, 1H), 7.42 (dd, 2H), 7.05 (dd, 2H), 6.76 (d, 1H), 4.16 (dd, 2H), 3.69 (s, 3H), 2.82 (dd, 2H), 2.09 (m, 2H), 1.88 (m, 2H).

Example of Process step [V10] from Scheme 7

2-(4-Fluorophenyl)-4,5,6,7-tetrahydropyrazolo[1,5-a]pyridine (VII-1)

A mixture of 2.44 g (16.5 mmol) of 4,5,6,7-tetrahydro[1,2,3]oxadiazolo[3,4-a]pyridin-8-ium 3-olate and 2.15 g (16.5 mmol) of 4-fluorophenylacetylene in 80 ml of mesitylene is stirred under argon at 165° C. for 16 h. After cooling, the reaction mixture is concentrated under reduced pressure. Purification by column chromatography on silica gel (cyclohexane/ethyl acetate) gives 888 mg (27%) of the desired product; log P(HCOOH): 2.76; $^1$H-NMR (MeCN-d3): 7.76 (dd, 2H), 7.11 (dd, 2H), 6.29 (s, 1H), 4.09 (dd, 2H), 2.79 (dd, 2H), 2.02 (m, 2H), 1.84 (m, 2H).

The following compounds can be prepared analogously:

2-(Phenyl)-5,6-dihydro-4H-pyrrolo[1,2-b]pyrazole (VII-2); log P(HCOOH): 2.19; $^1$H-NMR (DMSO-d6): 7.75 (d, 2H), 7.38 (dd, 2H), 7.25 (dd, 1H), 6.43 (s, 1H), 4.09 (dd, 2H), 2.86 (dd, 2H), 2.55 (m, 2H).

2-(4-Fluorophenyl)-5,6-dihydro-4H-pyrrolo[1,2-b]pyrazole (VII-3); log P(HCOOH): 2.42; $^1$H-NMR (DMSO-d6): 7.78 (dd, 2H), 7.19 (dd, 2H), 6.42 (s, 1H), 4.07 (dd, 2H), 2.85 (dd, 2H), 2.54 (m, 2H).

2-(4-Fluorophenyl)-5,6,7,8-tetrahydro-4H-pyrazolo[1,5-a]azepine (VII-3); log P(HCOOH): 3.27; $^1$H-NMR (DMSO-d6): 7.74 (dd, 2H), 7.19 (dd, 2H), 6.45 (s, 1H), 4.24 (m, 2H), 2.76 (m, 2H), 1.79 (m, 2H), 1.68 (m, 2H), 1.58 (m, 2H).

2-(4-Chlorophenyl)-5,6-dihydro-4H-pyrrolo[1,2-b]pyrazole (VII-4); log P(HCOOH): 2.86; $^1$H-NMR (DMSO-d6): 7.76 (d, 2H), 7.42 (d, 2H), 6.46 (s, 1H), 4.09 (dd, 2H), 2.86 (dd, 2H), 2.54 (m, 2H).

2-(Phenyl)-4,5,6,7-tetrahydropyrazolo[1,5-a]pyridine (VII-5); (log P(HCOOH): 2.57; $^1$H-NMR (MeCN-d3): 7.75 (dd, 2H), 7.36 (dd, 2H), 7.27 (dd, 1H), 6.33 (s, 1H), 4.10 (dd, 2H), 2.80 (dd, 2H), 2.05 (m, 2H), 1.84 (m, 2H).

2-[3-(Trifluoromethyl)phenyl]-5,6-dihydro-4H-pyrrolo[1,2-b]pyrazole (VII-6); log P(HCOOH): 3.25; $^1$H-NMR (DMSO-d6): 8.05 (m, 2H), 7.62 (m, 2H), 6.60 (s, 1H), 4.12 (dd, 2H), 2.88 (dd, 2H), 2.56 (m, 2H).

2-[4-(Methoxy)phenyl]-5,6-dihydro-4H-pyrrolo[1,2-b]pyrazole (VII-7); log P(HCOOH): 2.17; $^1$H-NMR (DMSO-d6): 7.66 (d, 2H), 6.93 (d, 2H), 6.34 (s, 1H), 4.06 (dd, 2H), 3.76 (s, 3H), 2.84 (dd, 2H), 2.54 (m, 2H).

2-[4-Methylphenyl]-5,6-dihydro-4H-pyrrolo[1,2-b]pyrazole (VII-8); log P(HCOOH): 2.64; $^1$H-NMR (DMSO-d6): 7.63 (d, 2H), 7.17 (d, 2H), 6.37 (s, 1H), 4.08 (dd, 2H), 2.85 (dd, 2H), 2.54 (m, 2H), 2.30 (s, 3H).

2-[4-(Trifluoromethyl)phenyl]-5,6-dihydro-4H-pyrrolo[1,2-b]pyrazole (VII-9); log P(HCOOH): 3.20; $^1$H-NMR (DMSO-d6): 7.66 (d, 2H), 7.71 (d, 2H), 6.57 (s, 1H), 4.13 (dd, 2H), 2.89 (dd, 2H), 2.57 (m, 2H).

2-[3-Fluorophenyl]-5,6-dihydro-4H-pyrrolo[1,2-b]pyrazole (VII-10); log P(HCOOH): 2.46; $^1$H-NMR (DMSO-d6): 7.60 (d, 1H), 7.52 (d, 1H), 7.42 (dd, 1H), 7.09 (dd, 1H), 6.51 (s, 1H), 4.10 (dd, 2H), 2.86 (dd, 2H), 2.55 (m, 2H).

2-(2-Thienyl)-4,5,6,7-tetrahydropyrazolo[1,5-a]pyridine (VII-11); log P(HCOOH): 2.42; $^1$H-NMR (MeCN-d3): 7.26 (m, 2H), 7.03 (dd, 1H), 6.23 (s, 1H), 4.06 (dd, 2H), 2.78 (dd, 2H), 2.02 (m, 2H), 1.86 (m 2H).

2-(3-Thienyl)-4,5,6,7-tetrahydropyrazolo[1,5-a]pyridine (VII-12); log P(HCOOH): 2.25; $^1$H-NMR (MeCN-d3): 7.53 (s, 1H), 7.42 (m, 2H), 6.22 (s, 1H), 4.07 (dd, 2H), 2.78 (dd, 2H), 2.02 (m, 2H), 1.86 (m 2H).

2-[3-Thienyl]-5,6-dihydro-4H-pyrrolo[1,2-b]pyrazole (VII-13); log P(HCOOH): 2.01; $^1$H-NMR (DMSO-d6): 7.66 (d, 1H), 7.53 (m, 1H), 7.42 (d, 1H), 6.30 (s, 1H), 4.05 (dd, 2H), 2.84 (dd, 2H), 2.55 (m, 2H).

Example of Process step [V11] from Scheme 7

2-(4-Fluorophenyl)-3-iodo-4,5,6,7-tetrahydropyrazolo[1,5-a]pyridine (VIII-1)

A solution of 2.20 g (13.5 mmol) of iodine monochloride in 5 ml of dichloromethane is added dropwise to a solution of 2.66 g (12.3 mmol) of 2-(4-fluorophenyl)-4,5,6,7-tetrahydropyrazolo[1,5-a]pyridine in 50 ml of dichloromethane, and the mixture is stirred for 12 h. 100 ml of water are added, and the reaction mixture is extracted with 3×50 ml of dichloromethane. The combined organic phases are dried over MgSO$_4$ and freed from the solvent under reduced pressure. This gives 4.40 g (98%) of the desired product; log P(HCOOH): 3.79; $^1$H-NMR (MeCN-d3): 7.82 (dd, 2H), 7.18 (dd, 2H), 4.11 (dd, 2H), 2.67 (dd, 2H), 2.06 (m, 2H), 1.94 (m, 2H).

The following compounds can be prepared analogously:

2-(4-Fluorophenyl)-3-iodo-5,6,7,8-tetrahydro-4H-pyrazolo[1,5-a]azepine (VIII-2); log P(HCOOH): 4.35 $^1$H-NMR (DMSO-d6): 7.77 (d, 2H), 7.28 (dd, 2H), 7.25 (dd, 1H), 4.33 (m, 2H), 2.84 (m, 2H), 1.82 (m, 2H), 1.72 (m, 2H), 1.61 (m, 2H).

2-[3-(Trifluoromethyl)phenyl]-3-iodo-5,6-dihydro-4H-pyrrolo[1,2-b]pyrazole (VIII-3); log P(HCOOH): 4.11 $^1$H-NMR (DMSO-d6): 8.10 (m, 2H), 7.72 (m, 2H), 4.24 (dd, 2H), 2.88 (dd, 2H), 2.56 (m, 2H).

2-(4-Chlorophenyl)-3-iodo-5,6-dihydro-4H-pyrrolo[1,2-b]pyrazole (VIII-4); log P(HCOOH): 3.88 $^1$H-NMR (DMSO-d6): 7.80 (d, 2H), 7.50 (d, 2H), 4.21 (dd, 2H), 2.83 (dd, 2H), 2.58 (m, 2H).

2-(Phenyl)-3-iodo-5,6-dihydro-4H-pyrrolo[1,2-b]pyrazole (VIII-5); log P(HCOOH): 3.09 $^1$H-NMR (DMSO-d6): 7.77 (d, 2H), 7.45 (dd, 2H), 7.34 (dd, 1H), 4.21 (dd, 2H), 2.82 (dd, 2H), 2.58 (m, 2H).

2-(4-Fluorophenyl)-3-iodo-5,6-dihydro-4H-pyrrolo[1,2-b]pyrazole (VIII-6); log P(HCOOH): 3.30 $^1$H-NMR (DMSO-d6): 7.78 (dd, 2H), 7.28 (dd, 2H), 4.20 (dd, 2H), 2.85 (dd, 2H), 2.52 (m, 2H).

2-[4-Methylphenyl]-3-iodo-5,6-dihydro-4H-pyrrolo[1,2-b]pyrazole (VIII-7); log P(HCOOH): 3.54 $^1$H-NMR (DMSO-d6): 7.64 (d, 2H), 7.23 (d, 2H), 4.20 (dd, 2H), 2.83 (dd, 2H), 2.55 (m, 2H), 2.33 (s, 3H).

2-[3-Thienyl]-3-iodo-5,6-dihydro-4H-pyrrolo[1,2-b]pyrazole (VIII-8); log P(HCOOH): 2.97 $^1$H-NMR (DMSO-d6): 7.93 (d, 1H), 7.59 (dd, 1H), 7.53 (d, 1H), 4.19 (dd, 2H), 2.81 (dd, 2H), 2.55 (m, 2H).

2-[4-(Methoxy)phenyl]-3-iodo-5,6-dihydro-4H-pyrrolo[1,2-b]pyrazole (VIII-9); log P(HCOOH): 3.01 $^1$H-NMR (DMSO-d6): 7.68 (d, 2H), 6.99 (d, 2H), 4.19 (dd, 2H), 3.79 (s, 3H), 2.82 (dd, 2H), 2.54 (m, 2H).

2-[4-(Trifluoromethyl)phenyl]-3-iodo-5,6-dihydro-4H-pyrrolo[1,2-b]pyrazole (VIII-10); log P(HCOOH): 4.13 $^1$H-NMR (DMSO-d6): 8.01 (d, 2H), 7.81 (d, 2H), 4.25 (dd, 2H), 2.88 (dd, 2H), 2.57 (m, 2H).

2-[3-Fluorophenyl]-3-iodo-5,6-dihydro-4H-pyrrolo[1,2-b]pyrazole (VIII-11); log P(HCOOH): 3.32 $^1$H-NMR (DMSO-d6): 7.65 (d, 1H), 7.52 (m, 2H), 7.20 (dd, 1H), 4.22 (dd, 2H), 2.81 (dd, 2H), 2.58 (m, 2H).

2-(Phenyl)-3-iodo-4,5,6,7-tetrahydropyrazolo[1,5-a]pyridine (VIII-12); (log P(HCOOH): 3.55; $^1$H-NMR (MeCN-d3): 7.80 (d, 2H), 7.39 (m, 3H), 4.12 (dd, 2H), 2.68 (dd, 2H), 2.05 (m, 2H), 1.84 (m, 2H).

2-(2-Thienyl)-3-iodo-4,5,6,7-tetrahydropyrazolo[1,5-a]pyridine (VIII-13); log P(HCOOH): 3.45 $^1$H-NMR (MeCN-d3): 7.74 (d, 1H), 7.37 (d, 1H), 7.11 (dd, 1H), 4.09 (dd, 2H), 2.66 (dd, 2H), 2.02 (m, 2H), 1.86 (m 2H).

2-(3-Thienyl)-3-iodo-4,5,6,7-tetrahydropyrazolo[1,5-a]pyridine (VIII-14); log P(HCOOH): 3.40 $^1$H-NMR (MeCN-d3): 7.95 (s, 1H), 7.57 (d, 1H), 7.44 (dd, 1H), 4.08 (dd, 2H), 2.66 (dd, 2H), 2.11 (m, 2H), 1.91 (m 2H).

3-Iodo-2-phenyl-6,7-dihydro-4H-pyrazolo[5,1-c][1,4]oxazine (VIII-15); log P(HCOOH): 2.82 $^1$H-NMR (DMSO-d6): 7.77 (d, 2H), 7.47 (dd, 2H), 7.39 (dd, 1H), 4.70 (s, 2H), 4.16 (m, 2H), 4.09 (m, 2H).

2-(4-Fluorophenyl)-3-iodo-7,7-dimethyl-4,5-dihydropyrazolo[1,5-c][1,3]oxazine (VIII-16); log P(HCOOH): 4.28 $^1$H-NMR (DMSO-d6): 7.81 (dd, 2H), 7.29 (dd, 2H), 4.09 (t, 2H), 2.76 (t, 2H), 1.68 (s, 6H).

3-Bromo-2-(4-fluorophenyl)-6,7-dihydro-4H-pyrazolo[5,1-c][1,4]oxazine (VIII-17); analogously with 2 eq. of NBS log P(HCOOH): 2.90 $^1$H-NMR (MeCN-d3): δ=7.90-7.86 (m, 2H), 7.21-7.17 (m, 2H), 4.75 (s, 2H), 4.14-4.09 (m, 4H)

3-Bromo-2-phenyl-6,7-dihydro-4H-pyrazolo[5,1-c][1,4]thiazine (VIII-18); analogously with 2 eq. of NBS log P(HCOOH): 3.42 mit MS (ESI): 296/298 [M+H]$^+$.

Example of Process step [V12] from Scheme 7

Example 61

3-(2-Fluoropyridin-4-yl)-2-phenyl-5,6-dihydro-4H-pyrrolo[1,2-b]pyrazole (Ia)

A mixture of 1.00 g (3.22 mmol) of 2-(phenyl)-3-iodo-5,6-dihydro-4H-pyrrolo[1,2-b]pyrazole, 1.80 g (8.06 mmol) of 2-fluoro-4-(4,4,5,5-tetramethyl-1,3,2-dioxaborolan-2-yl)pyridine, 2.63 g (8.06 mmol) of $Cs_2CO_3$ and 526 mg (0.65 mmol) of $Pd(dppf)Cl_2$ in 8 ml of THF is heated under argon at 60° C. for 16 h. 20 ml of water are added, and the reaction mixture is extracted with 3×50 ml of ethyl acetate. The combined organic phases are dried over $MgSO_4$ and freed from the solvent under reduced pressure. Purification by column chromatography on silica gel (cyclohexane/ethyl acetate) gives 507 mg (57%) of the desired product; log P(HCOOH): 2.53; $^1$H-NMR (DMSO-d6): 8.10 (d, 1H), 7.40 (m, 5H), 7.07 (d, 1H), 6.85 (s, 1H), 4.19 (dd, 2H), 3.11 (dd, 2H), 2.62 (m, 2H).

Example 5

N-{4-[2-(4-Fluorophenyl)-4,5,6,7-tetrahydropyrazolo[1,5-a]pyridin-3-yl]pyridin-2-yl}propanamide (If)

Under argon, 1.39 ml of a 2M aqueous $Na_2CO_3$ solution are added dropwise to a solution of 200 mg (0.55 mmol) of 2-(4-fluorophenyl)-3-iodo-4,5,6,7-tetrahydropyrazolo[1,5-a]pyridine, 168 g (0.61 mmol) of N-[4-(4,4,5,5-tetramethyl-1,3,2-dioxaborolan-2-yl)pyridin-2-yl]propanamide in 2 ml of dioxane, and 32 mg (0.04 mmol) of $Pd(PCy_3)_2Cl_2$ are added. In a microwave reactor, the reaction mixture is heated at 120° C. for 15 min. After cooling, 50 ml of ethyl acetate are added, the reaction mixture is filtered through kieselguhr and the filtrate is extracted with ethyl acetate. The combined organic phases are washed with water, dried over $MgSO_4$ and freed from the solvent under reduced pressure. Purification by column chromatography on silica gel (cyclohexane/ethyl acetate) gives 159 mg (78%) of the desired product; log P(HCOOH): 1.97; $^1$H-NMR (MeCN-d3): 8.54 (br.s, 1H), 8.11 (d, 1H), 8.02 (s, 1H), 7.42 (dd, 2H), 7.04 (dd, 2H), 6.77 (d, 1H), 4.16 (dd, 2H), 2.81 (dd, 2H), 2.40 (q, 2H), 1.77 (m, 2H), 1.11 (t, 3H).

Example of Process step [V14] from Scheme 9

Methyl 1-(2-chloroethyl)-3-(4-fluorophenyl)-1H-pyrazole-5-carboxylate (XI-1)

4.15 g (30 mmol) of potassium carbonate are added to a solution of 2.20 g (10 mmol) of methyl 3-(4-fluorophenyl)-1H-pyrazole-5-carboxylate (described in Zhejiang Daxue Xuebao, Lixueban 2008, 35, 641-643) in 30 ml of acetone. Over a period of 5 min, 7.17 g (50 mmol) of 1-bromo-2-chloroethane are added to this suspension. The reaction mixture is then stirred at 70° C. for 19 h. The insoluble components are then filtered off, and the solvent is concentrated. The crude oil obtained is purified by column chromatography on silica gel (mobile phase cyclohexane/ethyl acetate). This gives 2.5 g (80%) of the desired product; log P(HCOOH): 3.58; $^1$H-NMR (MeCN-d3): δ=7.86-7.84 (m, 2H), 7.20 (s, 1H), 7.19-7.16 (m, 2H), 6.53 (s, 1H), 4.89 (t, 2H), 4.00 (t, 2H), 3.88 (s, 3H).

Example of Process step [V15] from Scheme 9

[1-(2-Chloroethyl)-3-(4-fluorophenyl)-1H-pyrazol-5-yl]methanol (XIII-1)

Under argon and at 0° C., 4 ml of lithium aluminium hydride solution (1M in diethyl ether, 4.00 mmol) are added to a solution of 1.1 g (4.00 mmol) of methyl 1-(2-chloroethyl)-3-(4-fluorophenyl)-1H-pyrazole-5-carboxylate in 20 ml of tetrahydrofuran. The mixture is then stirred at 0° C. for 2 h. At 0° C., 5M of aqueous NaOH solution are then carefully added dropwise to the reaction mixture until the evolution of hydrogen has stopped. The suspension formed is decanted off and the solvent is removed. The crude product obtained is purified by column chromatography on silica gel (cyclohexane/ethyl acetate). This gives 900 mg (86%) of the desired product; log P(HCOOH): 1.84; $^1$H-NMR (MeCN-d3): δ=7.81-7.77 (m, 2H), 7.16-7.12 (m, 2H), 6.53 (s, 1H), 4.64 (d, 2H), 4.45 (t, 2H), 4.00 (t, 2H).

The following compound can be prepared analogously:
(3-Phenyl-1H-pyrazol-5-yl)methanol (XIV-1); log P(HCOOH): 1.14; LC-MS: m/z=175 [M+H].

Example of Process step [V16] from Scheme 9

2-(4-Fluorophenyl)-6,7-dihydro-4H-pyrazolo[5,1-c][1,4]oxazine (VIIa-1)

In a 100 ml round-bottom flask, 780 mg (3.00 mmol) of [1-(2-chloroethyl)-3-(4-fluorophenyl)-1H-pyrazol-5-yl]methanol are dissolved in 20 ml of N,N-dimethylformamide. Under argon and at 0° C., 120 mg of sodium hydride (3.00 mmol) are then added as a 60% suspension in oil. The mixture is then stirred at 25° C. for 18 h. The reaction mixture is then carefully poured into water and extracted repeatedly with ethyl acetate. The combined organic phases are then dried over $Na_2SO_4$ and concentrated. Purification is carried out by silica gel chromatography (cyclohexane/ethyl acetate). This gives 480 mg (49%) of the desired product; log P(HCOOH): 2.01; $^1$H-NMR (MeCN-d3): δ=7.81-7.77 (m, 2H), 7.15-7.11 (m, 2H), 6.36 (s, 1H), 4.81 (s, 2H), 4.14-4.12 (m, 2H), 4.10-4.08 (m, 2H).

Example of Process step [V17] from Scheme 9

5-(Chloromethyl)-3-phenyl-1H-pyrazole (XV-1)

At 20° C., 6.1 ml of thionyl chloride and 10 drops of dimethylformamide are added to a solution of 7.3 g (42.0 mmol) of (3-phenyl-1H-pyrazol-5-yl)methanol in 220 ml of dichloromethane. The mixture is then boiled under reflux for 12 h. The solvent is then removed from the reaction mixture. The residue is taken up in 100 ml of dichloromethane, and a saturated sodium bicarbonate solution is added to the mixture until a pH of from 6 to 7 is established. The mixture is then freed from the solvent under reduced pressure and dried. This gives 5.65 g of the desired product which is reacted further without further purification; log P(HCOOH): 2.05 with MS (ESI): 193.1/195.1 ([M+H]$^+$).

Example of Process steps [V18] and [V20] from Scheme 9

2-Phenyl-6,7-dihydro-4H-pyrazolo[5,1-c][1,4]thiazine (VIIb-1)

4.42 g (58 mmol) of thiourea are added to a solution of 5.59 g (29 mmol) of 5-(chloromethyl)-3-phenyl-1H-pyrazole in 200 ml of ethanol. The mixture is stirred at 20° C. for 2 days. Most of the solvent is then removed from the mixture, and 10-20 ml of dichloromethane are added. After brief stirring, the precipitate is filtered off with suction and dried. This gives 6.3 g of a product mixture which is used further without further purification. 4.19 g of this mixture are taken up again in 140 ml of N,N-dimethylformamide. 4.55 g of dried potassium carbonate and 4.74 ml of 1,2-dibromoethane are added to this mixture. The mixture is then stirred at 60° C. for 18 h. The reaction mixture is then carefully stirred into water. The aqueous phase is then decanted off, and ethyl acetate is added to the oily residue. The organic phase is dried over $Na_2SO_4$ and concentrated. Purification is carried out by silica gel chromatography (cyclohexane/ethyl acetate). This gives 620 mg of the desired product; log P(HCOOH): 2.46; $^1$H-NMR (ppm): δ (DMSO-d6)=3.20 (t, 2H), 3.94 (s, 2H), 4.32 (t, 2H), 6.54 (s, 1H), 7.31 (t, 1H), 7.40 (t, 2H), 7.65 (d, 2H).

Example of Process step [V21] from Scheme 10

5-(Benzyloxy)-1-(4-fluorophenyl)pent-2-yn-1-one (XX-1)

At −70° C., 2.56 ml of a 1.6 M butyllithium solution are added dropwise to a solution of 505 mg (3.15 mmol) of benzyl but-3-yn-1-yl ether in 10 ml of THF, and the mixture is stirred for 30 min. 500 mg (5.15 mmol) of 4-fluorobenzoyl chloride are added dropwise to this solution, and the temperature is allowed to rise to 0° C. After 1 h, 10 ml of a saturated ammonium chloride solution are added, and the reaction mixture is extracted with 3×50 ml of ethyl acetate. The combined organic phases are washed with water, dried over $MgSO_4$ and freed from the solvent under reduced pressure. Purification by column chromatography on silica gel (cyclohexane/ethyl acetate) gives 430 mg (45%) of the desired product; log P(HCOOH): 3.89; $^1$H-NMR (DMSO-d6): 8.15 (dd, 2H), 7.34 (m, 7H), 4.57 (s, 2H), 3.70 (t, 2H), 2.90 (t, 2H).

Example of Process step [V22] from Scheme 10

5-[2-(Benzyloxy)ethyl]-3-(4-fluorophenyl)-1H-pyrazole (XXI)

At room temperature, 0.17 ml (3.54 mmol) of hydrazine hydrate is added dropwise to a solution of 500 mg (1.77 mmol) of 5-(benzyloxy)-1-(4-fluorophenyl)pent-2-yn-1-one in 5 ml of ethanol, and the mixture is stirred under reflux for 2 h. After cooling, the reaction mixture is concentrated under reduced pressure and the residue is purified by column chromatography on silica gel (cyclohexane/ethyl acetate). This gives 470 mg (87%) of the desired product; log P(HCOOH): 3.09; $^1$H-NMR (DMSO-d6): 7.77 (dd, 2H), 7.34 (m, 8H), 6.49 (s, 1H), 4.51 (s, 2H), 3.70 (t, 2H), 2.89 (t, 2H).

Example of Process step [V23] from Scheme 10

2-[3-(4-Fluorophenyl)-1H-pyrazol-5-yl]ethanol (XXII)

39.4 g (242 mmol) of iron(III) chloride are initially charged in 200 ml of dichloromethane. At room temperature, a solution of 7.20 g (24.2 mmol) of 5-[2-(benzyloxy)ethyl]-3-(4-fluorophenyl)-1H-pyrazole in 90 ml of dichloromethane is added dropwise. After 20 min, the reaction mixture is washed with 2×100 ml of water. The combined aqueous phases are adjusted to pH 5-6 using sodium bicarbonate and extracted with 2×100 ml of ethyl acetate. The combined organic phases are washed with water, dried over $MgSO_4$ and freed from the solvent under reduced pressure. Purification by column chromatography on silica gel (cyclohexane/ethyl acetate) gives 3.40 g (67%) of the desired product; log P(HCOOH): 1.39; $^1$H-NMR (DMSO-d6): 7.79 (dd, 2H), 7.19 (dd, 2H), 6.47 (s, 1H), 4.79 (t, 1H), 3.65 (m, 2H), 2.76 (t, Example of Process step [V11] from Scheme 10

2-[3-(4-Fluorophenyl)-4-iodo-1H-pyrazol-5-yl]ethanol (XXII)

Analogously to Process step [11], 2-[3-(4-fluorophenyl)-1H-pyrazol-5-yl]ethanol can be reacted with 1.1 eq. of NIS in DMF. In a yield of 89%, the desired product is obtained as a mixture of isomers: log P(HCOOH): 1.99; $^1$H-NMR (DMSO-d6): 13.29 & 13.19 (s, 1H) 7.78 & 7.69 (dd, 2H), 7.38 & 7.28 (dd, 2H), 4.92 & 4.72 (t, 1H), 3.62 (m, 2H), 2.79 & 2.73 (t, 2H).

Example of Process step [V24] from Scheme 10

2-(4-Fluorophenyl)-3-iodo-4,5-dihydropyrazolo[1,5-c][1,3]oxazine (VIIIa-1)

A mixture of 200 mg (0.60 mmol) of 2-[3-(4-fluorophenyl)-4-iodo-1H-pyrazol-5-yl]ethanol, 36 mg (1.20 mmol) of paraformaldehyde and 10 mg (0.06 mmol) of 4-toluenesulphonic acid in 1 ml of dioxane is heated in a microwave reactor at 130° C. for 1 h. After cooling, the reaction mixture is concentrated under reduced pressure and the residue is purified by column chromatography on silica gel (cyclohexane/ethyl acetate). This gives 120 mg (57%) of the desired product; log P(HCOOH): 3.23; $^1$H-NMR (DMSO-d6): 7.81 (dd, 2H), 7.31 (dd, 2H), 5.54 (s, 2H), 4.12 (dd, 2H), 2.80 (dd, 2H).

Example of Process step [V25] from Scheme 11

4-Chloro-N'-(diphenylmethylene)pentane hydrazide (XXV-1)

At 0° C., a solution of 0.16 g (1.0 mmol) of 4-chloropentanoyl chloride in 15 ml dichloromethane is added to a solution of 0.20 g (1.0 mmol) of diphenylmethanone hydrazone and 0.08 ml of pyridine in 15 ml of dichloromethane. The reaction mixture is stirred at room temperature for 16 h. Ethyl acetate/saturated aqueous $NH_4Cl$ solution is added to the reaction mixture, the organic phase is separated off and the aqueous phase is extracted with 3×100 ml of ethyl acetate. The combined organic phases are dried over $Na_2SO_4$ and freed from the solvent under reduced pressure. Purification by column chromatography on silica gel (cyclohexane/ethyl acetate) gives 0.32 g (100%) of the desired product; log P(HCOOH): 3.76; $^1$H-NMR (ppm): δ (DMSO-d6)=1.45 (d, 0.9H), 1.52 (d, 2.1H), 1.81-2.12 (m, 1H), 2.30-2.42 (m, 1H), 2.88-3.00 (m, 2H), 4.13-4.20 (m, 0.3H), 4.28-4.34 (m, 0.7H), 7.26-7.61 (m, 10H), 9.19 (s, 1H); LC-MS: m/z=315 [M+H]$^+$

Example of Process step [V26] from Scheme 11

1-[(Diphenylmethylene)amino]-5-methylpyrrolidin-2-one (XXVI-1)

At 0° C., 2.7 g (68.0 mmol) of sodium hydride are added a little at a time to a solution of 33.0 g (68.0 mmol) of 4-bromo-N'-(diphenylmethylene)pentane hydrazide in 200 ml of tetrahydrofuran. The reaction mixture is stirred at room temperature for 16 h, and ethyl acetate/saturated aqueous $NH_4Cl$ solution is then added. The organic phase is separated off and the aqueous phase is extracted with 3×250 ml of ethyl acetate. The combined organic phases are dried over $Na_2SO_4$ and freed from the solvent under reduced pressure. Purification by column chromatography on silica gel (cyclohexane/ethyl acetate) gives 17.8 g (89%) of the desired product; log P(HCOOH): 2.73; $^1$H-NMR (ppm): δ (DMSO-d6)=1.22 (d, 3H), 2.05-2.15 (m, 4H), 3.86 (m, 1H), 7.24-7.26 (m, 2H), 7.40-7.43 (m, 4H), 7.48-7.53 (m, 4H); LC-MS: m/z=279 [M+H]$^+$ The following compounds can be prepared analogously:
1-[(Diphenylmethylene)amino]pyrrolidin-2-one (XXVI-2); log P(HCOOH): 2.23; $^1$H-NMR (ppm): δ (DMSO-d6) =1.83 (m, 2H), 2.15 (t, 2H), 3.31 (t, 2H), 7.25-7.28 (m, 2H), 7.37-7.50 (m, 8H); LC-MS: m/z=265 [M+H]$^+$
1-[(Diphenylmethylene)amino]-3-methylpyrrolidin-2-one (XXV-3); log P(HCOOH): 2.62; $^1$H-NMR (ppm): δ (DMSO-d6)=0.91 (d, 3H), 1.36-1.46 (m, 1H), 2.07-2.14 (m, 1H), 2.24-2.32 (m, 1H), 3.21-3.30 (m, 2H), 7.24-7.29 (m, 2H), 7.40-7.51 (m, 8H); LC-MS: m/z=279 [M+H]$^+$.

Example of Process step [V27] from Scheme 11

2-Methyl-5-oxopyrrolidin-1-aminium chloride (XXVII-1)

At room temperature 50 ml of 37% strength hydrochloric acid are added to a solution of 17.8 g (63.9 mmol) of 1-[(diphenylmethylene)amino]-5-methylpyrrolidin-2-one in 100 ml of tetrahydrofuran, and the mixture is stirred for 1 h. Ethyl acetate is then added to the reaction mixture, and the organic phase is separated off. Repeatedly, ethanol/toluene (1:1) is added to the hydrochloric acid phase and the mixture is concentrated under reduced pressure. The crude product obtained is reacted further without further purification. $^1$H-NMR (ppm): δ (DMSO-d6)=1.24 (d, 3H), 1.60-1.65 (m, 1H), 2.20-2.42 (m, 3H), 3.88 (m, 1H).

The following compounds can be prepared analogously:
3-Methyl-2-oxopyrrolidin-1-aminium chloride (XXVII-2); $^1$H-NMR (ppm): δ (DMSO-d6)=1.08 (d, 3H), 1.64-1.70 (m, 1H), 2.27-2.34 (m, 1H), 2.46-2.51 (m, 1H), 3.48 (dd, 1H), 3.48 (dd, 1H).
2-Oxopyrrolidin-1-aminium chloride (XXVII-2); $^1$H-NMR (ppm): δ (DMSO-d6)=1.97-2.07 (m, 2H), 2.22-2.36 (m, 2H), 3.59 (t, 2H).

Example of Process step [V28] from Scheme 11

Methyl 3-(4-fluorophenyl)-3-[(2-methyl-5-oxopyrrolidin-1-yl)imino]propanoate (XXVIII-1)

A mixture of 7.50 g (38.2 mmol) of methyl 3-(4-fluorophenyl)-3-oxopropanoate and 11.5 g (76.5 mmol) of 2-methyl-5-oxopyrrolidin-1-aminium chloride in 50 ml of pyridine is stirred at room temperature for 72 h. The reaction mixture is concentrated under reduced pressure. Purification by column chromatography on silica gel (cyclohexane/ethyl acetate) gives 10.4 g (93%) of the desired product as a mixture of isomers; log P(HCOOH): 2.13 and 2.45; $^1$H-NMR (ppm): δ (DMSO-d6)=1.16-1.19 (m, 3H), 1.58-1.62 (m, 2H), 2.20-2.22 (m, 1H), 2.36-2.41 (m, 1H), 3.54 (s, 2.25H), 3.64 (s, 0.75H), 3.80 (d, 1H), 3.90 (d, 1H), 3.80 (q, 1H), 7.24 (t, 0.6H), 7.29 (t, 1.4H), 7.44-7.47 (m, 0.6H), 7.89-7.92 (m, 1.4H); LC-MS: m/z=293 [M+H]$^+$.

The following compounds can be prepared analogously:
Methyl 3-(4-fluorophenyl)-3-[(2-methyl-5-oxopyrrolidin-1-yl)imino]propanoate (XXVIII-2); log P(HCOOH): 2.09 and 2.47; $^1$H-NMR (ppm): δ (DMSO-d6)=1.12 (d, 3H), 1.58-1.64 (m, 1H), 1.91-2.00 (m, 1H), 2.10-2.30 (m, 2H), 3.15 (td, 0.17H), 3.29 (td, 0.17H), 3.49 (td, 0.33H), 3.57 (s, 2H), 3.62 (td, 0.33H), 3.64 (s, 1H), 3.80 (d, 1H), 3.89 (d, 1H), 7.21-7.31 (m, 2H), 7.41-7.44 (m, 0.66H), 7.89-7.92 (m, 1.34H); LC-MS: m/z=293 [M+H]$^+$.
Ethyl 3-(2-fluorophenyl)-3-[(2-methyl-5-oxopyrrolidin-1-yl)imino]propanoate (XXVIII-3); log P(HCOOH): 2.34 and 2.74; $^1$H-NMR (ppm): δ (DMSO-d6)=0.99-1.06 (m, 3H), 1.15-1.24 (m, 3H), 1.58-1.64 (m, 1H), 1.81-2.45 (m, 3H), 3.64 (dd, 0.5H), 3.78-4.14 (m, 4.5H), 7.15-7.38 (m, 2H), 7.46-7.55 (m, 1H), 7.64-7.69 (m, 1H); LC-MS: m/z=307 [M+H]$^+$.
Ethyl 3-(2-fluorophenyl)-3-[(2-oxopyrrolidin-1-yl)imino] propanoate (XXVIII-4); log P(HCOOH): 1.97 and 2.39; $^1$H-NMR (ppm): δ (DMSO-d6)=0.99-1.22 (m, 3H), 1.59-1.66 (m, 1H), 1.95-2.09 (m, 2H), 2.30-2.41 (m, 1H), 3.39-3.49 (m, 2H), 3.62-4.01 (m, 4H), 7.19-7.79 (m, 4H); LC-MS: m/z=293 [M+H]$^+$.

Example of Process step [V29] from Scheme 11

Methyl 2-(4-fluorophenyl)-6-methyl-5,6-dihydro-4H-pyrrolo[1,2-b]pyrazole-3-carboxylate (XXX-1)

23.2 g (71.2 mmol) of caesium carbonate are added to a solution of 10.4 g (35.6 mmol) of methyl 3-(4-fluorophenyl)-3-[(2-methyl-5-oxopyrrolidin-1-yl)imino]propanoate in 100 ml of dimethylformamide. The reaction mixture is stirred at room temperature for 30 min and at 100° C. for 4 h. Ethyl acetate/water is then added, the organic phase separated off and the aqueous phase is extracted with 3×100 ml of ethyl acetate. The combined organic phases are dried over $Na_2SO_4$ and freed from the solvent under reduced pressure. Purification by column chromatography on silica gel (cyclohexane/ ethyl acetate) gives 6.6 g (64%) of the desired product; log P(HCOOH): 2.84; $^1$H-NMR (ppm): δ (DMSO-d6)=1.44 (d, 3H), 2.14-2.17 (m, 1H), 2.76-2.78 (m, 1H), 2.98-3.08 (m, 2H), 3.68 (s, 3H), 4.46 (m, 1H), 7.21-7.24 (m, 2H), 7.73-7.76 (m, 2H); LC-MS: m/z=275 [M+H]$^+$.

The following compounds can be prepared analogously:
Methyl 2-(4-fluorophenyl)-4-methyl-5,6-dihydro-4H-pyrrolo[1,2-b]pyrazole-3-carboxylate (XXX-2); log P(HCOOH): 2.71; $^1$H-NMR (ppm): δ (DMSO-d6)=1.34 (d, 3H), 2.16-2.21 (m, 1H), 2.81-2.86 (On, 1H), 3.45-3.52 (m, 1H), 3.70 (s, 3H), 4.11-4.29 (m, 2H), 7.20-7.25 (m, 2H), 7.69-7.72 (m, 2H); LC-MS: m/z=275 [M+H]$^+$.
Ethyl 2-(2-fluorophenyl)-5,6-dihydro-4H-pyrrolo[1,2-b] pyrazole-3-carboxylate (XXX-3); log P(HCOOH): 2.49; $^1$H-NMR (ppm): δ (DMSO-d6)=1.12 (t, 3H), 2.60 (quintet, 2H), 3.06 (ABq, 2H), 4.06 (q, 2H), 4.19 (ABq, 2H), 7.22-7.25 (m, 2H), 7.41-7.49 (m, 2H); LC-MS: m/z=275 [M+H]$^+$.

Example of Process step [V30] from Scheme 11

2-(4-Fluorophenyl)-6-methyl-5,6-dihydro-4H-pyrrolo[1,2-b]pyrazole-3-carboxylic acid (XXXI-1)

36.8 ml (73.6 mmol) of a 2 M aqueous NaOH solution are added to a solution of 7.0 g (25.5 mmol) of methyl 2-(4- fluorophenyl)-6-methyl-5,6-dihydro-4H-pyrrolo[1,2-b]pyrazole-3-carboxylate in 50 ml of methanol, and the mixture is stirred for 3 h. The reaction mixture is concentrated under reduced pressure, ethyl acetate/1 M hydrochloric acid is added, the organic phase is separated off and the aqueous phase is extracted with 3×100 ml of ethyl acetate. The combined organic phases are dried over $Na_2SO_4$ and freed from the solvent under reduced pressure. The 2-(4-fluorophenyl)-6-methyl-5,6-dihydro-4H-pyrrolo[1,2-b]pyrazole-3-carboxylic acid obtained (5.9 g) is reacted further without further purification.

The following compounds can be prepared analogously:

2-(4-Fluorophenyl)-4-methyl-5,6-dihydro-4H-pyrrolo[1,2-b]pyrazole-3-carboxylic acid (XXXI-2); log P(HCOOH): 1.84; $^1$H-NMR (ppm): δ (DMSO-d6)=1.33 (d, 3H), 2.12-2.19 (m, 1H), 2.76-2.86 (m, 1H), 3.40-3.49 (m, 1H), 4.08-4.26 (m, 2H), 7.17-7.23 (m, 2H), 7.69-7.74 (m, 2H); LC-MS: m/z=261 [M+H]$^+$.

2-(2-Fluorophenyl)-6-methyl-5,6-dihydro-4H-pyrrolo[1,2-b]pyrazole-3-carboxylic acid (XXXI-3); log P(HCOOH): 1.64; m/z=261 [M+H]$^+$.

2-(2-Fluorophenyl)-5,6-dihydro-4H-pyrrolo[1,2-b]pyrazole-3-carboxylic acid (XXXI-4); log P(HCOOH): 1.35; $^1$H-NMR (ppm): δ (DMSO-d6)=2.58 (quintet, 2H), 3.04 (ABq, 2H), 4.16 (ABq, 2H), 7.20-7.23 (m, 2H), 7.40-7.45 (m, 2H); LC-MS: m/z=247 [M+H]$^+$.

Example of Process step [V31] from Scheme 11

N'-(Diphenylmethylene)-4-hydroxypentane hydrazide (XXXIII-1)

At room temperature, 6.0 ml (12.0 mmol) of a 2.0 M trimethylaluminium solution in heptane are added dropwise to a solution of 0.78 g (4.0 mmol) of benzophenone hydrazone in 10 ml of dichloromethane, and the mixture is stirred for 30 min. A solution of 0.40 g (4.0 mmol) of γ-valerolactone in 5 ml of dichloromethane is then added dropwise to the reaction mixture. The reaction mixture is stirred at reflux for 2 h. A further 0.12 g (1.20 mmol) of γ-valerolactone is added, and the reaction mixture is stirred at reflux for 1 h. After cooling, dichloromethane/water is added to the reaction mixture. The organic phase is separated off and the aqueous phase is extracted with dichloromethane. The combined organic phases are dried over $Na_2SO_4$ and freed from the solvent under reduced pressure. Purification by column chromatography on silica gel (cyclohexane/ethyl acetate) gives 0.9 g (76%) of the desired product; (log P(HCOOH): 2.25); $^1$H-NMR (ppm): δ (DMSO-d6)=1.01 (d, 1H), 1.10 (d, 2H), 1.45-1.72 (m, 2H), 2.16-2.26 (m, 1H), 2.75-2.86 (m, 1H), 3.51-3.57 (m, 0.3H), 3.65-3.71 (m, 0.7H), 4.43 (d, 0.3H), 4.52 (d, 0.7H), 7.25-7.62 (m, 10H), 8.99 (s, 1H); LC-MS: m/z=297 [M+H]$^+$ The following compounds can be prepared analogously:

N'-(Diphenylmethylene)-4-hydroxy-4-phenylbutane hydrazide (XXXIII-2); log P(HCOOH): 3.07; $^1$H-NMR (ppm): δ (DMSO-D$_6$)=1.79-1.86 (m, 1H), 1.90-1.98 (m, 1H), 2.19-2.23 (m, 1H), 2.76-2.80 (m, 1H), 4.48-4.52 (m, 0.3H), 4.63-4.67 (m, 0.7H), 5.23 (d, 0.3H), 5.31 (d, 0.7H), 7.19-7.60 (m, 15H), 9.00 (s, 1H); LC-MS: m/z=359 [M+H]$^+$.

N'-(Diphenylmethylene)-4-hydroxy-2-methylbutane hydrazide (XXXIII-3); log P(HCOOH): 2.24; $^1$H-NMR (ppm): δ (DMSO-d6)=0.98 (d, 1.5H), 1.14 (d, 1.5H), 1.39-1.46 (m, 0.5H), 1.49-1.57 (m, 0.5H), 1.65-1.71 (m, 0.5H), 1.85-1.91 (m, 0.5H), 2.50-2.54 (m, 1H), 3.29-3.39 (m, 1H), 3.41-3.51 (m, 1H), 4.41 (dd, 0.5H), 4.51 (dd, 0.5H), 7.27-7.63 (m, 10H), 8.94 (s, 1H); LC-MS: m/z=297 [M+H]$^+$.

Example of Process step [V32] from Scheme 11

4-Bromo-N'-(diphenylmethylene)-2-methylbutane hydrazide (XXV-2)

At 0° C., 8.1 g (24.3 mmol) of carbon tetrabromide are added to a solution of 6.0 g (20.2 mmol) of N'-(diphenylmethylene)-4-hydroxy-2-methylbutane hydrazide and 6.3 g (24.3 mmol) of triphenylphosphane in 150 ml of dichloromethane. The reaction mixture is stirred at 0° C. for 1 h and then concentrated and purified by column chromatography on silica gel (cyclohexane/ethyl acetate). This gives 2.7 g (37%) of the desired product; (log P(HCOOH): 3.76); $^1$H-NMR (ppm): δ (DMSO-d6)=1.12 (d, 3H), 1.79-1.86 (m, 1H), 2.33-2.38 (m, 1H), 2.62-2.67 (m, 1H), 4.10-4.14 (m, 1H), 4.25-4.29 (m, 1H), 7.29-7.65 (m, 10H); LC-MS: m/z=359 [M+H]$^+$.

Example of Process step [V33] from Scheme 11

1-[(Diphenylmethylene)amino]-5-methylpyrrolidin-2-one (XXVI-4)

At 0° C., 0.25 ml (3.2 mmol) of methanesulphonyl chloride is added dropwise to a solution of 0.64 g (2.2 mmol) of N'-(diphenylmethylene)-4-hydroxypentane hydrazide, 0.19 ml (2.4 mmol) of pyridine and 0.01 mg of N—N-dimethylaminopyridine in 5 ml of dichloromethane. The reaction mixture is stirred at room temperature for 2 h, and ethyl acetate/water is then added. The organic phase is separated off and the aqueous phase is extracted with 3×100 ml of ethyl acetate. The combined organic phases are dried over $Na_2SO_4$ and freed from the solvent under reduced pressure. Purification by column chromatography on silica gel (cyclohexane/ethyl acetate) gives 0.38 g (44% pure) of 5-[2-(diphenylmethylene)hydrazino]-5-oxopentan-2-yl methanesulphonate; (log P(HCOOH): 2.82 with LC-MS: m/z=375 [M+]$^+$). The product is taken up again in 2 ml of tetrahydrofuran, and 0.04 g (1.0 mmol) of sodium hydride is added at 0° C. After 16 h of stirring at room temperature, ethyl acetate/saturated aqueous $NH_4Cl$ solution is added, the organic phase is separated off and the aqueous phase is extracted with 3×100 ml of ethyl acetate. The combined organic phases are dried over $Na_2SO_4$ and freed from the solvent under reduced pressure. This gives 0.21 g (61%) of the desired product; (log P(HCOOH): 2.73); $^1$H-NMR (ppm): δ (DMSO-d6)=1.22 (d, 3H), 2.05-2.15 (m, 4H), 3.86 (sextet, 1H), 7.24-7.26 (m, 2H), 7.40-7.43 (m, 4H), 7.48-7.53 (m, 4H); LC-MS: m/z=279 [M+H]$^+$.

Example of Process step [V36] from Scheme 11

2-(4-Fluorophenyl)-3-iodo-6-methyl-5,6-dihydro-4H-pyrrolo[1,2-b]pyrazole (VIII-19)

3.1 g (36.9 mmol) of $NaHCO_3$ and 2.8 g (12.3 mmol) of N-iodosuccinimide are added to a solution of 3.2 g (12.3 mmol) of 2-(4-fluorophenyl)-6-methyl-5,6-dihydro-4H-pyrrolo[1,2-b]pyrazole-3-carboxylic acid in 25 ml of dimethylformamide. The reaction mixture is stirred at room temperature for 16 h, water is added and the precipitated solid is filtered off and dried. This gives 3.30 g of the desired product in a purity of 77% which are reacted further without further purification: (log P(HCOOH): 3.82); $^1$H-NMR (ppm): δ

(DMSO-d6)=1.42 (d, 3H), 2.11-2.18 (m, 1H), 2.72-2.82 (m, 3H), 4.49 (m, 1H), 7.28 (dd, 2H), 7.79 (dd, 2H); LC-MS: m/z=343 [M+H]$^+$.

The following compounds can be prepared analogously:

2-(4-Fluorophenyl)-3-bromo-6-methyl-5,6-dihydro-4H-pyrrolo[1,2-b]pyrazole (VIII-20); Analogously with N-bromosuccinimide; log P(HCOOH): 3.77; $^1$H-NMR (ppm): δ (DMSO-d6)=1.43 (d, 3H), 2.12-2.18 (m, 1H), 2.73-2.89 (m, 3H), 4.47 (m, 1H), 7.29 (dd, 2H), 7.82 (dd, 2H); LC-MS: m/z=295 [M+H]$^+$ 2-(4-Fluorophenyl)-3-iodo-4-methyl-5,6-dihydro-4H-pyrrolo[1,2-b]pyrazole (VIII-21); log P(HCOOH): 3.67; $^1$H-NMR (ppm): δ (DMSO-d6)=1.40 (d, 3H), 2.09-2.19 (m, 1H), 2.74-2.83 (m, 1H), 3.24-3.32 (m, 1H), 4.07-4.13 (m, 1H), 4.20-4.26 (m, 1H), 7.28 (dd, 2H), 7.77 (dd, 2H); LC-MS: m/z=343 [M+H]$^+$.

3-Bromo-2-(2-fluorophenyl)-5,6-dihydro-4H-pyrrolo[1,2-b]pyrazole (VIII-22); analogously with N-bromosuccinimide; log P(HCOOH): 2.81; $^1$H-NMR (ppm): δ (DMSO-d6)=2.58 (quintet, 2H), 2.87 (ABq, 2H), 4.19 (ABq, 2H), 7.28-7.32 (m, 2H), 7.46-7.51 (m, 2H); LC-MS: m/z=281 [M+H]$^+$.

Analogously to the methods described above, it is possible to prepare the compounds of the general formula (Ik) listed in Table I below.

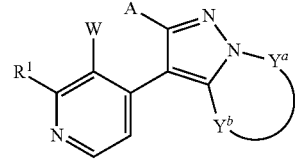
(Ik)

In the table below, $R^1$ represents, for example, $R^{1a}$, NH—$R^{1a}$ or NHCOR$^{1a}$.

TABLE 1

| Ex. | R$^1$ | R$^{1a}$ | W | A | —Y$^a$—Y$^b$— | log P |
|---|---|---|---|---|---|---|
| 1 | R$^{1a}$ | chloro | H | 4-fluorophenyl | —CH$_2$CH$_2$CH$_2$CH$_2$— | 3.26[a] |
| 2 | R$^{1a}$ | H | H | 4-fluorophenyl | —CH$_2$CH$_2$CH$_2$CH$_2$— | 1.03[a]; 2.43[b] |
| 3 | NH—R$^{1a}$ | H | H | 4-fluorophenyl | —CH$_2$CH$_2$CH$_2$CH$_2$— | 1.21[a]; 2.05[b] |
| 4 | NH—R$^{1a}$ | benzyl | H | 4-fluorophenyl | —CH$_2$CH$_2$CH$_2$CH$_2$— | 1.79[a] |
| 5 | NH—CO—R$^{1a}$ | ethyl | H | 4-fluorophenyl | —CH$_2$CH$_2$CH$_2$CH$_2$— | 1.97[a]; 2.58[b] |
| 6 | R$^{1a}$ | CH$_3$ | H | 4-fluorophenyl | —CH$_2$CH$_2$CH$_2$CH$_2$— | 1.22[a]; 2.67[b] |
| 7 | R$^{1a}$ | H | H | 4-fluorophenyl | —CH$_2$CH$_2$CH$_2$— | 2.08[b] |
| 8 | NH—CO—R$^{1a}$ | ethyl | H | phenyl | —CH$_2$CH$_2$CH$_2$CH$_2$— | 1.77[a]; 2.46[b] |
| 9 | R$^{1a}$ | H | H | phenyl | —CH$_2$CH$_2$CH$_2$CH$_2$— | 1.06[a]; 2.32[b] |
| 10 | R$^{1a}$ | H | H | phenyl | —CH$_2$CH$_2$CH$_2$— | 1.96[b] |
| 11 | R$^{1a}$ | H | H | 4-chlorophenyl | —CH$_2$CH$_2$CH$_2$— | 2.46[b] |
| 12 | R$^{1a}$ | H | H | 4-methoxyphenyl | —CH$_2$CH$_2$CH$_2$— | 0.72[a] |
| 13 | R$^{1a}$ | fluoro | H | 4-chlorophenyl | —CH$_2$CH$_2$CH$_2$— | 3.12[b] |
| 14 | NH—R$^{1a}$ | H | H | phenyl | —CH$_2$CH$_2$CH$_2$CH$_2$— | 1.12[a]; 1.89[b] |
| 15 | NH—CO—R$^{1a}$ | CH$_3$ | H | 4-fluorophenyl | —CH$_2$CH$_2$CH$_2$CH$_2$— | 1.66[a]; 2.14[b] |
| 16 | NH—CO—R$^{1a}$ | tert-butoxy | H | 4-fluorophenyl | —CH$_2$CH$_2$CH$_2$CH$_2$— | 1.73[a]; 3.04[b] |
| 17 | R$^{1a}$ | H | H | 4-(trifluoromethyl)phenyl | —CH$_2$CH$_2$CH$_2$— | 2.75[b] |
| 18 | NH—CO—R$^{1a}$ | tert-butoxy | H | 4-fluorophenyl | —CH$_2$CH$_2$CH$_2$— | 2.5[a] |
| 19 | NH—CO—R$^{1a}$ | CH$_3$ | H | phenyl | —CH$_2$CH$_2$CH$_2$CH$_2$— | 1.57[a]; 2.03[b] |
| 20 | NH—CO—R$^{1a}$ | cyclopropyl | H | 4-fluorophenyl | —CH$_2$CH$_2$CH$_2$CH$_2$— | 2.04[a]; 2.67[b] |
| 21 | NH—CO—R$^{1a}$ | cyclopropyl | H | Phenyl | —CH$_2$CH$_2$CH$_2$CH$_2$— | 1.85[a]; 2.52[b] |
| 22 | NH—CO—R$^{1a}$ | methoxymethyl | H | 4-fluorophenyl | —CH$_2$CH$_2$CH$_2$CH$_2$— | 2.3[a]; 2.54[b] |
| 23 | NH—CO—R$^{1a}$ | methoxymethyl | H | phenyl | —CH$_2$CH$_2$CH$_2$CH$_2$— | 2.12[a]; 2.39[b] |
| 24 | NH—CO—R$^{1a}$ | (1S)-1-hydroxyethyl | H | 4-fluorophenyl | —CH$_2$CH$_2$CH$_2$CH$_2$— | 1.91[a]; 2.14[b] |
| 25 | NH—CO—R$^{1a}$ | (1S)-1-hydroxyethyl | H | Phenyl | —CH$_2$CH$_2$CH$_2$CH$_2$— | 1.74[a]; 2.01[b] |
| 26 | NH—CO—R$^{1a}$ | methoxy | H | 4-fluorophenyl | —CH$_2$CH$_2$CH$_2$CH$_2$— | 2.11[a]; 2.56[b] |
| 27 | NH—CO—R$^{1a}$ | methoxy | H | phenyl | —CH$_2$CH$_2$CH$_2$CH$_2$— | 1.92[a]; 2.4[b] |
| 28 | NH—CO—R$^{1a}$ | propan-2-yl | H | 4-fluorophenyl | —CH$_2$CH$_2$CH$_2$CH$_2$— | 2.33[a]; 2.87[b] |
| 29 | NH—CO—R$^{1a}$ | propan-2-yl | H | phenyl | —CH$_2$CH$_2$CH$_2$CH$_2$— | 2.13[a]; 2.72[b] |
| 30 | NH—CO—R$^{1a}$ | 2-methylpropyl | H | 4-fluorophenyl | —CH$_2$CH$_2$CH$_2$CH$_2$— | 2.68[a]; 3.18[b] |
| 31 | NH—CO—R$^{1a}$ | 2-methylpropyl | H | phenyl | —CH$_2$CH$_2$CH$_2$CH$_2$— | 2.47[a]; 3.04[b] |

TABLE 1-continued

| Ex. | R$^1$ | R$^{1a}$ | W | A | —Y$^a$—Y$^b$— | log P |
|---|---|---|---|---|---|---|
| 32 | NH—CO—R$^{1a}$ | phenyl | H | 4-fluorophenyl | —CH$_2$CH$_2$CH$_2$CH$_2$— | 3[a]; 3.34[b] |
| 33 | NH—CO—R$^{1a}$ | phenyl | H | phenyl | —CH$_2$CH$_2$CH$_2$CH$_2$— | 2.78[a]; 3.2[b] |
| 34 | NH—CO—R$^{1a}$ | benzyl | H | 4-fluorophenyl | —CH$_2$CH$_2$CH$_2$CH$_2$— | 2.9[a]; 3.26[b] |
| 35 | NH—CO—R$^{1a}$ | benzyl | H | phenyl | —CH$_2$CH$_2$CH$_2$CH$_2$— | 2.7[a]; 3.12[b] |
| 36 | NH—CO—R$^{1a}$ | H | H | 4-fluorophenyl | —CH$_2$CH$_2$CH$_2$CH$_2$— | 1.28[a]; 2.12[b] |
| 37 | NH—CO—R$^{1a}$ | H | H | phenyl | —CH$_2$CH$_2$CH$_2$CH$_2$— | 1.87[a]; 1.98[b] |
| 38 | R$^{1a}$ | [(dimethylamino)methylidene]amino | H | phenyl | —CH$_2$CH$_2$CH$_2$CH$_2$— | 1.28[a]; 2.28[b] |
| 39 | R$^{1a}$ | [(dimethylamino)methylidene]amino | H | 4-fluorophenyl | —CH$_2$CH$_2$CH$_2$CH$_2$— | 1.44[a]; 2.47[b] |
| 40 | NH—CO—R$^{1a}$ | ethyl | H | 4-fluorophenyl | —CH$_2$CH$_2$CH$_2$— | 1.64[a] |
| 41 | R$^{1a}$ | H | H | 4-methylphenyl | —CH$_2$CH$_2$CH$_2$— | 2.34[b] |
| 42 | R$^{1a}$ | H | H | 3-(trifluoromethyl)phenyl | —CH$_2$CH$_2$CH$_2$— | 1.42[a] |
| 43 | R$^{1a}$ | H | H | 4-fluorophenyl | —CH$_2$CH$_2$CH$_2$CH$_2$CH$_2$— | 1.4[a] |
| 44 | R$^{1a}$ | H | H | 3-fluorophenyl | —CH$_2$CH$_2$CH$_2$— | 2.12[b] |
| 45 | R$^{1a}$ | fluoro | H | 4-fluorophenyl | —CH$_2$CH$_2$CH$_2$— | 2.69[a] |
| 46 | R$^{1a}$ | H | H | thiophen-3-yl | —CH$_2$CH$_2$CH$_2$— | 0.72[a] |
| 47 | NH—CO—R$^{1a}$ | thiophen-3-yl | H | 4-fluorophenyl | —CH$_2$CH$_2$CH$_2$CH$_2$— | 2.75[a]; 3.24[b] |
| 48 | NH—R$^{1a}$ | propan-2-yl | H | 4-chlorophenyl | —CH$_2$CH$_2$CH$_2$— | 3.25[b] |
| 49 | NH—CO—R$^{1a}$ | tert-butoxy | H | thiophen-3-yl | —CH$_2$CH$_2$CH$_2$CH$_2$— | 2.76[a] |
| 50 | NH—CO—R$^{1a}$ | 2-hydroxypropan-2-yl | H | phenyl | —CH$_2$CH$_2$CH$_2$CH$_2$— | 2[a]; 2.29[b] |
| 51 | NH—CO—R$^{1a}$ | thiophen-3-yl | H | phenyl | —CH$_2$CH$_2$CH$_2$CH$_2$— | 2.49[a]; 3.09[b] |
| 52 | NH—R$^{1a}$ | propan-2-yl | H | 4-fluorophenyl | —CH$_2$CH$_2$CH$_2$— | 1.4[a] |
| 53 | NH—R$^{1a}$ | H | H | thiophen-3-yl | —CH$_2$CH$_2$CH$_2$CH$_2$— | 0.82[a]; 1.8[b] |
| 54 | R$^{1a}$ | fluoro | H | 3-fluorophenyl | —CH$_2$CH$_2$CH$_2$— | 2.66[b] |
| 55 | NH—CO—R$^{1a}$ | 2-hydroxypropan-2-yl | H | 4-fluorophenyl | —CH$_2$CH$_2$CH$_2$CH$_2$— | 2.16[a]; 2.41[b] |
| 56 | NH—R$^{1a}$ | propan-2-yl | H | 3-fluorophenyl | —CH$_2$CH$_2$CH$_2$— | 2.86[b] |
| 57 | R$^{1a}$ | H | H | 5-chlorothiophen-2-yl | —CH$_2$CH$_2$C(Cl$_2$)CH(Cl)— | 3.23[a] |
| 58 | NH—CO—R$^{1a}$ | CH$_3$ | H | thiophen-3-yl | —CH$_2$CH$_2$CH$_2$CH$_2$— | 1.47[a]; 1.92[b] |
| 59 | NH—CO—R$^{1a}$ | ethyl | H | thiophen-3-yl | —CH$_2$CH$_2$CH$_2$CH$_2$— | 1.73[a]; 2.25[b] |
| 60 | NH—CO—R$^{1a}$ | methoxymethyl | H | thiophen-3-yl | —CH$_2$CH$_2$CH$_2$CH$_2$— | 2.06[a]; 2.27[b] |
| 61 | R$^{1a}$ | fluoro | H | phenyl | —CH$_2$CH$_2$CH$_2$— | 2.53[b] |
| 62 | R$^{1a}$ | H | H | thiophen-2-yl | —CH$_2$CH$_2$CH$_2$CH$_2$— | 1.05[a]; 2.2[b] |
| 63 | NH—CO—R$^{1a}$ | propan-2-yl | H | thiophen-3-yl | —CH$_2$CH$_2$CH$_2$CH$_2$— | 2.03[a]; 2.6[b] |
| 64 | NH—CO—R$^{1a}$ | 2-methylpropyl | H | thiophen-3-yl | —CH$_2$CH$_2$CH$_2$CH$_2$— | 2.37[a]; 2.91[b] |
| 65 | NH—CO—R$^{1a}$ | cyclopropyl | H | thiophen-3-yl | —CH$_2$CH$_2$CH$_2$CH$_2$— | 1.87[a]; 2.44[b] |
| 66 | NH—CO—R$^{1a}$ | (1R)-1-hydroxyethyl | H | thiophen-3-yl | —CH$_2$CH$_2$CH$_2$CH$_2$— | 1.73[a]; 1.95[b] |
| 67 | NH—CO—R$^{1a}$ | methoxy | H | thiophen-3-yl | —CH$_2$CH$_2$CH$_2$CH$_2$— | 1.92[a]; 2.32[b] |
| 68 | NH—CO—R$^{1a}$ | 2-hydroxypropan-2-yl | H | thiophen-3-yl | —CH$_2$CH$_2$CH$_2$CH$_2$— | 1.89[a]; 2.16[b] |
| 69 | NH—R$^{1a}$ | H | H | 4-fluorophenyl | —CH$_2$CH$_2$CH$_2$— | 1.8[b] |
| 70 | NH—R$^{1a}$ | propan-2-yl | H | phenyl | —CH$_2$CH$_2$CH$_2$— | 2.69[b] |
| 71 | NH—R$^{1a}$ | 2-methylpropyl | H | 4-fluorophenyl | —CH$_2$CH$_2$CH$_2$— | 3.18[b] |
| 72 | NH—R$^{1a}$ | 2-methylpropyl | H | phenyl | —CH$_2$CH$_2$CH$_2$— | 3.06[b] |
| 73 | NH—R$^{1a}$ | 2-methylpropyl | H | 3-fluorophenyl | —CH$_2$CH$_2$CH$_2$— | 1.54[b] |
| 74 | R$^{1a}$ | H | H | 4-fluorophenyl | —CH(CH$_3$)CH$_2$CH$_2$— | 1.13[a] |
| 75 | NH—CO—R$^{1a}$ | ethyl | H | thiophen-2-yl | —CH$_2$CH$_2$CH$_2$CH$_2$— | 1.89[a]; 2.35[b] |
| 76 | NH—CO—R$^{1a}$ | ethyl | H | 4-fluorophenyl | —CH(CH$_3$)CH$_2$CH$_2$— | 1.92[a] |
| 77 | NH—CO—R$^{1a}$ | propan-2-yl | H | 4-fluorophenyl | —CH(CH$_3$)CH$_2$CH$_2$— | 2.3[a] |
| 78 | NH—CO—R$^{1a}$ | cyclopropyl | H | 4-fluorophenyl | —CH(CH$_3$)CH$_2$CH$_2$— | 2.07[a] |
| 79 | NH—CO—R$^{1a}$ | cyclopropylmethyl | H | 4-fluorophenyl | —C(CH$_3$)$_2$OCH$_2$CH$_2$— | 2.97[a] |
| 80 | R$^{1a}$ | H | H | 5-chlorothiophen-2-yl | —CH$_2$CH$_2$CH$_2$CH(Cl)— | 2.21[a] |
| 81 | NH—R$^{1a}$ | H | H | thiophen-2-yl | —CH$_2$CH$_2$CH$_2$CH$_2$— | 1.04[a]; 1.89[b] |
| 82 | NH—CO—R$^{1a}$ | methoxymethyl | H | 4-fluorophenyl | —C(CH$_3$)$_2$OCH$_2$CH$_2$— | 2.92[a] |
| 83 | NH—CO—R$^{1a}$ | propan-2-yl | H | 4-fluorophenyl | —C(CH$_3$)$_2$OCH$_2$CH$_2$— | 2.81[a] |
| 84 | NH—CO—R$^{1a}$ | cyclopropyl | H | 4-fluorophenyl | —C(CH$_3$)$_2$OCH$_2$CH$_2$— | 2.67[a] |

TABLE 1-continued

| Ex. | $R^1$ | $R^{1a}$ | W | A | —$Y^a$—$Y^b$— | log P |
|---|---|---|---|---|---|---|
| 85 | $R^{1a}$ | H | H | 4-fluorophenyl | —$CH_2CH_2CH_2CH(OCH_3)$— | 1.23[a]; 2.27[b] |
| 86 | NH—CO—$R^{1a}$ | ethyl | H | 4-fluorophenyl | —$C(CH_3)_2OCH_2CH_2$— | 2.44[a] |
| 87 | NH—CO—$R^{1a}$ | $CH_3$ | H | thiophen-2-yl | —$CH_2CH_2CH_2CH_2$— | 1.54[a]; 2[b] |
| 88 | NH—CO—$R^{1a}$ | propan-2-yl | H | thiophen-2-yl | —$CH_2CH_2CH_2CH_2$— | 2.12[a]; 2.7[b] |
| 89 | NH—CO—$R^{1a}$ | cyclopropyl | H | thiophen-2-yl | —$CH_2CH_2CH_2CH_2$— | 1.9[a]; 2.51[b] |
| 90 | NH—CO—$R^{1a}$ | $CH_3$ | H | 4-fluorophenyl | —$C(CH_3)_2OCH_2CH_2$— | 2.17[a] |
| 91 | NH—CO—$R^{1a}$ | propan-2-yl | H | 4-fluorophenyl | —$CH_2OCH_2CH_2$— | 2.21[a] |
| 92 | NH—CO—$R^{1a}$ | propan-2-yl | H | 4-fluorophenyl | —$CH_2CH_2OCH_2$— | 2[a] |
| 93 | NH—CO—$R^{1a}$ | cyclopropyl | H | 4-fluorophenyl | —$CH_2CH_2OCH_2$— | 1.8[a] |
| 94 | NH—CO—$R^{1a}$ | methoxymethyl | H | 4-fluorophenyl | —$CH_2OCH_2CH_2$— | 2.14[a] |
| 95 | NH—CO—$R^{1a}$ | ethyl | H | 4-fluorophenyl | —$CH_2OCH_2CH_2$— | 1.87[a] |
| 96 | NH—CO—$R^{1a}$ | ethyl | H | 4-fluorophenyl | —$CH_2CH_2CH_2CH_2CH_2$— | 2.44[a] |
| 97 | NH—CO—$R^{1a}$ | propan-2-yl | H | 4-fluorophenyl | —$CH_2CH_2CH_2CH_2CH_2$— | 2.91[a] |
| 98 | NH—CO—$R^{1a}$ | benzyl | H | 4-fluorophenyl | —$CH_2CH_2CH_2CH_2CH_2$— | 3.52[a] |
| 99 | NH—CO—$R^{1a}$ | $CH_3$ | H | 4-fluorophenyl | —$CH_2CH_2CH_2CH_2CH_2$— | 2.2[a] |
| 100 | NH—CO—$R^{1a}$ | ethyl | H | phenyl | —$CH_2CH_2OCH_2$— | 1.57[a] |
| 101 | NH—CO—$R^{1a}$ | 2-methylcyclopropyl | H | 4-fluorophenyl | —$C(CH_3)_2OCH_2CH_2$— | 2.83[a] |
| 102 | NH—CO—$R^{1a}$ | cyclobutyl | H | 4-fluorophenyl | —$C(CH_3)_2OCH_2CH_2$— | 2.93[a] |
| 103 | NH—$R^{1a}$ | H | H | 4-fluorophenyl | —$CH_2OCH_2CH_2$— | 0.99[a] |
| 104 | NH—CO—$R^{1a}$ | ethyl | H | 4-fluorophenyl | —$CH_2OCH_2CH_2$— | 1.71[a] |
| 105 | NH—CO—$R^{1a}$ | 2-methylpropyl | H | 4-fluorophenyl | —$C(CH_3)_2OCH_2CH_2$— | 3.26[a] |
| 106 | NH—CO—$R^{1a}$ | $CH_3$ | H | 4-fluorophenyl | —$CH_2OCH_2CH_2$— | 1.6[a] |
| 107 | NH—CO—$R^{1a}$ | cyclopropyl | H | 4-fluorophenyl | —$CH_2OCH_2CH_2$— | 1.97[a] |
| 108 | NH—CO—$R^{1a}$ | 2-methylcyclopropyl | H | 4-fluorophenyl | —$CH_2OCH_2CH_2$— | 2.19[a] |
| 109 | NH—CO—$R^{1a}$ | cyclobutyl | H | 4-fluorophenyl | —$CH_2OCH_2CH_2$— | 2.26[a] |
| 110 | NH—CO—$R^{1a}$ | ethyl | H | 4-fluorophenyl | —$CH_2CH_2CH(CH_3)$— | 2.02[a] |
| 111 | NH—CO—$R^{1a}$ | propan-2-yl | H | 4-fluorophenyl | —$CH_2CH_2CH(CH_3)$— | 2.34[a] |
| 112 | NH—CO—$R^{1a}$ | 2-methylpropyl | H | 4-fluorophenyl | —$CH_2OCH_2CH_2$— | 2.51[a] |
| 113 | NH—CO—$R^{1a}$ | cyclopropylmethyl | H | 4-fluorophenyl | —$CH_2CH_2OCH_2$— | 2.22[a] |
| 114 | $R^{1a}$ | H | H | 5-chlorothiophen-2-yl | —$CH_2CH_2CH_2CH(OCH_3)$— | 1.59[a]; 2.88[b] |
| 115 | NH—CO—$R^{1a}$ | ethyl | H | phenyl | —$CH_2CH_2SCH_2$— | 1.98[a] |
| 116 | NH—CO—$R^{1a}$ | propan-2-yl | H | 4-fluorophenyl | —$CH(CH_3)OCH_2CH_2$— | 2.59[a] |
| 117 | $R^{1a}$ | H | F | 4-fluorophenyl | —$CH(CH_3)CH_2CH_2$— | 2.66[a] |
| 118 | $R^{1a}$ | H | F | 4-fluorophenyl | —$CH_2CH_2CH_2CH_2CH_2$— | 3.08[a] |

Calibration is carried out using unbranched alkan-2-ones (having 3 to 16 carbon atoms) with known log P values (determination of the log P values by the retention times using linear interpolation between two successive alkanones).

The lambda maX values were determined in the maxima of the chromatographic signals using the UV spectra from 200 nm to 400 nm.

The $^1$H-NMR of selected examples are listed in the form of $^1$H-NMR peak lists. For each signal peak, first the δ value in ppm and then, separated by a space, the signal intensity are given. The δ value/signal intensity number pairs of different signal peaks are listed separated by semicolons.

Accordingly, the peak list of an example takes the form:

$\delta_1$ intensity$_1$; $\delta_2$ intensity$_2$; ... ; $\delta_i$ intensity$_i$; ... ; $\delta_n$ intensity$_n$ The solvent in which the NMR spectrum was recorded is given in square brackets after the number of the example and before the peak list.

Example No. 2 [CD$_3$CN] 11.99 0.40; 8.47 12.97; 8.47 7.86; 8.46 7.66; 8.45 13.47; 8.22 0.39; 7.67 0.81; 7.66 1.21; 7.66 0.75; 7.65 1.49; 7.64 1.55; 7.64 1.17; 7.62 0.61; 7.62 1.58; 7.61 1.85; 7.61 1.01; 7.60 0.94; 7.59 0.87; 7.59 0.98; 7.58 0.43; 7.54 1.08; 7.54 0.85; 7.53 1.20; 7.52 1.57; 7.51 1.43; 7.49 0.70; 7.41 0.73; 7.41 7.03; 7.40 2.74; 7.39 7.75; 7.38 8.88; 7.38 2.97; 7.37 8.40; 7.36 1.09; 7.36 0.52; 7.12 15.59; 7.12 9.55; 7.11 9.27; 7.11 15.62; 7.08 0.87; 7.07 8.56; 7.07 2.55; 7.06 2.53; 7.05 16.00; 7.04 2.83; 7.03 2.53; 7.03 7.69; 7.02 0.70; 5.73 0.39; 5.45 0.48; 4.18 5.93; 4.16 10.77; 4.15 6.32; 3.55 0.40; 3.27 0.46; 3.14 0.37; 2.83 5.42; 2.81 10.85; 2.79 6.16; 2.76 0.40; 2.62 0.44; 2.18 0.54; 2.15 551.68; 2.13 4.84; 2.12 1.12; 2.11 1.33; 2.11 2.84; 2.10 2.13; 2.09 3.50; 2.08 3.26; 2.08 5.42; 2.07 3.21; 2.06 4.10; 2.05 1.23; 2.05 2.24; 2.00 0.44; 1.98 3.51; 1.96 13.95; 1.95 92.46; 1.95 172.38; 1.94 247.36; 1.93 168.83; 1.93 85.79; 1.90 0.61; 1.89 2.35; 1.89 1.48; 1.88 5.48; 1.87 2.91; 1.86 4.97; 1.86 2.75; 1.85 4.23; 1.84 1.23; 1.83 1.44; 1.79 3.22; 1.78 0.53; 1.77 1.31; 1.77 1.53; 1.76 0.96; 1.76 0.59; 1.38 0.40; 1.27 0.68; 1.20 0.78; 1.14 12.44; 1.11 1.17; 1.10 0.55; 0.97 0.41; 0.00 6.71; −0.56 0.38; −0.91 0.38

Example No. 3 [CD$_3$CN] 7.87 7.80; 7.86 6.71; 7.78 1.44; 7.77 1.50; 7.76 1.16; 7.75 1.04; 7.44 9.44; 7.44 4.07; 7.43 9.65; 7.43 8.10; 7.42 2.95; 7.42 7.08; 7.13 1.74; 7.11 2.77; 7.10 1.52; 7.07 9.74; 7.06 3.13; 7.06 4.53; 7.05 16.00; 7.05 2.20; 7.04 2.43; 7.04 6.56; 6.37 7.59; 6.36 7.23; 6.36 6.66; 6.35 6.10; 6.32 10.23; 6.32 10.42; 6.30 1.41; 4.82 5.76; 4.16 8.39; 4.15 14.05; 4.14 7.58; 4.10 1.14; 4.09 2.01; 4.08 1.12; 4.07 0.54; 4.05 0.56; 3.68 0.43; 3.60 2.65; 3.53 0.62; 3.52 0.49; 2.81 1.58; 2.80 2.56; 2.79 8.07; 2.78 14.32; 2.77 7.81; 2.28 2.05; 2.19 1484.50; 2.08 2.72; 2.07 5.29; 2.07 4.98; 2.06 8.04; 2.06 5.25; 2.05 6.72; 2.05 4.22; 2.04 3.86; 2.03 1.81; 2.02 1.52; 1.97 5.85; 1.97 111.79; 1.96 16.95; 1.95 18.95; 1.95 136.97; 1.95 254.23; 1.94 364.32; 1.94 249.63; 1.93 135.01; 1.87 3.21; 1.87 2.52; 1.86 7.43; 1.86 5.06; 1.85 8.47; 1.85 5.29; 1.84 7.14; 1.84 3.12; 1.83 4.76; 1.83 3.15; 1.82 2.23; 1.45 5.08; 1.27 4.10; 1.22 1.13; 1.20 2.13; 1.20 2.53; 1.19 1.09; 1.13 7.78; 1.11 0.95; 0.91 1.33; 0.88 0.75; 0.00 3.34

Example No. 5 [CD$_3$CN] 8.56 0.33; 8.53 1.20; 8.12 3.16; 8.12 3.17; 8.11 3.14; 8.11 3.19; 8.02 3.46; 7.44 0.52; 7.43 3.23; 7.43 1.41; 7.42 3.61; 7.41 3.85; 7.40 1.60; 7.40 3.57; 7.07 0.61; 7.07 3.81; 7.06 1.27; 7.05 1.73; 7.04

6.89; 7.04 1.51; 7.03 1.20; 7.02 3.20; 6.78 3.10; 6.78 3.06; 6.77 2.97; 6.77 2.94; 5.45 3.87; 4.18 3.04; 4.16 5.56; 4.14 3.17; 4.07 0.41; 4.05 0.45; 3.60 0.62; 2.83 2.87; 2.82 5.71; 2.80 3.12; 2.58 0.32; 2.47 0.39; 2.42 2.28; 2.40 7.10; 2.38 7.25; 2.36 2.60; 2.32 0.39; 2.30 0.47; 2.16 3440.79; 2.13 13.90; 2.12 7.86; 2.11 7.71; 2.11 7.72; 2.10 6.49; 2.09 5.91; 2.09 4.54; 2.08 5.30; 2.07 3.92; 2.07 4.12; 2.05 2.75; 1.96 348.62; 1.96 48.76; 1.95 229.54; 1.95 416.81; 1.94 574.60; 1.93 393.69; 1.93 202.54; 1.90 4.69; 1.88 4.85; 1.88 3.70; 1.87 4.13; 1.86 3.41; 1.84 1.76; 1.79 2.58; 1.78 1.98; 1.77 2.97; 1.77 3.77; 1.76 2.92; 1.76 1.71; 1.73 0.70; 1.71 0.63; 1.70 0.58; 1.65 0.50; 1.62 0.44; 1.60 0.41; 1.59 0.44; 1.58 0.48; 1.55 0.42; 1.50 0.39; 1.46 0.34; 1.44 0.38; 1.41 0.35; 1.40 0.34; 1.39 0.38; 1.33 0.34; 1.33 0.33; 1.27 1.81; 1.25 0.38; 1.23 0.40; 1.22 0.85; 1.20 1.36; 1.19 0.75; 1.14 1.26; 1.13 7.97; 1.11 16.00; 1.09 7.52; 0.91 1.43; 0.90 0.33; 0.15 1.39; 0.05 0.43; 0.01 17.04; 0.00 336.21; −0.01 14.03; −0.15 1.41

Example No. 6 [CD$_3$CN] 8.34 1.99; 8.33 2.00; 7.40 2.57; 7.40 0.94; 7.39 2.72; 7.39 2.84; 7.38 1.00; 7.38 2.70; 7.06 2.91; 7.06 0.85; 7.05 0.93; 7.05 5.48; 7.04 0.92; 7.04 0.83; 7.03 2.62; 7.01 2.33; 6.91 1.32; 6.90 1.27; 6.90 1.29; 6.90 1.23; 5.45 1.02; 4.17 2.21; 4.16 3.92; 4.15 2.28; 2.81 2.08; 2.80 4.07; 2.79 2.26; 2.42 16.00; 2.16 311.44; 2.09 0.67; 2.09 0.47; 2.08 1.29; 2.08 1.40; 2.07 2.04; 2.07 1.13; 2.06 1.50; 2.06 0.96; 2.05 1.58; 2.05 0.73; 2.04 0.36; 1.97 0.69; 1.97 86.82; 1.96 2.30; 1.95 3.09; 1.95 63.52; 1.95 122.98; 1.94 177.45; 1.94 117.58; 1.93 60.40; 1.93 1.80; 1.92 0.85; 1.88 0.77; 1.87 0.45; 1.87 1.85; 1.86 1.06; 1.86 1.70; 1.85 1.03; 1.85 0.96; 1.85 1.64; 1.84 0.43; 1.84 0.61; 1.84 0.43; 1.83 0.71; 1.83 1.04; 1.82 0.71; 1.82 0.36; 1.27 0.37; 1.13 2.93; 0.91 0.69; 0.01 0.95; 0.00 35.06; −0.01 1.01

Example No. 7 [DMSO-D$_6$] 8.45 14.21; 8.45 9.47; 8.44 9.73; 8.44 14.23; 7.95 1.10; 7.44 1.27; 7.43 7.47; 7.42 3.71; 7.41 8.66; 7.41 9.90; 7.40 4.10; 7.39 8.79; 7.39 1.33; 7.24 1.58; 7.24 9.24; 7.23 3.34; 7.22 4.25; 7.21 15.98; 7.21 3.93; 7.20 3.19; 7.19 7.37; 7.18 1.16; 7.15 16.00; 7.14 10.41; 7.14 10.38; 7.13 15.31; 4.19 6.64; 4.17 10.29; 4.15 6.85; 4.10 0.38; 3.91 0.56; 3.48 0.35; 3.47 0.35; 3.32 762.33; 3.08 6.00; 3.06 9.64; 3.04 6.98; 2.89 8.51; 2.73 6.85; 2.68 0.65; 2.67 0.83; 2.67 0.74; 2.66 0.58; 2.65 2.17; 2.63 5.71; 2.61 7.80; 2.59 4.97; 2.58 1.94; 2.56 0.69; 2.54 1.36; 2.51 39.75; 2.51 71.47; 2.50 91.33; 2.50 64.50; 2.49 32.07; 2.33 0.46; 2.33 0.60; 2.32 0.50; 2.07 1.53; 1.99 1.14; 1.19 0.33; 1.18 0.65; 1.16 1.37; 1.07 3.83; 0.01 0.66; 0.00 11.20; −0.01 0.56

Example No. 8 [CD$_3$CN] 8.53 1.12; 8.11 3.09; 8.11 3.15; 8.10 3.15; 8.10 3.18; 8.03 3.46; 7.42 2.54; 7.41 1.89; 7.41 1.96; 7.41 3.74; 7.40 2.68; 7.40 3.90; 7.39 4.04; 7.33 0.32; 7.33 0.34; 7.31 2.13; 7.31 5.95; 7.30 3.89; 7.30 6.48; 7.29 6.44; 7.28 0.74; 6.78 3.01; 6.77 2.95; 6.77 2.96; 6.76 2.81; 5.45 0.50; 4.18 3.17; 4.17 5.71; 4.15 3.27; 2.83 3.01; 2.82 5.88; 2.80 3.25; 2.42 2.29; 2.40 7.11; 2.38 7.35; 2.36 2.55; 2.15 675.49; 2.12 3.68; 2.11 3.82; 2.11 3.64; 2.10 3.87; 2.09 2.99; 2.08 3.90; 2.08 2.67; 2.07 2.97; 2.06 1.44; 2.05 1.66; 2.03 0.64; 1.97 4.46; 1.96 34.85; 1.96 16.18; 1.95 78.40; 1.95 145.50; 1.94 202.52; 1.93 139.85; 1.93 71.95; 1.90 2.62; 1.90 2.01; 1.89 3.55; 1.88 2.55; 1.87 3.23; 1.87 2.22; 1.86 2.62; 1.84 1.11; 1.81 0.33; 1.79 0.43; 1.78 0.62; 1.77 1.02; 1.77 1.30; 1.76 0.96; 1.76 0.59; 1.27 0.63; 1.22 0.44; 1.20 0.80; 1.19 0.44; 1.14 0.77; 1.13 7.90; 1.11 1.86; 1.11 16.00; 1.10 1.03; 1.09 7.46; 0.91 0.59; 0.01 4.13; 0.00 79.89; −0.01 3.62

Example No. 9 [CD$_3$CN] 8.46 12.86; 8.46 7.80; 8.45 7.80; 8.45 13.17; 7.39 0.50; 7.39 0.79; 7.39 5.54; 7.38 5.31; 7.38 4.64; 7.38 5.42; 7.38 6.38; 7.37 4.19; 7.37 8.36; 7.36 1.28; 7.32 2.03; 7.32 5.24; 7.32 16.00; 7.31 7.73; 7.31 14.42; 7.31 7.23; 7.30 13.01; 7.30 2.39; 7.30 0.96; 7.12 15.56; 7.12 9.27; 7.11 9.12; 7.11 15.39; 5.45 0.33; 4.18 6.91; 4.17 12.35; 4.16 7.20; 4.05 0.33; 2.83 6.58; 2.82 12.77; 2.81 7.06; 2.17 1619.57; 2.10 2.17; 2.10 1.46; 2.09 4.14; 2.09 3.59; 2.08 6.62; 2.08 5.09; 2.07 4.82; 2.07 1.47; 2.06 2.53; 2.06 1.93; 2.05 2.74; 2.05 1.86; 2.04 0.98; 1.97 2.98; 1.97 279.75; 1.96 6.42; 1.95 8.89; 1.95 167.54; 1.95 322.73; 1.94 461.38; 1.94 316.75; 1.93 161.66; 1.93 5.13; 1.92 2.45; 1.89 2.50; 1.88 1.49; 1.88 6.01; 1.87 3.41; 1.87 5.52; 1.86 3.27; 1.86 5.30; 1.85 1.40; 1.85 2.11; 1.85 2.01; 1.84 1.01; 1.83 1.90; 1.83 2.76; 1.82 1.89; 1.82 0.96; 1.28 0.43; 1.27 1.33; 1.22 0.44; 1.20 0.85; 1.20 1.84; 1.19 0.43; 1.13 2.71; 1.13 0.55; 1.11 1.07; 1.10 0.56; 0.91 3.98; 0.89 0.34; 0.88 0.34; 0.00 3.57

Example No. 10 [DMSO-D$_6$] 8.44 5.14; 8.43 3.87; 8.42 4.95; 8.13 1.10; 7.39 4.34; 7.38 16.00; 7.37 3.75; 7.36 3.33; 7.35 1.23; 7.35 1.19; 7.15 6.72; 7.14 4.32; 7.14 4.38; 7.13 6.19; 6.49 5.26; 5.75 0.40; 4.20 3.14; 4.18 4.79; 4.16 3.14; 4.02 0.35; 3.71 0.42; 3.69 0.44; 3.67 0.43; 3.65 0.41; 3.62 0.47; 3.60 0.47; 3.56 0.53; 3.53 0.59; 3.51 0.72; 3.49 0.78; 3.48 0.80; 3.47 0.90; 3.31 912.25; 3.08 2.62; 3.07 4.22; 3.05 3.01; 2.69 0.46; 2.67 1.30; 2.67 1.62; 2.67 1.29; 2.65 1.31; 2.63 2.95; 2.62 3.96; 2.60 2.80; 2.58 1.47; 2.54 6.96; 2.51 88.21; 2.50 153.79; 2.50 192.19; 2.50 132.85; 2.33 0.89; 2.33 1.19; 2.32 0.89; 2.30 0.89; 2.07 1.54; 1.24 0.76; 0.00 20.61

Example No. 11 [DMSO-D$_6$] 8.47 10.09; 8.46 6.48; 8.46 6.68; 8.45 10.02; 7.45 5.95; 7.45 2.75; 7.44 4.42; 7.43 16.00; 7.43 3.64; 7.41 4.20; 7.41 15.79; 7.40 3.94; 7.39 2.73; 7.39 5.59; 7.16 10.84; 7.16 6.93; 7.15 6.97; 7.15 10.30; 4.20 4.19; 4.18 6.43; 4.16 4.24; 4.06 0.59; 4.04 1.68; 4.02 1.69; 4.00 4.08; 3.90 0.40; 3.31 291.79; 3.28 4.09; 3.07 3.76; 3.06 6.02; 3.04 4.32; 2.67 0.50; 2.67 0.63; 2.66 0.53; 2.66 0.41; 2.65 1.38; 2.63 3.57; 2.61 4.91; 2.59 3.09; 2.58 1.21; 2.54 1.07; 2.51 32.86; 2.51 58.60; 2.50 74.75; 2.50 52.07; 2.49 25.07; 2.33 0.37; 2.33 0.47; 2.32 0.34; 2.07 0.67; 1.99 7.32; 1.47 0.42; 1.31 0.45; 1.19 2.10; 1.18 4.13; 1.16 2.08; 1.07 2.72; 0.01 0.60; 0.00 10.19; −0.01 0.41

Example No. 12 [DMSO-D$_6$] 8.73 0.63; 8.73 0.44; 8.72 0.45; 8.72 0.67; 8.44 3.45; 8.43 2.24; 8.42 3.53; 7.83 0.76; 7.83 0.50; 7.82 0.49; 7.82 0.73; 7.32 0.50; 7.31 3.47; 7.31 1.27; 7.30 1.39; 7.29 3.92; 7.28 0.52; 7.15 3.71; 7.15 2.38; 7.14 2.37; 7.14 3.56; 6.96 0.58; 6.95 3.90; 6.95 1.36; 6.93 1.29; 6.93 3.42; 6.92 0.47; 4.17 1.42; 4.15 2.23; 4.14 1.48; 3.78 16.00; 3.31 295.82; 3.07 1.33; 3.05 2.10; 3.03 1.54; 2.67 0.40; 2.67 0.52; 2.66 0.40; 2.64 0.49; 2.62 1.27; 2.60 1.75; 2.58 1.16; 2.57 0.54; 2.54 1.05; 2.51 29.97; 2.50 54.32; 2.50 69.80; 2.50 49.02; 2.49 24.18; 2.33 0.40; 2.33 0.49; 2.32 0.37; 2.07 0.44; 1.99 0.83; 1.17 0.46; 0.00 3.60

Example No. 13 [DMSO-D$_6$] 8.13 0.67; 8.12 0.68; 7.47 0.74; 7.47 0.34; 7.46 0.52; 7.45 1.81; 7.45 0.41; 7.43 0.45; 7.42 1.82; 7.42 0.50; 7.41 0.35; 7.40 0.73; 7.08 0.40; 7.07 0.32; 7.07 0.39; 6.89 0.87; 4.21 0.50; 4.19 0.78; 4.17 0.51; 3.91 2.62; 3.32 17.61; 3.11 0.45; 3.09 0.74; 3.08 0.52; 2.64 0.43; 2.62 0.59; 2.60 0.37; 2.51 1.32; 2.51 2.34; 2.50 2.98; 2.50 2.11; 1.99 0.80; 1.18 0.44; 1.07 16.00

Example No. 14 [CD$_3$CN] 7.78 0.55; 7.77 0.57; 7.44 0.48; 7.43 0.37; 7.43 0.65; 7.42 0.80; 7.41 0.74; 7.40 0.38; 7.34 0.33; 7.33 0.91; 7.33 0.96; 7.32 1.37; 7.31 1.18; 6.44 0.86; 6.42 0.63; 6.42 0.46; 6.40 0.55; 6.40 0.46; 4.18 0.60; 4.16 1.06; 4.15 0.62; 3.77 0.88; 3.67 1.75; 2.82 0.57; 2.80 1.10; 2.79 0.62; 2.35 1.03; 2.17 15.08; 2.11 1.47; 2.11 1.47; 2.10 1.17; 2.09 1.08; 2.08 0.95; 2.08 1.09; 2.07 0.80; 2.06 0.84; 2.01 0.53; 1.96 18.43; 1.96 4.21; 1.95 20.77; 1.95 37.93; 1.94 52.45; 1.93 36.36; 1.93 18.80; 1.90 0.50; 1.89 0.40; 1.88 0.69; 1.88 0.51; 1.87 0.63; 1.86 0.45; 1.85 0.53; 1.77 0.37; 1.20 1.20; 1.14 16.00; 0.01 0.40; 0.00 7.38; −0.01 0.33

Example No. 15 [CD$_3$CN] 8.64 1.88; 8.13 7.15; 8.13 6.86; 8.12 7.11; 8.12 7.02; 7.99 3.30; 7.97 0.38; 7.43 0.74; 7.42 7.82; 7.42 2.89; 7.41 8.21; 7.41 8.52; 7.40 3.04; 7.40 8.16; 7.39 0.86; 7.07 0.87; 7.06 8.62; 7.06 2.57; 7.05 2.79; 7.05 16.00; 7.04 2.85; 7.03 2.47; 7.03 7.75; 7.03 0.78; 6.80 6.93; 6.80 6.87; 6.79 6.72; 6.79 6.75; 5.45 1.03; 4.17 6.62; 4.16 11.98; 4.15 6.87; 4.08 0.41; 4.07 1.17; 4.05 1.19; 4.04 0.40; 3.55 0.33; 3.54 0.35; 3.53 0.35; 3.53 0.34; 2.82 6.30; 2.81 12.42; 2.80 6.75; 2.54 0.36; 2.20 3758.35; 2.10 2.22; 2.09 67.52; 2.08 4.51; 2.08 6.46; 2.07 3.66; 2.07 4.64; 2.06 2.54; 2.06 3.55; 2.05 3.65; 2.05 2.41; 1.98 0.54; 1.97 6.08; 1.97 102.59; 1.96 15.98; 1.95 19.90; 1.95 220.52; 1.95 409.99; 1.94 602.47; 1.94 409.64; 1.93 205.63; 1.93 6.76; 1.93 3.04; 1.89 2.11; 1.88 1.35; 1.87 5.38; 1.87 3.28; 1.86 5.16; 1.86 3.13; 1.86 4.74; 1.85 1.26; 1.84 1.73; 1.84 1.28; 1.83 2.32; 1.83 3.36; 1.82 2.31; 1.82 1.21; 1.27 1.52; 1.22 1.53; 1.20 3.03; 1.19 1.51; 1.13 1.41; 1.11 2.77; 1.10 1.45; 0.91 2.34; 0.00 5.81

Example No. 16 [CD$_3$CN] 8.09 0.54; 8.09 0.59; 7.72 0.69; 7.43 0.64; 7.42 0.73; 7.41 0.79; 7.41 0.35; 7.40 0.76; 7.06 0.69; 7.05 1.37; 7.03 0.70; 6.75 0.50; 6.74 0.53; 6.74 0.54; 6.74 0.56; 4.17 0.66; 4.16 1.21; 4.15 0.69; 2.82

-continued 0.68; 2.81 1.17; 2.80 0.63; 2.25 0.43; 2.24 0.60; 2.21 281.02; 2.09 0.60; 2.08 0.67; 2.08 0.44; 2.07 0.51; 2.05 0.35; 1.97 3.93; 1.96 1.61; 1.96 2.05; 1.95 19.68; 1.95 36.83; 1.94 52.56; 1.94 34.71; 1.93 17.69; 1.88 0.55; 1.88 0.40; 1.87 0.58; 1.86 0.48; 1.83 0.32; 1.45 16.00; 1.31 0.38; 1.27 1.83; 0.93 0.34; 0.88 0.37

Example No. 17 [DMSO-D$_6$] 8.49 7.10; 8.49 4.64; 8.48 4.71; 8.47 7.19; 7.83 0.32; 7.75 4.48; 7.73 6.06; 7.63 5.84; 7.61 4.30; 7.19 7.71; 7.18 5.00; 7.18 4.93; 7.17 7.46; 5.75 0.36; 4.23 2.98; 4.21 4.57; 4.19 3.07; 4.06 1.23; 4.04 3.65; 4.02 3.68; 4.00 1.25; 3.78 0.61; 3.31 319.54; 3.29 2.38; 3.08 2.68; 3.06 4.34; 3.05 3.16; 2.67 0.37; 2.67 0.54; 2.66 1.06; 2.64 2.53; 2.63 3.49; 2.61 2.21; 2.59 0.83; 2.54 0.88; 2.52 1.90; 2.51 21.87; 2.51 39.93; 2.50 51.66; 2.50 36.22; 2.49 17.70; 2.33 0.36; 1.99 16.00; 1.91 1.60; 1.19 4.47; 1.18 8.89; 1.16 4.40; 1.07 1.32; 0.00 0.54

Example No. 18 [DMSO-D$_6$] 9.57 1.03; 8.09 0.83; 8.08 0.89; 7.69 1.06; 7.43 0.76; 7.43 0.38; 7.42 0.90; 7.41 0.98; 7.40 0.44; 7.40 0.86; 7.22 0.91; 7.21 0.34; 7.19 1.56; 7.18 0.34; 7.17 0.74; 6.74 0.72; 6.73 0.69; 6.72 0.70; 6.72 0.67; 4.19 0.60; 4.17 0.93; 4.15 0.61; 3.30 299.11; 3.28 3.24; 3.05 0.53; 3.03 0.86; 3.01 0.59; 2.67 0.38; 2.67 0.50; 2.66 0.42; 2.66 0.38; 2.64 0.58; 2.62 0.75; 2.60 0.55; 2.59 0.33; 2.54 1.28; 2.51 26.66; 2.50 47.67; 2.50 60.62; 2.50 41.83; 2.49 20.06; 2.33 0.38; 2.07 1.33; 1.47 1.00; 1.42 16.00; 1.31 0.45; 1.21 0.44; 1.20 0.45; 1.18 1.06; 1.16 1.02; 0.00 3.28

Example No. 19 [CD$_3$CN] 8.63 1.93; 8.12 7.24; 8.12 7.35; 8.11 7.63; 8.11 7.35; 8.00 3.39; 7.42 0.50; 7.41 0.52; 7.41 2.30; 7.41 6.15; 7.41 3.47; 7.40 3.65; 7.40 8.80; 7.40 5.33; 7.40 8.74; 7.39 9.03; 7.39 0.97; 7.39 0.95; 7.39 1.00; 7.38 0.52; 7.32 0.44; 7.32 0.37; 7.31 1.39; 7.31 3.34; 7.31 2.63; 7.30 11.84; 7.30 9.56; 7.30 14.41; 7.29 16.00; 7.29 1.52; 6.79 6.84; 6.79 6.87; 6.78 7.01; 6.78 6.88; 4.18 6.83; 4.17 12.43; 4.16 7.13; 4.08 0.97; 4.06 2.83; 4.05 2.84; 4.04 0.95; 2.82 6.50; 2.81 12.83; 2.80 7.00; 2.29 0.40; 2.28 0.49; 2.27 0.45; 2.26 0.47; 2.21 1.58; 2.19 3.13; 2.16 5.28; 2.11 2.10; 2.10 2.67; 2.09 2.30; 2.08 69.67; 2.08 8.12; 2.07 4.29; 2.07 5.19; 2.06 1.89; 2.06 2.63; 2.06 1.23; 2.05 1.23; 2.05 0.90; 2.04 0.60; 2.01 0.43; 1.99 0.44; 1.99 0.40; 1.97 12.82; 1.97 8.69; 1.96 8.56; 1.96 4.73; 1.95 5.10; 1.95 52.78; 1.95 101.61; 1.94 147.51; 1.94 96.93; 1.93 48.66; 1.92 0.88; 1.89 2.29; 1.88 1.51; 1.88 5.68; 1.87 3.50; 1.87 5.52; 1.86 3.36; 1.86 4.94; 1.85 1.40; 1.85 1.80; 1.83 0.40; 1.83 0.65; 1.83 0.94; 1.82 0.68; 1.82 0.38; 1.27 1.25; 1.22 3.81; 1.20 7.66; 1.19 3.62; 1.16 0.44; 1.15 0.51; 1.13 1.08; 1.11 0.56; 1.10 0.36; 1.10 0.34; 1.06 0.50; 0.92 0.32; 0.88 0.36; 0.01 1.35; 0.00 47.40; −0.01 1.39

Example No. 20 [CD$_3$CN] 8.86 2.00; 8.13 6.39; 8.13 6.65; 8.12 6.76; 8.12 6.49; 8.00 5.69; 7.43 0.71; 7.42 7.59; 7.42 2.70; 7.41 7.94; 7.41 8.15; 7.40 2.80; 7.40 7.87; 7.39 0.80; 7.06 0.87; 7.05 8.49; 7.05 2.45; 7.04 2.65; 7.04 16.00; 7.04 2.63; 7.03 2.38; 7.02 7.62; 7.02 0.74; 6.77 6.95; 6.77 6.87; 6.77 6.64; 6.76 6.59; 5.45 1.47; 4.16 5.76; 4.15 10.28; 4.14 5.91; 2.80 5.43; 2.79 10.67; 2.78 5.81; 2.16 685.93; 2.09 1.73; 2.04 0.95; 1.97 3.32; 1.97 2.08; 2.08 3.34; 2.08 3.58; 2.08 3.08; 2.07 5.24; 2.06 3.12; 2.06 4.74; 2.06 2.59; 2.05 3.17; 2.05 2.05; 2.05 2.21; 2.04 1.00; 1.97 2.65; 1.97 353.50; 1.96 13.17; 1.95 15.55; 1.95 169.29; 1.95 311.80; 1.94 474.83; 1.94 324.65; 1.93 157.51; 1.93 4.26; 1.92 1.93; 1.92 0.44; 1.88 1.84; 1.87 1.18; 1.87 4.60; 1.86 2.85; 1.86 4.35; 1.85 2.83; 1.85 3.48; 1.85 4.10; 1.84 1.10; 1.84 1.49; 1.84 1.32; 1.83 1.87; 1.83 2.56; 1.82 1.81; 1.82 0.95; 1.80 0.92; 1.79 1.94; 1.78 2.07; 1.78 3.38; 1.77 1.37; 1.77 2.17; 1.76 2.12; 1.76 1.05; 1.45 0.33; 1.28 0.42; 1.27 1.43; 1.13 1.16; 1.11 2.38; 1.10 1.20; 0.91 1.52; 0.88 0.36; 0.88 2.12; 0.87 5.56; 0.86 8.14; 0.86 5.13; 0.86 4.88; 0.86 7.78; 0.85 3.11; 0.85 1.58; 0.84 4.26; 0.83 7.98; 0.83 4.80; 0.82 3.83; 0.82 8.93; 0.82 4.13; 0.81 1.41; 0.81 1.57; 0.01 1.27; 0.00 46.54; −0.01 1.28

Example No. 21 [CD$_3$CN] 8.87 2.15; 8.12 6.63; 8.12 6.93; 8.11 6.97; 8.11 6.79; 8.01 6.02; 7.41 0.53; 7.41 0.60; 7.41 2.20; 7.40 5.95; 7.40 3.38; 7.40 3.53; 7.40 8.34; 7.40 5.18; 7.39 8.48; 7.39 8.64; 7.39 0.96; 7.38 1.02; 7.38 0.49; 7.32 0.46; 7.32 0.41; 7.31 1.52; 7.31 3.04; 7.31 2.73; 7.30 10.96; 7.30 9.17; 7.30 6.52; 7.30 13.60; 7.29 16.00; 7.28 1.55; 6.77 6.75; 6.77 6.72; 6.76 6.84; 6.76 6.62; 5.45 2.85; 4.17 6.19; 4.16 11.15; 4.15 6.46; 3.54 0.41; 3.53 0.41; 2.81 5.81; 2.80 11.47; 2.79 6.30; 2.17 121.73; 2.09 2.36; 2.09 1.92; 2.08 4.14; 2.08 3.88; 2.08 3.85; 2.07 6.16; 2.07 3.86; 2.06 4.57; 2.06 2.02; 2.06 1.84; 2.06 2.37; 2.05 2.49; 2.05 2.80; 2.05 1.73; 2.04 0.95; 1.97 3.34; 1.97 257.13; 1.96 11.13; 1.95 15.26; 1.95 129.36; 1.95 246.94; 1.94 355.17; 1.94 233.11; 1.93 114.36; 1.93 4.21; 1.92 2.10; 1.88 2.11; 1.88 1.49; 1.87 5.18; 1.87 3.30; 1.86 4.96; 1.86 3.17; 1.85 5.85; 1.85 1.34; 1.84 1.70; 1.84 0.95; 1.83 1.50; 1.83 2.13; 1.82 1.49; 1.82 0.80; 1.80 1.09; 1.79 2.23; 1.78 2.36; 1.78 3.76; 1.77 1.70; 1.77 2.45; 1.76 2.37; 1.75 1.22; 1.51 0.57; 1.50 1.09; 1.49 1.16; 1.49 0.68; 1.49 1.86; 1.48 0.73; 1.48 1.19; 1.47 1.17; 1.47 0.61; 1.27 1.12; 1.22 0.87; 1.20 0.90; 1.19 0.45; 1.13 0.60; 1.13 1.11; 1.11 2.15; 1.10 1.04; 0.91 1.01; 0.88 0.34; 0.87 2.22; 0.87 6.00; 0.86 8.75; 0.86 5.69; 0.86 5.37; 0.85 8.51; 0.85 3.90; 0.84 1.78; 0.84 1.22; 0.84 1.23; 0.84 4.36; 0.83 8.44; 0.83 5.12; 0.82 4.24; 0.82 9.09; 0.81 4.27; 0.81 1.54; 0.80 1.65; 0.75 0.81; 0.74 0.85; 0.74 2.83; 0.74 4.26; 0.73 2.38; 0.73 2.14; 0.73 3.86; 0.72 1.08; 0.72 1.51; 0.71 0.64; 0.71 0.84; 0.70 1.65; 0.70 4.33; 0.69 2.37; 0.69 1.80; 0.69 1.23; 0.68 4.04; 0.68 2.05; 0.68 1.01; 0.67 0.82; 0.01 0.72; 0.00 21.79; −0.01 0.67

Example No. 22 [CD$_3$CN] 8.73 0.33; 8.17 1.22; 8.16 1.30; 8.16 1.32; 8.16 1.32; 8.02 1.10; 8.02 1.12; 7.43 1.48; 7.42 0.51; 7.42 1.57; 7.42 0.60; 7.41 0.60; 7.41 1.56; 7.41 0.52; 7.40 1.52; 7.06 1.55; 7.06 0.46; 7.05 0.50; 7.05 3.02; 7.04 0.49; 7.04 0.46; 7.03 1.50; 6.85 1.40; 6.85 1.36; 6.84 1.30; 6.84 1.23; 5.45 4.31; 4.17 1.04; 4.16 1.88; 4.15 1.09; 3.97 7.87; 3.45 16.00; 2.84 0.99; 2.82 1.95; 2.81 1.07; 2.17 25.36; 2.09 0.59; 2.08 0.54; 2.08 0.95; 2.07 0.55; 2.07 0.69; 2.06 0.36; 1.97 1.99; 1.96 0.47; 1.95 0.57; 1.95 6.22; 1.95 11.65; 1.94 18.33; 1.94 12.52; 1.93 5.86; 1.89 0.33; 1.88 0.85; 1.87 0.52; 1.87 0.79; 1.86 0.50; 1.86 0.75; 0.00 0.88

Example No. 23 [CD$_3$CN] 8.72 0.43; 8.15 1.44; 8.15 1.40; 8.15 1.45; 8.14 1.45; 8.03 1.48; 7.41 1.13; 7.41 0.66; 7.41 0.68; 7.41 1.69; 7.40 1.06; 7.40 1.65; 7.40 1.70; 7.31 0.62; 7.31 2.30; 7.31 1.84; 7.31 1.28; 7.30 2.79; 7.30 3.09; 6.84 1.33; 6.84 1.34; 6.84 1.32; 6.83 1.31; 4.18 1.34; 4.17 2.44; 4.16 1.40; 3.97 8.57; 3.45 16.00; 3.36 0.42; 2.84 1.27; 2.83 2.53; 2.82 1.37; 2.16 56.22; 2.10 0.38; 2.09 0.79; 2.09 0.71; 2.08 1.27; 2.08 0.75; 2.07 0.93; 2.06 0.45; 1.97 0.63; 1.97 10.22; 1.96 1.18; 1.95 1.42; 1.95 14.78; 1.95 28.14; 1.94 41.34; 1.94 27.46; 1.93 13.53; 1.89 0.43; 1.88 1.10; 1.88 0.68; 1.87 1.07; 1.87 0.65; 1.86 0.97; 1.85 0.35; 0.00 3.68

Example No. 24 [CD$_3$CN] 9.00 0.94; 8.16 3.12; 8.16 3.14; 8.15 3.18; 8.15 3.20; 8.04 2.84; 7.43 0.37; 7.43 3.55; 7.43 1.35; 7.42 3.77; 7.41 3.86; 7.41 1.38; 7.41 3.68; 7.40 0.40; 7.07 0.40; 7.06 3.90; 7.06 1.15; 7.05 1.26; 7.05 7.37; 7.05 1.26; 7.04 1.12; 7.03 3.56; 7.03 0.36; 6.83 3.22; 6.83 3.18; 6.82 3.13; 6.82 3.14; 4.25 0.42; 4.24 1.26; 4.23 1.29; 4.22 0.44; 4.17 2.68; 4.16 4.74; 4.15 2.84; 4.06 0.61; 4.05 0.63; 4.05 0.63; 4.00 0.39; 3.78 1.62; 3.49 1.12; 3.36 2.74; 2.84 2.14; 2.83 4.25; 2.82 2.45; 2.17 153.67; 2.10 0.87; 2.10 0.63; 2.09 1.70; 2.09 1.70; 2.08 2.87; 2.08 1.66; 2.07 1.97; 2.07 0.66; 2.06 1.06; 2.06 0.71; 2.05 0.93; 2.05 0.66; 2.04 0.34; 1.97 2.84; 1.97 0.47; 1.97 53.39; 1.96 4.42; 1.95 4.98; 1.95 56.63; 1.95 105.31; 1.94 154.76; 1.94 105.89; 1.93 52.70; 1.93 1.80; 1.92 0.82; 1.92 0.35; 1.89 0.90; 1.89 0.60; 1.88 2.23; 1.88 1.39; 1.87 2.22; 1.87 1.38; 1.86 1.73; 1.86 0.61; 1.85 0.89; 1.84 0.37; 1.83 0.64; 1.83 0.92; 1.82 0.63; 1.82 0.34; 1.37 16.00; 1.36 15.93; 1.27 0.47; 1.22 0.86; 1.20 1.58; 1.19 0.80; 1.13 0.53; 1.11 1.07; 1.10 0.55; 0.91 0.55; 0.01 0.36; 0.00 14.03; −0.01 0.42

Example No. 25 [CD$_3$CN] 9.00 1.02; 8.15 2.86; 8.14 2.91; 8.06 3.11; 7.42 0.97; 7.41 2.70; 7.41 1.61; 7.41 1.66; 7.41 3.85; 7.41 2.52; 7.40 4.01; 7.40 4.04; 7.39 0.54; 7.32 0.65; 7.32 1.22; 7.31 5.11; 7.31 4.58; 7.31 3.15; 7.30 6.65; 7.30 7.97; 7.29 0.81; 6.82 3.13; 6.82 3.20; 6.82 3.16; 6.81 3.14; 5.45 1.47; 4.25 0.42; 4.24 1.27; 4.23 1.29; 4.22 0.45; 4.18 2.92; 4.17 5.19; 4.16 3.06; 4.00 0.54; 2.84 2.47; 2.83 4.88; 2.82 2.77; 2.16 349.12; 2.11 0.94; 2.10 0.72; 2.10 1.86; 2.09 1.75; 2.09 3.12; 2.08 1.80; 2.08 2.52; 2.07 0.75; 2.07 1.05; 2.06 0.48; 2.06 0.75; 2.05 1.10; 2.05 0.76; 2.04 0.39; 1.97 1.32; 1.97 135.15; 1.96 5.99; 1.95 6.98; 1.95 67.53; 1.95 129.20; 1.94 187.18; 1.94 124.02; 1.93 62.30; 1.92 1.31; 1.90 1.06; 1.89 0.73; 1.89 2.51; 1.88 1.57; 1.88 2.50; 1.87 1.53; 1.87 1.97; 1.85 0.68; 1.85 0.91; 1.84

0.43; 1.83 0.75; 1.83 1.09; 1.82 0.78; 1.82 0.41; 1.37 15.89; 1.36 16.00; 1.27 0.40; 1.13 0.47; 1.11 0.90; 1.10 0.43; 0.91 0.61; 0.01 0.56; 0.00 17.88; −0.01 0.57
Example No. 26 [CD$_3$CN] 8.13 0.49; 8.11 1.39; 8.11 1.42; 8.10 1.39; 8.10 1.37; 7.76 1.50; 7.43 1.49; 7.43 0.59; 7.42 1.60; 7.42 1.66; 7.41 0.60; 7.41 1.58; 7.07 1.71; 7.06 0.56; 7.05 0.55; 7.05 3.17; 7.05 0.59; 7.04 0.46; 7.04 1.51; 6.77 1.33; 6.77 1.33; 6.76 1.34; 6.76 1.33; 5.45 0.72; 4.17 1.26; 4.16 2.30; 4.15 1.32; 3.69 16.00; 2.83 1.22; 2.82 2.38; 2.81 1.28; 2.16 220.97; 2.10 0.39; 2.09 0.76; 2.09 0.71; 2.08 1.21; 2.08 0.72; 2.07 0.88; 2.06 0.49; 2.06 0.41; 2.05 0.59; 2.05 0.40; 1.97 0.39; 1.97 12.90; 1.96 2.70; 1.95 3.15; 1.95 36.26; 1.95 69.14; 1.94 99.80; 1.94 65.90; 1.93 33.48; 1.93 1.12; 1.92 0.51; 1.89 0.43; 1.88 1.06; 1.88 0.68; 1.87 1.03; 1.87 0.64; 1.86 0.93; 1.85 0.38; 1.83 0.40; 1.83 0.59; 1.82 0.40; 1.27 0.37; 1.13 0.33; 1.11 0.62; 0.00 8.16
Example No. 27 [CD$_3$CN] 8.10 1.34; 8.09 1.28; 8.09 1.34; 8.09 1.32; 8.06 0.39; 7.78 1.16; 7.77 1.33; 7.77 1.32; 7.42 1.30; 7.41 0.75; 7.41 0.73; 7.41 1.36; 7.41 1.00; 7.40 1.68; 7.40 1.69; 7.32 0.45; 7.32 0.77; 7.32 0.66; 7.31 1.97; 7.31 1.93; 7.31 1.30; 7.30 2.71; 7.30 3.57; 7.30 0.40; 6.76 1.32; 6.76 1.31; 6.75 1.33; 6.75 1.31; 5.45 0.51; 4.18 1.20; 4.17 2.12; 4.16 1.24; 3.77 0.32; 3.72 0.68; 3.68 16.00; 3.68 0.42; 3.55 0.77; 2.83 1.16; 2.82 2.19; 2.81 1.22; 2.19 0.59; 2.16 494.63; 2.13 0.37; 2.11 0.43; 2.10 0.32; 2.10 0.75; 2.09 0.71; 2.09 1.19; 2.08 0.71; 2.08 2.88; 2.07 0.34; 2.07 0.44; 2.06 0.64; 2.06 1.10; 2.05 1.56; 2.05 1.11; 2.04 0.55; 1.97 2.91; 1.97 395.06; 1.96 8.76; 1.95 9.24; 1.95 102.32; 1.95 189.07; 1.94 284.13; 1.94 194.04; 1.93 96.18; 1.93 3.13; 1.92 1.46; 1.92 0.61; 1.92 0.40; 1.92 0.35; 1.89 0.51; 1.89 0.39; 1.88 1.07; 1.88 0.71; 1.87 1.04; 1.87 0.69; 1.86 0.95; 1.86 0.34; 1.85 0.41; 1.85 2.24; 1.84 0.40; 1.84 0.62; 1.83 1.13; 1.83 1.60; 1.82 1.12; 1.82 0.60; 1.29 0.34; 1.27 1.09; 1.13 0.73; 1.11 1.45; 1.10 0.74; 0.91 1.06; 0.01 0.68; 0.00 27.09; −0.01 0.83
Example No. 28 [CD$_3$CN] 8.53 0.63; 8.13 1.51; 8.12 1.58; 8.11 1.62; 8.11 1.70; 8.04 1.90; 7.43 1.65; 7.43 0.78; 7.42 1.88; 7.41 2.03; 7.40 0.86; 7.40 1.89; 7.07 1.88; 7.06 0.69; 7.05 0.85; 7.04 3.43; 7.04 0.81; 7.03 0.66; 7.02 1.63; 6.78 1.47; 6.77 1.51; 6.77 1.48; 6.76 1.43; 4.17 1.63; 4.16 2.91; 4.14 1.65; 2.83 1.54; 2.82 3.05; 2.80 1.72; 2.66 0.38; 2.64 0.96; 2.63 1.31; 2.61 1.01; 2.59 0.42; 2.15 400.60; 2.12 1.80; 2.11 1.81; 2.11 1.68; 2.10 1.58; 2.09 1.71; 2.09 1.53; 2.08 2.02; 2.07 1.43; 2.07 1.54; 2.06 0.76; 2.05 0.86; 2.03 0.35; 1.97 2.43; 1.96 24.07; 1.96 7.56; 1.95 38.73; 1.95 71.16; 1.94 98.81; 1.93 68.31; 1.93 35.30; 1.90 1.33; 1.90 1.06; 1.89 1.84; 1.88 1.36; 1.87 1.73; 1.86 1.22; 1.86 1.37; 1.84 0.60; 1.78 0.34; 1.77 0.52; 1.77 0.68; 1.76 0.49; 1.45 1.04; 1.27 0.65; 1.20 0.45; 1.15 16.00; 1.13 15.73; 1.11 0.60; 1.07 1.04; 1.05 1.01; 0.01 2.02; 0.00 37.39; −0.01 1.74
Example No. 29 [CD$_3$CN] 8.53 0.63; 8.11 1.70; 8.10 1.67; 8.10 1.70; 8.05 2.05; 7.42 1.35; 7.41 1.00; 7.41 1.06; 7.41 2.01; 7.40 1.44; 7.40 2.05; 7.39 2.11; 7.39 0.47; 7.31 1.12; 7.31 3.10; 7.30 2.08; 7.30 3.46; 7.29 3.34; 7.28 0.41; 6.77 1.55; 6.77 1.54; 6.76 1.54; 6.75 1.47; 4.18 1.72; 4.17 3.08; 4.15 1.75; 2.84 1.66; 2.82 3.20; 2.80 1.76; 2.66 0.43; 2.64 1.02; 2.63 1.37; 2.61 1.07; 2.59 0.46; 2.15 356.74; 2.12 1.56; 2.11 1.60; 2.11 1.60; 2.11 1.61; 2.10 1.93; 2.09 1.50; 2.09 1.99; 2.08 1.34; 2.07 1.54; 2.06 0.70; 2.06 0.85; 1.97 2.60; 1.96 18.27; 1.96 7.76; 1.95 37.89; 1.95 68.94; 1.94 95.23; 1.93 65.84; 1.93 33.89; 1.91 1.17; 1.90 0.86; 1.89 1.71; 1.88 1.20; 1.88 1.57; 1.87 1.04; 1.86 1.23; 1.85 0.46; 1.85 0.46; 1.77 0.39; 1.77 0.54; 1.76 0.39; 1.27 0.37; 1.21 1.01; 1.19 0.93; 1.15 16.00; 1.13 15.71; 1.12 1.88; 1.11 0.55; 1.11 0.95; 0.01 2.16; 0.00 36.54; −0.01 1.73
Example No. 30 [CD$_3$CN] 8.54 0.65; 8.13 1.64; 8.12 1.66; 8.01 1.64; 7.43 1.85; 7.42 1.94; 7.41 2.01; 7.40 1.02; 7.39 1.86; 7.06 1.85; 7.04 3.52; 7.02 1.57; 6.80 1.34; 6.80 1.59; 6.79 1.44; 6.79 1.11; 6.04 0.33; 6.03 0.38; 6.02 0.35; 6.01 0.35; 5.99 0.40; 5.52 0.37; 5.48 0.40; 4.17 1.85; 4.16 3.14; 4.14 1.63; 4.07 0.65; 4.05 0.57; 3.57 0.38; 3.55 0.61; 3.54 0.75; 3.54 0.66; 3.52 0.60; 3.50 0.33; 3.27 0.33; 2.96 0.48; 2.84 1.86; 2.82 3.29; 2.81 1.88; 2.71 0.36; 2.66 0.35; 2.61 0.37; 2.57 0.36; 2.49 0.59; 2.46 1.44; 2.39 0.87; 2.37 0.88; 2.35 0.93; 2.34 1.04; 2.32 1.12; 2.30 1.25; 2.28 1.49; 2.24 5.60; 2.22 7.93; 2.15 3170.97; 2.12 12.27; 2.11 11.19; 2.11 10.36; 2.10 7.82; 2.09 6.11; 2.09 4.76; 2.08 4.49; 2.07 3.79; 2.05 2.81; 2.00 8.49; 1.99 11.64; 1.99 10.01; 1.96 131.70; 1.96 60.56; 1.95 308.30; 1.95 561.87; 1.94 776.89; 1.93 536.23; 1.93 275.81; 1.89 3.51; 1.88 2.84; 1.87 2.84; 1.86 2.03; 1.80 0.73; 1.79 1.05; 1.78 1.92; 1.77 3.39; 1.77 4.67; 1.76 3.38; 1.76 1.63; 1.65 0.33; 1.45 1.22; 1.44 0.42; 1.27 2.35; 1.22 0.70; 1.20 1.46; 1.19 0.66; 1.13 1.58; 1.11 2.80; 1.10 1.35; 1.07 5.03; 1.05 4.94; 0.96 15.92; 0.94 16.00; 0.93 15.83; 0.92 7.02; 0.92 6.89; 0.91 15.68; 0.89 0.92; 0.15 1.21; 0.01 15.64; 0.00 294.13; −0.01 14.71; −0.15 1.27
Example No. 31 [CD$_3$CN] 8.54 0.64; 8.12 1.65; 8.10 1.68; 8.03 1.86; 7.41 1.29; 7.41 0.98; 7.41 1.02; 7.41 1.94; 7.40 1.45; 7.40 2.10; 7.39 2.11; 7.30 2.92; 7.30 2.65; 7.30 2.07; 7.29 3.54; 7.29 3.52; 6.79 1.51; 6.79 1.53; 6.78 1.50; 6.77 1.47; 4.18 1.68; 4.17 3.05; 4.15 1.72; 2.84 1.62; 2.82 3.12; 2.81 1.70; 2.24 3.77; 2.23 5.35; 2.15 417.05; 2.11 2.57; 2.11 2.84; 2.10 2.55; 2.09 2.32; 2.09 2.60; 2.07 2.30; 2.05 1.29; 2.04 0.53; 2.02 0.48; 1.97 2.43; 1.96 8.32; 1.96 8.85; 1.95 47.32; 1.95 86.75; 1.94 120.02; 1.93 82.95; 1.93 42.90; 1.90 1.60; 1.89 2.01; 1.88 1.48; 1.87 1.82; 1.87 1.30; 1.86 1.44; 1.84 0.67; 1.78 0.42; 1.77 0.63; 1.77 0.82; 1.76 0.61; 1.76 0.36; 1.27 0.46; 1.20 0.55; 1.11 0.47; 1.00 0.76; 0.99 0.81; 0.96 16.00; 0.95 3.04; 0.94 15.57; 0.93 1.49; 0.91 0.52; 0.01 2.62; 0.00 45.26; −0.01 2.08
Example No. 32 [CD$_3$CN] 9.03 3.06; 8.21 7.74; 8.20 7.84; 8.18 9.33; 7.94 8.49; 7.94 10.32; 7.93 2.84; 7.93 11.48; 7.93 9.55; 7.83 1.14; 7.83 8.01; 7.82 10.18; 7.82 2.89; 7.81 11.51; 7.81 9.74; 7.62 1.27; 7.62 2.47; 7.62 1.54; 7.61 1.72; 7.61 6.32; 7.59 2.50; 7.59 4.51; 7.59 2.56; 7.56 1.25; 7.56 2.48; 7.55 1.51; 7.55 1.71; 7.54 6.27; 7.54 2.37; 7.53 9.89; 7.53 8.22; 7.53 3.32; 7.52 12.14; 7.51 2.13; 7.51 5.56; 7.48 8.32; 7.47 3.78; 7.46 13.24; 7.46 3.71; 7.45 10.30; 7.45 9.09; 7.44 3.17; 7.44 8.17; 7.43 0.92; 7.08 0.86; 7.08 8.35; 7.08 2.69; 7.07 2.92; 7.06 16.00; 7.06 2.49; 7.05 7.88; 7.04 0.98; 6.87 6.69; 6.86 6.94; 6.86 6.62; 6.86 6.82; 6.74 0.50; 5.98 0.45; 4.19 6.53; 4.18 11.96; 4.17 6.82; 4.08 0.72; 4.06 2.14; 4.05 2.13; 4.04 0.71; 3.61 0.36; 3.54 0.44; 3.53 0.44; 2.88 6.17; 2.87 12.30; 2.86 6.61; 2.17 354.13; 2.12 3.04; 2.11 2.50; 2.11 4.76; 2.10 4.39; 2.10 6.77; 2.09 4.24; 2.09 5.06; 2.08 1.99; 2.08 2.60; 2.06 1.38; 2.06 2.22; 2.05 3.14; 2.05 2.17; 2.04 1.24; 1.97 9.88; 1.97 12.68; 1.96 14.29; 1.95 15.61; 1.95 183.09; 1.95 345.53; 1.94 504.89; 1.94 352.39; 1.93 178.21; 1.92 2.73; 1.91 2.30; 1.91 1.62; 1.90 5.34; 1.90 3.49; 1.89 5.41; 1.89 3.41; 1.88 4.67; 1.87 1.70; 1.84 1.05; 1.83 1.97; 1.83 2.89; 1.82 1.96; 1.82 1.01; 1.45 2.51; 1.44 0.42; 1.27 1.82; 1.22 2.61; 1.20 5.23; 1.19 2.51; 1.13 0.35; 1.13 1.99; 1.11 3.88; 1.10 1.90; 0.91 1.88; 0.88 0.33; 0.10 0.60; 0.01 4.27; 0.00 149.10; −0.01 5.07; −0.10 0.60
Example No. 33 [CD$_3$CN] 9.03 2.43; 8.74 0.34; 8.19 16.00; 8.19 7.83; 8.19 6.92; 8.02 0.41; 8.01 0.96; 8.00 0.71; 8.00 0.64; 7.94 8.46; 7.93 2.60; 7.93 9.41; 7.93 7.71; 7.83 4.74; 7.82 5.99; 7.82 1.85; 7.81 6.90; 7.81 5.69; 7.62 1.32; 7.62 2.14; 7.61 1.33; 7.60 5.26; 7.60 1.96; 7.59 2.31; 7.59 3.80; 7.59 2.12; 7.57 0.36; 7.56 0.70; 7.55 1.68; 7.55 1.32; 7.55 1.11; 7.54 3.72; 7.54 1.57; 7.53 8.21; 7.53 4.41; 7.52 9.79; 7.51 1.87; 7.51 4.48; 7.50 0.77; 7.49 0.55; 7.48 0.92; 7.48 1.21; 7.48 4.93; 7.47 2.29; 7.46 6.93; 7.45 1.53; 7.45 3.60; 7.45 3.15; 7.45 2.13; 7.45 6.32; 7.44 4.79; 7.44 3.57; 7.44 3.59; 7.44 3.41; 7.43 8.45; 7.43 7.43; 7.42 0.96; 7.42 0.35; 7.34 1.02; 7.33 0.80; 7.33 2.39; 7.33 2.06; 7.32 7.53; 7.32 4.97; 7.32 5.02; 7.31 12.81; 7.31 13.01; 7.31 2.75; 7.30 1.48; 7.29 0.44; 7.29 0.42; 6.86 5.49; 6.86 4.25; 6.85 4.34; 6.85 5.58; 4.20 5.27; 4.19 9.71; 4.18 5.53; 4.06 0.65; 4.05 0.63; 3.54 0.81; 3.53 0.81; 2.89 5.00; 2.88 9.93; 2.87 5.40; 2.17 62.37; 2.12 3.51; 2.12 2.94; 2.11 4.68; 2.11 4.26; 2.10 6.14; 2.10 4.02; 2.09 4.61; 2.09 2.06; 2.08 2.39; 2.06 1.00; 2.06 1.49; 2.05 1.92; 2.05 1.41; 2.04 0.86; 1.97 3.10; 1.97 7.03; 1.96 7.15; 1.95 9.61; 1.95 97.58; 1.95 187.06; 1.94 266.43; 1.94 180.73; 1.93 95.01; 1.92 2.43; 1.91 1.80; 1.91 4.72; 1.90 3.22; 1.89 4.75; 1.89 3.08; 1.89 4.00; 1.88 1.56; 1.83 0.65; 1.83 1.14; 1.83 1.65; 1.82 1.18; 1.82 0.65; 1.27 0.65; 1.22 0.82; 1.20 1.62; 1.19 0.82; 1.13 1.63; 1.11 3.31; 1.10 1.67; 0.91 1.01; 0.01 2.68; 0.00 80.69; −0.01 3.13

-continued

Example No. 34 [CD$_3$CN] 8.69 1.30; 8.17 0.45; 8.16 0.47; 8.15 0.48; 8.15 0.47; 8.12 3.61; 8.12 3.71; 8.11 3.65; 8.11 3.76; 7.98 3.81; 7.48 0.41; 7.47 0.51; 7.46 0.66; 7.45 0.64; 7.42 0.61; 7.41 4.11; 7.41 1.96; 7.40 4.66; 7.40 3.21; 7.39 2.80; 7.39 5.25; 7.38 2.22; 7.38 5.01; 7.37 2.16; 7.37 1.89; 7.37 1.06; 7.36 2.20; 7.35 4.50; 7.35 4.42; 7.34 1.60; 7.33 11.56; 7.33 11.26; 7.33 9.87; 7.32 1.61; 7.32 1.78; 7.31 3.19; 7.30 1.64; 7.29 1.43; 7.28 2.98; 7.28 2.70; 7.27 1.21; 7.27 1.48; 7.26 0.68; 7.25 0.32; 7.06 0.65; 7.05 4.63; 7.05 1.95; 7.04 0.67; 7.03 1.84; 7.03 8.62; 7.02 2.52; 7.01 1.51; 7.01 4.20; 7.00 0.92; 7.00 0.60; 6.83 0.47; 6.83 0.48; 6.82 0.48; 6.82 0.48; 6.79 3.70; 6.79 3.70; 6.78 3.61; 6.77 3.58; 5.45 2.16; 5.16 0.51; 4.16 3.88; 4.14 6.94; 4.13 3.95; 3.70 16.00; 3.61 3.16; 2.81 3.48; 2.79 6.94; 2.78 3.76; 2.29 0.35; 2.27 0.47; 2.16 45.32; 2.11 2.47; 2.11 2.20; 2.10 1.79; 2.09 1.57; 2.09 2.03; 2.08 1.79; 2.07 2.94; 2.07 2.82; 2.06 4.09; 2.05 2.72; 2.04 3.13; 2.04 1.35; 2.03 1.66; 1.99 0.51; 1.97 1.52; 1.97 2.82; 1.96 74.42; 1.95 5.26; 1.95 30.94; 1.95 58.82; 1.94 84.49; 1.93 58.28; 1.93 29.86; 1.88 1.56; 1.87 1.23; 1.86 3.34; 1.85 2.36; 1.85 3.27; 1.84 2.21; 1.83 2.67; 1.82 1.00; 1.82 1.06; 1.79 0.60; 1.78 0.37; 1.77 0.50; 1.77 0.63; 1.76 0.57; 1.45 0.87; 1.28 0.44; 1.27 1.35; 1.22 0.43; 1.20 0.73; 1.19 0.40; 1.14 0.33; 0.91 0.48; 0.01 1.02; 0.00 26.47; −0.01 1.01

Example No. 35 [CD$_3$CN] 8.84 0.42; 8.66 1.38; 8.46 0.84; 8.36 0.79; 8.34 0.73; 8.15 0.57; 8.14 0.56; 8.11 3.83; 8.10 3.74; 8.10 3.70; 7.99 3.95; 7.81 0.42; 7.57 0.32; 7.54 0.37; 7.52 0.39; 7.50 0.50; 7.48 1.10; 7.46 1.16; 7.43 0.77; 7.40 3.91; 7.39 4.30; 7.39 4.34; 7.38 4.93; 7.38 5.93; 7.38 4.56; 7.37 6.73; 7.37 6.83; 7.36 4.22; 7.36 5.13; 7.35 6.55; 7.35 6.07; 7.34 12.99; 7.33 12.57; 7.32 3.25; 7.31 7.48; 7.30 4.40; 7.30 6.31; 7.30 11.28; 7.29 8.22; 7.29 12.07; 7.28 14.06; 7.28 14.65; 7.27 5.41; 7.25 1.54; 7.22 0.83; 7.21 1.27; 7.20 1.00; 7.19 1.02; 7.17 0.67; 7.16 0.86; 7.15 0.77; 7.14 1.19; 7.12 0.87; 7.11 0.62; 7.09 0.59; 7.09 0.65; 7.07 0.59; 7.06 0.40; 7.02 0.70; 7.00 0.50; 6.83 0.60; 6.82 0.52; 6.81 0.58; 6.81 0.65; 6.78 3.48; 6.78 3.43; 6.77 3.36; 6.77 3.46; 5.45 3.76; 5.41 0.41; 5.16 0.41; 4.41 0.49; 4.20 0.39; 4.19 0.42; 4.17 4.24; 4.15 7.40; 4.14 4.79; 4.12 0.58; 4.11 0.41; 4.08 0.44; 4.07 0.67; 4.05 0.84; 3.80 0.36; 3.78 0.40; 3.76 3.63; 3.70 16.00; 3.62 1.09; 3.61 2.52; 3.60 14.42; 3.53 0.40; 3.52 0.35; 3.52 0.41; 3.50 0.37; 3.49 0.40; 3.48 0.35; 3.35 0.76; 2.81 3.72; 2.80 7.21; 2.78 3.82; 2.47 0.43; 2.47 0.57; 2.46 0.44; 2.36 0.47; 2.34 0.79; 2.33 0.72; 2.31 0.64; 2.30 0.86; 2.29 0.93; 2.28 1.02; 2.15 1291.20; 2.11 14.42; 2.11 13.14; 2.10 10.32; 2.09 8.15; 2.08 6.61; 2.07 5.87; 2.07 6.83; 2.06 4.98; 2.05 5.34; 2.04 3.33; 2.01 2.18; 1.97 10.97; 1.96 534.49; 1.96 47.42; 1.95 285.56; 1.95 539.00; 1.94 772.69; 1.93 533.69; 1.93 274.84; 1.88 4.03; 1.87 5.27; 1.86 4.07; 1.85 4.82; 1.85 3.54; 1.84 3.89; 1.82 2.12; 1.80 1.32; 1.79 4.02; 1.78 2.61; 1.77 4.01; 1.77 5.27; 1.76 4.18; 1.76 2.29; 1.75 1.25; 1.73 1.07; 1.72 1.11; 1.69 1.12; 1.66 0.84; 1.62 0.60; 1.61 0.62; 1.60 0.68; 1.59 0.65; 1.57 0.62; 1.55 0.74; 1.53 0.77; 1.51 0.74; 1.50 0.81; 1.49 0.70; 1.48 0.69; 1.46 0.50; 1.44 0.64; 1.43 0.51; 1.41 0.57; 1.41 0.60; 1.39 1.11; 1.38 0.61; 1.36 0.71; 1.34 1.17; 1.32 0.94; 1.31 0.93; 1.29 2.24; 1.27 7.40; 1.24 1.06; 1.24 0.91; 1.23 1.11; 1.22 1.56; 1.22 1.01; 1.20 2.69; 1.19 1.34; 1.18 0.67; 1.17 0.70; 1.16 0.56; 1.15 0.53; 1.14 1.30; 1.12 0.54; 1.10 0.57; 1.09 0.47; 1.08 0.79; 1.06 0.81; 1.04 0.48; 1.00 0.34; 1.00 0.32; 0.99 0.38; 0.97 0.53; 0.95 0.54; 0.93 0.44; 0.91 3.89; 0.89 0.87; 0.88 1.31; 0.86 0.75; 0.84 0.52; 0.82 0.39; 0.82 0.33; 0.79 0.32; 0.57 0.32; 0.15 1.03; 0.01 9.80; 0.00 232.46; −0.01 9.70; −0.05 0.33; −0.06 0.33; −0.15 1.01

Example No. 36 [CD$_3$CN] 19.94 0.65; 9.24 1.88; 9.22 1.96; 8.68 1.19; 8.46 1.03; 8.32 3.19; 8.16 2.28; 8.15 2.62; 8.14 2.64; 8.13 3.02; 8.12 1.13; 7.98 3.50; 7.43 9.12; 7.42 9.99; 7.41 10.29; 7.40 9.29; 7.09 2.01; 7.07 4.09; 7.06 4.23; 7.05 4.33; 7.04 3.59; 7.04 2.02; 6.85 5.66; 6.84 5.65; 6.80 0.77; 6.79 0.75; 6.67 3.50; 6.38 0.58; 4.17 8.76; 4.16 16.00; 4.15 9.11; 4.13 0.68; 4.13 0.66; 4.06 1.22; 4.05 1.40; 4.04 0.63; 3.55 0.62; 3.53 0.60; 3.52 0.52; 2.83 7.78; 2.82 15.96; 2.81 9.19; 2.80 0.96; 2.78 0.63; 2.74 0.71; 2.47 0.58; 2.15 1619.61; 2.10 3.30; 2.09 6.91; 2.09 12.26; 2.08 10.47; 2.08 6.56; 2.07 7.89; 2.07 3.38; 2.06 6.46; 2.06 6.45; 2.05 8.27; 2.05 5.80; 2.04 3.05; 1.97 7.23; 1.97 84.42; 1.96 46.87; 1.95 58.29; 1.95 539.35; 1.95 972.69; 1.94 1413.07; 1.94 974.09; 1.93 494.81; 1.92 6.87; 1.89 3.43; 1.89 2.52; 1.88 8.56; 1.88 5.52; 1.87 8.87; 1.87 5.57; 1.86 7.71; 1.85 2.81; 1.85 3.39; 1.83 3.27; 1.83 5.72; 1.83 8.02; 1.82 5.44; 1.82 2.80; 1.27 3.78; 1.22 1.70; 1.20 3.25; 1.19 1.65; 1.13 1.55; 1.11 3.17; 1.10 1.61; 0.88 0.77; 0.87 0.67; 0.10 1.64; 0.01 12.44; 0.00 406.61; −0.01 12.14; 0.10 1.66

Example No. 37 [CD$_3$CN] 9.22 1.12; 9.20 1.14; 8.70 0.82; 8.54 2.28; 8.48 0.72; 8.32 1.93; 8.13 3.54; 8.11 2.20; 8.09 1.91; 8.07 0.47; 8.05 0.51; 7.99 2.00; 7.84 0.53; 7.60 0.75; 7.58 0.82; 7.44 2.13; 7.43 1.98; 7.42 2.99; 7.42 8.16; 7.41 5.64; 7.41 5.88; 7.41 10.34; 7.40 7.94; 7.40 10.61; 7.40 8.08; 7.39 11.23; 7.39 2.55; 7.38 1.90; 7.31 8.44; 7.14 0.75; 7.12 0.74; 7.08 2.41; 7.08 1.00; 7.07 1.65; 7.06 4.42; 7.05 1.31; 7.04 1.81; 7.04 2.28; 7.02 0.60; 6.85 5.39; 6.84 5.68; 6.83 5.47; 6.83 5.25; 6.79 2.24; 6.78 1.75; 6.77 1.48; 6.76 1.18; 6.69 2.22; 6.68 0.97; 6.67 0.88; 5.45 10.12; 4.19 8.35; 4.17 16.00; 4.16 6.70; 4.16 10.13; 4.15 3.31; 3.68 0.88; 3.29 1.63; 3.17 7.82; 3.06 7.96; 2.96 8.28; 2.89 0.74; 2.84 7.25; 2.82 14.80; 2.81 8.89; 2.80 2.28; 2.77 0.72; 2.67 0.55; 2.47 0.40; 2.46 0.32; 2.32 3.06; 2.16 501.04; 2.11 9.58; 2.11 9.73; 2.10 11.02; 2.09 9.42; 2.08 12.19; 2.08 9.37; 2.07 9.56; 2.06 5.49; 2.05 5.26; 2.02 1.40; 1.96 90.22; 1.96 17.48; 1.95 147.07; 1.95 278.25; 1.94 400.28; 1.93 276.42; 1.93 142.35; 1.90 5.44; 1.90 4.39; 1.89 9.51; 1.88 7.12; 1.87 9.50; 1.87 7.02; 1.86 8.19; 1.84 3.43; 1.79 1.13; 1.78 1.40; 1.77 2.09; 1.77 2.80; 1.76 2.03; 1.76 1.33; 1.72 0.56; 1.62 0.39; 1.60 0.60; 1.56 0.43; 1.49 0.45; 1.49 0.37; 1.39 0.40; 1.34 0.52; 1.27 4.21; 1.22 0.52; 1.20 0.79; 1.19 0.46; 1.16 0.41; 1.14 1.01; 1.06 1.12; 1.04 2.04; 1.02 1.06; 0.91 2.16; 0.90 0.48; 0.89 0.45; 0.88 0.67; 0.86 0.45; 0.15 0.50; 0.01 5.19; 0.00 127.20; −0.01 4.91; −0.02 0.64; −0.15 0.52

Example No. 38 [CD$_3$CN] 8.43 5.82; 8.43 4.66; 8.09 3.36; 8.09 3.45; 8.09 3.00; 8.09 2.73; 8.08 3.45; 8.08 3.42; 8.07 2.89; 8.07 2.57; 7.86 0.53; 7.85 0.56; 7.45 0.50; 7.44 3.29; 7.43 2.06; 7.42 4.25; 7.42 3.09; 7.42 4.02; 7.42 5.23; 7.41 4.19; 7.40 5.47; 7.39 3.65; 7.39 0.61; 7.33 0.43; 7.33 0.45; 7.31 1.56; 7.31 4.18; 7.30 4.18; 7.30 2.88; 7.29 6.18; 7.29 5.81; 7.28 0.64; 7.07 0.56; 7.06 3.68; 7.06 1.20; 7.05 1.48; 7.04 6.62; 7.04 1.30; 7.02 1.13; 7.02 3.05; 7.01 0.33; 6.67 2.18; 6.66 2.39; 6.65 4.25; 6.65 4.85; 6.64 2.38; 6.64 2.95; 6.62 3.88; 6.62 4.25; 6.61 3.66; 6.61 3.23; 6.61 3.23; 6.61 3.31; 6.60 2.87; 6.36 0.48; 6.36 0.54; 6.35 0.45; 6.35 0.55; 6.33 0.78; 5.45 2.73; 4.78 0.38; 4.18 2.76; 4.17 4.19; 4.16 5.20; 4.15 6.54; 4.15 3.47; 4.14 3.50; 4.07 0.51; 4.05 0.54; 3.06 16.00; 3.05 14.00; 2.97 13.85; 2.97 11.10; 2.96 1.38; 2.89 0.35; 2.84 0.36; 2.81 2.43; 2.81 3.50; 2.80 5.03; 2.79 5.97; 2.78 3.16; 2.77 3.43; 2.76 0.73; 2.16 496.75; 2.13 3.97; 2.12 2.23; 2.11 2.30; 2.11 2.49; 2.10 2.59; 2.10 2.28; 2.09 2.34; 2.08 3.59; 2.07 4.48; 2.06 3.86; 2.04 1.81; 2.04 1.54; 1.99 0.78; 1.97 5.39; 1.96 104.98; 1.96 9.99; 1.95 72.03; 1.95 135.24; 1.94 193.59; 1.93 132.82; 1.93 67.88; 1.89 1.67; 1.89 2.27; 1.88 3.21; 1.87 4.48; 1.85 4.09; 1.85 3.03; 1.84 2.96; 1.83 1.25; 1.83 1.08; 1.79 0.75; 1.78 0.56; 1.77 0.90; 1.77 1.23; 1.76 0.89; 1.76 0.52; 1.27 1.10; 1.22 0.72; 1.20 1.38; 1.19 0.73; 0.91 1.02; 0.01 2.42; 0.00 61.98; −0.01 2.38

Example No. 39 [CD$_3$CN] 8.43 5.24; 8.09 3.23; 8.09 3.08; 8.08 3.22; 8.08 3.19; 7.77 0.33; 7.76 0.35; 7.44 0.38; 7.43 3.36; 7.43 1.23; 7.42 3.69; 7.42 1.57; 7.42 1.56; 7.42 3.76; 7.41 1.32; 7.41 3.55; 7.40 0.41; 7.13 0.35; 7.11 0.65; 7.10 0.34; 7.06 0.45; 7.06 3.80; 7.06 1.15; 7.05 1.26; 7.04 6.98; 7.04 1.20; 7.03 1.12; 7.03 3.43; 7.02 0.35; 6.65 2.80; 6.64 3.20; 6.64 2.77; 6.63 3.12; 6.61 3.28; 6.61 3.80; 6.60 3.33; 6.60 2.96; 6.30 0.48; 4.16 2.66; 4.15 4.67; 4.14 2.67; 4.09 0.44; 3.06 16.00; 2.97 15.08; 2.96 0.39; 2.80 2.45; 2.79 4.77; 2.78 2.61; 2.17 1355.00; 2.14 0.68; 2.09 0.83; 2.08 0.66; 2.08 1.57; 2.07 1.42; 2.07 2.38; 2.06 2.22; 2.06 3.39; 2.05 3.14; 2.05 2.28; 2.04 1.13; 1.97 13.95; 1.96 12.79; 1.95 15.39; 1.95 165.58; 1.95 329.59; 1.94 489.99; 1.94 325.35; 1.93 155.14; 1.93 4.91; 1.92 2.32; 1.88 1.00; 1.87 0.70; 1.87 2.23; 1.86 1.48; 1.86 2.07; 1.85 1.53; 1.85 1.99; 1.84 0.74; 1.84 1.68; 1.83 1.96; 1.83 2.79; 1.82 1.99; 1.82 1.02; 1.44 5.93; 1.27 1.08; 1.11 0.55; 0.91 1.77; 0.01 1.11; 0.00 43.04; −0.01 1.34

Example No. 40 [DMSO-D$_6$] 10.36 4.02; 8.15 4.48; 8.13 4.63; 8.09 4.10; 7.46 0.33; 7.46 3.35; 7.45 1.36; 7.44 3.80; 7.43 4.54; 7.43 1.68; 7.42 4.10; 7.41 0.53; 7.24 0.47; 7.24 4.14; 7.23 1.29; 7.22 1.46; 7.21 7.43; 7.21 1.47; 7.20 1.15; 7.19 3.52; 7.18 0.34; 6.76 3.13; 6.76 3.12; 6.75 3.10; 6.74 3.15; 4.20 2.51; 4.18 4.06; 4.16 2.62; 3.36 405.89; 3.34

0.50; 3.06 2.19; 3.04 3.78; 3.02 2.66; 2.67 0.72; 2.65 2.08; 2.63 2.82; 2.61 1.78; 2.59 0.58; 2.52 17.00; 2.52 23.32; 2.51 16.38; 2.40 1.88; 2.39 6.33; 2.37 6.52; 2.35 2.11; 2.00 0.40; 1.10 0.39; 1.07 7.47; 1.05 16.00; 1.03 7.16

Example No. 41 [DMSO-$D_6$] 8.44 5.92; 8.43 3.68; 8.43 3.83; 8.42 6.02; 7.28 4.34; 7.27 2.33; 7.26 6.88; 7.19 5.40; 7.17 3.72; 7.15 6.23; 7.15 3.84; 7.14 5.91; 4.18 2.47; 4.14 2.52; 4.10 0.66; 4.06 0.64; 4.04 1.87; 4.02 1.90; 4.00 0.65; 3.31 284.17; 3.07 2.21; 3.06 3.49; 3.04 2.58; 2.89 0.82; 2.73 0.65; 2.67 0.36; 2.67 0.46; 2.67 0.34; 2.64 0.79; 2.62 2.05; 2.61 2.87; 2.59 1.80; 2.57 0.72; 2.54 0.64; 2.51 24.14; 2.50 45.26; 2.50 59.28; 2.50 40.96; 2.49 19.54; 2.33 16.00; 1.99 8.22; 1.91 0.81; 1.19 2.27; 1.17 4.49; 1.16 2.23; 1.07 0.48; 0.92 0.40; 0.01 0.62; 0.00 13.23; −0.01 0.53

Example No. 42 [DMSO-$D_6$] 8.73 10.76; 8.73 7.01; 8.72 7.15; 8.72 11.09; 8.48 14.87; 8.48 9.20; 8.47 9.36; 8.47 15.18; 8.43 0.36; 8.42 0.35; 7.83 12.62; 7.83 8.14; 7.82 7.99; 7.82 12.12; 7.72 3.32; 7.70 12.43; 7.67 2.99; 7.65 6.03; 7.63 4.72; 7.61 4.80; 7.59 1.74; 7.56 0.33; 7.26 0.45; 7.18 16.00; 7.18 9.84; 7.17 9.90; 7.17 15.59; 7.15 0.51; 7.15 0.33; 7.13 0.42; 4.22 5.88; 4.21 8.79; 4.19 6.03; 4.16 0.35; 4.10 0.74; 4.04 0.45; 4.02 0.46; 3.91 0.50; 3.61 0.33; 3.60 0.34; 3.59 0.37; 3.56 0.39; 3.54 0.47; 3.53 0.47; 3.51 0.57; 3.48 0.62; 3.47 0.70; 3.31 2137.05; 3.29 34.04; 3.08 5.11; 3.07 8.13; 3.05 6.08; 2.89 0.32; 2.73 0.39; 2.68 0.95; 2.67 1.72; 2.67 2.34; 2.67 2.74; 2.64 4.95; 2.63 6.91; 2.61 4.43; 2.59 1.89; 2.54 3.03; 2.52 8.68; 2.51 111.92; 2.51 208.40; 2.50 272.43; 2.50 187.67; 2.49 89.14; 2.34 0.67; 2.33 1.40; 2.33 2.48; 2.18 0.46; 2.07 1.06; 1.99 1.30; 1.91 1.87; 1.24 0.78; 1.19 0.39; 1.18 0.79; 1.16 0.49; 1.07 2.34; 0.89 0.33; 0.00 1.84

Example No. 43 [DMSO-$D_6$] 8.55 3.50; 8.54 2.14; 8.54 2.20; 8.53 3.62; 7.95 1.92; 7.32 1.62; 7.31 0.73; 7.30 1.85; 7.30 2.22; 7.29 0.85; 7.28 2.01; 7.15 2.10; 7.14 0.72; 7.13 0.95; 7.13 4.57; 7.12 4.66; 7.12 2.89; 7.11 2.49; 7.11 4.14; 7.10 1.97; 4.35 1.40; 4.34 1.24; 4.33 1.32; 3.33 69.85; 2.89 16.00; 2.73 13.14; 2.73 12.88; 2.72 1.37; 2.70 1.46; 2.51 4.08; 2.51 7.74; 2.50 10.22; 2.50 7.17; 2.49 3.53; 1.91 2.30; 1.85 1.02; 1.84 0.96; 1.77 0.92; 1.76 1.09; 1.65 0.89; 1.63 1.10

Example No. 44 [DMSO-$D_6$] 8.73 2.30; 8.73 1.57; 8.72 1.56; 8.72 2.40; 8.47 11.10; 8.47 7.35; 8.46 7.60; 8.46 11.41; 8.44 0.39; 8.33 0.70; 8.31 0.73; 7.95 0.47; 7.91 0.45; 7.83 2.92; 7.83 1.97; 7.82 1.85; 7.82 2.75; 7.60 0.35; 7.59 0.34; 7.56 0.33; 7.55 0.40; 7.54 0.40; 7.53 0.42; 7.53 0.45; 7.51 0.37; 7.49 0.40; 7.47 0.36; 7.44 1.68; 7.43 2.92; 7.42 3.90; 7.41 4.18; 7.39 2.91; 7.38 1.26; 7.36 0.53; 7.35 0.99; 7.33 0.52; 7.32 0.43; 7.31 0.42; 7.25 0.38; 7.24 0.48; 7.21 6.27; 7.21 7.51; 7.19 10.12; 7.18 6.82; 7.18 15.23; 7.17 9.62; 7.16 10.33; 7.16 16.00; 7.15 2.33; 7.14 1.12; 7.12 0.61; 7.12 0.85; 4.22 0.38; 4.21 5.27; 4.19 8.07; 4.17 5.51; 4.10 1.27; 4.04 0.44; 4.02 0.49; 4.00 0.33; 3.91 2.04; 3.62 0.32; 3.58 0.38; 3.58 0.38; 3.57 0.41; 3.56 0.47; 3.54 0.55; 3.52 0.62; 3.51 0.74; 3.44 1.00; 3.32 2064.37; 3.22 0.68; 3.15 0.35; 3.07 4.82; 3.06 7.57; 3.04 5.62; 2.89 2.26; 2.73 1.91; 2.67 1.46; 2.67 1.20; 2.66 0.89; 2.65 1.78; 2.63 4.63; 2.62 6.32; 2.60 4.05; 2.58 1.71; 2.56 0.76; 2.54 1.97; 2.51 82.20; 2.51 153.58; 2.50 201.23; 2.50 140.41; 2.49 68.02; 2.33 0.90; 2.33 1.28; 2.32 0.88; 2.28 0.42; 2.07 0.72; 1.99 1.57; 1.91 14.77; 1.66 0.51; 1.61 0.45; 1.40 5.58; 1.37 0.36; 1.30 0.41; 1.28 0.34; 1.26 0.37; 1.24 1.07; 1.19 0.65; 1.18 1.13; 1.16 5.74; 1.12 0.42; 1.09 0.77; 1.07 15.92; 1.06 0.96; 1.04 0.62; 0.91 0.32; 0.89 0.42; 0.85 0.42; 0.83 0.37; 0.01 0.36; 0.00 6.83

Example No. 45 [DMSO-$D_6$] 8.12 0.72; 8.10 0.72; 7.45 0.62; 7.43 0.71; 7.42 0.80; 7.42 0.32; 7.41 0.71; 7.26 0.77; 7.24 0.32; 7.24 1.31; 7.22 0.58; 7.07 0.42; 7.06 0.33; 7.06 0.32; 7.05 0.40; 6.85 0.92; 4.20 0.54; 4.18 0.82; 4.17 0.54; 3.32 27.82; 3.12 0.48; 3.10 0.77; 3.08 0.56; 2.64 0.45; 2.62 0.62; 2.60 0.39; 2.51 2.57; 2.51 4.72; 2.50 6.09; 2.50 4.24; 2.49 2.06; 1.99 0.58; 1.18 0.33; 1.16 0.93; 1.07 16.00; 0.00 0.34

Example No. 46 [DMSO-$D_6$] 8.48 4.80; 8.47 3.50; 8.46 3.35; 8.46 4.96; 7.83 0.35; 7.82 0.35; 7.58 2.60; 7.57 3.11; 7.57 2.95; 7.56 3.23; 7.55 0.43; 7.47 2.82; 7.47 3.29; 7.46 2.90; 7.46 2.71; 7.45 0.41; 7.22 6.37; 7.21 4.15; 7.21 4.08; 7.20 6.43; 7.16 0.33; 7.12 3.22; 7.12 3.27; 7.11 3.16; 7.10 3.15; 7.07 0.34; 4.19 0.38; 4.17 2.83; 4.15 4.15; 4.14 2.89; 4.10 0.51; 4.06 1.24; 4.04 3.65; 4.02 3.67; 4.00 1.27; 3.31 237.71; 3.06 2.38; 3.04 3.72; 3.02 2.85; 2.67 0.41; 2.66 0.33; 2.65 0.36; 2.64 1.07; 2.62 2.39; 2.60 3.18; 2.58 2.01; 2.57 0.84; 2.54 0.51; 2.51 16.14; 2.50 30.00; 2.50 39.24; 2.50 27.23; 2.49 13.12; 1.99 16.00; 1.91 5.55; 1.24 0.51; 1.19 4.51; 1.17 8.85; 1.16 4.44; 1.07 0.50; 0.06 0.61; 0.01 0.39; 0.00 7.70

Example No. 47 [CD$_3$CN] 8.89 2.33; 8.86 0.35; 8.20 5.77; 8.19 9.08; 8.18 6.36; 8.18 6.14; 8.18 5.51; 8.14 7.12; 8.06 0.35; 7.58 4.64; 7.58 4.85; 7.57 6.50; 7.57 6.22; 7.50 5.90; 7.49 5.94; 7.49 4.73; 7.48 4.25; 7.47 1.28; 7.46 6.10; 7.46 2.97; 7.45 6.65; 7.44 6.96; 7.43 2.86; 7.43 6.45; 7.42 1.11; 7.40 0.39; 7.30 0.33; 7.08 6.81; 7.07 2.15; 7.06 2.74; 7.06 12.48; 7.05 2.65; 7.04 2.15; 7.03 5.97; 7.03 0.82; 6.85 5.42; 6.85 5.42; 6.84 5.34; 6.84 5.28; 5.45 16.00; 4.19 5.51; 4.17 9.99; 4.16 5.76; 4.09 0.35; 4.07 1.06; 4.05 1.10; 4.03 0.36; 3.61 0.33; 2.88 5.15; 2.86 10.23; 2.85 5.40; 2.47 0.38; 2.46 0.36; 2.40 0.38; 2.35 0.42; 2.28 0.60; 2.27 0.68; 2.25 0.83; 2.15 1423.35; 2.11 8.07; 2.11 8.55; 2.10 7.55; 2.09 8.22; 2.09 5.22; 2.08 5.66; 2.06 3.05; 2.04 1.40; 2.03 1.38; 2.00 2.03; 1.97 11.74; 1.96 113.50; 1.96 35.82; 1.95 189.71; 1.95 349.30; 1.94 485.27; 1.93 334.49; 1.93 171.63; 1.90 7.16; 1.90 5.07; 1.89 5.99; 1.87 4.65; 1.86 1.99; 1.82 0.69; 1.79 0.92; 1.78 1.43; 1.77 2.41; 1.77 2.96; 1.76 2.33; 1.76 1.31; 1.72 0.66; 1.69 0.94; 1.67 0.68; 1.65 0.63; 1.62 0.57; 1.59 0.41; 1.57 0.35; 1.55 0.33; 1.51 0.41; 1.50 1.20; 1.49 0.67; 1.47 0.35; 1.45 0.73; 1.45 0.39; 1.44 0.42; 1.42 0.35; 1.40 0.34; 1.39 0.32; 1.36 0.32; 1.35 0.34; 1.34 0.40; 1.32 0.33; 1.32 1.24; 1.27 2.73; 1.23 0.42; 1.22 1.69; 1.20 3.29; 1.19 1.80; 1.17 0.58; 1.13 0.48; 1.11 0.63; 1.10 0.46; 1.07 0.37; 1.03 0.36; 1.02 0.35; 0.98 0.47; 0.95 0.49; 0.91 1.72; 0.88 0.60; 0.86 0.57; 0.00 29.99

Example No. 48 [DMSO-$D_6$] 7.85 2.31; 7.83 2.30; 7.44 0.61; 7.42 16.00; 7.41 0.46; 7.40 0.41; 7.40 0.42; 6.27 2.89; 6.23 1.95; 6.22 1.68; 6.21 2.13; 6.21 2.14; 6.21 1.50; 6.19 1.33; 4.17 1.59; 4.15 2.49; 4.13 1.60; 4.04 0.56; 4.02 0.55; 3.89 0.54; 3.87 0.84; 3.86 0.81; 3.84 0.52; 3.57 0.37; 3.41 0.33; 3.39 0.47; 3.38 0.63; 3.31 414.21; 3.29 3.89; 2.99 5.49; 2.98 2.28; 2.96 1.59; 2.67 0.37; 2.63 0.53; 2.61 1.35; 2.59 1.82; 2.57 1.22; 2.55 0.58; 2.54 0.53; 2.51 20.36; 2.50 37.33; 2.50 48.05; 2.50 33.38; 2.49 16.08; 2.07 0.51; 1.99 2.34; 1.24 0.36; 1.19 0.72; 1.17 1.41; 1.16 0.79; 1.10 15.32; 1.08 15.16; 1.04 0.40; 1.01 0.60; 0.99 0.55; 0.00 2.20

Example No. 50 [CD$_3$CN] 9.19 0.34; 8.14 1.01; 8.13 1.01; 8.07 1.21; 7.41 0.71; 7.41 0.47; 7.41 1.01; 7.40 1.11; 7.40 1.05; 7.32 0.37; 7.32 0.37; 7.31 1.42; 7.30 2.07; 7.30 2.07; 6.81 0.79; 6.80 0.79; 6.80 0.78; 6.80 0.77; 4.18 0.91; 4.17 1.68; 4.16 0.96; 4.02 0.46; 2.84 0.86; 2.83 1.73; 2.82 0.94; 2.21 0.34; 2.21 0.36; 2.19 434.90; 2.16 0.56; 2.10 0.58; 2.09 0.52; 2.09 1.02; 2.08 0.56; 2.08 1.60; 2.07 0.33; 2.06 0.43; 2.05 0.43; 1.97 1.35; 1.97 168.54; 1.96 5.33; 1.95 5.13; 1.95 41.91; 1.95 76.84; 1.94 112.13; 1.94 75.93; 1.93 38.25; 1.93 0.78; 1.90 0.36; 1.89 0.81; 1.88 0.53; 1.88 0.85; 1.87 0.52; 1.87 0.72; 1.85 0.99; 1.83 0.46; 1.83 0.67; 1.82 0.46; 1.41 16.00; 1.27 0.48; 0.00 5.09

Example No. 51 [CD$_3$CN] 8.91 2.39; 8.19 12.95; 8.19 8.38; 8.18 7.52; 8.18 9.08; 8.18 7.33; 8.16 6.98; 8.15 7.62; 8.15 7.95; 7.58 6.53; 7.58 6.42; 7.57 8.01; 7.57 7.72; 7.50 7.61; 7.49 7.68; 7.49 6.31; 7.49 6.13; 7.47 0.34; 7.46 0.33; 7.44 1.08; 7.44 7.16; 7.43 4.64; 7.43 4.96; 7.43 2.36; 7.43 9.55; 7.42 8.66; 7.42 0.90; 7.41 0.36; 7.34 1.01; 7.33 0.69; 7.33 2.74; 7.32 1.71; 7.32 8.28; 7.32 6.68; 7.31 15.75; 7.31 16.00; 7.30 2.36; 7.30 2.28; 7.30 1.39; 7.29 0.41; 7.29 0.37; 6.85 6.79; 6.84 6.68; 6.84 6.81; 6.83 6.76; 5.45 0.63; 4.19 5.98; 4.18 10.88; 4.17 6.24; 4.06 0.69; 4.05 0.72; 3.27 0.53; 2.88 5.68; 2.87 11.22; 2.86 6.08; 2.19 573.93; 2.12 2.37; 2.11 1.86; 2.11 3.96; 2.10 3.63; 2.10 5.91; 2.09 3.61; 2.09 4.37; 2.08 1.60; 2.08 5.98; 2.06 1.13; 2.06 1.91; 2.05 2.65; 2.05 1.83; 2.04 1.02; 1.99 0.35; 1.97 7.01; 1.97 691.81; 1.96 14.81; 1.95 15.36; 1.95 162.44; 1.95 294.97; 1.94 434.82; 1.94 299.80; 1.93 150.79; 1.93 4.41; 1.93 2.05; 1.91 2.19; 1.91 1.50; 1.90 5.02; 1.90 3.20; 1.89 4.84; 1.89 3.04; 1.88 4.39; 1.88 1.30; 1.87 1.63; 1.85 3.96; 1.84 0.96; 1.83

-continued 1.78; 1.83 2.54; 1.82 1.74; 1.82 0.93; 1.38 0.72; 1.34 0.34; 1.28 0.72; 1.27 2.14; 1.22 1.05; 1.20 1.81; 1.19 0.98; 1.11 0.48; 0.91 1.94; 0.88 0.47; 0.00 7.31
Example No. 52 [DMSO-D$_6$] 7.83 2.30; 7.82 2.30; 7.45 2.09; 7.45 0.96; 7.44 2.42; 7.43 2.61; 7.42 1.06; 7.42 2.30; 7.22 0.43; 7.21 2.47; 7.21 0.87; 7.19 1.08; 7.19 4.29; 7.18 1.00; 7.17 0.78; 7.17 1.98; 6.26 2.96; 6.22 2.03; 6.21 1.78; 6.20 2.00; 6.20 1.79; 6.18 1.36; 6.16 1.36; 4.16 1.59; 4.14 2.51; 4.13 1.61; 3.88 0.54; 3.86 0.83; 3.84 0.82; 3.83 0.54; 3.31 221.49; 3.29 1.63; 3.00 1.39; 2.98 2.33; 2.96 1.66; 2.63 0.51; 2.61 1.36; 2.59 1.83; 2.57 1.18; 2.55 0.48; 2.51 9.30; 2.50 17.10; 2.50 22.16; 2.50 15.45; 2.49 7.50; 2.08 11.04; 1.99 1.28; 1.19 0.41; 1.18 0.74; 1.16 0.39; 1.10 16.00; 1.08 15.81; 1.01 0.43; 0.99 0.41; 0.00 1.00
Example No. 53 [DMSO-D$_6$] 7.86 8.61; 7.85 8.75; 7.66 0.52; 7.66 0.52; 7.66 0.61; 7.65 0.54; 7.54 0.61; 7.53 0.52; 7.53 0.75; 7.52 0.74; 7.50 8.18; 7.49 9.36; 7.48 8.86; 7.48 9.40; 7.42 0.67; 7.42 0.63; 7.41 0.58; 7.41 0.61; 7.36 8.91; 7.35 9.69; 7.35 8.61; 7.35 7.93; 7.14 10.18; 7.13 9.95; 7.12 9.72; 7.12 9.31; 6.33 16.00; 6.33 13.52; 6.32 6.73; 6.31 9.35; 6.31 7.01; 6.30 1.55; 5.88 0.56; 5.84 13.46; 4.17 0.38; 4.12 7.18; 4.11 13.20; 4.09 7.17; 4.06 0.97; 4.05 1.37; 4.04 0.78; 4.03 0.88; 4.02 0.61; 4.02 0.34; 4.01 0.39; 4.00 0.42; 3.99 0.37; 3.96 0.34; 3.93 0.41; 3.92 0.41; 3.91 0.40; 3.90 0.47; 3.88 0.42; 3.87 0.41; 3.86 0.38; 3.82 0.45; 3.82 0.51; 3.81 0.49; 3.80 0.45; 3.78 0.46; 3.75 0.59; 3.69 0.67; 3.68 0.63; 3.63 0.81; 3.61 0.89; 3.59 0.96; 3.57 3.27; 3.55 1.27; 3.51 1.52; 3.33 3424.42; 3.20 0.61; 3.19 0.55; 3.18 0.67; 3.16 0.36; 2.77 0.66; 2.75 1.03; 2.74 0.84; 2.71 6.56; 2.69 13.04; 2.68 7.88; 2.61 0.48; 2.61 0.51; 2.54 2.77; 2.51 94.24; 2.51 172.97; 2.50 224.40; 2.50 156.69; 2.49 76.49; 2.44 0.38; 2.33 1.07; 2.33 1.44; 2.32 1.04; 2.09 0.40; 2.07 3.85; 2.06 0.39; 2.04 1.93; 2.02 4.58; 2.01 5.21; 2.01 6.80; 2.00 5.50; 1.99 5.59; 1.99 4.48; 1.98 2.41; 1.96 0.60; 191 0.51; 1.81 6.10; 1.80 5.44; 1.80 6.62; 1.78 5.12; 1.40 0.32; 1.24 0.47; 1.19 0.47; 1.18 0.79; 1.16 0.52; 0.00 3.11
Example No. 54 [DMSO-D$_6$] 8.13 8.66; 8.12 8.74; 8.10 0.33; 7.92 0.41; 7.90 0.41; 7.75 0.34; 7.47 2.03; 7.45 4.39; 7.43 4.74; 7.43 3.40; 7.41 2.68; 7.40 0.68; 7.36 0.35; 7.26 0.41; 7.24 1.76; 7.24 2.49; 7.23 3.23; 7.22 16.00; 7.21 14.95; 7.20 7.22; 7.19 10.48; 7.19 5.28; 7.12 0.63; 7.10 4.07; 7.09 5.29; 7.09 4.31; 7.08 4.10; 7.08 4.89; 7.07 3.60; 6.89 11.11; 6.39 0.42; 6.39 0.46; 4.21 6.84; 4.20 10.38; 4.18 6.91; 3.90 0.73; 3.51 0.37; 3.46 0.40; 3.44 0.39; 3.43 0.51; 3.42 0.53; 3.30 747.94; 3.28 10.29; 3.17 0.35; 3.12 6.19; 3.10 9.77; 3.08 7.05; 2.91 0.42; 2.67 1.55; 2.66 1.55; 2.66 2.44; 2.64 5.91; 2.62 8.16; 2.60 5.39; 2.58 2.32; 2.51 81.79; 2.50 146.04; 2.50 185.15; 2.50 128.60; 2.33 0.97; 2.33 1.28; 2.29 0.38; 2.27 0.34; 2.07 1.84; 1.99 0.44; 1.40 1.95; 1.35 0.33; 1.30 1.39; 1.26 0.42; 1.24 1.25; 1.16 0.97; 1.07 4.07; 0.00 32.19; −0.01 1.43
Example No. 55 [CD$_3$CN] 9.18 0.36; 8.16 0.92; 8.15 0.94; 8.06 1.15; 7.44 0.99; 7.43 0.45; 7.42 1.08; 7.41 1.07; 7.41 0.47; 7.40 0.97; 7.07 1.12; 7.05 1.92; 7.03 0.35; 7.02 0.89; 6.82 0.87; 6.82 0.79; 6.81 0.83; 6.80 0.81; 4.18 0.90; 4.16 1.62; 4.15 0.89; 3.95 2.02; 2.84 0.91; 2.83 1.69; 2.81 0.91; 2.47 0.33; 2.16 856.19; 2.13 4.46; 2.12 1.58; 2.11 1.73; 2.11 1.82; 2.10 1.68; 2.09 1.31; 2.08 1.44; 2.08 1.12; 2.07 1.19; 2.05 0.84; 2.04 0.69; 1.96 389.96; 1.95 62.01; 1.95 106.27; 1.94 145.13; 1.93 99.91; 1.93 51.45; 1.89 1.30; 1.88 0.96; 1.88 1.09; 1.86 0.82; 1.79 2.20; 1.78 0.40; 1.77 0.59; 1.77 0.86; 1.76 0.60; 1.76 0.34; 1.41 16.00; 1.27 0.40; 0.91 0.75; 0.01 0.69; 0.00 15.01; −0.01 0.74
Example No. 56 [DMSO-D$_6$] 7.86 2.18; 7.85 2.22; 7.42 0.61; 7.41 0.73; 7.40 1.20; 7.39 1.23; 7.39 0.86; 7.38 0.78; 7.25 1.11; 7.25 1.66; 7.25 1.28; 7.24 1.01; 7.24 1.46; 7.24 1.10; 7.20 0.76; 7.19 0.79; 7.19 0.98; 7.19 0.84; 7.18 0.73; 7.18 0.82; 7.17 0.97; 7.17 0.92; 7.17 0.79; 7.17 0.69; 7.16 0.46; 7.16 0.44; 7.15 1.12; 7.15 0.80; 7.14 0.54; 7.14 0.55; 7.14 0.40; 7.13 0.38; 6.28 2.62; 6.26 1.27; 6.25 1.32; 6.24 1.91; 6.23 1.72; 6.23 1.86; 6.23 1.74; 4.17 1.54; 4.16 2.37; 4.15 1.59; 4.03 0.41; 4.02 0.41; 3.88 0.36; 3.87 0.57; 3.86 0.58; 3.85 0.37; 3.35 80.05; 3.33 1.48; 2.99 1.35; 2.98 2.08; 2.96 1.57; 2.62 0.62; 2.60 1.27; 2.59 1.73; 2.58 1.05; 2.57 0.37; 2.51 5.24; 2.51 11.62; 2.50 16.15; 2.50 11.61; 2.50 5.26; 2.08 0.46; 1.99 1.79; 1.19 0.53; 1.17 1.01; 1.16 0.50; 1.10 16.00; 1.09 15.96; 1.01 0.72; 1.00 0.72; 0.00 6.89
Example No. 57 [CD$_3$CN] 8.70 7.26; 8.70 4.26; 8.69 4.42; 8.68 7.66; 8.67 0.53; 8.65 0.38; 8.63 0.56; 8.62 0.39; 8.59 1.12; 8.58 0.71; 8.57 0.83; 8.57 1.19; 7.57 0.54; 7.55 0.66; 7.50 8.38; 7.49 4.92; 7.48 8.26; 7.42 1.10; 7.42 0.64; 7.41 1.01; 7.40 0.43; 7.39 0.58; 7.37 0.41; 7.26 0.63; 7.25 0.58; 6.80 6.76; 6.79 7.20; 6.78 0.73; 6.77 1.57; 6.76 1.09; 6.48 6.83; 6.47 6.42; 6.45 0.32; 6.44 0.33; 6.44 0.33; 6.43 0.35; 6.39 0.99; 6.38 0.99; 5.48 5.89; 5.00 2.53; 4.99 2.68; 4.97 2.81; 4.97 2.65; 4.68 0.43; 4.68 0.51; 4.67 0.43; 4.67 0.36; 4.51 0.78; 4.50 1.76; 4.49 0.99; 4.48 1.61; 4.47 3.31; 4.45 1.63; 4.42 1.76; 4.40 1.90; 4.39 2.38; 4.38 2.51; 4.37 1.06; 4.36 1.13; 4.35 1.01; 4.34 0.93; 4.33 0.64; 4.32 0.68; 4.31 0.50; 4.30 0.46; 4.29 0.35; 4.27 0.62; 4.25 0.35; 4.12 0.52; 4.10 1.47; 4.08 1.56; 4.06 0.56; 3.58 0.33; 3.57 0.41; 3.55 0.39; 3.46 0.40; 3.44 0.41; 3.18 0.62; 3.16 0.59; 3.13 0.43; 3.12 0.48; 2.88 0.58; 2.88 0.66; 2.87 1.17; 2.86 1.13; 2.86 0.61; 2.85 1.18; 2.84 0.94; 2.83 1.75; 2.83 1.72; 2.82 0.84; 2.81 0.75; 2.77 0.95; 2.75 0.96; 2.75 1.09; 2.73 1.53; 2.72 0.94; 2.72 0.64; 2.71 1.35; 2.69 0.64; 2.69 0.62; 2.67 0.45; 2.50 0.60; 2.42 0.34; 2.39 0.37; 2.36 0.36; 2.35 0.65; 2.34 0.60; 2.33 0.49; 2.32 0.75; 2.30 1.06; 2.25 144.20; 2.24 210.43; 2.16 1.66; 2.15 0.72; 2.14 0.91; 2.14 1.06; 2.13 0.75; 2.12 0.55; 2.01 2.16; 2.00 8.74; 1.99 191.01; 1.99 6.63; 1.98 40.96; 1.98 75.96; 1.97 108.11; 1.96 73.24; 1.96 37.20; 1.83 0.41; 1.82 1.25; 1.81 0.44; 1.80 0.62; 1.80 0.77; 1.79 0.54; 1.79 0.33; 1.30 1.21; 1.28 0.49; 1.25 2.02; 1.23 3.66; 1.21 2.02; 1.19 0.34; 1.00 1.36; 0.98 2.76; 0.97 1.40; 0.96 1.39; 0.94 2.94; 0.92 1.34; 0.03 0.38
Example No. 58 [CD$_3$CN] 8.64 2.38; 8.18 9.09; 8.17 9.01; 8.04 4.38; 7.36 6.82; 7.35 8.54; 7.35 7.26; 7.34 9.17; 7.31 8.37; 7.31 8.80; 7.30 7.04; 7.30 6.78; 7.18 8.82; 7.18 8.56; 7.17 8.20; 7.17 7.67; 6.90 8.19; 6.89 8.10; 6.89 8.21; 6.89 7.98; 5.45 0.99; 4.15 8.52; 4.14 15.37; 4.13 8.72; 2.78 8.12; 2.77 16.00; 2.76 8.68; 2.21 0.60; 2.20 0.48; 2.19 1.42; 2.16 872.77; 2.14 1.02; 2.10 76.19; 2.09 2.51; 2.08 1.78; 2.08 5.50; 2.07 4.41; 2.07 7.95; 2.06 5.30; 2.06 7.22; 2.05 3.46; 2.05 2.48; 2.05 2.83; 1.99 0.42; 1.97 2.84; 1.97 264.26; 1.96 15.21; 1.95 17.71; 1.95 146.93; 1.95 270.28; 1.94 396.53; 1.94 268.16; 1.93 133.53; 1.92 0.44; 1.92 0.39; 1.91 0.38; 1.87 2.67; 1.87 1.70; 1.86 6.86; 1.86 4.14; 1.85 7.01; 1.85 3.94; 1.84 6.02; 1.84 1.64; 1.83 2.87; 1.83 2.29; 1.82 1.52; 1.82 0.81; 1.27 0.69; 0.01 0.95; 0.00 31.85; −0.01 0.87
Example No. 59 [CD$_3$CN] 8.57 1.21; 8.17 3.52; 8.16 3.62; 8.07 3.46; 7.36 2.32; 7.35 2.95; 7.35 2.69; 7.34 3.13; 7.31 3.03; 7.31 3.45; 7.30 2.75; 7.30 2.66; 7.18 3.18; 7.18 3.36; 7.17 2.94; 7.17 3.01; 6.89 2.95; 6.88 3.11; 6.88 2.90; 6.87 3.04; 5.45 3.47; 4.15 3.33; 4.14 6.15; 4.13 3.44; 4.08 0.99; 4.06 3.02; 4.05 3.07; 4.04 1.02; 2.79 3.18; 2.78 6.32; 2.77 3.41; 2.42 2.26; 2.41 6.99; 2.40 7.18; 2.39 2.42; 2.16 57.06; 2.09 1.30; 2.08 5.07; 2.07 4.11; 2.06 2.13; 2.06 2.86; 2.05 1.64; 2.05 1.49; 2.04 0.56; 1.99 0.67; 1.98 0.63; 1.97 19.43; 1.97 586.60; 1.96 10.34; 1.96 8.32; 1.95 9.95; 1.95 65.34; 1.95 118.42; 1.94 170.03; 1.94 118.14; 1.93 60.29; 1.88 1.04; 1.87 0.72; 1.87 2.74; 1.86 1.77; 1.86 2.85; 1.85 4.62; 1.85 2.57; 1.84 0.88; 1.83 0.70; 1.83 1.00; 1.82 0.68; 1.82 0.34; 1.27 0.36; 1.22 3.56; 1.20 7.06; 1.19 3.52; 1.13 7.88; 1.12 16.00; 1.11 7.61; 0.01 0.42; 0.00 13.95; −0.01 0.45
Example No. 60 [CD$_3$CN] 8.75 0.39; 8.21 1.41; 8.21 1.42; 8.21 1.39; 8.21 1.46; 8.08 1.43; 7.36 1.16; 7.36 1.43; 7.35 1.37; 7.35 1.65; 7.31 1.36; 7.31 1.50; 7.31 1.29; 7.31 1.25; 7.18 1.54; 7.18 1.49; 7.17 1.37; 7.17 1.33; 6.95 1.37; 6.95 1.37; 6.94 1.33; 6.94 1.34; 5.45 0.77; 4.15 1.26; 4.14 2.29; 4.13 1.34; 4.08 0.55; 4.06 1.68; 4.05 1.67; 4.04 0.57; 3.98 8.38; 3.46 16.00; 2.80 1.20; 2.79 2.38; 2.78 1.30; 2.17 14.59; 2.09 0.45; 2.08 0.35; 2.08 0.83; 2.07 0.75; 2.07 1.25; 2.06 0.79; 2.06 1.02; 2.06 0.51; 2.05 0.45; 2.05 0.53; 2.05 0.53; 1.97 7.67; 1.97 16.34; 1.96 2.15; 1.95 2.09; 1.95 19.24; 1.95 34.64; 1.94 51.63; 1.94 35.91; 1.93 18.25; 1.92 0.38; 1.88 0.42; 1.87 1.05; 1.86 0.67; 1.86 1.03; 1.85 0.68; 1.85 0.97; 1.84 0.33; 1.84 0.39; 1.83 0.34; 1.22 2.21; 1.20 4.18; 1.19 2.18; 0.00 3.45
Example No. 61 [DMSO-D$_6$] 8.10 4.76; 8.10 4.86; 7.43 0.48; 7.42 0.85; 7.42 0.49; 7.42 0.91; 7.41 2.11; 7.41 2.38; 7.41 3.51; 7.40 15.14; 7.40 16.00; 7.39 3.43; 7.39 2.45; 7.38 2.55; 7.38 0.42; 7.38 0.38; 7.37 0.60; 7.07 1.64; 7.07

2.34; 7.07 1.70; 7.07 1.69; 7.06 2.25; 7.06 1.58; 6.85 5.37; 4.20 3.12; 4.19 4.71; 4.18 3.22; 3.38 0.58; 3.38 0.77; 3.38 0.56; 3.37 1.26; 3.35 992.34; 3.33 3.42; 3.32 0.41; 3.12 2.81; 3.11 4.11; 3.10 3.22; 2.64 0.92; 2.63 2.39; 2.62 3.93; 2.61 1.27; 2.61 2.17; 2.59 0.79; 2.54 0.38; 2.52 1.03; 2.52 1.29; 2.52 1.27; 2.51 40.31; 2.51 89.93; 2.50 125.16; 2.50 90.10; 2.50 40.68; 2.39 0.56; 2.39 0.74; 2.38 0.53; 2.08 0.90; 1.99 0.69; 1.17 0.38; 0.00 5.87

Example No. 62 [CD$_3$CN] 8.54 13.69; 8.54 7.82; 8.53 8.02; 8.53 13.64; 7.31 6.31; 7.31 6.26; 7.30 6.64; 7.30 6.44; 7.26 16.00; 7.26 9.18; 7.25 9.20; 7.25 15.58; 6.95 6.21; 6.94 7.63; 6.94 5.84; 6.93 7.53; 6.89 7.27; 6.89 7.53; 6.89 6.07; 6.89 5.75; 5.45 2.59; 4.15 6.33; 4.14 11.20; 4.13 6.60; 2.75 6.07; 2.74 11.71; 2.73 6.51; 2.20 0.49; 2.19 0.68; 2.19 0.60; 2.17 523.59; 2.16 0.50; 2.08 1.91; 2.08 1.37; 2.07 3.62; 2.07 3.10; 2.06 5.83; 2.06 3.58; 2.05 5.08; 2.05 1.37; 2.04 2.30; 1.97 0.32; 1.97 28.74; 1.96 5.43; 1.95 6.64; 1.95 58.15; 1.95 105.93; 1.94 157.71; 1.94 107.34; 1.93 52.87; 1.93 1.19; 1.92 0.46; 1.86 2.22; 1.86 1.22; 1.85 5.44; 1.85 2.99; 1.84 4.53; 1.84 4.86; 1.84 2.86; 1.83 4.94; 1.83 1.28; 1.83 1.13; 1.83 1.27; 1.82 1.81; 1.82 0.35; 1.27 0.42; 1.13 0.59; 0.00 5.72

Example No. 63 [CD$_3$CN] 8.58 0.51; 8.18 1.70; 8.17 1.56; 8.17 1.71; 8.08 1.75; 7.36 1.22; 7.35 1.55; 7.35 1.37; 7.35 1.66; 7.31 1.61; 7.31 1.70; 7.30 1.39; 7.30 1.27; 7.18 1.68; 7.18 1.60; 7.17 1.52; 7.17 1.50; 6.89 1.47; 6.88 1.39; 6.88 1.44; 6.87 1.39; 5.45 0.44; 4.15 1.52; 4.14 2.78; 4.13 1.60; 3.61 0.56; 2.79 1.41; 2.78 2.80; 2.77 1.52; 2.66 0.32; 2.65 0.84; 2.64 1.14; 2.63 0.87; 2.62 0.35; 2.18 415.81; 2.09 0.42; 2.09 0.43; 2.09 0.32; 2.08 0.91; 2.08 0.82; 2.08 0.79; 2.07 1.41; 2.07 0.83; 2.06 1.19; 2.06 0.60; 2.05 0.70; 2.05 0.53; 1.97 0.53; 1.97 60.62; 1.96 3.38; 1.95 3.70; 1.95 32.80; 1.95 60.37; 1.94 88.12; 1.94 59.46; 1.93 30.14; 1.93 0.49; 1.88 0.47; 1.87 1.20; 1.86 0.76; 1.86 1.20; 1.85 0.74; 1.85 1.08; 1.84 0.39; 1.83 0.36; 1.83 0.51; 1.82 0.35; 1.27 0.49; 1.15 16.00; 1.14 15.84; 0.97 0.53; 0.95 0.51; 0.00 5.59

Example No. 64 [CD$_3$CN] 8.58 0.47; 8.18 1.49; 8.18 1.55; 8.17 1.50; 8.17 1.65; 8.08 1.29; 7.35 1.32; 7.35 1.75; 7.35 1.48; 7.34 1.87; 7.31 1.71; 7.31 1.85; 7.30 1.47; 7.30 1.47; 7.18 1.66; 7.18 1.65; 7.17 1.52; 7.17 1.51; 6.90 1.52; 6.89 1.52; 6.89 1.50; 6.88 1.53; 4.15 1.33; 4.14 2.44; 4.13 1.44; 3.27 0.36; 2.79 1.29; 2.78 2.52; 2.77 1.39; 2.25 3.64; 2.24 4.55; 2.16 187.11; 2.13 0.83; 2.11 0.87; 2.10 0.88; 2.09 0.86; 2.09 0.78; 2.08 1.18; 2.08 1.28; 2.07 0.83; 2.07 1.37; 2.06 0.88; 2.06 1.30; 2.06 1.17; 2.05 1.39; 2.05 1.12; 2.04 0.53; 1.97 1.48; 1.97 125.29; 1.96 8.47; 1.95 8.35; 1.95 77.11; 1.95 141.39; 1.94 210.88; 1.94 144.04; 1.93 71.86; 1.93 2.48; 1.92 0.89; 1.88 0.44; 1.87 1.10; 1.86 0.71; 1.86 1.05; 1.85 1.13; 1.85 1.03; 1.84 0.40; 1.84 0.41; 1.84 0.55; 1.83 0.90; 1.83 1.21; 1.82 0.83; 1.82 0.43; 1.48 0.34; 1.44 0.33; 1.27 0.65; 1.22 0.35; 1.20 0.41; 0.97 16.00; 0.95 15.50; 0.94 0.61; 0.93 0.57; 0.01 1.30; 0.00 44.51; −0.01 1.22

Example No. 65 [CD$_3$CN] 8.88 2.87; 8.18 9.34; 8.18 9.71; 8.17 9.31; 8.17 9.80; 8.04 8.90; 7.35 8.26; 7.35 9.82; 7.34 8.90; 7.34 10.57; 7.30 9.48; 7.30 10.16; 7.29 8.16; 7.29 7.89; 7.18 10.24; 7.17 10.03; 7.17 9.49; 7.17 9.10; 6.88 9.46; 6.88 9.25; 6.87 9.12; 6.87 9.28; 5.45 11.62; 4.14 8.65; 4.13 15.38; 4.12 8.87; 4.06 0.38; 4.05 0.36; 3.28 1.09; 3.27 1.01; 2.89 1.16; 2.77 1.60; 2.77 8.04; 2.76 16.00; 2.75 8.74; 2.20 0.51; 2.19 1.79; 2.18 1.59; 2.18 3.31; 2.16 2864.50; 2.15 3.12; 2.14 1.52; 2.14 1.10; 2.13 0.90; 2.12 0.38; 2.08 2.30; 2.08 1.74; 2.07 4.95; 2.07 4.48; 2.06 9.35; 2.06 6.41; 2.05 8.65; 2.05 4.98; 2.04 2.78; 2.04 2.75; 1.98 0.34; 1.97 2.80; 1.97 210; 1.96 23.95; 1.95 28.58; 1.95 315.03; 1.95 583.14; 1.94 830.07; 1.94 575.58; 1.93 291.99; 1.93 9.01; 1.92 4.13; 1.92 1.05; 1.91 0.67; 1.91 0.52; 1.87 2.78; 1.86 1.82; 1.86 6.98; 1.85 4.46; 1.85 6.61; 1.84 4.17; 1.84 6.37; 1.83 4.78; 1.83 6.13; 1.82 3.54; 1.82 1.79; 1.81 1.32; 1.80 2.76; 1.80 2.97; 1.79 1.75; 1.79 5.06; 1.78 3.17; 1.78 2.92; 1.77 1.47; 1.27 1.88; 1.22 0.46; 1.20 0.85; 1.19 0.59; 0.89 2.33; 0.89 1.94; 0.88 8.28; 0.88 12.08; 0.87 7.33; 0.87 6.18; 0.87 11.16; 0.86 4.31; 0.85 1.64; 0.85 2.10; 0.84 4.76; 0.84 11.77; 0.83 6.52; 0.83 5.42; 0.83 12.12; 0.82 6.09; 0.82 2.49; 0.81 2.31; 0.10 1.08; 0.01 8.35; 0.00 298.98; −0.01 9.20; −0.10 1.12

Example No. 66 [CD$_3$CN] 9.02 0.50; 8.21 1.75; 8.21 1.81; 8.20 1.85; 8.20 1.77; 8.09 1.58; 7.36 1.83; 7.36 2.23; 7.35 1.86; 7.35 2.53; 7.31 2.04; 7.31 2.30; 7.31 1.87; 7.31 1.70; 7.18 2.27; 7.18 2.32; 7.18 2.16; 7.17 2.09; 6.94 2.04; 6.93 1.96; 6.93 1.94; 6.93 1.96; 5.45 16.00; 4.26 0.49; 4.25 0.51; 4.25 0.51; 4.24 0.51; 4.15 1.60; 4.14 2.78; 4.13 1.68; 4.06 0.58; 4.05 0.57; 4.01 0.58; 4.00 0.56; 2.80 1.39; 2.79 2.75; 2.78 1.56; 2.19 0.45; 2.18 0.47; 2.18 0.72; 2.16 404.88; 2.14 0.40; 2.09 0.46; 2.09 0.36; 2.08 0.94; 2.08 1.11; 2.07 1.54; 2.07 0.96; 2.06 1.13; 2.06 1.10; 2.05 1.53; 2.05 0.81; 2.04 0.42; 1.97 2.83; 1.97 39.03; 1.96 0.53; 1.96 4.80; 1.95 5.85; 1.95 65.22; 1.95 118.44; 1.94 182.94; 1.94 127.17; 1.93 61.91; 1.93 1.84; 1.92 0.80; 1.88 0.55; 1.88 0.35; 1.87 1.35; 1.87 0.81; 1.86 1.27; 1.86 0.77; 1.85 1.34; 1.84 0.34; 1.84 0.41; 1.84 0.45; 1.83 0.76; 1.83 1.01; 1.82 0.72; 1.82 0.39; 1.39 9.59; 1.37 9.73; 1.27 0.44; 1.22 0.91; 1.20 1.64; 1.19 0.84; 1.11 0.63; 0.01 1.73; 0.00 66.64; −0.01 1.82

Example No. 67 [CD$_3$CN] 8.16 1.25; 8.16 1.28; 8.15 1.33; 8.15 1.26; 8.12 0.43; 7.82 1.39; 7.36 1.12; 7.36 1.38; 7.35 1.27; 7.35 1.53; 7.31 1.34; 7.31 1.40; 7.31 1.20; 7.31 1.14; 7.19 1.41; 7.18 1.30; 7.18 1.28; 6.87 1.31; 6.87 1.29; 6.86 1.28; 6.86 1.27; 5.45 2.80; 4.15 1.16; 4.14 2.10; 4.13 1.22; 4.06 0.49; 4.05 0.49; 3.70 16.00; 2.79 1.12; 2.78 2.19; 2.77 1.21; 2.16 399.73; 2.15 0.76; 2.14 0.32; 2.09 0.33; 2.08 0.67; 2.08 0.77; 2.07 1.08; 2.07 0.67; 2.06 0.84; 2.06 0.85; 2.05 1.14; 2.05 0.62; 2.04 0.35; 1.97 2.44; 1.97 33.49; 1.96 3.95; 1.95 4.93; 1.95 52.98; 1.95 96.11; 1.94 144.50; 1.94 99.18; 1.93 49.40; 1.93 1.38; 1.92 0.61; 1.88 0.40; 1.87 0.98; 1.86 0.61; 1.86 0.93; 1.85 0.58; 1.85 0.86; 1.84 0.36; 1.84 0.35; 1.83 0.61; 1.83 0.82; 1.82 0.58; 1.22 0.64; 1.20 1.26; 1.19 0.62; 1.11 0.51; 0.01 1.41; 0.00 49.91; −0.01 1.40

Example No. 68 [CD$_3$CN] 9.20 0.37; 8.21 0.99; 8.20 1.02; 8.10 1.30; 7.36 0.69; 7.36 0.82; 7.35 0.75; 7.35 0.85; 7.31 0.87; 7.31 0.95; 7.30 0.80; 7.30 0.76; 7.18 0.91; 7.18 0.92; 7.17 0.86; 6.93 0.83; 6.92 0.87; 6.92 0.81; 6.91 0.85; 4.15 0.93; 4.14 1.71; 4.13 0.97; 3.93 0.80; 2.80 0.86; 2.79 1.74; 2.78 0.97; 2.16 367.05; 2.08 0.61; 2.08 0.53; 2.07 0.92; 2.07 0.57; 2.06 0.71; 2.06 0.58; 2.06 0.77; 2.05 1.08; 2.05 0.65; 1.97 12.84; 1.96 6.06; 1.95 8.11; 1.95 62.38; 1.95 113.23; 1.94 163.35; 1.94 112.62; 1.93 58.71; 1.87 0.77; 1.87 0.51; 1.86 0.80; 1.85 0.66; 1.83 0.37; 1.83 0.65; 1.83 0.95; 1.82 0.63; 1.82 0.36; 1.42 16.00; 1.27 0.32; 1.11 0.62; 0.01 1.19; 0.00 33.11; −0.01 1.31

Example No. 69 [DMSO-D$_6$] 7.82 0.47; 7.80 0.44; 7.49 0.39; 7.47 0.45; 7.47 0.50; 7.45 0.44; 7.29 0.47; 7.27 0.34; 7.27 0.84; 7.24 0.73; 6.73 0.49; 6.72 0.50; 6.57 0.33; 6.55 0.33; 4.22 0.34; 4.20 0.50; 4.18 0.37; 4.07 0.35; 3.93 4.17; 3.09 0.40; 2.51 5.19; 2.51 10.41; 2.50 13.89; 2.50 10.12; 2.50 5.02; 1.30 6.27; 1.16 2.70; 1.07 16.00; 0.00 0.54

Example No. 70 [DMSO-D$_6$] 8.10 0.52; 8.10 0.52; 7.82 2.25; 7.81 2.31; 7.42 1.96; 7.42 2.86; 7.42 0.85; 7.41 1.82; 7.41 3.98; 7.41 3.27; 7.40 2.21; 7.40 1.84; 7.40 0.66; 7.39 0.36; 7.37 1.11; 7.37 1.87; 7.36 0.63; 7.35 3.83; 7.35 1.68; 7.34 0.99; 7.34 2.06; 7.34 0.34; 7.33 0.88; 7.32 1.67; 7.32 0.89; 7.32 0.56; 7.31 1.81; 7.31 0.37; 7.30 0.54; 6.85 0.58; 6.28 2.55; 6.28 2.60; 6.21 1.35; 6.21 2.25; 6.21 1.97; 6.20 3.14; 6.20 2.40; 4.20 0.34; 4.19 0.52; 4.18 0.37; 4.16 1.52; 4.15 2.36; 4.14 1.57; 4.05 0.33; 4.03 1.02; 4.02 1.02; 4.01 0.34; 3.85 0.35; 3.84 0.55; 3.83 0.56; 3.82 0.35; 3.35 117.16; 3.33 1.19; 3.11 0.45; 3.10 0.35; 2.99 1.35; 2.98 2.04; 2.97 1.56; 2.62 0.75; 2.61 0.35; 2.60 1.31; 2.59 1.72; 2.58 1.04; 2.57 0.36; 2.51 8.24; 2.51 18.33; 2.50 25.54; 2.50 18.54; 2.50 8.47; 1.99 4.60; 1.19 1.27; 1.17 2.51; 1.16 1.32; 1.09 16.00; 1.08 15.90; 1.06 0.33; 1.01 0.95; 0.99 0.95; 0.00 9.01

Example No. 71 [DMSO-D$_6$] 7.83 1.95; 7.82 2.02; 7.45 1.91; 7.44 0.78; 7.43 2.20; 7.43 2.45; 7.42 0.91; 7.41 2.23; 7.22 2.37; 7.21 0.75; 7.20 0.82; 7.19 4.23; 7.19 0.89; 7.18 0.68; 7.17 2.00; 6.44 0.61; 6.43 1.27; 6.41 0.63; 6.25 2.65; 6.25 1.32; 6.24 1.87; 6.23 1.40; 4.16 1.37; 4.15 2.19; 4.13 1.43; 4.04 0.48; 4.02 0.48; 3.35 24.21; 3.35 25.51; 3.34 49.43; 3.31 1.33; 3.00 1.20; 2.99 2.03; 2.97 1.49; 2.94 1.39; 2.92 2.43; 2.91 1.78; 2.89 0.36; 2.63 0.45; 2.61 1.13; 2.59 1.54; 2.57 0.97; 2.55 0.32; 2.51 6.42; 2.51 13.24; 2.50 17.92; 2.50 13.08; 2.49 6.27; 1.99 2.16; 1.75 0.35; 1.74 0.69; 1.72 0.88; 1.70 0.73; 1.69 0.40; 1.24 0.59; 1.19 0.61; 1.17 1.19; 1.16 0.59; 0.99 0.39; 0.98 0.37; 0.85 16.00; 0.83 15.38; 0.82 2.16; 0.81 0.47; 0.81 0.63; 0.81 1.69; 0.00 5.51

Example No. 72 [DMSO-D$_6$] 8.02 0.59; 7.81 1.82; 7.80 1.87; 7.43 1.31; 7.42 1.62; 7.42 0.65; 7.40 2.85; 7.40 2.69; 7.37 0.84; 7.37 1.05; 7.36 0.52; 7.35 2.78; 7.35 1.13; 7.33 2.72; 7.33 2.04; 7.32 1.03; 7.32 0.59; 7.31 0.98; 6.42 0.53; 6.41 1.10; 6.39 0.56; 6.29 2.10; 6.24 1.50; 6.24 1.34; 6.23 1.48; 6.23 1.35; 4.17 1.22; 4.15 1.94; 4.13 1.27; 4.06 0.88; 4.04 2.69; 4.02 2.72; 4.00 0.91; 3.35 35.16; 3.34 65.44; 3.32 1.52; 3.01 1.08; 2.99 1.81; 2.97 1.31; 2.94 1.23; 2.92 2.13; 2.91 1.69; 2.90 1.81; 2.89 0.75; 2.82 0.42; 2.80 0.50; 2.79 0.37; 2.63 0.37; 2.61 1.03; 2.59 1.39; 2.58 0.86; 2.52 0.33; 2.51 7.77; 2.51 15.73; 2.50 21.07; 2.50 15.30; 2.49 7.23; 1.99 12.05; 1.76 0.32; 1.74 0.63; 1.72 0.81; 1.71 0.70; 1.69 0.52; 1.67 0.44; 1.65 0.33; 1.40 0.52; 1.24 1.00; 1.22 0.42; 1.19 3.46; 1.18 1.18; 1.17 6.92; 1.16 3.35; 1.05 0.42; 1.03 0.42; 0.99 0.72; 0.98 0.63; 0.87 0.69; 0.85 16.00; 0.83 15.89; 0.82 3.66; 0.81 0.72; 0.81 1.07; 0.81 2.83; 0.00 1.75

Example No. 73 [DMSO-D$_6$] 7.85 2.33; 7.85 2.30; 7.84 2.36; 7.84 2.38; 7.42 0.66; 7.41 0.87; 7.40 1.28; 7.39 1.28; 7.39 0.89; 7.38 0.77; 7.26 1.21; 7.25 1.73; 7.25 1.38; 7.24 1.08; 7.24 1.49; 7.24 1.16; 7.19 0.68; 7.19 1.03; 7.18 0.90; 7.17 1.34; 7.17 1.21; 7.17 1.44; 7.17 1.19; 7.16 1.26; 7.16 0.98; 7.15 0.78; 7.15 0.60; 7.14 0.60; 7.14 0.42; 7.14 0.38; 6.49 0.69; 6.48 1.44; 6.47 0.71; 6.29 2.07; 6.27 1.79; 6.27 1.49; 6.26 1.74; 6.26 1.52; 4.17 1.58; 4.16 2.46; 4.15 1.69; 4.05 0.32; 4.03 0.97; 4.02 0.99; 4.01 0.32; 3.37 166.66; 3.35 0.70; 2.99 1.43; 2.98 2.18; 2.97 1.67; 2.95 1.08; 2.94 1.81; 2.93 1.12; 2.62 0.54; 2.61 1.28; 2.59 1.84; 2.58 1.13; 2.57 0.40; 2.51 4.37; 2.51 9.64; 2.51 13.51; 2.50 9.63; 2.50 4.35; 1.99 4.49; 1.75 0.32; 1.74 0.65; 1.73 0.83; 1.72 0.68; 1.71 0.35; 1.24 0.42; 1.19 1.32; 1.17 2.61; 1.16 1.23; 0.85 16.00; 0.85 3.05; 0.84 15.75; 0.84 2.67; 0.82 0.39; 0.82 1.46; 0.81 1.40; 0.00 3.26

Example No. 74 [DMSO-D$_6$] 8.45 5.48; 8.44 5.69; 7.44 0.44; 7.43 4.66; 7.43 1.82; 7.42 5.17; 7.41 6.28; 7.40 2.07; 7.40 5.73; 7.39 0.66; 7.25 0.64; 7.24 5.99; 7.23 1.71; 7.22 1.89; 7.22 10.60; 7.21 1.92; 7.20 1.58; 7.19 4.90; 7.19 0.48; 7.15 6.49; 7.15 4.39; 7.14 4.32; 7.14 6.40; 5.76 1.18; 4.49 1.07; 4.48 2.04; 4.46 2.07; 4.44 1.11; 3.93 1.99; 3.34 110.22; 3.31 0.83; 3.13 0.58; 3.12 0.69; 3.11 0.71; 3.10 0.80; 3.09 1.24; 3.08 1.34; 3.06 1.27; 3.02 1.14; 3.01 1.49; 3.00 1.73; 2.99 1.94; 2.97 0.70; 2.96 0.86; 2.95 0.78; 2.84 0.64; 2.83 0.63; 2.83 0.77; 2.82 0.84; 2.81 1.32; 2.80 1.09; 2.79 1.26; 2.78 0.87; 2.77 0.64; 2.76 0.49; 2.51 14.76; 2.50 20.10; 2.24 0.60; 2.22 1.23; 2.21 0.78; 2.20 1.16; 2.20 1.26; 2.19 1.31; 2.18 1.06; 2.17 0.83; 2.17 1.02; 2.15 0.50; 1.99 0.41; 1.49 16.00; 1.47 15.92; 1.16 0.38; 1.07 11.85; 0.00 4.14

Example No. 75 [CD$_3$CN] 8.21 0.50; 8.21 0.51; 8.20 0.50; 8.20 0.51; 8.10 0.43; 7.30 0.50; 7.30 0.54; 7.29 0.52; 7.29 0.55; 6.96 0.54; 6.96 0.59; 6.96 0.44; 6.96 0.45; 6.95 0.61; 6.95 0.85; 6.95 0.87; 6.94 0.74; 6.94 0.41; 6.93 0.66; 6.93 0.42; 5.45 7.73; 4.14 0.46; 4.13 0.83; 4.12 0.49; 2.76 0.44; 2.75 0.86; 2.74 0.47; 2.43 0.36; 2.42 1.14; 2.40 1.17; 2.39 0.38; 2.17 123.39; 2.06 0.44; 2.06 0.43; 2.05 0.34; 2.05 0.52; 2.05 0.35; 1.97 0.72; 1.97 14.22; 1.96 2.29; 1.95 2.60; 1.95 24.64; 1.95 46.24; 1.94 66.64; 1.94 44.02; 1.93 22.38; 1.93 0.57; 1.86 0.38; 1.85 0.36; 1.84 0.35; 1.83 0.42; 1.20 0.39; 1.20 0.40; 1.13 16.00; 1.12 2.98; 1.11 1.38; 0.00 2.77

Example No. 76 [DMSO-D$_6$] 10.36 0.59; 8.14 0.61; 8.14 0.66; 8.13 0.62; 8.12 0.70; 8.09 0.59; 7.45 0.57; 7.44 0.64; 7.43 0.73; 7.42 0.66; 7.23 0.70; 7.21 1.25; 7.18 0.59; 6.76 0.54; 6.75 0.53; 6.74 0.53; 6.74 0.55; 3.94 2.56; 3.35 55.42; 2.51 4.65; 2.51 6.42; 2.51 4.32; 2.38 1.01; 2.36 1.04; 2.34 0.34; 2.00 0.58; 1.49 1.72; 1.48 1.72; 1.18 0.33; 1.08 16.00; 1.06 1.28; 1.04 2.83; 1.02 1.21

Example No. 77 [DMSO-D$_6$] 10.39 0.32; 8.13 0.37; 8.12 0.73; 7.43 0.35; 7.20 0.55; 5.76 1.66; 3.96 2.81; 3.35 11.07; 2.51 1.15; 2.51 2.51; 2.50 3.45; 2.50 2.49; 2.50 1.13; 1.48 0.85; 1.47 0.85; 1.12 0.36; 1.11 0.35; 1.07 16.00; 1.06 2.11; 0.00 0.42

Example No. 78 [DMSO-D$_6$] 10.72 0.46; 8.14 0.47; 8.12 0.49; 8.07 0.51; 7.44 0.41; 7.43 0.47; 7.42 0.53; 7.41 0.48; 7.22 0.50; 7.20 0.88; 7.17 0.41; 6.74 0.37; 6.73 0.36; 6.73 0.37; 6.72 0.37; 3.93 0.93; 3.34 6.37; 3.34 9.96; 3.34 8.90; 2.51 1.52; 2.51 2.89; 2.50 3.94; 2.50 2.73; 2.50 1.34; 1.48 1.28; 1.46 1.27; 1.07 16.00; 0.79 1.33; 0.77 1.24; 0.00 0.67

Example No. 79 [DMSO-D$_6$] 10.23 0.80; 8.05 0.76; 8.05 0.74; 8.04 0.79; 8.04 0.77; 7.87 0.54; 7.26 0.65; 7.25 0.74; 7.24 0.76; 7.23 0.69; 7.04 0.73; 7.03 1.35; 7.01 0.64; 6.64 0.63; 6.64 0.61; 6.64 0.62; 6.63 0.63; 3.93 0.49; 3.93 1.05; 3.92 0.51; 3.19 16.00; 2.76 0.50; 2.75 0.99; 2.74 0.47; 2.35 3.21; 2.35 7.13; 2.35 9.90; 2.35 7.10; 2.34 3.17; 2.10 1.14; 2.09 1.16; 1.58 8.13; 0.30 0.75; 0.30 0.77; 0.29 0.35; 0.29 0.35; 0.29 0.73; 0.28 0.75; 0.01 0.78; 0.01 0.81; 0.00 0.75; 0.00 0.81; −0.16 0.69

Example No. 80 [CD$_3$CN] 10.78 0.46; 10.24 0.42; 8.66 7.23; 8.64 7.23; 8.56 0.78; 8.55 0.99; 8.54 0.50; 8.52 0.46; 8.50 1.12; 8.49 1.22; 8.48 1.11; 8.47 1.13; 8.45 1.49; 8.44 1.80; 7.83 0.85; 7.82 1.53; 7.80 0.94; 7.44 8.66; 7.44 5.44; 7.43 5.20; 7.43 8.55; 7.34 1.02; 7.33 1.03; 7.13 0.76; 7.12 0.93; 7.11 1.25; 7.10 0.50; 7.03 1.50; 7.02 1.32; 6.96 1.37; 6.84 6.20; 6.83 6.98; 6.82 1.04; 6.81 0.92; 6.66 6.81; 6.65 6.68; 6.64 1.44; 6.63 0.68; 6.61 0.86; 6.60 0.70; 6.58 0.97; 6.57 0.72; 6.37 0.48; 6.22 0.54; 5.56 0.75; 5.48 0.44; 5.39 2.05; 5.38 4.01; 5.37 2.06; 5.34 0.58; 5.31 0.67; 4.47 0.45; 4.42 1.75; 4.40 2.12; 4.39 2.45; 4.38 2.41; 4.37 1.98; 4.36 0.48; 4.13 0.61; 4.12 1.91; 4.10 1.76; 4.10 1.00; 4.08 2.19; 4.07 2.00; 4.05 1.55; 4.04 1.16; 2.75 0.56; 2.72 0.95; 2.68 0.49; 2.59 0.55; 2.58 0.55; 2.56 0.94; 2.55 1.28; 2.54 1.18; 2.53 1.34; 2.51 1.45; 2.49 1.26; 2.48 1.06; 2.46 0.69; 2.44 0.57; 2.40 0.78; 2.40 0.84; 2.38 0.98; 2.37 1.19; 2.35 1.95; 2.34 1.99; 2.31 4.71; 2.30 7.50; 2.29 7.23; 2.26 949.77; 2.25 2035.07; 2.18 2.50; 2.16 3.88; 2.15 1.77; 2.14 2.57; 2.14 2.95; 2.13 2.32; 2.11 0.47; 2.09 0.46; 2.03 0.54; 1.99 450.00; 1.98 121.96; 1.98 222.61; 1.97 311.09; 1.96 209.77; 1.96 105.49; 1.82 2.57; 1.81 0.73; 1.80 1.11; 1.80 1.74; 1.79 1.19; 1.79 0.83; 1.34 0.55; 1.30 3.25; 1.26 0.43; 1.25 0.68; 1.23 1.24; 1.22 0.44; 1.22 0.70; 1.16 16.00; 0.98 0.44; 0.94 0.70; 0.91 0.53; 0.87 0.51

Example No. 81 [DMSO-D$_6$] 7.89 3.88; 7.88 4.32; 7.43 0.33; 7.42 3.60; 7.42 4.28; 7.41 3.93; 7.40 4.52; 6.98 3.00; 6.97 4.31; 6.97 3.09; 6.96 4.57; 6.94 4.63; 6.94 5.58; 6.93 3.14; 6.93 3.25; 6.60 0.32; 6.39 0.37; 6.38 4.47; 6.37 16.00; 5.99 0.36; 5.91 0.49; 5.88 7.99; 5.85 0.41; 5.75 0.38; 5.53 0.34; 4.12 3.02; 4.10 5.56; 4.09 3.00; 4.04 0.81; 4.02 0.77; 4.00 0.37; 3.34 1573.87; 3.28 0.75; 3.26 0.44; 3.23 0.34; 2.68 3.14; 2.67 6.30; 2.65 2.91; 2.54 0.46; 2.52 1.95; 2.51 157.17; 2.50 217.14; 2.50 157.72; 2.44 0.33; 2.33 1.30; 2.07 1.41; 2.01 2.29; 2.00 2.89; 1.99 5.53; 1.82 1.08; 1.80 2.52; 1.79 2.74; 1.77 2.02; 1.58 0.71; 1.40 0.36; 1.19 0.88; 1.17 1.69; 1.16 0.88; 0.89 0.36; 0.00 7.16

Example No. 82 [DMSO-D$_6$] 9.95 1.49; 8.23 1.63; 8.22 1.70; 7.95 1.50; 7.42 1.19; 7.40 1.36; 7.40 1.64; 7.39 0.60; 7.38 1.45; 7.20 1.50; 7.18 2.71; 7.16 1.26; 6.87 1.20; 6.87 1.22; 6.86 1.26; 6.86 1.23; 4.09 0.94; 4.08 2.08; 4.06 1.32; 4.03 5.64; 3.37 1.07; 3.34 65.63; 3.34 63.22; 3.33 84.69; 3.33 101.81; 2.93 0.98; 2.91 1.98; 2.90 0.92; 2.52 0.45; 2.51 31.47; 2.50 42.95; 2.50 30.28; 1.73 16.00; 1.40 4.84; 1.07 1.52; 0.00 1.73

Example No. 83 [DMSO-D$_6$] 10.41 1.81; 8.20 1.62; 8.19 1.66; 8.02 2.10; 7.42 1.21; 7.40 1.39; 7.40 1.75; 7.38 1.52; 7.20 1.48; 7.18 2.68; 7.15 1.26; 6.78 1.11; 6.77 1.28; 6.76 1.11; 6.76 1.29; 4.09 0.99; 4.08 2.18; 4.07 1.07; 3.32 81.59; 2.92 1.07; 2.90 2.13; 2.89 1.02; 2.75 0.64; 2.73 0.86; 2.71 0.65; 2.51 22.25; 2.50 30.78; 2.50 24.82; 2.07 0.35; 1.73 16.00; 1.09 0.36; 1.07 9.66; 1.05 9.53; 0.00 5.33

Example No. 84 [DMSO-D$_6$] 10.78 1.74; 8.21 1.64; 8.20 1.70; 7.98 1.96; 7.41 1.28; 7.40 0.55; 7.40 1.55; 7.39 1.63; 7.37 1.46; 7.20 1.58; 7.17 2.75; 7.15 1.24; 6.79 1.34; 6.78 1.13; 6.77 1.25; 6.77 1.11; 5.76 0.71; 4.08 0.95; 4.07 2.10; 4.05 0.99; 3.32 51.77; 2.90 0.99; 2.88 2.00; 2.87 0.94; 2.52 0.35; 2.51 23.23; 2.50 29.15; 2.50 20.09; 2.00 0.49; 1.99 0.75; 1.97 0.49; 1.72 16.00; 1.40 2.00; 0.79 2.23; 0.78 2.32; 0.77 4.47; 0.00 5.87

Example No. 85 [CD$_3$CN] 18.32 0.43; 17.36 0.42; 12.09 0.40; 9.25 0.43; 8.50 3.39; 8.49 2.77; 8.49 3.49; 8.47 0.53; 8.45 0.59; 7.40 1.90; 7.39 2.19; 7.38 2.41; 7.37 1.97; 7.23 3.83; 7.22 2.82; 7.22 2.77; 7.21 3.70; 7.15 0.43; 7.12 0.71; 7.11 0.69; 7.08 2.43; 7.05 3.86; 7.03 2.00; 5.45 1.04; 4.38 1.72; 4.34 0.70; 4.30 0.73; 4.18 0.41; 4.17 0.45; 4.07

0.67; 4.05 0.62; 4.03 0.84; 4.03 0.95; 4.01 0.51; 3.99 0.59; 3.81 0.41; 3.45 0.41; 3.28 0.52; 3.24 16.00; 2.81 0.57; 2.60 3.11; 2.47 0.43; 2.41 0.41; 2.39 0.42; 2.29 1.62; 2.27 2.00; 2.25 2.03; 2.18 1032.82; 2.12 0.98; 2.11 1.48; 2.11 1.68; 2.10 1.14; 2.08 0.49; 2.06 0.46; 2.05 0.49; 1.96 24.10; 1.95 101.96; 1.95 188.93; 1.94 255.59; 1.93 181.67; 1.93 92.41; 1.88 0.44; 1.86 0.49; 1.86 0.42; 1.79 0.62; 1.78 1.09; 1.77 1.92; 1.76 1.72; 1.72 0.76; 1.69 0.69; 1.69 0.57; 1.66 0.41; 1.57 0.41; 1.56 0.51; 1.55 0.50; 1.54 0.60; 1.51 0.50; 1.41 0.47; 1.37 0.50; 1.36 0.78; 1.34 0.87; 1.27 12.86; 1.21 0.80; 1.18 0.53; 1.16 0.50; 1.14 0.78; 1.11 0.46; 1.09 0.51; 1.08 0.40; 0.93 0.41; 0.92 0.73; 0.90 1.27; 0.88 1.91; 0.86 1.56; 0.82 0.51; 0.81 0.51; 0.00 3.40

Example No. 86 [DMSO-$D_6$] 10.41 1.53; 8.20 1.66; 8.19 1.69; 8.00 1.58; 7.42 1.29; 7.40 1.40; 7.39 1.72; 7.39 0.62; 7.38 1.46; 7.20 1.71; 7.18 2.86; 7.15 1.37; 6.79 1.12; 6.79 1.32; 6.78 1.24; 6.78 1.22; 5.76 0.61; 4.09 1.02; 4.08 1.99; 4.06 1.04; 4.04 1.21; 4.02 1.19; 4.00 0.38; 3.93 0.53; 3.38 0.38; 3.36 0.74; 3.33 1004.40; 3.30 3.22; 3.28 0.49; 3.27 0.42; 2.91 0.90; 2.90 1.81; 2.88 0.90; 2.68 1.17; 2.67 1.62; 2.67 1.21; 2.54 0.84; 2.52 2.75; 2.52 3.94; 2.51 95.26; 2.51 187.51; 2.50 261.60; 2.50 181.42; 2.49 89.34; 2.39 0.76; 2.38 2.58; 2.36 2.50; 2.34 1.29; 2.33 1.34; 2.33 1.70; 2.32 2.15; 2.07 2.93; 1.99 5.51; 1.73 16.00; 1.71 0.52; 1.40 0.44; 1.19 1.42; 1.17 3.01; 1.16 1.33; 1.07 2.92; 1.05 3.01; 1.03 6.50; 1.01 2.68; 0.86 4.57; 0.00 5.61

Example No. 87 [$CD_3CN$] 8.67 2.40; 8.21 9.20; 8.21 9.26; 8.21 9.38; 8.20 9.13; 8.08 4.62; 7.30 8.59; 7.30 9.02; 7.29 8.95; 7.29 9.32; 7.29 0.48; 7.28 0.35; 7.28 0.35; 6.97 9.37; 6.97 9.17; 6.96 9.32; 6.96 9.34; 6.96 6.59; 6.95 7.46; 6.95 12.63; 6.95 11.85; 6.94 12.62; 6.93 6.71; 6.93 11.57; 6.93 6.68; 6.43 0.40; 5.45 4.58; 4.14 8.54; 4.13 15.44; 4.12 8.96; 4.11 0.39; 2.75 8.14; 2.74 16.00; 2.73 8.72; 2.72 0.46; 2.71 0.59; 2.21 0.48; 2.20 0.38; 2.19 0.67; 2.16 598.75; 2.14 1.14; 2.13 0.63; 2.13 0.42; 2.11 79.56; 2.08 2.44; 2.08 1.88; 2.07 5.10; 2.07 4.65; 2.06 8.52; 2.06 3.96; 2.06 5.02; 2.05 5.54; 2.05 6.21; 2.04 2.64; 2.04 2.94; 2.00 0.40; 1.97 1.57; 1.97 17.47; 1.96 11.11; 1.95 15.22; 1.95 144.24; 1.95 260.73; 1.94 388.20; 1.94 269.48; 1.93 134.42; 1.93 4.26; 1.93 2.06; 1.92 0.65; 1.86 2.84; 1.86 1.84; 1.85 7.15; 1.85 4.38; 1.84 6.97; 1.84 4.29; 1.83 6.51; 1.83 3.64; 1.82 3.80; 1.82 1.08; 1.28 0.59; 1.27 2.87; 1.22 0.42; 1.20 0.74; 1.19 0.40; 0.88 0.55; 0.87 0.34; 0.01 1.64; 0.00 50.02; −0.01 1.37

Example No. 88 [$CD_3CN$] 8.59 0.45; 8.21 1.46; 8.21 1.54; 8.20 1.52; 8.20 1.53; 8.11 1.54; 8.11 1.55; 7.30 1.40; 7.30 1.54; 7.30 1.57; 7.29 1.58; 6.97 1.58; 6.96 1.60; 6.96 1.57; 6.96 2.26; 6.95 2.07; 6.94 2.25; 6.94 1.09; 6.93 2.03; 6.93 1.11; 5.45 12.41; 4.14 1.33; 4.13 2.39; 4.12 1.37; 3.28 1.31; 3.27 1.31; 2.76 1.26; 2.75 2.48; 2.74 1.35; 2.66 0.78; 2.65 1.07; 2.63 0.81; 2.62 0.32; 2.17 110.60; 2.08 0.40; 2.07 0.80; 2.07 0.74; 2.07 1.25; 2.06 0.69; 2.06 0.79; 2.06 1.06; 2.06 0.99; 2.05 1.21; 2.05 0.81; 2.04 0.71; 1.97 0.43; 1.97 7.43; 1.96 3.90; 1.95 5.42; 1.95 49.59; 1.95 95.69; 1.94 142.35; 1.94 95.75; 1.93 46.25; 1.93 1.58; 1.93 0.81; 1.92 0.39; 1.87 0.49; 1.87 0.32; 1.86 1.11; 1.86 0.69; 1.85 1.05; 1.85 0.65; 1.84 0.97; 1.84 0.52; 1.83 0.71; 1.83 0.87; 1.82 0.58; 1.44 10.41; 1.27 1.05; 1.16 16.00; 1.15 0.63; 1.14 15.64; 1.11 0.41; 0.01 0.64; 0.00 19.73; −0.01 0.54

Example No. 89 [$CD_3CN$] 8.91 3.39; 8.22 9.14; 8.22 9.10; 8.21 9.33; 8.21 9.05; 8.08 10.05; 7.30 8.23; 7.29 8.04; 7.29 8.42; 7.29 8.46; 6.96 8.77; 6.96 8.85; 6.95 9.07; 6.95 12.85; 6.95 7.54; 6.95 6.71; 6.94 11.34; 6.94 12.05; 6.93 6.06; 6.93 10.26; 6.92 5.85; 5.45 14.46; 4.13 8.67; 4.12 15.55; 4.11 8.69; 2.74 8.22; 2.73 16.00; 2.72 8.58; 2.30 0.35; 2.17 733.24; 2.14 1.75; 2.12 0.52; 2.07 2.55; 2.07 2.23; 2.06 5.54; 2.06 5.23; 2.05 8.79; 2.05 6.31; 2.05 6.79; 2.04 2.15; 2.03 2.85; 1.97 48.89; 1.96 14.99; 1.95 20.59; 1.95 148.87; 1.95 268.38; 1.94 374.42; 1.94 263.39; 1.93 136.32; 1.93 2.36; 1.92 1.21; 1.92 1.06; 1.91 0.88; 1.91 0.69; 1.90 0.46; 1.89 0.46; 1.88 0.36; 1.86 2.88; 1.85 2.17; 1.85 7.14; 1.84 4.76; 1.84 7.57; 1.83 5.88; 1.83 8.22; 1.82 3.28; 1.82 2.67; 1.81 2.79; 1.80 2.99; 1.80 2.08; 1.79 5.00; 1.79 3.14; 1.78 2.80; 1.77 1.41; 1.44 1.74; 1.28 0.80; 1.27 4.07; 1.06 0.35; 1.14 0.33; 1.06 1.45; 1.05 1.34; 0.89 2.75; 0.89 2.48; 0.88 7.97; 0.88 12.18; 0.88 8.02; 0.88 6.93; 0.87 10.69; 0.87 4.10; 0.87 4.76; 0.86 1.63; 0.85 2.17; 0.85 4.92; 0.84 10.80; 0.84 6.31; 0.83 5.69; 0.83 11.40; 0.82 5.69; 0.82 2.53; 0.82 2.22; 0.01 1.88; 0.00 46.53; −0.01 1.45

Example No. 90 [DMSO-$D_6$] 10.49 1.22; 8.21 1.56; 8.21 1.61; 7.96 0.72; 7.41 1.30; 7.40 0.59; 7.40 1.54; 7.39 1.50; 7.39 0.70; 7.38 1.34; 7.20 1.47; 7.19 0.51; 7.18 2.64; 7.17 0.54; 7.17 1.23; 6.82 1.23; 6.82 1.13; 6.81 1.21; 6.81 1.10; 5.77 4.47; 4.08 1.10; 4.07 2.25; 4.06 1.10; 4.03 0.47; 4.02 0.47; 3.39 0.37; 3.35 38.82; 3.33 0.66; 2.90 1.09; 2.89 2.14; 2.88 1.03; 2.51 12.38; 2.50 16.01; 2.50 11.43; 2.09 0.94; 2.05 7.29; 1.99 2.01; 1.76 0.40; 1.73 16.00; 1.48 0.32; 1.19 0.55; 1.17 1.08; 1.16 0.54; 0.00 5.33

Example No. 91 [DMSO-$D_6$] 10.46 2.46; 8.21 2.38; 8.21 2.35; 8.20 2.49; 8.20 2.44; 8.05 2.44; 7.42 2.02; 7.41 0.89; 7.41 2.31; 7.40 2.39; 7.40 1.02; 7.39 2.19; 7.20 2.30; 7.20 0.79; 7.19 0.99; 7.19 4.25; 7.18 0.97; 7.18 0.78; 7.17 2.03; 6.78 1.96; 6.78 1.90; 6.78 1.93; 6.77 1.92; 5.61 7.16; 4.13 1.64; 4.12 3.53; 4.11 1.69; 4.05 0.66; 4.03 1.98; 4.02 2.01; 4.01 0.67; 3.39 0.73; 3.35 19.15; 3.33 0.55; 2.98 1.50; 2.97 2.97; 2.96 1.43; 2.76 0.33; 2.75 0.82; 2.74 1.11; 2.72 0.83; 2.71 0.33; 2.52 0.33; 2.52 0.35; 2.51 8.34; 2.51 17.69; 2.50 24.06; 2.50 17.58; 2.50 8.24; 1.99 8.76; 1.91 0.81; 1.40 0.47; 1.19 2.41; 1.17 4.69; 1.16 2.38; 1.12 1.45; 1.11 1.44; 1.06 16.00; 1.05 15.89; 0.00 6.78

Example No. 92 [$CD_3CN$] 8.56 1.50; 8.38 0.47; 8.37 0.48; 8.13 2.13; 8.12 2.14; 7.95 2.64; 7.46 1.92; 7.46 0.87; 7.46 2.19; 7.45 2.17; 7.44 0.97; 7.44 1.94; 7.38 0.38; 7.38 0.35; 7.38 0.37; 7.37 0.33; 7.09 2.05; 7.09 0.71; 7.08 3.83; 7.07 0.87; 7.06 1.82; 6.75 1.72; 6.75 1.62; 6.74 1.71; 6.74 1.55; 4.88 8.24; 4.21 1.04; 4.20 2.67; 4.19 2.73; 4.17 2.85; 4.16 2.88; 4.15 1.12; 2.65 0.39; 2.64 1.01; 2.63 1.35; 2.61 1.02; 2.60 0.41; 2.16 55.53; 1.97 0.92; 1.97 2.31; 1.96 1.61; 1.95 14.67; 1.95 25.87; 1.94 36.51; 1.94 25.07; 1.93 12.62; 1.20 3.58; 1.19 3.51; 1.14 16.00; 1.13 15.75; 0.00 1.38

Example No. 93 [$CD_3CN$] 8.90 1.86; 8.56 0.37; 8.17 4.01; 8.15 4.09; 7.94 5.40; 7.92 0.48; 7.89 0.48; 7.49 3.82; 7.49 1.74; 7.48 4.32; 7.47 4.68; 7.46 2.09; 7.46 4.31; 7.25 0.33; 7.22 0.68; 7.20 0.37; 7.12 4.26; 7.10 7.95; 7.07 3.80; 6.78 3.58; 6.78 3.49; 6.77 3.53; 6.76 3.47; 4.88 16.00; 4.78 1.63; 4.23 1.66; 4.22 4.51; 4.21 6.00; 4.19 6.12; 4.18 4.37; 4.17 5.30; 4.16 2.29; 4.15 0.93; 4.14 0.54; 4.12 0.79; 4.10 2.19; 4.08 2.21; 4.06 0.77; 2.50 0.52; 2.48 0.53; 2.31 0.33; 2.27 0.33; 2.25 0.52; 2.19 929.12; 2.15 0.91; 2.14 1.08; 2.14 1.41; 2.13 0.86; 2.00 10.09; 1.99 10.55; 1.98 80.75; 1.98 150.71; 1.97 207.03; 1.96 142.18; 1.96 72.27; 1.84 0.56; 1.82 1.45; 1.80 2.81; 1.80 1.80; 1.79 2.21; 1.78 1.52; 1.77 0.69; 1.47 2.07; 1.37 0.36; 1.30 1.25; 1.25 2.61; 1.23 5.20; 1.22 2.74; 1.20 1.07; 1.18 0.53; 1.17 0.67; 0.94 0.53; 0.92 0.75; 0.91 2.85; 0.90 5.74; 0.90 4.91; 0.89 4.64; 0.88 3.17; 0.87 5.35; 0.86 2.66; 0.86 3.23; 0.85 4.72; 0.84 2.34; 0.83 0.76

Example No. 94 [DMSO-$D_6$] 9.97 4.26; 8.24 4.07; 8.23 4.20; 7.98 3.81; 7.43 0.37; 7.42 3.59; 7.42 1.48; 7.41 4.07; 7.40 4.53; 7.39 1.69; 7.39 4.24; 7.38 0.55; 7.21 0.53; 7.21 4.35; 7.20 1.36; 7.19 1.49; 7.18 7.75; 7.18 1.52; 7.17 1.17; 7.16 3.53; 7.15 0.39; 6.89 3.28; 6.88 3.23; 6.87 3.22; 6.87 3.24; 5.61 12.18; 4.13 2.51; 4.12 5.71; 4.10 2.63; 4.03 16.00; 3.34 42.63; 3.32 250.73; 3.30 0.69; 3.00 2.35; 2.98 4.86; 2.97 2.24; 2.67 0.59; 2.67 0.43; 2.52 1.00; 2.51 33.04; 2.51 62.61; 2.50 85.72; 2.50 59.64; 2.49 29.53; 2.33 0.53; 2.32 0.35; 2.07 1.55; 1.99 0.34; 1.91 0.44; 1.87 0.56; 1.07 0.36; 0.96 0.64; 0.01 0.40; 0.00 13.78; −0.01 0.38

Example No. 95 [DMSO-$D_6$] 10.42 2.84; 8.21 2.90; 8.21 2.86; 8.20 3.02; 8.20 3.01; 8.03 2.86; 7.42 2.54; 7.42 1.00; 7.41 2.90; 7.40 3.25; 7.39 1.16; 7.39 2.96; 7.38 0.36; 7.20 3.14; 7.20 0.93; 7.19 1.01; 7.18 5.61; 7.18 1.06; 7.16 0.86; 7.16 2.56; 6.81 2.42; 6.80 2.38; 6.79 2.39; 6.79 2.43; 5.61 8.42; 4.13 1.69; 4.11 3.95; 4.10 1.79; 4.06 0.78; 4.04 2.39; 4.02 2.41; 4.00 0.80; 3.93 2.73; 3.33 126.38; 2.98 1.62; 2.97 3.35; 2.95 1.51; 2.52 0.40; 2.51 9.40; 2.51 18.18; 2.50 25.24; 2.50 17.35; 2.49 8.54; 2.40 1.35; 2.38 4.63; 2.36 4.76; 2.34 1.49; 2.07 0.63; 1.99 10.81; 1.91 0.45; 1.19 3.00; 1.17 6.01; 1.16 2.94; 1.07 16.00; 1.05 5.63; 1.03 12.51; 1.01 5.45; 0.00 0.89

Example No. 96 [DMSO-$D_6$] 10.48 2.56; 8.24 2.60; 8.24 2.54; 8.23 2.68; 8.23 2.65; 7.95 1.94; 7.34 2.22; 7.33 0.88; 7.33 2.49; 7.32 2.64; 7.32 1.03; 7.31 2.43; 7.14 2.52; 7.14 0.78; 7.13 0.94; 7.13 4.65; 7.13 0.90; 7.12 0.76; 7.11

-continued 2.18; 6.76 2.19; 6.76 2.12; 6.75 2.17; 6.75 2.16; 4.35 1.64; 4.34 1.45; 4.33 1.65; 3.96 1.90; 3.36 141.41; 3.34 0.62; 2.73 1.46; 2.73 1.32; 2.72 1.51; 2.52 0.33; 2.51 9.66; 2.51 21.18; 2.50 29.04; 2.50 20.95; 2.50 9.52; 2.40 1.22; 2.39 0.37; 2.38 3.83; 2.37 3.84; 2.36 1.23; 1.99 0.53; 1.84 1.22; 1.83 1.06; 1.75 1.19; 1.63 0.91; 1.62 1.12; 1.40 6.79; 1.07 16.00; 1.04 5.31; 1.03 11.30; 1.02 5.23

Example No. 97 [DMSO-$D_6$] 10.47 2.11; 8.24 2.00; 8.23 2.04; 8.23 1.90; 7.96 2.00; 7.34 1.66; 7.34 0.74; 7.33 1.90; 7.33 1.94; 7.32 0.81; 7.32 1.74; 7.14 1.96; 7.14 0.67; 7.13 0.81; 7.13 3.50; 7.13 0.75; 7.12 0.62; 7.11 1.64; 6.76 1.62; 6.76 1.55; 6.75 1.58; 6.75 1.56; 4.35 1.33; 4.34 1.18; 4.33 1.28; 3.96 2.28; 3.38 0.37; 3.35 68.69; 3.33 0.53; 2.76 0.36; 2.75 0.87; 2.74 1.90; 2.73 1.66; 2.72 1.32; 2.71 0.48; 2.53 0.48; 2.52 0.57; 2.52 0.64; 2.51 6.76; 2.51 14.02; 2.50 18.81; 2.50 13.44; 2.50 6.20; 1.84 1.02; 1.83 0.89; 1.75 0.99; 1.62 0.93; 1.40 3.72; 1.09 0.35; 1.07 16.00; 1.07 14.01; 1.05 12.94; 0.00 1.82

Example No. 98 [DMSO-$D_6$] 10.78 2.37; 8.26 2.53; 8.26 2.44; 8.25 2.62; 8.25 2.55; 7.92 1.83; 7.33 0.85; 7.33 0.78; 7.32 16.00; 7.32 5.70; 7.31 7.18; 7.31 2.92; 7.30 1.40; 7.30 2.88; 7.29 0.33; 7.25 0.72; 7.25 0.93; 7.24 1.02; 7.24 1.13; 7.23 0.80; 7.23 0.65; 7.22 0.32; 7.13 0.34; 7.13 2.57; 7.12 0.84; 7.12 1.04; 7.11 0.94; 7.10 0.83; 7.10 2.17; 6.77 2.17; 6.77 2.07; 6.77 2.14; 6.76 2.13; 5.77 11.89; 4.33 1.63; 4.32 1.46; 4.32 1.59; 4.03 0.81; 4.02 0.82; 3.70 6.48; 3.57 0.97; 3.36 45.81; 2.72 1.46; 2.71 1.33; 2.70 1.44; 2.53 0.35; 2.52 0.45; 2.52 0.53; 2.51 6.82; 2.51 14.16; 2.50 19.07; 2.50 13.75; 2.50 6.17; 1.99 3.67; 1.82 1.22; 1.81 1.06; 1.73 1.20; 1.59 1.14; 1.19 0.98; 1.17 2.00; 1.16 0.97; 1.07 1.30; 0.00 3.09

Example No. 99 [DMSO-$D_6$] 10.50 1.50; 8.24 1.69; 8.23 1.71; 8.23 1.72; 7.92 1.25; 7.34 1.48; 7.34 0.65; 7.33 1.70; 7.32 1.97; 7.31 0.70; 7.31 1.80; 7.14 1.85; 7.14 0.60; 7.13 0.64; 7.12 3.28; 7.12 0.71; 7.10 0.52; 7.10 1.52; 6.77 1.42; 6.77 1.39; 6.76 1.40; 6.76 1.44; 4.35 1.05; 4.34 0.96; 4.33 1.04; 4.06 1.13; 4.04 3.57; 4.02 3.64; 4.00 1.21; 3.33 60.54; 3.32 111.85; 2.73 0.95; 2.71 1.01; 2.52 0.47; 2.51 30.09; 2.50 28.24; 2.06 10.48; 1.99 16.00; 1.91 0.49; 1.84 0.80; 1.75 1.66; 1.62 0.82; 1.36 0.78; 1.19 4.25; 1.17 8.53; 1.16 4.17; 0.00 1.16

Example No. 100 [DMSO-$D_6$] 10.42 3.63; 8.18 3.78; 8.17 3.79; 8.16 3.92; 8.16 3.96; 7.92 3.77; 7.41 2.07; 7.40 2.09; 7.40 1.94; 7.39 1.43; 7.39 2.12; 7.39 5.47; 7.38 5.79; 7.37 1.31; 7.36 2.14; 7.36 1.25; 7.35 4.99; 7.35 2.26; 7.34 2.59; 7.34 5.94; 7.33 5.57; 7.32 1.35; 7.32 0.88; 6.73 3.10; 6.73 3.06; 6.72 3.07; 6.71 3.13; 4.87 10.04; 4.23 1.22; 4.22 3.22; 4.21 3.13; 4.17 3.20; 4.16 3.49; 4.15 1.27; 4.06 0.39; 4.04 1.20; 4.02 1.21; 4.00 0.42; 3.93 1.21; 3.34 44.41; 3.34 47.95; 3.33 89.77; 2.52 0.48; 2.51 20.91; 2.50 28.27; 2.40 1.77; 2.38 6.05; 2.36 6.24; 2.34 1.95; 1.99 5.34; 1.19 1.45; 1.17 2.92; 1.16 1.40; 1.11 0.32; 1.09 0.73; 1.07 9.81; 1.06 7.28; 1.04 16.00; 1.02 6.97; 0.00 0.79

Example No. 101 [DMSO-$D_6$] 10.69 1.52; 10.64 0.61; 8.21 0.62; 8.20 1.49; 8.20 1.49; 8.20 0.72; 8.19 1.52; 8.19 1.49; 7.97 2.12; 7.41 1.69; 7.40 0.70; 7.39 1.94; 7.39 2.11; 7.38 0.79; 7.37 1.88; 7.19 1.61; 7.19 0.60; 7.19 0.80; 7.18 0.60; 7.17 2.87; 7.16 1.31; 7.16 0.52; 7.15 1.33; 7.14 0.59; 6.82 0.50; 6.81 0.47; 6.80 0.48; 6.80 0.48; 6.78 1.22; 6.77 1.19; 6.77 1.19; 6.76 1.24; 5.76 8.22; 4.08 1.03; 4.07 1.08; 4.07 1.95; 4.06 0.85; 4.05 0.89; 4.04 0.85; 4.02 0.81; 3.33 37.17; 3.33 70.41; 3.30 0.54; 2.91 0.48; 2.90 0.53; 2.89 0.93; 2.87 1.73; 2.86 0.82; 2.52 0.41; 2.51 16.66; 2.50 22.81; 2.50 15.48; 1.99 3.69; 1.76 0.61; 1.75 0.69; 1.73 8.51; 1.72 16.00; 1.24 0.41; 1.23 0.47; 1.22 0.54; 1.21 0.55; 1.20 0.53; 1.20 0.61; 1.19 1.46; 1.18 0.48; 1.18 2.27; 1.17 0.34; 1.16 0.36; 1.16 1.09; 1.09 0.71; 1.08 4.37; 1.06 3.62; 1.05 2.38; 1.04 1.77; 1.03 0.87; 1.02 0.36; 0.99 0.42; 0.98 0.59; 0.97 0.71; 0.96 0.56; 0.95 0.41; 0.66 0.35; 0.65 0.40; 0.64 0.39; 0.63 0.51; 0.63 0.47; 0.63 0.40; 0.62 0.38; 0.00 5.15

Example No. 102 [DMSO-$D_6$] 10.29 1.60; 8.19 1.50; 8.19 1.51; 8.18 1.53; 8.18 1.56; 8.03 1.33; 7.42 1.35; 7.41 0.56; 7.41 1.55; 7.40 1.71; 7.39 0.64; 7.38 1.53; 7.20 1.65; 7.20 0.53; 7.18 0.59; 7.18 2.91; 7.17 0.59; 7.16 0.46; 7.16 1.35; 6.78 1.25; 6.78 1.23; 6.77 1.23; 6.77 1.27; 5.76 0.49; 4.10 0.87; 4.08 1.95; 4.07 0.91; 3.36 0.55; 3.34 1.05; 3.33 44.43; 3.30 0.46; 2.92 0.91; 2.91 1.84; 2.90 0.86; 2.50 15.50; 2.20 0.55; 2.19 0.50; 2.17 0.79; 2.17 1.00; 2.15 0.63; 2.15 0.91; 2.13 0.45; 2.11 0.33; 2.11 0.56; 2.09 0.68; 2.08 0.95; 2.07 0.38; 2.07 0.61; 2.06 0.76; 1.99 0.33; 1.91 0.49; 1.89 0.68; 1.87 0.33; 1.78 0.47; 1.77 0.34; 1.77 0.34; 1.76 0.43; 1.73 16.00; 0.00 3.15

Example No. 103 [DMSO-$D_6$] 7.98 0.34; 7.97 0.34; 7.85 5.61; 7.84 1.67; 7.84 1.71; 7.83 5.91; 7.45 0.45; 7.44 4.48; 7.44 1.84; 7.43 5.08; 7.42 5.87; 7.41 2.08; 7.41 5.39; 7.40 0.73; 7.21 0.67; 7.20 5.45; 7.20 1.72; 7.19 1.86; 7.18 9.84; 7.18 2.00; 7.16 1.51; 7.16 4.62; 7.15 0.46; 6.64 0.42; 6.29 2.62; 6.28 5.68; 6.28 4.37; 6.27 13.56; 6.04 0.46; 5.85 8.08; 5.76 1.39; 5.58 16.00; 4.10 3.26; 4.09 7.56; 4.07 3.42; 3.93 0.53; 3.57 1.58; 3.32 103.95; 3.30 1.31; 2.94 3.07; 2.92 6.41; 2.91 2.91; 2.67 0.35; 2.52 0.59; 2.51 39.53; 2.50 53.86; 2.50 37.13; 2.33 0.37; 2.07 0.43; 1.07 2.95; 0.00 2.93

Example No. 104 [$CD_3CN$] 8.58 1.44; 8.56 0.60; 8.16 3.63; 8.15 3.72; 7.96 4.63; 7.50 3.50; 7.49 1.49; 7.49 3.97; 7.47 1.78; 7.46 3.83; 7.13 3.89; 7.10 7.32; 7.09 1.44; 7.08 3.43; 6.78 3.16; 6.77 3.26; 6.77 3.08; 4.90 14.71; 4.24 1.43; 4.23 4.05; 4.22 5.38; 4.20 5.60; 4.19 3.76; 4.18 4.54; 4.17 1.66; 4.12 0.51; 4.10 1.66; 4.08 1.64; 4.06 0.56; 2.50 0.43; 2.48 0.48; 2.45 2.32; 2.43 7.17; 2.41 7.38; 2.39 2.50; 2.19 450.42; 2.17 0.90; 2.16 0.47; 2.15 0.37; 2.14 0.56; 2.14 0.58; 2.13 0.38; 2.00 7.36; 1.99 4.85; 1.98 38.06; 1.98 71.36; 1.97 98.93; 1.96 67.61; 1.96 34.11; 1.80 0.38; 1.80 0.57; 1.79 0.36; 1.47 0.57; 1.37 0.40; 1.30 0.57; 1.25 1.88; 1.23 3.77; 1.22 2.02; 1.20 0.97; 1.18 0.50; 1.16 7.95; 1.14 16.00; 1.12 7.43

Example No. 105 [DMSO-$D_6$] 10.39 1.59; 8.21 1.54; 8.21 1.53; 8.20 1.60; 8.20 1.59; 7.98 1.54; 7.41 1.31; 7.41 0.53; 7.40 1.55; 7.39 1.69; 7.38 0.62; 7.38 1.53; 7.19 1.63; 7.19 0.51; 7.17 0.58; 7.17 2.90; 7.16 0.57; 7.15 0.44; 7.15 1.32; 6.82 1.23; 6.82 1.22; 6.81 1.24; 6.81 1.25; 4.09 0.87; 4.08 1.94; 4.06 0.92; 3.32 71.04; 3.30 1.70; 2.92 0.91; 2.91 1.86; 2.90 0.88; 2.89 1.45; 2.73 0.97; 2.52 0.55; 2.52 0.83; 2.51 18.44; 2.51 35.30; 2.50 48.54; 2.50 33.69; 2.49 16.77; 2.24 2.35; 2.22 2.85; 2.07 0.65; 2.07 0.36; 2.04 0.51; 2.02 0.64; 2.00 0.50; 1.73 16.00; 1.40 3.01; 0.90 1.42; 0.90 11.40; 0.89 1.97; 0.88 11.08; 0.86 0.37; 0.01 0.41; 0.00 13.55; −0.01 0.41

Example No. 106 [DMSO-$D_6$] 10.47 2.01; 8.22 2.45; 8.22 2.58; 8.21 2.55; 8.21 2.67; 7.98 1.71; 7.42 2.27; 7.41 0.90; 7.40 2.59; 7.40 2.96; 7.39 1.05; 7.38 2.67; 7.21 0.33; 7.20 2.82; 7.20 0.89; 7.18 0.92; 7.18 5.07; 7.17 0.97; 7.16 0.76; 7.16 2.31; 6.84 2.14; 6.83 2.11; 6.83 2.11; 6.82 2.15; 5.76 0.91; 5.61 7.37; 4.12 1.53; 4.11 3.50; 4.09 1.56; 3.34 47.42; 3.33 44.00; 3.33 52.21; 3.32 49.40; 3.30 0.61; 2.97 1.42; 2.96 2.95; 2.95 1.37; 2.52 0.49; 2.52 0.70; 2.51 15.64; 2.51 28.39; 2.50 39.07; 2.50 26.13; 2.07 0.35; 2.05 16.00; 0.01 0.46; 0.00 16.26; −0.01 0.48

Example No. 107 [DMSO-$D_6$] 10.78 3.48; 8.22 3.72; 8.22 3.74; 8.21 3.85; 8.20 3.83; 8.01 3.86; 7.42 0.40; 7.41 3.36; 7.41 1.38; 7.40 3.88; 7.39 4.20; 7.38 1.52; 7.38 3.81; 7.37 0.44; 7.21 0.48; 7.20 4.15; 7.20 1.26; 7.18 1.41; 7.18 7.38; 7.17 1.36; 7.16 1.15; 7.16 3.36; 6.80 3.22; 6.79 3.12; 6.78 3.18; 6.78 3.20; 5.76 16.00; 5.60 10.42; 4.12 2.14; 4.10 4.91; 4.09 2.24; 3.34 50.57; 3.33 51.49; 3.33 57.39; 3.33 66.01; 3.30 0.71; 3.18 0.34; 2.96 2.03; 2.95 4.15; 2.93 1.90; 2.52 0.57; 2.52 0.84; 2.51 18.33; 2.51 32.88; 2.50 45.30; 2.50 29.95; 2.49 15.00; 2.33 0.32; 2.02 0.35; 2.01 1.10; 1.99 1.74; 1.98 1.10; 1.96 0.38; 1.21 0.32; 1.17 0.51; 0.79 6.19; 0.77 10.98; 0.63 0.39; 0.63 0.43; 0.62 0.35; 0.01 0.48; 0.00 18.65; −0.01 0.57

Example No. 108 [DMSO-$D_6$] 10.73 3.94; 10.68 1.45; 8.22 1.61; 8.22 1.60; 8.21 4.05; 8.20 3.86; 8.00 4.82; 7.41 0.52; 7.41 4.10; 7.40 1.94; 7.40 4.85; 7.39 5.05; 7.39 2.22; 7.38 4.37; 7.38 0.62; 7.20 0.49; 7.20 3.58; 7.19 1.37; 7.19 2.37; 7.18 6.74; 7.18 1.79; 7.17 3.11; 7.17 3.42; 7.16 0.72; 7.16 1.27; 6.83 1.20; 6.83 1.17; 6.82 1.19; 6.82 1.18; 6.79 2.99; 6.79 2.92; 6.78 2.98; 6.78 2.98; 5.77 16.00; 5.60 11.84; 5.59 0.42; 4.12 0.79; 4.11 3.46; 4.10 5.95; 4.09 2.70; 3.35 80.58; 3.33 0.60; 2.99 0.53; 2.98 1.15; 2.97 1.19; 2.96 0.65; 2.95 2.42; 2.94 4.69; 2.93 2.26; 2.52 0.34; 2.51 10.03; 2.51 21.21; 2.51 28.69; 2.50 21.16; 2.50 10.09; 2.01 0.37; 2.00 0.51; 1.99 0.65; 1.99 0.37; 1.76 0.70; 1.76 1.31; 1.75 1.37; 1.74 1.30; 1.74 0.75; 1.25 0.45; 1.25 0.60; 1.24 0.80; 1.23 0.79; 1.23 0.88; 1.22 0.86; 1.22 0.88; 1.21 1.25; 1.21

1.18; 1.20 1.31; 1.20 1.23; 1.19 1.11; 1.19 0.86; 1.18 0.76; 1.18 0.35; 1.10 0.59; 1.09 0.56; 1.08 0.42; 1.07 11.46; 1.06 10.13; 1.05 5.88; 1.04 5.04; 1.04 0.41; 1.03 0.48; 1.03 2.32; 1.02 0.89; 0.99 0.99; 0.98 1.49; 0.97 1.79; 0.96 1.40; 0.96 0.95; 0.93 0.40; 0.93 0.49; 0.92 0.71; 0.91 0.69; 0.91 0.52; 0.90 0.35; 0.82 0.34; 0.75 0.38; 0.74 0.58; 0.74 0.54; 0.74 0.50; 0.73 0.52; 0.73 0.51; 0.73 0.34; 0.65 0.93; 0.65 1.05; 0.64 1.16; 0.64 1.39; 0.64 1.30; 0.63 1.05; 0.63 1.10; 0.62 0.78; 0.00 5.93

Example No. 109 [DMSO-$D_6$] 10.33 5.34; 8.20 5.37; 8.19 5.33; 8.19 5.42; 8.06 3.12; 7.42 0.40; 7.42 0.82; 7.42 4.50; 7.41 2.07; 7.41 5.13; 7.40 5.43; 7.40 2.23; 7.39 4.85; 7.39 0.61; 7.21 0.68; 7.20 5.15; 7.20 1.88; 7.19 2.14; 7.19 9.54; 7.18 1.67; 7.17 4.49; 7.17 0.52; 6.79 4.34; 6.79 4.34; 6.78 4.32; 6.78 4.35; 5.62 16.00; 4.13 3.67; 4.12 7.87; 4.11 3.71; 3.58 0.37; 3.37 0.76; 3.35 338.69; 3.33 1.44; 3.33 2.71; 2.99 3.38; 2.98 6.68; 2.97 3.15; 2.95 0.62; 2.95 0.68; 2.94 0.46; 2.93 0.46; 2.62 0.55; 2.62 0.76; 2.61 0.56; 2.52 1.45; 2.52 1.93; 2.52 2.31; 2.51 41.63; 2.51 87.11; 2.50 117.52; 2.50 85.88; 2.50 39.66; 2.39 0.47; 2.39 0.67; 2.38 0.47; 2.20 0.73; 2.20 0.46; 2.19 2.33; 2.18 1.90; 2.17 2.94; 2.17 3.52; 2.16 2.17; 2.15 3.09; 2.14 0.73; 2.14 1.04; 2.10 0.57; 2.09 1.04; 2.09 1.34; 2.08 1.37; 2.08 3.15; 2.07 3.16; 2.07 2.22; 2.07 2.30; 2.06 2.91; 2.06 1.78; 2.05 0.84; 2.05 0.87; 2.04 0.88; 2.04 0.72; 2.00 0.42; 1.99 0.61; 1.98 0.35; 1.98 0.54; 1.94 0.49; 1.93 1.25; 1.93 0.85; 1.91 1.89; 1.91 1.80; 1.90 1.21; 1.90 2.26; 1.88 1.25; 1.87 0.41; 1.86 0.36; 1.86 0.35; 1.84 0.48; 1.80 0.41; 1.79 0.69; 1.78 0.85; 1.78 1.44; 1.77 0.99; 1.77 0.91; 1.77 0.88; 1.76 1.21; 1.75 0.72; 1.74 0.47; 1.74 0.35; 1.73 0.32; 1.49 0.50; 1.31 0.53; 1.23 0.38; 1.08 0.34; 1.07 0.39; 0.01 0.98; 0.00 25.43; −0.01 0.78

Example No. 110 [DMSO-$D_6$] 10.40 1.02; 8.16 0.99; 8.16 1.04; 8.15 1.03; 8.15 1.07; 8.09 0.98; 7.40 0.88; 7.40 0.35; 7.39 1.01; 7.38 1.15; 7.37 0.41; 7.37 1.04; 7.20 1.09; 7.18 0.35; 7.17 1.95; 7.17 0.38; 7.15 0.90; 6.76 0.85; 6.76 0.83; 6.75 0.84; 6.75 0.84; 4.04 0.84; 4.02 0.85; 3.94 2.79; 3.34 31.11; 2.51 4.74; 2.50 6.50; 2.50 4.43; 2.40 0.42; 2.38 1.45; 2.36 1.59; 2.35 0.53; 1.99 3.78; 1.40 0.53; 1.19 1.01; 1.18 2.06; 1.16 3.63; 1.14 2.65; 1.07 16.00; 1.06 2.01; 1.04 4.34; 1.02 1.90

Example No. 111 [DMSO-$D_6$] 10.39 0.56; 8.16 0.55; 8.16 0.56; 8.15 0.56; 8.15 0.59; 8.09 0.60; 7.40 0.48; 7.39 0.55; 7.38 0.62; 7.37 0.57; 7.20 0.59; 7.17 1.06; 7.15 0.49; 6.76 0.47; 6.75 0.46; 6.74 0.46; 6.74 0.48; 3.94 2.46; 3.34 27.70; 2.51 3.07; 2.50 4.21; 2.50 2.82; 1.99 0.34; 1.16 1.44; 1.15 1.43; 1.07 16.00; 1.05 2.92

Example No. 112 [DMSO-$D_6$] 10.41 2.31; 8.22 2.22; 8.21 2.29; 8.01 2.21; 7.83 0.35; 7.82 0.36; 7.43 0.41; 7.42 2.11; 7.41 0.83; 7.40 2.39; 7.39 2.48; 7.39 0.93; 7.38 2.23; 7.34 0.56; 7.33 0.43; 7.31 1.42; 7.31 1.82; 7.29 1.20; 7.27 0.49; 7.25 0.41; 7.20 0.81; 7.20 2.57; 7.19 0.92; 7.18 1.44; 7.18 4.29; 7.17 0.99; 7.16 0.89; 7.15 1.94; 6.84 1.77; 6.83 1.75; 6.82 1.75; 6.82 1.81; 6.26 0.36; 6.26 0.42; 6.25 0.61; 5.84 0.50; 5.61 6.29; 4.13 1.29; 4.11 2.96; 4.10 1.37; 4.05 0.41; 3.70 2.22; 3.34 70.98; 2.99 1.23; 2.98 2.51; 2.96 1.15; 2.86 0.38; 2.52 0.51; 2.52 0.76; 2.51 17.53; 2.51 34.04; 2.50 47.12; 2.50 33.07; 2.49 16.51; 2.24 3.42; 2.22 4.15; 2.06 0.42; 2.04 0.77; 2.02 0.91; 2.01 0.73; 1.99 0.41; 1.91 0.43; 1.87 0.92; 1.71 3.25; 0.90 16.00; 0.88 15.65; 0.86 1.17; 0.00 1.83

Example No. 113 [$CD_3CN$] 8.59 1.60; 8.56 0.71; 8.56 0.71; 8.38 0.65; 8.38 0.67; 8.37 0.68; 8.37 0.68; 8.14 4.03; 8.14 4.16; 8.13 4.11; 8.13 4.21; 7.95 3.76; 7.68 0.33; 7.67 0.33; 7.47 0.47; 7.47 4.23; 7.46 1.73; 7.46 4.60; 7.45 4.82; 7.45 1.84; 7.44 4.47; 7.44 0.54; 7.39 0.62; 7.39 0.64; 7.39 0.64; 7.38 0.64; 7.10 0.55; 7.09 4.60; 7.09 1.51; 7.08 1.78; 7.08 8.87; 7.08 1.79; 7.07 1.48; 7.06 4.33; 7.06 0.49; 6.76 3.77; 6.76 3.90; 6.76 3.90; 6.75 3.80; 5.45 2.55; 4.88 16.00; 4.21 1.80; 4.20 4.70; 4.19 4.88; 4.17 4.86; 4.17 5.10; 4.16 3.79; 4.16 5.61; 4.15 2.15; 4.15 1.96; 4.08 0.34; 4.06 0.97; 4.05 0.98; 4.04 0.34; 2.34 1.48; 2.33 1.52; 2.27 9.09; 2.26 9.27; 2.18 87.47; 2.09 31.03; 2.08 0.55; 1.97 4.58; 1.97 3.02; 1.96 2.10; 1.96 2.73; 1.95 21.51; 1.95 39.41; 1.94 55.04; 1.94 37.15; 1.94 19.43; 1.34 1.11; 1.22 1.29; 1.20 2.46; 1.20 0.81; 1.19 1.28; 1.14 1.03; 1.13 0.87; 1.11 0.33; 1.09 0.39; 1.08 0.47; 1.08 0.48; 1.07 0.94; 1.07 0.97; 1.07 0.91; 1.07 0.68; 1.06 0.64; 1.06 1.70; 1.06 0.62; 1.06 0.69; 1.05 0.95; 1.05 0.96; 1.05 1.04; 1.04 0.49; 1.04 0.54; 1.04 0.41; 0.58 0.78; 0.58 0.74; 0.58 0.35; 0.57 0.38; 0.57 0.84; 0.57 0.75; 0.56 1.73; 0.55 4.37; 0.55 4.57; 0.54 2.10; 0.54 2.18; 0.54 4.56; 0.53 4.30; 0.53 1.75; 0.26 0.75; 0.26 0.74; 0.25 0.76; 0.25 0.83; 0.24 0.33; 0.23 1.51; 0.22 4.61; 0.22 4.58; 0.21 4.27; 0.21 4.75; 0.20 1.33; 0.00 6.10

Example No. 114 [$CD_3CN$] 8.59 2.54; 8.59 1.53; 8.58 1.54; 8.58 2.57; 7.37 3.17; 7.37 1.88; 7.36 1.84; 7.36 3.12; 6.82 2.59; 6.81 2.86; 6.67 2.84; 6.67 2.67; 4.32 0.65; 4.32 1.32; 4.31 0.57; 4.28 0.34; 4.28 0.33; 4.27 0.33; 4.27 0.32; 4.26 0.42; 4.26 0.38; 4.25 0.37; 4.02 0.40; 4.01 0.53; 4.00 0.47; 4.00 0.43; 3.99 0.57; 3.99 0.50; 3.98 0.37; 3.97 0.42; 3.17 16.00; 2.24 0.62; 2.23 0.43; 2.23 0.40; 2.23 0.38; 2.21 0.39; 2.21 0.40; 2.20 0.45; 2.20 0.37; 2.18 0.36; 2.16 394.92; 2.15 0.79; 2.14 0.54; 2.14 0.85; 2.06 0.40; 2.06 0.74; 2.05 1.10; 2.05 0.75; 2.04 0.38; 1.98 0.34; 1.97 0.52; 1.97 9.52; 1.96 5.44; 1.95 7.79; 1.95 72.73; 1.95 131.74; 1.94 197.34; 1.94 136.52; 1.93 68.11; 1.93 1.17; 1.92 0.67; 1.92 0.57; 1.91 0.34; 1.84 0.41; 1.83 0.78; 1.83 1.10; 1.82 0.76; 1.82 0.38; 1.78 0.44; 1.76 0.33; 1.75 0.49; 1.75 0.48; 1.27 1.08; 0.01 0.97; 0.00 30.82; −0.01 0.89

Example No. 115 [DMSO-$D_6$] 8.20 0.32; 7.35 0.40; 7.35 0.54; 7.32 0.46; 7.31 0.41; 7.30 0.42; 3.93 2.43; 3.89 0.85; 3.34 21.37; 2.51 1.65; 2.51 3.53; 2.50 4.82; 2.50 3.58; 2.49 1.79; 2.38 0.51; 2.36 0.53; 1.99 0.94; 1.17 0.51; 1.16 0.35; 1.07 16.00; 1.05 0.70; 1.03 1.31; 1.02 0.60; 0.00 0.48

Example No. 116 [DMSO-$D_6$] 10.41 1.98; 8.21 1.89; 8.19 1.97; 8.03 2.31; 7.42 1.56; 7.41 0.75; 7.41 1.83; 7.40 2.12; 7.39 0.87; 7.38 1.88; 7.33 0.38; 7.20 1.92; 7.20 0.75; 7.18 0.78; 7.18 3.43; 7.16 0.60; 7.16 1.60; 6.78 1.51; 6.77 1.48; 6.77 1.53; 5.69 0.34; 5.67 1.21; 5.66 1.23; 5.64 0.36; 4.31 0.50; 4.30 0.54; 4.28 0.65; 4.27 0.59; 4.06 1.23; 4.04 3.73; 4.02 3.79; 4.00 1.29; 3.94 0.33; 3.93 0.47; 3.93 0.70; 3.91 0.72; 3.91 0.77; 3.89 0.42; 3.88 0.34; 3.57 0.45; 3.32 28.64; 3.30 0.55; 3.12 0.54; 3.10 0.38; 3.09 0.40; 2.81 0.66; 2.81 0.72; 2.77 0.82; 2.75 0.80; 2.73 1.07; 2.72 0.80; 2.51 7.58; 2.51 15.92; 2.50 21.76; 2.50 16.77; 2.49 8.99; 1.99 16.00; 1.72 5.27; 1.71 5.31; 1.40 0.42; 1.20 0.33; 1.19 4.44; 1.17 8.71; 1.16 4.36; 1.09 0.44; 1.07 13.25; 1.05 12.16; 0.00 3.20

Example No. 117 [DMSO-$D_6$] 8.54 6.04; 8.54 6.22; 8.34 3.94; 8.34 4.00; 8.33 4.08; 8.33 4.10; 7.40 0.44; 7.39 4.29; 7.38 1.85; 7.38 4.83; 7.37 5.80; 7.36 2.11; 7.35 5.24; 7.35 0.67; 7.26 3.11; 7.25 3.29; 7.24 3.51; 7.23 3.12; 7.20 0.65; 7.20 5.66; 7.19 1.80; 7.18 1.92; 7.17 10.00; 7.17 2.10; 7.16 1.59; 7.15 4.54; 7.14 0.50; 4.53 1.17; 4.51 2.29; 4.49 2.31; 4.48 1.15; 3.94 1.70; 3.46 0.35; 3.41 0.63; 3.35 757.79; 3.34 820.12; 3.01 0.46; 3.00 0.61; 2.98 0.56; 2.97 1.30; 2.96 1.51; 2.94 1.43; 2.93 1.61; 2.91 2.04; 2.89 1.87; 2.87 0.78; 2.85 0.84; 2.83 0.87; 2.82 0.74; 2.82 0.92; 2.80 1.57; 2.79 1.11; 2.78 1.40; 2.77 0.98; 2.76 0.70; 2.75 0.51; 2.68 0.42; 2.68 0.85; 2.67 1.18; 2.67 0.86; 2.66 0.43; 2.54 0.57; 2.54 0.53; 2.53 3.59; 2.52 5.35; 2.51 62.19; 2.51 127.34; 2.50 169.68; 2.50 125.11; 2.49 62.31; 2.34 0.43; 2.33 0.86; 2.33 1.19; 2.33 0.89; 2.32 0.45; 2.23 0.65; 2.21 1.34; 2.21 0.89; 2.20 1.22; 2.19 1.37; 2.18 1.43; 2.17 1.06; 2.16 0.90; 2.16 1.09; 2.14 0.56; 2.07 1.40; 1.50 16.00; 1.49 15.95; 1.24 0.51; 1.16 2.81; 1.07 13.39; 0.01 0.78; 0.00 25.60

Example No. 118 [DMSO-$D_6$] 8.61 9.62; 8.60 9.81; 8.44 6.16; 8.44 6.08; 8.43 6.35; 8.43 6.19; 7.33 0.68; 7.32 6.73; 7.31 2.80; 7.31 7.54; 7.30 9.22; 7.29 3.29; 7.28 8.37; 7.28 1.18; 7.26 4.65; 7.25 4.96; 7.25 5.29; 7.23 4.63; 7.16 1.02; 7.16 9.31; 7.15 2.73; 7.14 2.89; 7.13 16.00; 7.13 3.09; 7.12 2.41; 7.11 7.12; 7.10 0.79; 5.76 0.46; 4.37 5.36; 4.36 4.78; 4.35 5.03; 3.35 80.36; 2.65 4.89; 2.64 4.16; 2.62 5.19; 2.52 0.44; 2.52 8.56; 2.51 18.70; 2.51 25.30; 2.50 18.15; 2.50 8.58; 1.85 3.90; 1.84 3.74; 1.77 3.55; 1.76 4.08; 1.64 3.24; 1.63 4.07; 1.26 0.41; 1.23 0.52; 1.07 1.69; 0.00 2.91

The intensity of sharp signals correlates with the height of the signals in a printed example of an NMR spectrum in cm and shows the true ratios of the signal intensities. In the case of broad signals, a plurality of peaks or the middle of the signal and their relative intensities compared to the most intensive signal in the spectrum may be shown.

The lists of the $^1$H-NMR peaks are similar to the classic $^1$H-NMR prints and thus usually comprise all peaks listed in classic NMR interpretations.

In addition, like classic $^1$H-NMR prints, they may show solvent signals, signals of stereoisomers of the target compounds, which are likewise part of the subject matter of the invention, and/or peaks of impurities.

In the list of compound signals in the delta range of solvents and/or water, in our lists of $^1$H-NMR peaks the usual solvent peaks, for example peaks of DMSO in DMSO-d$_6$ and the peak of water, which usually on average have a high intensity, are shown.

Usually, on average, the peaks of stereoisomers of the target compounds and/or peaks of impurities have a lower intensity than the peaks of the target compounds (for example of a purity of >90%).

Such stereoisomers and/or impurities may be typical for the preparation process in question. Thus, their peaks may help to identify any reproduction of our preparation process using "by-product fingerprints".

If required, an expert calculating the peaks of the target compounds with known methods (MestreC, ACD simulation, but also using empirically evaluated expected values) can isolate the peaks of the target compounds, using, if appropriate, additional intensity filters. This isolation would be similar to the corresponding peak picking of the classic $^1$H-NMR interpretation.

If, as the case may be, signals having identical δ values occur as a result of rounding of the δ value to two decimal places, their intensities after addition give the same image which can also be observed in a print of a classic NMR in the range of this δ value.

USE EXAMPLES

Example A

*Alternaria* Test (Tomato)/Protective

Solvent: 49 parts by weight of N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the active compound preparation at the stated application rate. 1 day after the treatment, the plants are inoculated with a spore suspension of *Alternaria solani* and then remain at 100% rel. humidity and 22° C. for 24 h. The plants then remain at 96% rel. atmospheric humidity and a temperature of 20° C.

Evaluation is carried out 7 days after the inoculation. 0% means an efficacy which corresponds to that of the control, whereas an efficacy of 100% means that no infection is observed.

In this test, the compounds according to the invention below show, at an active compound concentration of 500 ppm, an efficacy of 70% or more.

Example No. [Table 1] (efficacy in %):
2 (94%), 3 (95%), 5 (100%), 6 (95%), 7 (95%), 8 (100%), 9 (100%), 10 (70%), 15 (100%), 19 (100%), 20 (100%), 21 (100%), 22 (95%), 23 (95%), 24 (95%), 25 (100%), 26 (100%), 27 (100%), 28 (100%), 29 (100%), 30 (100%), 31 (94%), 32 (78%), 33 (89%), 34 (100%), 35 (94%), 37 (95%), 38 (95%), 39 (80%), 40 (100%), 41 (70%), 43 (94%), 44 (80%), 45 (95%), 46 (70%), 47 (90%), 50 (95%), 51 (95%), 52 (90%), 54 (80%), 55 (80%), 58 (80%), 59 (70%), 62 (94%), 63 (100%), 64 (100%), 65 (100%), 66 (70%), 67 (80%), 70 (90%), 74 (95%), 75 (95%), 76 (100%), 77 (89%), 82 (89%), 83 (89%), 86 (90%), 87 (80%), 88 (90%), 89 (90%), 90 (95%), 91 (90%), 92 (90%), 93 (95%), 94 (90%), 95 (80%), 96 (90%), 97 (70%), 98 (90%), 99 (80%), 100 (80%), 101 (90%), 102 (95%), 104 (80%), 106 (80%), 108 (80%), 109 (90%), 112 (90%), 113 (90%) 117 (94%).

Example B

*Botrytis* Test (Bean)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the active compound preparation at the stated application rate. After the spray coating has dried on, 2 small pieces of agar colonized by *Botrytis cinerea* are placed onto each leaf. The inoculated plants are placed in a dark chamber at about 20° C. and 100% relative atmospheric humidity.

2 days after the inoculation, the size of the infected areas on the leaves is evaluated. 0% means an efficacy which corresponds to that of the control, whereas an efficacy of 100% means that no infection is observed.

In this test, the compounds according to the invention below show, at an active compound concentration of 100 ppm, an efficacy of 70% or more.

Example No. [Table 1] (efficacy in %):
2 (100%), 5 (100%), 7 (95%), 8 (99%), 9 (93%), 15 (82%), 19 (99%), 20 (98%), 21 (98%), 22 (89%), 23 (100%), 24 (76%), 25 (90%), 26 (93%), 27 (92%), 28 (95%), 29 (100%), 30 (100%), 31 (90%), 32 (98%), 33 (98%), 34 (99%), 35 (96%), 40 (100%), 43 (99%), 51 (99%), 52 (78%), 58 (100%), 59 (100%), 63 (94%), 64 (100%), 65 (97%), 74 (100%), 76 (100%), 77 (100%), 78 (100%), 85 (100%), 86 (100%), 87 (100%), 89 (100%), 91 (100%) 117 (100%).

Example C

*Fusarium graminearum* Test (Barley)/Protective

Solvent: 49 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the active compound preparation at the stated application rate.

After the spray coating has dried on, the plants are sprayed with spores of a spore suspension of *Fusarium graminearum*.

The plants are placed in a greenhouse chamber under a translucent incubation hood at 22° C. and 100% relative atmospheric humidity.

Evaluation is carried out 5 days after the inoculation. 0% means an efficacy which corresponds to that of the control, whereas an efficacy of 100% means that no infection is observed.

In this test, the compounds according to the invention below show, at an active compound concentration of 1000 ppm, an efficacy of 70% or more.

Example No. [Table 1] (efficacy in %):
5 (100%), 8 (88%), 15 (100%), 19 (100%), 20 (94%), 21 (100%), 22 (100%), 23 (88%), 24 (100%), (94%), 26 (88%), 27 (94%), 28 (100%), 29 (94%), 30 (88%), 31 (100%), 32 (86%), 34 (100%), 36 (93%), 40 (100%), 50 (83%), 55 (83%), 58 (100%), 59 (94%), 63 (83%), 65 (83%), 76 (90%), 77 (90%) 117 (100%).

Example D

*Fusarium nivale* (var. *majus*) Test (Wheat)/Protective

Solvent: 49 parts by weight of N,N-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the active compound preparation at the stated application rate.

After the spray coating has dried on, the plants are sprayed with spores of a spore suspension of *Fusarium nivale* (var. *majus*).

The plants are placed in a greenhouse chamber under a translucent incubation hood at 10° C. and 100% relative atmospheric humidity.

Evaluation is carried out 5 days after the inoculation. 0% means an efficacy which corresponds to that of the control, whereas an efficacy of 100% means that no infection is observed.

In this test, the compounds according to the invention below show, at an active compound concentration of 1000 ppm, an efficacy of 70% or more.

Example No. [Table 1] (efficacy in %):
5 (100%), 8 (100%), 15 (100%), 19 (100%), 20 (100%), 21 (100%), 22 (86%), 23 (86%), 24 (100%), 25 (100%), 26 (86%), 27 (86%), 28 (100%), 29 (86%), 30 (86%), 31 (100%), 32 (86%), 34 (100%), 36 (88%), 37 (86%), 38 (86%), 40 (100%), 43 (80%), 47 (80%), 50 (83%), 55 (100%), 58 (100%), 59 (100%), 63 (83%), 65 (100%), 76 (100%), 77 (100%) 117 (100%).

Example E

*Leptosphaeria nodorum* Test (Wheat)/Protective

Solvent: 49 parts by weight of N,N-dimethylformamide
Emulsifier: 1 part by weight of alkylaryl polyglycol ether To produce a suitable preparation of active compounds, 1 part by weight of active compound is mixed with the stated amounts of solvent and emulsifier, and the concentrate is diluted with water to the desired concentration.

To test for protective activity, young wheat plants are sprayed with the active compound preparation at the stated application rate. 1 day after the treatment, the plants are inoculated with an aqueous spore suspension of *Leptosphaeria nodorum* and then remain at 100% rel. atmospheric humidity and 22° C. for 48 h. The plants are then placed in a greenhouse at 90% rel. atmospheric humidity and a temperature of 22° C.

Evaluation is carried out 7-9 days after the inoculation. 0% means an efficacy which corresponds to that of the control, whereas an efficacy of 100% means that no infection is observed.

In this test, the compounds according to the invention below show, at an active compound concentration of 500 ppm, an efficacy of 70% or more.

Example No. [Table 1] (efficacy in %):
2 (80%), 3 (89%), 5 (94%), 6 (70%), 8 (95%), 9 (95%), 10 (80%), 11 (70%), 15 (95%), 19 (95%), 20 (95%), 21 (95%), 22 (80%), 23 (90%), 24 (90%), 25 (95%), 26 (80%), 28 (90%), 29 (90%), 30 (90%), 31 (90%), 32 (90%), 33 (70%), 34 (95%), 35 (90%), 36 (90%), 37 (90%), 40 (95%), 43 (90%), 55 (90%), 58 (94%), 59 (89%), 60 (78%), 62 (78%), 63 (94%), 64 (94%), 65 (94%), 70 (90%), 74 (88%), 76 (89%), 77 (94%), 78 (100%), 82 (88%), 83 (75%), 84 (88%), 85 (75%), 86 (70%), 87 (70%), 89 (80%), 90 (89%), 91 (78%), 92 (90%), 93 (80%), 95 (90%), 96 (90%), 97 (80%), 99 (95%), 100 (70%), 101 (70%), 102 (90%), 107 (90%), 108 (70%), 112 (90%), 113 (78%) 117 (86%).

Example F

*Phytophthora* Test (Tomato)/Protective

Solvent: 49 parts by weight of N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the active compound preparation at the stated application rate. 1 day after the treatment, the plants are inoculated with a spore suspension of *Phytophthora infestans* and then remain at 100% rel. humidity and 22° C. for 24 h. The plants are then placed in a climatized chamber at about 96% relative atmospheric humidity and a temperature of about 20° C.

Evaluation is carried out 7 days after the inoculation. 0% means an efficacy which corresponds to that of the control, whereas an efficacy of 100% means that no infection is observed.

In this test, the compounds according to the invention below show, at an active compound concentration of 500 ppm, an efficacy of 70% or more.

Example No. [Table 1] (efficacy in %):
2 (94%), 3 (90%), 5 (95%), 7 (95%), 8 (95%), 9 (90%), 10 (70%), 11 (80%), 14 (70%), 15 (95%), 17 (80%), 19 (100%), 20 (100%), 21 (90%), 22 (90%), 23 (80%), 24 (90%), 25 (80%), 26 (95%), 27 (80%), 28 (95%), 29 (90%), 30 (80%), 31 (80%), 32 (70%), 33 (70%), 34 (95%), 35 (80%), 36 (80%), 37 (70%), 38 (70%), 39 (80%), 40 (70%), 41 (70%), 43 (70%), 44 (70%), 45 (90%), 46 (70%), 47 (80%), 48 (70%), 52 (95%), 56 (80%), 58 (70%), 62 (80%), 63 (95%), 64 (80%), 65 (90%), 66 (80%), 67 (70%), 69 (70%), 70 (95%), 71 (80%), 74 (90%), 75 (80%), 82 (70%), 83 (70%), 85 (90%), 87 (90%), 88 (80%), 89 (90%), 90 (78%), 92 (80%), 93 (90%), 96 (70%), 113 (70%).

Example G

*Puccinia triticina* Test (Wheat)/Protective

Solvent: 49 parts by weight of INN-dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the active compound preparation at the stated application rate.

After the spray coating has dried on, the plants are sprayed with spores of a spore suspension of Puccinia triticina. The plants remain in an incubation cabin at 20° C. and 100% relative atmospheric humidity for 48 hours.

The plants are placed in greenhouse at a temperature of about 20° C. and a relative atmospheric humidity of about 80%.

Evaluation is carried out 8 days after the inoculation. 0% means an efficacy which corresponds to that of the control, whereas an efficacy of 100% means that no infection is observed.

In this test, the compounds according to the invention below show, at an active compound concentration of 1000 ppm, an efficacy of 70% or more.

Example No. [Table 1] (efficacy in %):
5 (100%), 8 (100%), 15 (94%), 19 (100%), 19 (95%), 20 (100%), 21 (95%), 22 (75%), 23 (75%), 24 (100%), 25 (88%), 26 (100%), 27 (75%), 28 (100%), 29 (94%), 30 (88%), 31 (94%), 32 (89%), 34 (94%), 36 (78%), 37 (78%), 40 (100%), 43 (100%), 50 (86%), 55 (100%), 58 (100%), 59 (100%), 63 (86%), 65 (86%), 76 (88%), 77 (88%) 117 (100%).

Example H

Pyrenophora teres Test (Barley)/Protective

Solvent: 49 parts by weight of N,N-dimethylformamide
Emulsifier: 1 part by weight of alkylaryl polyglycol ether To produce a suitable preparation of active compounds, 1 part by weight of active compound is mixed with the stated amounts of solvent and emulsifier, and the concentrate is diluted with water to the desired concentration.

To test for protective activity, young barley plants are sprayed with the active compound preparation at the stated application rate. 1 day after the treatment, the plants are inoculated with an aqueous spore suspension of Pyrenophora teres and then remain at 100% rel. atmospheric humidity and 22° C. for 48 h. The plants are then placed in a greenhouse at 80% rel. atmospheric humidity and a temperature of 20° C.

Evaluation is carried out 7-9 days after the inoculation. 0% means an efficacy which corresponds to that of the control, whereas an efficacy of 100% means that no infection is observed.

In this test, the compounds according to the invention below show, at an active compound concentration of 500 ppm, an efficacy of 70% or more.

Example No. [Table 1] (efficacy in %): 2 (95%), 3 (95%), 5 (100%), 6 (70%), 7 (80%), 8 (100%), 9 (94%), 10 (80%), 11 (70%), 13 (80%), 15 (100%), 19 (100%), 20 (100%), 21 (100%), 22 (95%), 23 (95%), 24 (95%), 25 (100%), 26 (95%), 27 (90%), 28 (100%), 29 (100%), 30 (100%), 31 (100%), 32 (78%), 33 (78%), 34 (94%), 35 (78%), 36 (89%), 37 (100%), 38 (95%), 39 (95%), 40 (95%), 41 (95%), 43 (95%), 44 (90%), 45 (95%), 46 (70%), 47 (90%), 50 (95%), 51 (90%), 52 (80%), 55 (95%), 58 (90%), 59 (90%), 60 (90%), 61 (70%), 62 (95%), 63 (95%), 64 (100%), 65 (95%), 66 (95%), 67 (95%), 70 (80%), 71 (80%), 72 (80%), 73 (70%), 74 (100%), 75 (100%), 78 (95%), 82 (94%), 83 (94%), 84 (94%), 85 (100%), 86 (100%), 87 (90%), 88 (90%), 89 (95%), 90 (95%), 91 (95%), 92 (95%), 93 (100%), 94 (95%), 95 (100%), 96 (100%), 97 (100%), 98 (95%), 99 (95%), 100 (100%), 101 (95%), 102 (95%), 103 (90%), 104 (95%), 105 (95%), 106 (95%), 107 (95%), 108 (95%), 109 (95%), 112 (95%), 113 (94%) 117 (100%).

Example I

Septoria tritici Test (Wheat)/Protective

Solvent: 49 parts by weight of N,N-dimethylacetamide
Emulsifier: 1 part by weight of alkylaryl polyglycol ether To produce a suitable preparation of active compound, 1 part by weight of active compound is mixed with the stated amount of solvent and emulsifier, and the concentrate is diluted with water to the desired concentration.

To test for protective activity, young plants are sprayed with the active compound preparation at the stated application rate. After the spray coating has dried on, the plants are sprayed with a spore suspension of Septoria tritici. The plants remain in an incubation cabin at 20° C. and 100% relative atmospheric humidity for 48 hours. The plants are then placed under a translucent hood at 15° C. and 100% relative atmospheric humidity for a further 60 hours.

The plants are placed in a greenhouse at a temperature of about 15° C. and a relative atmospheric humidity of 80%.

Evaluation is carried out 21 days after the inoculation. 0% means an efficacy which corresponds to that of the control, whereas an efficacy of 100% means that no infection is observed.

In this test, the compounds according to the invention below show, at an active compound concentration of 1000 ppm, an efficacy of 70% or more.

Example No. [Table 1] (efficacy in %):
8 (100%), 15 (100%), 19 (100%), 21 (100%), 22 (86%), 23 (86%), 24 (100%), 25 (86%), 26 (86%), 28 (100%), 29 (71%), 30 (100%), 31 (100%), 32 (100%), 34 (93%), 36 (100%), 40 (90%), 43 (100%), 47 (100%), 50 (90%), 55 (90%), 58 (89%), 63 (100%), 65 (90%), 76 (100%), 77 (100%) 117 (100%).

Example J

Sphaerotheca Test (Cucumber)/Protective

Solvent: 49 parts by weight of N,N-dimethylformamide
Emulsifier: 1 part by weight of alkylaryl polyglycol ether To produce a suitable preparation of active compounds, 1 part by weight of active compound is mixed with the stated amounts of solvent and emulsifier, and the concentrate is diluted with water to the desired concentration.

To test for protective activity, young cucumber plants are sprayed with the active compound preparation at the stated application rate. 1 day after the treatment, the plants are inoculated with a spore suspension of Sphaerotheca fuliginea. The plants are then placed in a greenhouse at 70% rel. atmospheric humidity and a temperature of 23° C.

Evaluation is carried out 7 days after the inoculation. 0% means an efficacy which corresponds to that of the control, whereas an efficacy of 100% means that no infection is observed.

In this test, the compounds according to the invention below show, at an active compound concentration of 500 ppm, an efficacy of 70% or more.

Example No. [Table 1] (efficacy in %):
2 (91%), 5 (95%), 7 (90%), 8 (99%), 9 (86%), 10 (94%), 11 (88%), 15 (98%), 19 (98%), 20 (100%), 21 (100%), 22 (90%), 23 (89%), 24 (94%), 25 (94%), 26 (98%), 28 (100%), 29 (83%), 30 (95%), 31 (95%), 33 (95%), 34 (100%), 36 (94%), 40 (94%), 47 (96%), 50 (94%), 55 (95%), 58 (96%), 59 (98%), 60 (90%), 63 (93%), 64 (86%), 65 (100%), 70 (94%), 74 (93%), 75 (95%), 76 (100%), 78 (100%), 82 (95%), 83 (98%), 84 (98%), 85 (85%), 86 (100%), 87 (95%), 88 (95%), 89 (100%), 90 (95%), 91 (100%), 92 (98%), 93 (98%), 94 (93%), 95 (95%), 96 (95%), 97 (100%), 98 (90%), 99 (98%), 100 (95%), 101 (98%), 102 (100%), 104 (93%), 106 (75%), 107 (100%), 108 (95%), 109 (93%), 112 (95%), 113 (98%) 117 (95%).

Example K

*Uromyces* Test (Bean)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the active compound preparation at the stated application rate. After the spray coating has dried on, the plants are inoculated with an aqueous spore suspension of the bean rust pathogen *Uromyces appendiculatus* and then remain in an incubation cabin at about 20° C. and 100% relative atmospheric humidity for 1 day.

The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

In this test, the compounds according to the invention below show, at an active compound concentration of 100 ppm, an efficacy of 70% or more.

Example No. [Table 1] (efficacy in %):
5 (98%), 8 (100%), 15 (94%), 19 (94%), 20 (94%), 21 (94%), 22 (94%), 23 (95%), 24 (91%), 25 (94%), 26 (94%), 27 (94%), 28 (95%), 29 (94%), 30 (95%), 31 (94%), 32 (96%), 33 (95%), 34 (95%), 36 (85%), 40 (81%), 40 (75%), 43 (90%), 51 (86%), 63 (75%), 64 (78%), 65 (95%), 76 (95%), 77 (98%), 78 (94%), 85 (85%), 86 (95%), 87 (93%), 89 (95%), 91 (95%) 117 (90%).

Example L

*Venturia* Test (Apple)/Protective

Solvents: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the active compound preparation at the stated application rate. After the spray coating has dried on, the plants are inoculated with an aqueous conidia suspension of the apple scab pathogen *Venturia inaequalis* and then remain in an incubation cabin at about 20° C. and 100% relative atmospheric humidity for 1 day.

The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

In this test, the compounds according to the invention below show, at an active compound concentration of 100 ppm, an efficacy of 70% or more.

Example No. [Table 1] (efficacy in %): 2 (95%), 5 (98%), 7 (76%), 8 (96%), 9 (95%), 15 (94%), 19 (93%), 20 (99%), 21 (99%), 22 (76%), 23 (98%), 24 (83%), 25 (94%), 26 (93%), 27 (89%), 28 (100%), 29 (95%), 30 (99%), 31 (100%), 32 (90%), 33 (95%), 34 (95%), 35 (95%), 40 (94%), 43 (98%), 50 (88%), 51 (74%), 52 (94%), 58 (99%), 59 (97%), 63 (99%), 64 (99%), 65 (96%), 70 (100%), 74 (95%), 76 (100%), 77 (100%), 78 (100%), 86 (95%), 89 (94%), 91 (95%) 117 (100%).

Example M

*Pyricularia* Test (Rice)/Protective

Solvent: 28.5 parts by weight of acetone
Emulsifier: 1.5 parts by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the active compound preparation at the stated application rate. 1 day after the treatment, the plants are inoculated with an aqueous spore suspension of *Pyricularia oryzae*. The plants are then placed in a greenhouse at 100% relative atmospheric humidity and 25° C.

Evaluation is carried out 5 days after the inoculation. 0% means an efficacy which corresponds to that of the control, whereas an efficacy of 100% means that no infection is observed.

In this test, the compounds according to the invention below show, at an active compound concentration of 250 ppm, an efficacy of 80% or more.

Example No. [Table 1] (efficacy in %):
19 (92%), 20 (92%), 21 (98%), 28 (90%), 29 (95%), 30 (94%), 31 (98%), 34 (95%).

Example N

*Rhizoctonia* Test (Rice)/Protective

Solvent: 28.5 parts by weight of acetone
Emulsifier: 1.5 parts by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the active compound preparation at the stated application rate. 1 day after the treatment, the plants are inoculated with hyphae of *Rhizoctonia solani*. The plants are then placed in a greenhouse at 100% relative atmospheric humidity and 25° C.

Evaluation is carried out 4 days after the inoculation. 0% means an efficacy which corresponds to that of the control, whereas an efficacy of 100% means that no infection is observed.

In this test, the compounds according to the invention below show, at an active compound concentration of 250 ppm, an efficacy of 80% or more.

Example No. [Table 1] (efficacy in %):
19 (100%), 20 (100%), 21 (100%), 28 (100%), 29 (100%), 30 (100%), 31 (100%), 34 (85%).

Example O

Cochliobolus Test (Rice)/Protective

Solvent: 28.5 parts by weight of acetone
Emulsifier: 1.5 parts by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the active compound preparation at the stated application rate. 1 day after the treatment, the plants are inoculated with an aqueous spore suspension of Cochliobolus miyabeanus. The plants are then placed in a greenhouse at 100% relative atmospheric humidity and 25° C.

Evaluation is carried out 4 days after the inoculation. 0% means an efficacy which corresponds to that of the control, whereas an efficacy of 100% means that no infection is observed.

In this test, the compounds according to the invention below show, at an active compound concentration of 250 ppm, an efficacy of 80% or more.

Example No. [Table 1] (efficacy in %):
19 (96%), 20 (96%), 21 (96%), 28 (95%), 29 (95%), 30 (96%), 31 (95%), 34 (90%).

Example P

Gibberella Test (Rice)/Protective

Solvent: 28.5 parts by weight of acetone
Emulsifier: 1.5 parts by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the active compound preparation at the stated application rate. 1 day after the treatment, the plants are inoculated with an aqueous spore suspension of Gibberella zeae. The plants are then placed in a greenhouse at 100% relative atmospheric humidity and 25° C.

Evaluation is carried out 5 days after the inoculation. 0% means an efficacy which corresponds to that of the control, whereas an efficacy of 100% means that no infection is observed.

In this test, the compounds according to the invention below show, at an active compound concentration of 250 ppm, an efficacy of 80% or more.

Example No. [Table 1] (efficacy in %):
28 (85%), 29 (80%), 31 (80%), 34 (80%).

Example Q

Phakopsora Test (Sojabohnen)/Protective

Solvent: 28.5 parts by weight of acetone
Emulsifier: 1.5 parts by weight of alkylaryl polyglycol ether To produce a suitable preparation of active compound, 1 part by weight of active compound is mixed with the stated amount of solvent, and the concentrate is diluted with water and the stated amount of emulsifier to the desired concentration.

To test for protective activity, young rice plants are sprayed with the active compound preparation at the stated application rate. 1 day after the treatment, the plants are inoculated with an aqueous spore suspension of Phakopsora pachyrhizi. The plants are then placed in a greenhouse at 80% relative atmospheric humidity and 20° C.

Evaluation is carried out 1 day after the inoculation. 0% means an efficacy which corresponds to that of the control, whereas an efficacy of 100% means that no infection is observed.

In this test, the compounds according to the invention below show, at an active compound concentration of 250 ppm, an efficacy of 80% or more.

Example No. [Table 1] (efficacy in %):
5 (80%).

Example R

Production of DON/Acetyl-DON by Fusarium graminearum

The compounds were tested in microtitre plates in a DON-inducing liquid medium (1 g of $(NH_4)_2HPO_4$, 0.2 g of $MgSO_4 \times 7H_2O$, 3 g of $KH_2PO_4$, 10 g of glycerol, 5 g of NaCl and 40 g of sucrose per liter) and DMSO (0.5%). Inoculation was carried out using a concentrated spore suspension of Fusarium graminearum at a final concentration of 2000 spores/ml.

The plate was incubated at 28° C. and high atmospheric humidity for 7 days.

At the beginning and after 3 days, the OD was measured at OD620 (repeat measurements: 3×3 measurements per well) to calculate the inhibition of growth.

After 7 days, 1 volume of an 84/16 acetonitrile/water mixture was added, and a sample of the liquid medium from each well was then removed and diluted 1:100 in 10% strength acetonitrile. The proportions of DON and acetyl-DON of the samples were analysed by HPLC-MS/MS, and the measured values were used to calculate the inhibition of DON/AcDON production compared to an active compound-free control.

HPLC-MS/MS measurements were carried out using the following parameters:
Ionization: ESI negative
Ion spray voltage: −4500 V
Spray gas temperature: 500° C.
Decluster potential: −40 V
Collision energy: −22 eV
Collision gas: $N_2$
NMR trace: 355.0>264.9;
HPLC column: Waters Atlantis T3 (trifunctionally C18-bonded, sealed)
Particle size: 3 μm
Column dimensions: 50×2 mm
Temperature: 40° C.
Solvent A: water/2.5 mM $NH_4OAc$+0.05% $CH_3COOH$ (v/v)
Solvent B: methanol/2.5 mM $NH_4OAc$+0.05% $CH_3COOH$ (v/v)
Flow rate: 400 μl/minute
Injection volume: 11 μl Gradient:

| Time [min] | A % | B % |
|---|---|---|
| 0 | 100 | 0 |
| 0.75 | 100 | 0 |
| 1.5 | 5 | 95 |
| 4 | 5 | 95 |
| 5 | 100 | 0 |
| 10 | 100 | 0 |

Examples of DON Inhibition

The following examples showed an activity of >80% for the inhibition of DON/AcDON production at 50 μM. The inhibition of growth of *Fusarium graminearum* of the examples mentioned varied from 0 to 100% at 50 μM.

| Example No. | % inhibition of DON/AcDON at 50 μM | % inhibition of the fungal growth of *Fusarium graminearum* at 50 μM |
|---|---|---|
| 2 | 100 | 99 |
| 3 | 94 | 30 |
| 5 | 99 | 100 |
| 6 | 99 | 70 |
| 7 | 99 | 100 |
| 8 | 99 | 100 |
| 9 | 99 | 100 |
| 10 | 100 | 87 |
| 11 | 100 | 92 |
| 13 | 96 | 17 |
| 14 | 93 | 24 |
| 15 | 99 | 88 |
| 16 | 93 | 0 |
| 19 | 100 | 100 |
| 20 | 100 | 95 |
| 21 | 100 | 97 |
| 22 | 100 | 97 |
| 23 | 100 | 97 |
| 24 | 99 | 74 |
| 25 | 99 | 92 |
| 26 | 98 | 57 |
| 27 | 99 | 56 |
| 28 | 99 | 100 |
| 29 | 99 | 100 |
| 30 | 99 | 88 |
| 31 | 99 | 97 |
| 32 | 99 | 94 |
| 33 | 99 | 100 |
| 34 | 99 | 98 |
| 36 | 99 | 94 |
| 37 | 99 | 93 |
| 38 | 99 | 89 |
| 41 | 98 | 100 |
| 42 | 98 | 100 |
| 43 | 98 | 100 |
| 44 | 100 | 61 |
| 45 | 100 | 21 |
| 46 | 100 | 52 |
| 47 | 100 | 76 |
| 50 | 92 | 57 |
| 51 | 100 | 41 |
| 52 | 99 | 19 |
| 54 | 100 | 0 |
| 56 | 92 | 27 |
| 58 | 100 | 100 |
| 59 | 100 | 100 |
| 60 | 100 | 100 |
| 61 | 100 | 0 |
| 62 | 100 | 35 |
| 63 | 100 | 100 |
| 64 | 100 | 100 |
| 65 | 100 | 100 |
| 66 | 98 | 50 |
| 67 | 100 | 60 |

The invention claimed is:

1. A compound of formula (I), or an agrochemically active salt thereof,

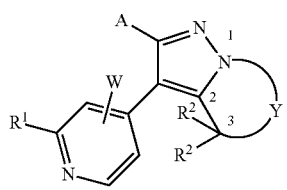

(I)

in which:

Y together with the adjacent nitrogen atom "1" and the two carbon atoms "2" and "3" forms a 5- to 7-membered non-aromatic heterocyclic ring whose further ring members are selected from the group consisting of $C(R^2)_2$, O, S, $NR^3$, $C(R^2)=C(R^2)$, $C(R^2)=N$, $N=N$, $C(=O)$, $C(=S)$, $C(=NR^4)$, $S(=O)_p(=NR^4)_q$ and $SiR^{5a}R^{5b}$;

$R^2$ represent in each case independently of one another H, halogen, cyano, —CHO, —NHCHO, —$N_3$, —N=C=O, —N=C=S, —SH, —C(=O)$NH_2$, —C(=O)NHCN, —C(=O)$OR^6$, —C(=O)$NHOR^{6a}$, $C_1$-$C_5$-alkyl, $C_2$-$C_5$-alkenyl, $C_2$-$C_5$-alkynyl, $C_3$-$C_6$-cycloalkyl, $C_3$-$C_6$-halocycloalkyl, $C_3$-$C_6$-cycloalkenyl, $C_1$-$C_5$-haloalkyl, $C_1$-$C_5$-alkoxy, $C_1$-$C_5$-haloalkoxy, $C_3$-$C_6$-cycloalkoxy, $C_2$-$C_5$-alkenyloxy, $C_3$-$C_5$-haloalkenyloxy, $C_2$-$C_5$-alkynyloxy, $C_2$-$C_5$-alkylcarbonyl, $C_2$-$C_5$-alkylcarbonyloxy, $C_2$-$C_5$-haloalkylcarbonyloxy, $C_3$-$C_5$-alkoxycarbonylalkoxy, $C_1$-$C_5$-alkylthio, $C_1$-$C_5$-haloalkylthio, $C_3$-$C_6$-cycloalkylthio, $C_2$-$C_5$-alkyl(thiocarbonyl), $C_2$-$C_5$-alkylthio(thiocarbonyl), $C_1$-$C_5$-alkylsulphinyl, $C_1$-$C_5$-haloalkylsulphinyl, $C_3$-$C_6$-cycloalkylsulphinyl, $C_1$-$C_5$-alkylsulphonyl, $C_1$-$C_5$-haloalkylsulphonyl, $C_3$-$C_6$-cycloalkylsulphonyl, $C_3$-$C_5$-trialkylsilyl, $C_3$-$C_5$-halotrialkylsilyl, $C_1$-$C_5$-alkylamino, $C_2$-$C_5$-haloalkylamino, $C_3$-$C_6$-cycloalkylamino, $C_2$-$C_5$-dialkylamino or $C_3$-$C_5$-halodialkylamino;

$R^3$ represents H, —CN, —C(=O)$NH_2$, —C(=O)NHCN, —CHO, —NHCHO, —C(=O)$OR^6$, —C(=O)NHOR$^{6a}$, hydroxyl, $C_1$-$C_5$-alkyl, $C_2$-$C_5$-alkenyl, $C_2$-$C_5$-alkynyl, $C_3$-$C_6$-cycloalkyl, $C_3$-$C_6$-halocycloalkyl, $C_3$-$C_6$-cycloalkenyl, $C_4$-$C_{10}$-cycloalkylalkyl, $C_4$-$C_7$-alkylcycloalkyl, $C_5$-$C_7$-alkylcycloalkylalkyl, $C_2$-$C_5$-haloalkyl, $C_1$-$C_4$-alkylcarbonyl, $C_1$-$C_4$-haloalkylcarbonyl, $C_3$-$C_7$-cycloalkylcarbonyl, $C_1$-$C_6$-alkoxycarbonyl, $C_1$-$C_4$-haloalkoxycarbonyl, $C_3$-$C_6$-cycloalkoxycarbonyl, $C_2$-$C_6$-alkoxyalkylcarbonyl, $C_2$-$C_6$-alkoxyalkoxycarbonyl, $C_1$-$C_6$-(alkylthio)carbonyl, $C_1$-$C_6$-alkoxy(thiocarbonyl), $C_1$-$C_6$-alkyl(thiocarbonyl), $C_1$-$C_6$-alkylthio(thiocarbonyl), $C_1$-$C_6$-alkylaminocarbonyl, $C_3$-$C_6$-cycloalkylaminocarbonyl, $C_2$-$C_6$-dialkylaminocarbonyl, $C_1$-$C_6$-alkylamino (thiocarbonyl), $C_2$-$C_6$-dialkylamino(thiocarbonyl), $C_2$-$C_6$-alkoxy(alkyl)aminocarbonyl, $C_3$-$C_6$-alkoxy, $C_1$-$C_5$-haloalkoxy, $C_1$-$C_5$-alkylthio, $C_1$-$C_5$-haloalkylthio, $C_3$-$C_6$-cycloalkylthio, $C_1$-$C_5$-alkylaminosulphonyl, $C_3$-$C_5$-trialkylsilyl or $C_3$-$C_5$-halotrialkylsilyl;

$R^4$ in each case represents H, cyano, amino, hydroxyl, $C_1$-$C_6$-alkyl, $C_3$-$C_6$-cycloalkyl, $C_1$-$C_4$-alkylcarbonyl, $C_1$-$C_4$-haloalkylcarbonyl, $C_1$-$C_4$-alkoxy, phenyl or benzoyl;

$R^{5a}$ and $R^{5b}$ independently of one another represent $C_1$-$C_4$-alkyl, $C_2$-$C_5$-alkenyl, $C_2$-$C_5$-alkynyl, $C_3$-$C_5$-cycloalkyl, $C_3$-$C_6$-halocycloalkyl, $C_4$-$C_7$-cycloalkylalkyl, $C_4$-$C_7$-alkylcycloalkyl, $C_5$-$C_7$-alkylcycloalkylalkyl, $C_1$-$C_5$-haloalkyl, $C_1$-$C_5$-alkoxy or $C_1$-$C_5$-haloalkoxy;

$R^6$ in each case represents H, $C_1$-$C_6$-alkyl, $C_1$-$C_6$-haloalkyl, $C_3$-$C_6$-cycloalkyl, $C_4$-$C_7$-cycloalkylalkyl, $C_4$-$C_7$-alkylcycloalkyl or benzyl;

$R^{6a}$ in each case represents $C_1$-$C_6$-alkyl, $C_1$-$C_6$-haloalkyl, $C_3$-$C_6$-cycloalkyl, $C_4$-$C_7$-cycloalkylalkyl or $C_4$-$C_7$-alkylcycloalkyl;

A represents a phenyl ring which may optionally be mono- or polysubstituted by $R^7$, or represents a thiophenyl ring which may optionally be mono- or polysubstituted by $R^8$;

$R^7$ independently of one another represent halogen, $C_1$-$C_6$-alkyl, $C_2$-$C_6$-alkenyl, $C_2$-$C_6$-alkynyl, $C_3$-$C_6$-cycloalkyl, $C_3$-$C_6$-halocycloalkyl, $C_4$-$C_7$-alkylcycloalkyl, $C_1$-$C_6$-haloalkyl, $C_2$-$C_6$-haloalkenyl, cyano, nitro, $C_1$-$C_6$-alkoxy, $C_1$-$C_6$-haloalkoxy, $C_1$-$C_6$-alkylthio, $C_1$-$C_6$-alkylsulphinyl, $C_1$-$C_6$-alkylsulphonyl, $C_1$-$C_6$-haloalkylthio, $C_1$-$C_6$-haloalkylsulphinyl, $C_1$-$C_6$-haloalkylsulphonyl, $C_1$-$C_6$-alkylamino, $C_2$-$C_6$-dialkylamino, $C_1$-$C_6$-alkylcarbonyl, $C_1$-$C_6$-alkoxycarbonyl, $C_1$-$C_6$-alkylaminocarbonyl, $C_2$-$C_6$-dialkylaminocarbonyl or $C_3$-$C_6$-trialkylsilyl;

$R^8$ independently of one another represent halogen, cyano, $C_1$-$C_3$-alkyl, $C_1$-$C_3$-alkoxy, $C_1$-$C_3$-haloalkyl, or $C_1$-$C_3$-haloalkoxy;

$R^1$ represents H, halogen, cyano, hydroxyl, $C_1$-$C_4$-alkyl, $CONR^{9a}R^{9b}$, COOH, $COOR^{12}$, $-NR^{9a}R^{9b}$, $-N(R^{9b})COR^{9a}$, $-N(R^{9b})CSR^{9a}$, $-N(R^{9b})COOR^{12}$, $-N(R^{9b})SO_2R^{12}$, $-NR^{10}-NR^{11a}R^{11b}$, $-S(O)_mR^{12}$, $-OR^{12}$, $-N=CR^{13a}R^{13b}$ or $-NR^{10}N=CR^{14a}R^{14b}$;

$R^{9a}$ and $R^{11a}$ independently of one another each represent H, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_2$-$C_6$-alkoxyalkyl, $C_3$-$C_6$-alkoxyalkoxyalkyl, $C_3$-$C_6$-alkoxyalkenyl, $C_3$-$C_6$-alkoxyalkynyl, $C_3$-$C_6$-dialkoxyalkyl, $C_4$-$C_{10}$-trialkoxyalkyl, $C_2$-$C_6$-haloalkoxyalkyl, $C_2$-$C_6$-alkoxyhaloalkyl, $C_2$-$C_6$-haloalkoxyhaloalkyl, $C_1$-$C_6$-hydroxyalkyl, $C_1$-$C_{10}$-cyanoalkyl, $C_2$-$C_6$-alkylthioalkyl, $C_2$-$C_6$-alkylsulphinylalkyl, $C_3$-$C_6$-alkylaminoalkyl, $C_3$-$C_6$-haloalkylaminoalkyl, $C_5$-$C_{10}$-cycloalkylaminoalkyl, $C_4$-$C_{10}$-dialkylaminoalkyl, $C_4$-$C_{10}$-halodialkylaminoalkyl, $C_5$-$C_{10}$-cycloalkyl(alkyl)aminoalkyl or $-(CR^{15a}R^{15b})_mR^{16}$;

$R^{9b}$ and $R^{11b}$ independently of one another each represent H, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_2$-$C_6$-alkoxyalkyl, $C_3$-$C_6$-alkoxyalkoxyalkyl, $C_3$-$C_6$-alkoxyalkenyl, $C_3$-$C_6$-alkoxyalkynyl, $C_3$-$C_6$-dialkoxyalkyl, $C_4$-$C_{10}$-trialkoxyalkyl, $C_2$-$C_6$-haloalkoxyalkyl, $C_2$-$C_6$-alkoxyhaloalkyl, $C_2$-$C_6$-haloalkoxyhaloalkyl, $C_1$-$C_6$-hydroxyalkyl, $C_1$-$C_{10}$-cyanoalkyl, $C_2$-$C_6$-alkylthioalkyl, $C_2$-$C_6$-alkylsulphinylalkyl, $C_3$-$C_6$-alkylaminoalkyl, $C_3$-$C_6$-haloalkylaminoalkyl, $C_5$-$C_{10}$-cycloalkylaminoalkyl, $C_4$-$C_{10}$-dialkylaminoalkyl, $C_4$-$C_{10}$-halodialkylammoalkyl, $C_5$-$C_{10}$-cycloalkyl(alkyl)aminoalkyl or $-(CR^{15a}R^{15b})_mR^{16}$;

or $R^{9a}$ and $R^{9b}$ or $R^{11a}$ and $R^{11b}$ in each case together with the nitrogen atom or the (NCO) unit or the (NCS) unit to which they are attached form a 3- to 6-membered ring which may optionally additionally comprise ring members selected from the group consisting of O, $NR^3$, C(=O), C(=S), C(=$NR^4$), $SiR^{5a}R^{5b}$ and $S(=O)_p$(=$NR^4$)$_q$ and which may optionally be substituted at the ring carbon atoms by 1 to 4 substituents selected from the group consisting of halogen, $-CN$, $C_1$-$C_2$-alkyl and $C_1$-$C_2$-alkoxy;

$R^{12}$ in each case represents $C_1$-$C_{10}$-alkyl, $C_2$-$C_{10}$-alkenyl, $C_2$-$C_{10}$-alkynyl, $C_1$-$C_{10}$-haloalkyl, $C_2$-$C_{10}$-haloalkenyl, $C_2$-$C_{10}$-haloalkynyl, $C_2$-$C_{10}$-alkoxyalkyl, $C_3$-$C_{10}$-alkoxyalkoxyalkyl, $C_3$-$C_{10}$-alkoxyalkenyl, $C_3$-$C_{10}$-alkoxyalkynyl, $C_3$-$C_{10}$-dialkoxyalkyl, $C_4$-$C_{10}$-trialkoxyalkyl, $C_2$-$C_{10}$-haloalkoxyalkyl, $C_2$-$C_{10}$-alkoxyhaloalkyl, $C_2$-$C_{10}$-haloalkoxyhaloalkyl, $C_2$-$C_{10}$-hydroxyalkyl, $C_2$-$C_{10}$-cyanoalkyl, $C_2$-$C_{10}$-alkylthioalkyl, $C_2$-$C_{10}$-alkylsulphinylalkyl, $C_3$-$C_{10}$-alkylaminoalkyl, $C_3$-$C_{10}$-haloalkylaminoalkyl, $C_5$-$C_{10}$-cycloalkylaminoalkyl, $C_4$-$C_{10}$-dialkylaminoalkyl, $C_4$-$C_{10}$-halodialkylaminoalkyl, $C_6$-$C_{10}$-cycloalkyl(alkyl)-aminoalkyl or $-(CR^{15a}R^{15b})_mR^{16}$;

$R^{15a}$ and $R^{15b}$ independently of one another represent H, halogen, $C_1$-$C_5$-alkyl, $C_1$-$C_5$-haloalkyl or $C_1$-$C_5$-alkoxy;

or a geminal pair of $R^{15a}$ and $R^{15b}$ together with the carbon atom to which it is attached forms C(=O) or a $C_3$-$C_6$-cycloalkyl ring or a $C_3$-$C_6$-halocycloalkyl ring;

$R^{16}$ represents phenyl, $C_3$-$C_8$-cycloalkyl, $C_3$-$C_8$-cycloalkenyl, a 5- or 6-membered heteroaromatic ring or naphthalenyl or an 8-, 9- or 10-membered heteroaromatic bicyclic ring system, or a 5- or 6-membered heterocyclic non-aromatic ring which optionally contains ring members selected from the group consisting of C(=O), C(=S), C(=$NR^4$), $SiR^{5a}R^{5b}$ and $S(=O)_p$(=$NR^4$)$_q$; where each ring or each ring system may optionally be substituted at the ring carbon atoms by up to 5 substituents independently of one another selected from $R^{17}$;

$R^{17}$ in each case independently of one another represent halogen, $C_1$-$C_6$-alkyl, $C_2$-$C_6$-alkenyl, $C_2$-$C_6$-alkynyl, $C_3$-$C_6$-cycloalkyl, $C_4$-$C_{10}$-alkylcycloalkyl, $C_3$-$C_6$-halocycloalkyl, $C_1$-$C_6$-haloalkyl, $C_2$-$C_6$-haloalkenyl, cyano, nitro, $C_1$-$C_6$-alkoxy, $C_3$-$C_8$-cycloalkoxy, $C_3$-$C_8$-halocycloalkoxy, $C_1$-$C_6$-haloalkoxy, $C_1$-$C_6$-alkylthio, $C_1$-$C_6$-alkylsulphinyl, $C_1$-$C_6$-alkylsulphonyl, $C_1$-$C_6$-haloalkylthio, $C_1$-$C_6$-haloalkylsulphinyl, $C_1$-$C_6$-haloalkylsulphonyl, $C_1$-$C_6$-alkylamino, $C_1$-$C_6$-dialkylamino, $C_1$-$C_6$-alkylcarbonyl, $C_1$-$C_6$-alkoxycarbonyl, $C_1$-$C_6$-alkylaminocarbonyl, $C_3$-$C_6$-dialkylaminocarbonyl, $C_3$-$C_6$-trialkylsilyl, phenyl, naphthalenyl or a 5- or 6-membered heteroaromatic ring;

m represents 0, 1 or 2;

$R^{10}$ in each case represents H, $C_1$-$C_5$-alkyl, $C_2$-$C_5$-alkenyl, $C_2$-$C_5$-alkynyl, $C_3$-$C_6$-cycloalkyl, $C_3$-$C_6$-halocycloalkyl, $C_1$-$C_5$-haloalkyl, $C_2$-$C_5$-haloalkenyl, $C_2$-$C_5$-haloalkynyl, $C_2$-$C_5$-alkoxyalkyl, $C_2$-$C_5$-alkylcarbonyl or $C_1$-$C_5$-alkoxy;

$R^{13a}$ and $R^{13b}$ independently of one another represent H, $-CN$, $-C(=O)OR^{18}$, $C_1$-$C_6$-alkyl, $C_2$-$C_6$-alkenyl, $C_2$-$C_6$-alkynyl, $C_3$-$C_8$-cycloalkyl, $C_3$-$C_8$-halocycloalkyl, $C_3$-$C_8$-cycloalkenyl, $C_4$-$C_{10}$-cycloalkylalkyl, $C_4$-$C_{10}$-alkylcycloalkyl, $C_5$-$C_{10}$-alkylcycloalkylalkyl, $C_1$-$C_6$-alkylamino, $C_2$-$C_6$-dialkylamino, $C_2$-$C_6$-alkylaminoalkyl, $C_2$-$C_6$-haloalkylaminoalkyl, $C_4$-$C_6$-cycloalkylaminoalkyl, $C_3$-$C_6$-dialkylaminoalkyl, $C_3$-$C_6$-halodialkylaminoalkyl, $C_5$-$C_{10}$-cycloalkyl(alkyl)aminoalkyl, $C_1$-$C_6$-alkoxy, $C_1$-$C_6$-haloalkoxy, $C_3$-$C_{10}$-cycloalkoxy, $C_1$-$C_{10}$-alkylthio, $C_1$-$C_{10}$-haloalkylthio, $C_3$-$C_{10}$-cycloalkylthio, $C_3$-$C_{10}$-trialkylsilyl or $C_3$-$C_{10}$-halotrialkylsilyl, or phenyl or a 5- or 6-membered heteroaromatic ring, or an 8-, 9- or 10-membered heteroaromatic bicyclic ring system, or a 5- or 6-membered heterocyclic non-aromatic ring which optionally contains ring members selected from the group consisting of $NR^3$, $C(=O)$, $C(=S)$, $C(=NR^4)$, $SiR^{5a}R^{5b}$ and $S(=O)_p(=NR^4)_q$; where each ring or each ring system may optionally be substituted at the ring carbon atoms by 1 to 5 substituents selected from the group consisting of $C_1$-$C_3$-alkyl, halogen, —CN and $C_1$-$C_3$-alkoxy;

or $R^{13a}$ and $R^{13b}$ together with the carbon atom to which they are attached form a 3- to 6-membered ring, where said ring may optionally contain ring members selected from the group consisting of $NR^3$, $C(=O)$, $C(=S)$, $C(=NR^4)$, $SiR^{5a}R^{5b}$ and $S(=O)_p(=NR^4)_q$ and may optionally be substituted at the ring carbon atoms by 1 to 4 substituents selected from the group consisting of $C_1$-$C_2$-alkyl, halogen, —CN and $C_1$-$C_2$-alkoxy;

$R^{14a}$ and $R^{14b}$ independently of one another represent H, —CN, —C(=O)OR$^{18}$, $C_1$-$C_6$-alkyl, $C_2$-$C_6$-alkenyl, $C_2$-$C_6$-alkynyl, $C_3$-$C_8$-cycloalkyl, $C_3$-$C_8$-halocycloalkyl, $C_3$-$C_8$-cycloalkenyl, $C_4$-$C_{10}$-cycloalkylalkyl, $C_4$-$C_{10}$-alkylcycloalkyl, $C_5$-$C_{10}$-alkylcycloalkylalkyl, $C_1$-$C_6$-alkylamino, $C_2$-$C_6$-dialkylamino, $C_2$-$C_6$-alkylaminoalkyl, $C_2$-$C_6$-haloalkylaminoalkyl, $C_4$-$C_6$-cycloalkylaminoalkyl, $C_3$-$C_6$-dialkylaminoalkyl, $C_3$-$C_6$-halodialkylaminoalkyl, $C_5$-$C_{10}$-cycloalkyl(alkyl)aminoalkyl, $C_1$-$C_6$-alkoxy, $C_1$-$C_6$-haloalkoxy, $C_3$-$C_{10}$-cycloalkoxy, $C_1$-$C_{10}$-alkylthio, $C_1$-$C_{10}$-haloalkylthio, $C_3$-$C_{10}$-cycloalkylthio, $C_3$-$C_{10}$-trialkylsilyl or $C_3$-$C_{10}$-halotrialkylsilyl, or phenyl or a 5- or 6-membered heteroaromatic ring, or an 8-, 9- or 10-membered heteroaromatic bicyclic ring system, or a 5- or 6-membered heterocyclic non-aromatic ring which optionally contains ring members selected from the group consisting of $NR^3$, $C(=O)$, $C(=S)$, $C(=NR^4)$, $SiR^{5a}R^{5b}$ and $S(=O)_p(=NR^4)_q$; where each ring or each ring system may optionally be substituted at the ring carbon atoms by 1 to 5 substituents selected from the group consisting of $C_1$-$C_3$-alkyl, halogen, —CN and $C_1$-$C_3$-alkoxy;

or $R^{14a}$ and $R^{14b}$ together with the carbon atom to which they are attached form a 3- to 6-membered ring, where said ring may optionally contain ring components selected from the group consisting of $NR^3$, $C(=O)$, $C(=S)$, $C(=NR^4)$, $SiR^{5a}R^{5b}$ and $S(=O)p(=NR^4)_q$ and may optionally be substituted at the ring carbon atoms by 1 to 4 substituents selected from the group consisting of $C_1$-$C_2$-alkyl, halogen, —CN and $C_1$-$C_2$-alkoxy;

p and q independently of one another represent 0, 1 or 2, provided the sum of p and q is 1 or 2;

$R^{18}$ represents $C_1$-$C_6$-alkyl, $C_1$-$C_6$-haloalkyl, $C_3$-$C_6$-cycloalkyl, $C_4$-$C_7$-cycloalkylalkyl or $C_4$-$C_7$-alkylcycloalkyl, W represents H or W represents halogen, CN, $C_1$-$C_4$-haloalkyl, $C_1$-$C_4$-alkyl, or $C_1$-$C_4$-alkoxy.

2. The compound of formula (I), or the agrochemically active salt thereof, of claim 1, in which:

Y together with the adjacent nitrogen atom "1" and the two carbon atoms "2" and "3" forms a 5- to 7-membered non-aromatic heterocyclic ring whose further ring members are selected from the group consisting of $C(R^2)_2$, O, S, $SO_2$, $NR^3$, —$C(R^2)=C(R^2)$—, $C(=O)$ and $C(=S)$;

$R^2$ represent in each case independently of one another H, halogen, cyano, —CHO, —C(=O)OR$^6$, —C(=O)NHOR$^{6a}$, $C_1$-$C_5$-alkyl, $C_2$-$C_5$-alkenyl, $C_2$-$C_5$-alkynyl, $C_3$-$C_6$-cycloalkyl, $C_3$-$C_6$-halocycloalkyl, $C_3$-$C_6$-cycloalkenyl, $C_1$-$C_5$-haloalkyl, $C_1$-$C_5$-alkoxy, $C_1$-$C_5$-haloalkoxy, $C_3$-$C_6$-cycloalkoxy, $C_2$-$C_5$-alkenyloxy, $C_3$-$C_5$-haloalkenyloxy, $C_2$-$C_5$-alkynyloxy, $C_2$-$C_5$-alkylcarbonyl, $C_1$-$C_5$-alkylthio, $C_1$-$C_5$-haloalkylthio or $C_3$-$C_6$-cycloalkylthio;

$R^3$ represents H, —CN, —C(=O)NH$_2$, —C(=O)NHCN, —CHO, —C(=O)OR$^6$, —C(=O)NHOR$^{6a}$, $C_1$-$C_5$-alkyl, $C_2$-$C_5$-haloalkyl, $C_1$-$C_4$-alkylcarbonyl, $C_1$-$C_4$-haloalkylcarbonyl, $C_3$-$C_6$-cycloalkylcarbonyl, $C_1$-$C_4$-alkoxycarbonyl, $C_1$-$C_4$-haloalkoxycarbonyl, $C_3$-$C_6$-cycloalkoxycarbonyl, $C_3$-$C_6$-alkoxyalkylcarbonyl, $C_3$-$C_6$-alkoxyalkoxycarbonyl, $C_1$-$C_4$-(alkylthio)carbonyl, $C_1$-$C_4$-alkoxy(thiocarbonyl), $C_1$-$C_4$-alkyl(thiocarbonyl), $C_1$-$C_4$-alkylthio(thiocarbonyl), $C_1$-$C_4$-alkylaminocarbonyl, $C_3$-$C_6$-cycloalkylaminocarbonyl, $C_2$-$C_6$-dialkylaminocarbonyl, $C_2$-$C_6$-alkylamino(thiocarbonyl), $C_2$-$C_6$-dialkylamino(thiocarbonyl) or $C_3$-$C_6$-alkoxy(alkyl)aminocarbonyl;

$R^6$ in each case represents H or $C_1$-$C_4$-alkyl;

$R^{6a}$ in each case represents $C_1$-$C_4$-alkyl;

A represents a phenyl ring which may optionally be mono- or polysubstituted by $R^7$, or represents a thiophenyl ring which may optionally be mono- or polysubstituted by $R^8$;

$R^7$ independently of one another represent halogen, $C_1$-$C_4$-alkyl, $C_1$-$C_4$-haloalkyl, cyano, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl or $C_1$-$C_4$-haloalkylthio;

$R^8$ independently of one another represent halogen, cyano, $C_1$-$C_3$-alkyl, $C_1$-$C_3$-alkoxy, or $C_1$-$C_3$-haloalkyl;

$R^1$ represents H, halogen, $C_1$-$C_3$-alkyl, cyano, —NR$^{9a}$R$^{9b}$, —N(R$^{9b}$)COR$^{9a}$, —N(R$^{9b}$)CSR$^{9a}$, —N(R$^{9b}$)COOR$^{12}$, —OR$^{12}$, —S(O)mR$^{6a}$, COOR$^{12}$ or —CONR$^{9a}$R$^{9b}$;

$R^{9a}$ in each case represents H, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_2$-$C_6$-alkoxyalkyl, $C_3$-$C_6$-alkoxyalkoxyalkyl, $C_3$-$C_6$-alkoxyalkenyl, $C_3$-$C_6$-alkoxyalkynyl, $C_3$-$C_6$-dialkoxyalkyl, $C_2$-$C_6$-haloalkoxyalkyl, $C_2$-$C_6$-alkoxyhaloalkyl, $C_2$-$C_6$-haloalkoxyhaloalkyl, $C_1$-$C_6$-hydroxyalkyl, $C_1$-$C_6$-cyanoalkyl, $C_2$-$C_6$-alkylthioalkyl, $C_2$-$C_6$-alkylsulphinylalkyl, $C_3$-$C_6$-alkylaminoalkyl, $C_3$-$C_6$-haloalkylaminoalkyl, $C_5$-$C_{10}$-cycloalkylaminoalkyl, $C_4$-$C_{10}$-dialkylaminoalkyl, $C_4$-$C_{10}$-halodialkylaminoalkyl or —(CR$^{15a}$R$^{15b}$)$_m$R$^{16}$;

$R^{9b}$ in each case represents H, $C_1$-$C_6$-alkyl, $C_2$-$C_6$-alkenyl, $C_2$-$C_6$-alkynyl, $C_1$-$C_6$-haloalkyl or —(CR$^{15a}$R$^{15b}$)$_m$R$^{16}$;

or $R^{9a}$ and $R^{9b}$ in each case together with the nitrogen atom or the (NCO) or the (NCS) unit to which they are attached form a 3- to 6-membered ring which may optionally additionally also comprise ring members selected from the group consisting of $NR^3$, $C(=O)$, $C(=S)$, and O and which is optionally substituted at the ring carbon atoms by 1 to 4 substituents selected from the group consisting of halogen, —CN, $C_1$-$C_2$-alkyl and $C_1$-$C_2$-alkoxy;

$R^{12}$ in each case represents $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl or —$(CR^{15a}R^{15b})_m R^{16}$;

$R^{15a}$ and $R^{15}$ independently of one another represent H, halogen or $C_1$-$C_4$-alkyl;

$R^{16}$ represents phenyl, $C_3$-$C_8$-cycloalkyl, $C_3$-$C_8$-cycloalkenyl, a 5- or 6-membered heteroaromatic ring or naphthalenyl or an 8-, 9- or 10-membered heteroaromatic bicyclic ring system, or a 5- or 6-membered heterocyclic non-aromatic ring which optionally contains ring members selected from the group consisting of C(=O), C(=S), and C(=NR$^4$); where each ring or each ring system may optionally be substituted at the ring carbon atoms by up to 3 substituents independently of one another selected from $R^{17}$;

$R^{17}$ in each case independently of one another represent halogen, cyano, $C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, or $C_1$-$C_6$-alkoxy;

m represents 0, 1 or 2,

W represents H or

W represents fluorine, chlorine, CN, CF$_3$, methyl, ethyl, or methoxy.

3. The compound of formula (I), or the agrochemically active salt thereof, of claim 1 in which:

Y together with the adjacent nitrogen atom "1" and the two carbon atoms "2" and "3" forms a 5- to 7-membered non-aromatic heterocyclic ring selected from the group consisting of: H-1, H-2, H-3, H-4, H-5, H-6, H-7, H-8, H-9 and H-10 shown in Scheme 1, where s is a number from 0 to 4;

Scheme 1

H-1

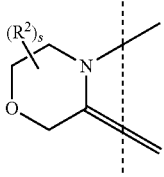

H-2

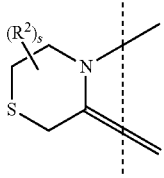

H-3

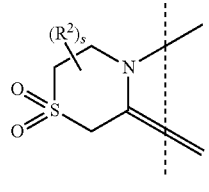

H-4

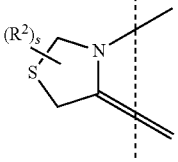

H-5

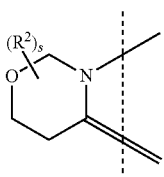

H-6

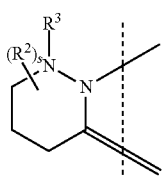

H-7

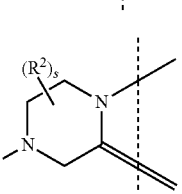

H-8

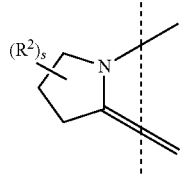

H-9

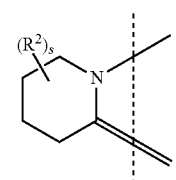

H-10

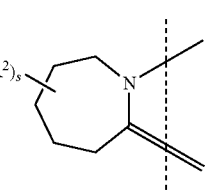

$R^2$ in each case independently of one another represent H, F, Cl, Br, I, cyano, —CHO, —C(=O)OR$^6$, methyl, ethyl, isopropyl, n-propyl, trifluoromethyl, difluoromethyl, dichloromethyl, pentafluoroethyl, methoxy, ethoxy, n-propoxy, isopropoxy, trifluoromethoxy, difluoromethoxy or acetyl, propionyl, isobutyryl, or 2,2-dimethylpropanoyl;

$R^3$ represents H, —CHO, methyl, ethyl, isopropyl, n-propyl, acetyl, propionyl, isobutyryl, 2,2-dimethylpropanoyl, trifluoroacetyl, difluoroacetyl, CH$_3$OC(O), CH$_3$CH$_2$C(O), (CH$_3$)$_2$CHC(O)CF$_3$OC(O), or CF$_2$HOC(O);

$R^6$ in each case represents H, methyl, ethyl, isopropyl, or n-propyl;

A represents a phenyl or thiophene ring which is optionally substituted by radicals selected from the group consisting of F, Cl, Br, I, cyano, methyl, ethyl, isopropyl, n-propyl, trifluoromethyl, difluoromethyl, dichloromethyl, pentafluoroethyl, methoxy, ethoxy, and n-propoxy, isopropoxy;

$R^1$ represents H, F, Cl, Br, I, $CH_3$, $S(O)_m Me$, $-NR^{9a}R^{9b}$, $(R^{9b})COR^{9a}$, or $N(R^{9b})COOR^{12}$;

$R^{9a}$ in each case represents H, methyl, ethyl, isopropyl, n-propyl, n-butyl, sec-butyl, tert-butyl, isobutyl, n-pentyl, n-hexyl, $-CH=CH_2$, $-CH_2CH=CH_2$, $-CH=CHCH_3$, $-CH_2C\equiv CH$, $-C\equiv CH$, trifluoromethyl, difluoromethyl, dichloromethyl, pentafluoroethyl, methoxymethyl, ethoxymethyl, methoxyethyl, tert-butoxymethyl, hydroxymethyl, 1-hydroxyethyl, 2-hydroxypropan-2-yl or $-(CH_2)_m R^{16}$;

$R^{9b}$ in each case represents H, methyl, ethyl, isopropyl, n-propyl, n-butyl, sec-butyl, tert-butyl, isobutyl, n-pentyl, n-hexyl, $-CH_2CH=CH_2$, $-CH=CHCH_3$, $-CH_2C\equiv CH$, or $-C\equiv CH$;

$R^{9a}$ and $R^{9b}$ in each case together with the nitrogen to which they are attached form a 5- or 6-membered ring which is optionally substituted at the ring carbon atoms by 1 or 2 substituents selected from the group consisting of F, Cl, Br, I, —CN and methyl, ethyl;

$R^{12}$ represents methyl, ethyl, isopropyl, n-propyl, n-butyl, sec-butyl, tert-butyl, isobutyl, $-CH_2CH=CH_2$, $-CH=CHCH_3$, $CH_2C\equiv CH$, $-C\equiv CH$, trifluoromethyl, difluoromethyl, dichloromethyl or $-(CH_2)_m R^{16}$;

$R^{16}$ represents cyclopropyl, cyclobutyl, cyclopentyl, cyclohexyl, cyclopentenyl, cyclohexenyl, phenyl or thienyl, each of which may optionally be substituted by up to 2 radicals selected from the group $R^{17}$;

$R^{17}$ in each case independently of one another represent F, Cl, Br, I, methyl, ethyl, isopropyl, n-propyl, n-butyl, sec-butyl, tert-butyl, isobutyl, trifluoromethyl, difluoromethyl, dichloromethyl, methoxy, ethoxy or cyano;

m represents 0, 1 and 2,

W represents H or

W represents fluorine, chlorine, CN, $CF_3$, methyl, or ethyl.

4. The compound of formula (I), or the agrochemically active salt thereof, of claim 1, in which:

Y together with the adjacent nitrogen atom "1" and the two carbon atoms "2" and "3" forms a 5- to 7-membered non-aromatic heterocyclic ring selected from the group consisting of: H-1, H-2, H-3, H-4, H-5 and H-8 shown in Scheme 2, where s is a number from 0 to 4;

Scheme 2

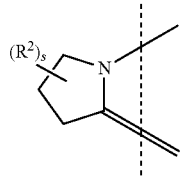

H-1

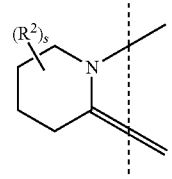

H-2

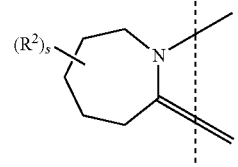

H-3

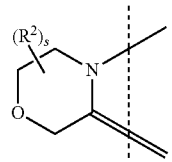

H-4

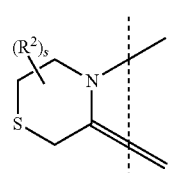

H-5

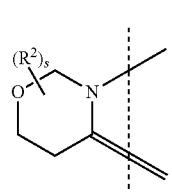

H-8

$R^2$ in each case independently of one another represent H, fluorine, chlorine, cyano, $CF_3$, methyl or methoxy;

A represents a phenyl or thiophene ring which is optionally substituted by radicals selected from the group consisting of F, Cl, cyano, $CH_3$, and $CF_3$;

$R^1$ represents H, fluorine, chlorine, $S(O)_m Me$, $NR^{9a}R^{9b}$, $(R^{9b})COR^{9a}$, or $N(R^{9b})COOR^{12}$;

$R^{9a}$ in each case represents H, methyl, ethyl, n-propyl, isopropyl, n-butyl, isobutyl, sec-butyl, tert-butyl, n-pentyl, n-hexyl, methoxymethyl, ethoxymethyl, ethoxyethyl, methoxyethyl, methoxypropyl, hydroxymethyl, 1-hydroxyethyl, 2-hydroxyethyl, hydroxypropyl or $-(CH_2)_m R^6$;

$R^{9b}$ in each case represents H, methyl, ethyl, n-propyl, isopropyl, n-butyl, allyl or propargyl;

$R^{12}$ represents methyl, ethyl, n-propyl, isopropyl, t-butyl, allyl, propargyl or $-(CH_2)_m R^{16}$;

$R^{16}$ represents cyclopropyl, cyclopentyl, cyclobutyl, cyclohexyl, thienyl or phenyl, each of which may be substituted by a radical selected from the group $R^{17}$;

m represents 0, 1 or 2;

$R^{17}$ represents methyl, ethyl, fluorine, chlorine, $CF_3$, OMe, or cyano;

W represents H, or

W represents fluorine, chlorine, or cyano.

5. A method for controlling phytopathogenic and mycotoxin-producing fungi, comprising, applying one or more bicyclic pyridinylpyrazoles of the formula (I), or agrochemically active salts thereof, of claim 1, to the fungi, their habitat, or a combination thereof.

6. A composition, comprising at least one compound of the formula (I), or an agrochemically active salt thereof, of claim 1, and an extender, a surfactant, or a combination thereof.

7. A method for controlling phytopathogenic harmful fungi, comprising applying a compound of the formula (I), or an agrochemically active salt thereof, of claim 1, to the phytopathogenic harmful fungi.

8. A process for preparing a composition, comprising mixing one or more compounds of the formula (I), or agrochemically active salts thereof, of claim 1 with an extender, a surfactant, or a combination thereof.

9. A method for treating a plant, comprising contacting one or more compounds of the formula (I), or agrochemically active salts thereof, of claim 1, with the plant.

10. A method for treating a seed of a transgenic plant, a transgenic plant, or a combination thereof, comprising contacting one or more compounds of formula (I), or agrochemically active salts thereof, of claim 1, with the seed of the transgenic plant, the transgenic plant, or a combination thereof.

11. The method of claim 10, comprising treating the seed of the transgenic plant.

12. The method of claim 10, comprising treating the transgenic plant.

13. The method of claim 11, wherein the seed of the transgenic plant comprises a heterologous gene from a microorganism species of: *Bacillus, Rhizobium, Pseudomonas, Serratia, Trichoderma, Clavibacter, Glomus,* or *Gliocladium.*

14. The method of claim 13, wherein the seed of the transgenic plant comprises a heterologous gene from *Bacillus* sp.

15. A compound of formula (I) of claim 1.

16. A agrochemically active salt of the compound of formula (I) of claim 1.

17. A compound of formula (I) of claim 2.

18. A agrochemically active salt of the compound of formula (I) of claim 2.

19. A compound of formula (I) of claim 3.

20. A agrochemically active salt of the compound of formula (I) of claim 3.

* * * * *